(12) United States Patent
Baumann et al.

(10) Patent No.: US 8,557,847 B2
(45) Date of Patent: Oct. 15, 2013

(54) SYNERGISTIC MODULATION OF FLT3 KINASE USING A FLT3 INHIBITOR AND A FARNESYL TRANSFERASE INHIBITOR

(75) Inventors: Christian Andrew Baumann, Exton, PA (US); Michael David Gaul, Yardley, PA (US); Dana L. Johnson, Upper Black Eddy, PA (US); Robert W. Tuman, Chalfont, PA (US)

(73) Assignee: Janssen Pharmaceutica, N.V., Beerse (BE)

( * ) Notice: Subject to any disclaimer, the term of this patent is extended or adjusted under 35 U.S.C. 154(b) by 216 days.

(21) Appl. No.: 12/421,778

(22) Filed: Apr. 10, 2009

(65) Prior Publication Data

US 2009/0197913 A1 Aug. 6, 2009

Related U.S. Application Data

(63) Continuation of application No. 11/422,413, filed on Jun. 6, 2006, now abandoned.

(60) Provisional application No. 60/793,320, filed on Apr. 19, 2006, provisional application No. 60/690,070, filed on Jun. 10, 2005.

(51) Int. Cl.
 *A61K 31/445* (2006.01)
 *C07D 293/10* (2006.01)

(52) U.S. Cl.
 USPC ............................... 514/326; 514/908; 544/1

(58) Field of Classification Search
 USPC ..................................... 514/326, 908; 544/1
 See application file for complete search history.

(56) References Cited

U.S. PATENT DOCUMENTS

| | | | |
|---|---|---|---|
| 2,466,420 A | 4/1949 | Hagemeyer et al. | |
| 3,226,394 A | 12/1965 | Schipper | |
| 4,551,540 A | 11/1985 | Hechenbleikner et al. | |
| 5,190,541 A | 3/1993 | Abele et al. | |
| 5,474,765 A | 12/1995 | Thorpe | |
| 5,762,918 A | 6/1998 | Thorpe | |
| 5,855,866 A | 1/1999 | Thorpe et al. | |
| 5,874,442 A | 2/1999 | Doll et al. | |
| 5,944,718 A | 8/1999 | Austin et al. | |
| 5,968,952 A | 10/1999 | Venet et al. | |
| 6,037,350 A | 3/2000 | Venet et al. | |
| 6,100,254 A | 8/2000 | Budde et al. | |
| 6,117,432 A | 9/2000 | Ganne et al. | |
| 6,169,096 B1 | 1/2001 | Venet et al. | |
| 6,187,786 B1 | 2/2001 | Venet et al. | |
| 6,235,746 B1 | 5/2001 | Davis et al. | |
| 6,342,219 B1 | 1/2002 | Thorpe et al. | |
| 6,346,625 B1 | 2/2002 | Karabelaset et al. | |
| 6,383,790 B1 | 5/2002 | Shokat | |
| 6,420,387 B1 | 7/2002 | Venet et al. | |
| 6,458,800 B1 | 10/2002 | Angibaud et al. | |
| 6,596,746 B1 | 7/2003 | Das et al. | |
| 6,692,491 B1 | 2/2004 | Phan | |
| 7,157,456 B2 | 1/2007 | Straub et al. | |
| 7,208,493 B2 | 4/2007 | Wrasidlo et al. | |
| 7,414,050 B2 | 8/2008 | Illig et al. | |
| 7,427,683 B2 | 9/2008 | Player et al. | |
| 7,429,603 B2 | 9/2008 | Player et al. | |
| 7,645,755 B2 | 1/2010 | Illig et al. | |
| 7,662,837 B2 | 2/2010 | Illig et al. | |
| 7,790,724 B2 | 9/2010 | Player et al. | |
| 7,795,279 B2 * | 9/2010 | Ballentine et al. | 514/326 |
| 7,973,035 B2 | 7/2011 | Illig et al. | |
| 2002/0016625 A1 | 2/2002 | Falotico et al. | |
| 2004/0049032 A1 | 3/2004 | Charrier et al. | |
| 2005/0113566 A1 | 5/2005 | Player et al. | |
| 2006/0040995 A1 | 2/2006 | Bacque et al. | |
| 2006/0100619 A1 | 5/2006 | McClurken et al. | |
| 2006/0122181 A1 | 6/2006 | Ikemoto et al. | |
| 2006/0148812 A1 | 7/2006 | Illig | |
| 2006/0189623 A1 | 8/2006 | Illig et al. | |
| 2006/0258666 A1 | 11/2006 | Player et al. | |

(Continued)

FOREIGN PATENT DOCUMENTS

| | | |
|---|---|---|
| EP | 1566379 A1 | 8/2005 |
| GB | 1189719 | 4/1970 |
| WO | 94/10138 | 5/1994 |
| WO | 96/11932 | 4/1996 |
| WO | 96/21452 | 7/1996 |
| WO | 96/32907 | 10/1996 |
| WO | 97/16443 | 5/1997 |
| WO | 97/21701 | 6/1997 |
| WO | 97/30992 | 8/1997 |
| WO | 98/06700 | 2/1998 |
| WO | 98/28264 | 7/1998 |
| WO | 98/28303 | 7/1998 |

(Continued)

OTHER PUBLICATIONS

Cortes. Farnesyltransferase inhibitors in acute myeloid leukemia and myelodysplastic syndromes. Clinical Lymphoma, vol. 4, Suppl. 1, S30-S35, 2003.*

(Continued)

*Primary Examiner* — Anna Pagonakis

(57) ABSTRACT

The invention is directed to a method of inhibiting FLT3 tyrosine kinase activity or expression or reducing FLT3 kinase activity or expression in a cell or a subject comprising the administration of a farnesyl transferase inhibitor and a FLT3 kinase inhibitor selected from compounds of Formula I':

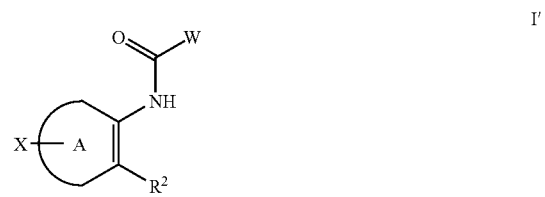

Included within the present invention is both prophylactic and therapeutic methods for treating a subject at risk of (or susceptible to) developing a cell proliferative disorder or a disorder related to FLT3.

15 Claims, 40 Drawing Sheets

(56) References Cited

U.S. PATENT DOCUMENTS

| | | | |
|---|---|---|---|
| 2006/0258724 | A1 | 11/2006 | Straub et al. |
| 2006/0281788 | A1 | 12/2006 | Baumann et al. |
| 2007/0249593 | A1 | 10/2007 | Illig et al. |
| 2007/0249608 | A1 | 10/2007 | Illig et al. |
| 2007/0249649 | A1 | 10/2007 | Illig et al. |
| 2007/0249680 | A1 | 10/2007 | Illig et al. |
| 2007/0249685 | A1 | 10/2007 | Illig et al. |
| 2008/0051402 | A1 | 2/2008 | Illig et al. |
| 2009/0105296 | A1 | 4/2009 | Chen et al. |
| 2011/0195960 | A1 | 8/2011 | Illig et al. |

FOREIGN PATENT DOCUMENTS

| | | |
|---|---|---|
| WO | 98/40383 | 9/1998 |
| WO | 98/49157 | 11/1998 |
| WO | 98/54174 | 12/1998 |
| WO | 99/45712 | 9/1999 |
| WO | 99/45912 | 9/1999 |
| WO | 00/01691 | 1/2000 |
| WO | 00/02871 | 1/2000 |
| WO | 00/12498 | 3/2000 |
| WO | 00/12499 | 3/2000 |
| WO | WO 00/27820 A1 | 5/2000 |
| WO | 00/39082 | 7/2000 |
| WO | 01/49667 | 7/2001 |
| WO | WO 01/47897 A1 | 7/2001 |
| WO | WO 01/47919 A1 | 7/2001 |
| WO | WO 02/32861 A2 | 4/2002 |
| WO | WO 02/068406 A2 | 9/2002 |
| WO | WO 02/092599 A1 | 11/2002 |
| WO | WO 03/024931 A1 | 3/2003 |
| WO | WO 03/024969 A1 | 3/2003 |
| WO | WO 03/035009 A2 | 5/2003 |
| WO | WO 03/037347 A1 | 5/2003 |
| WO | WO 03/057690 A1 | 7/2003 |
| WO | 03/099796 | 12/2003 |
| WO | WO 03/099771 A2 | 12/2003 |
| WO | WO 2004/005281 A1 | 1/2004 |
| WO | WO 2004/016597 A2 | 2/2004 |
| WO | 2004/022525 | 3/2004 |
| WO | WO 2004/018419 A2 | 3/2004 |
| WO | WO 2004/039782 A1 | 5/2004 |
| WO | WO 2004/043389 A2 | 5/2004 |
| WO | WO 2004/046120 A2 | 6/2004 |
| WO | WO 2004/058749 A1 | 7/2004 |
| WO | 2004/085388 | 10/2004 |
| WO | 2004/096795 | 11/2004 |
| WO | 2005/012220 | 2/2005 |
| WO | 2005/040139 | 5/2005 |
| WO | 2005/047273 | 5/2005 |
| WO | 2005/073225 | 8/2005 |
| WO | 2006/047504 A1 | 5/2006 |
| WO | WO 2006/047277 * | 5/2006 |
| WO | WO 2006/047277 A2 | 5/2006 |
| WO | 2006/135630 | 12/2006 |
| WO | 2006/135636 | 12/2006 |
| WO | 2006/135713 | 12/2006 |
| WO | 2006/135718 | 12/2006 |
| WO | WO 2006/138155 A1 | 12/2006 |
| WO | 2007/048088 | 4/2007 |
| WO | 2009/058968 | 5/2009 |

OTHER PUBLICATIONS

ChemBlink. Tipifarnib. Electronic Resource. Retrived on Dec. 18, 2010: [http://www.chemblink.com/products/192185-72-1.html].*

Thalhammer et al. Duration of second complete remission in patients with acute myeloid leukemia treated with chemotherapy: a retrospective single-center study. Ann. Hematology, 1996, 72: 216-222.*

Acute myeloid leukemia: MedlinePlus Medical Encyclopedia. Retrieved on Dec. 28, 2010. Electronic Resource: http://www.nlm.nih.gov/medlineplus/ency/article/000542.htm].*

Berenbaum et al. What is synergy? Pharmacological Reviews, 1989.*

Yee et al. Synergistic effect of SU11248 with cytarabine or daunorubicin on FLT3 ITD-positive leukemic cells. Blood, 2004, 104: 42-2-4209. Published online Aug. 10, 2004.*

Zhu et al. Farnesyltransferase inhibitor R115777 (Zarnestra, Tipifarnib) synergizes with paclitaxel to induce apoptosis and mitotic arrest and to inhibit tumor growth of multiple myeloma cells. Blood, vol. 105, No. 12, 4759-4766, Published online Feb. 22, 2005.*

Abdel-Magid, J Org. Chem. 61 pp. 3849-3862 (1996).

Abdel-Magid et al, "Reductive Amination of Aldehydes and Ketones with Sodium Triacetoxyborohydride.Studies on Direct and Indirect Reductive Amination Procedures", J Org. Chem., vol. 61 pp. 3849-3862 (1996).

Ansari-Lari, A. et al., "FLT3 mutations in myeloid sarcoma" British Journal of Haematology. Sep. 2004 126(6):785-91.

Arnon et al., "Monoclonal Antibodies for Immunotargeting of Drugs in Cancer Therapy", in Monoclonal Antibodies and Cancer Therapy, Reisfeld et al. (eds.), pp. 243-256 (Alan R. Liss, Inc. 1985).

Baumann CA, Zeng L, Donatelli RR, Maroney AC. Development of a quantitative, high-throughput cell-based enzyme-linked immunosorbent assay for detection of colony-stimulating factor-1 receptor tyrosine kinase inhibitors. J Biochem Biophys Methods. 2004; 60:69-79.

Berge, S., et al, "Pharmaceutical Salts", J. Pharm. Sci., Jan. 1977, 66(1): 1-19.

Bodansky, M. et al., "The Practice of Peptide Synthesis", Springer-Verlag, NY (1984).

British Journal of Haematology, "Flt3 mutations and leukaemia", 2003,122(4):523-38.

Buchwald, E.L. et al., Top. Curr. Chem., 219:131-209 (2001).

Canibano, V. et al., Synthesis 14, 2175 (2001).

Comprehensive Organic Transformations: Larock, R.S.; Wiley and Sons Inc., USA 1999.

Drexler, H. G. et al. (2004), "FLT3: receptor and ligand"; Growth Factors 22(2):71-3.

Drexler, H.G., "The Leukemia-Lymphoma Cell Line Factsbook", Academic Pres:SanDiego, CA, 2000.

Gray, M., et al. "Practical Methylation of Aryl Halides by Suzuki-Miyaura Coupling" Tetrahedron Letters, 41:6237-40 (2000).

Gilliand, G., et.al, "The roles of FLT3 in mematopoiesis and leukemia", Blood. 2002; 100:1532-42.

Gould, P., "Salt selection for basic drugs", Ref. International J. Pharm. 1986, 33, 201-217.

Gray, M. et al., Tetrahedron Lett., 41:6237-40 (2000).

Griswold, I. J. et al., "Effects of MLN518, A Dual FLT3 and KIT inhibitor, on Normal and Malignant Hematopoiesis" Blood, Jul. 2004 [Epub ahead of print].

Hartwig, J.F., "Organopalladium Chemistry for Organic Synthesis," Wiley Interscience, NY (2002).

Hellstrom et al., "Antibodies for Drug Delivery", in Controlled Drug Delivery (2nd Ed.), Robinson et al. (eds.), pp. 623-653 (Marcel Dekker, Inc. 1987).

Iddon. B. et al., J. Chem. Soc. Perkin Trans. 1., 1370, (1980).

Kamwakami J., et al. "A Convenient Synthesis of 4(5)-Alkylacyl-1H-imidazoles from 4(5)-Imidazolecarboxaldehyde" Synthesis, No. 5, pp. 677-680 (2003).

Katritsky, A. et al., "para-Formylation of Nitroarenes via Vicarious Nucleophilic Substitution of Hydrogen with Tris(benzotriazol-1-yl)methane", Tetrahedron Lett., 37:347-50 (1996).

Kolder, C.R., et al, "Synthesis and Reactivity of 5-Chloro-2,4-Dihydrosypyridine", x Recl. Tray. Chim. Pays-Bas; 285 (1953).

Levis, M. et al. 2001, "A FLT3 tyrosine kinase inhibitor is selectively cytoxic to acute myeloid leukemia blasts harboring FLT3 internal tandem duplication mutations", Blood 98(3):885-7.

Levis, M. et al., "Novel FLT3 tyrosine kinase inhibitors" Expert Opin. Investing. Drugs (2003) 12 (12) 1951-1962.

Levis, M. et al., "Small Molecule FLT3 Tyrosine Kinase Inhibitors" Current Pharmaceutical Design, 2004, 10, 1183-1193.

Lewis, et al. "Diacetoxypiperidinium Analogs of Acetylcholine", Junal of Medicinal Chemistry, 1973, vol. 16, No. 2 pp. 156-159.

Loader, C., et al., "Pyrrole chemistry. XXIII. The cyanation of substituted pyrroles with chlorosulfonyl isocyanate (CSI). New syntheses of pyrrole-3-carbonitriles.", Can. J. Chem, 59, 2673 (1981).

(56) References Cited

OTHER PUBLICATIONS

Lyon, R., et al., "Synthesis and Evaluation of Phenyl- and Benzoylpiperazines as Potential Serotonergic Agents", J. Med. Chem., 29: 630-4 (1986).
Major, R., et al. "1-Alkoxy-4-phenyl-4-propionoxypiperdines and Their 3-Methyl Homologs as New Analgesics", vol. 26, pp. 1867-1847, (1961).
McKenna, H.J. et al., "Mice lacking flt3 ligand having deficient hematopoiesis affecting hematopoietic progenitor cells, dendritic cells and natural killer cells", Blood Jun. 2000; 95:3489-3497.
Miyaura, N. et al., "Palladium-Catalyzed Cross-Coupling Reactions of Organoboron Compounds", Chem. Rev. 95:2457 (1995).
Modern Amination Methods: Ricci, A., Ed., Wiley-VCH: Weinheim, 2000.
Muci, et al., "Practical Palladium Catalysts for C—N and C—O Bond Formation", Top. Curr., Chem. 219-131-209 (2001.
Murata, K. et al., "Synthesis of Alkenylboronates via Palladium-Catalyzed Borylation of Alkenyl Triflates (or Iodindes) with Pinacolborane" Synthesis, 2000, No. 6, pp. 778-780.
Murata, K. et al., "Selective cytotoxic mechanism of GTP-14564, a novel tyrosine kinase inhibitor in leukemia cells expressing a constitutively active Fms-like tyrosine kinase 3 (FLT3)" J Biol Chem. Aug. 29, 2003; 278(35):32892-8.
Nicolai, E., et al., "New Process for the Synthesis of Imidazo[4-5-b] pyridine Derivatives as Potent Orally Active Thromboxane $A_2$ Receptor Antagonists", J. Heterocyclic Chemistry, 31, (73) (1994).
O'Farrell, A.M. et al. "SU11248 is a novel FLT3 tyrosine kinase inhibitor with potent activity in vitro and in vivo" Blood, May 2003; 101:3597-3605.
Olah, G.A. et al., "Formylating Agents", Chemical Reviews, vol. 87, No. 4, 1987.
Protecting Groups, P, Kocienski Thieme Medical Publishers, 2000.
Quentmeier H, et al. FLT3 mutations in acute myeloid leukemia cell lines. Leukemia. Jan. 2003;17:120-124.
Regan, J., et al., Structure-Activity Relationships of the p38* MAP Kinsase Inhibitor 1-)5-*tert*-Butyl-2-*p*-tolyl-2h-pyrazol-3-yl)-3-[4-(2-morpholin-4-yl-ethoxy)naph-thalen-1-yl-)urea (BIRB 796)J. Med. Chem., 46:4676-86 (2003).
Romeo, G., et al, "New Pyrimido [5,4-b_indoles as Ligands for *1-Adrenoceptor Subtypes", J. Med. Chem., 46: 2877-2894 (2003).
Sadick, M. et al., Analysis of Heregulin-Induced ErbB2 Phosphorylation with a High-Throughput Kinase Receptor Activation Enzyme-Linked Immunsorbent Assay, Analytical Biochemistry. 1996; 235:207-214.
Scheijen, B. et al. (2002), "Tyrosine kinase oncogenes innormal hematopoiesis and hematological disease", Oncogene 21(21):3314-33.
Simpson WG, The calcium channel blocker verapamil and cancer chemotherapy. Cell Calcium. Dec. 1985;6(6):449-67.
Smith, B. D. et al., "Single-agent CEP-701, a novel FLT3 inhibitor, shows biologic and clinical activity in patients with relapsed or refractory acute myeloid leukemia" Blood, May 2004; 103:3669-3676.
Smith, P, "The Curtius Reaction", Organic Reactions 3:337 (1947).
Stille, J.K., "The Palladium-Catalyzed Cross-Coupling Reactions of Organotin Reagents with Organic Electrophiles", Angew, Chem, Int. Ed. Engl., 25:508024 (1986).
Stirewalt, D.L. et al. (2003), "The role of FLT3 in haematopoietic malignancies", NatRev Cancer 3(9):650-65.
Stone, R.M. et al. "PKC 412 FLT3 inhibitor therapy in AML: results of a phase II trial" An Hematol 2004; 83 Suppl 1:S89-90.
Thorpe, "Antibody Carriers of Cytotoxic Agents in Cancer Therapy: A Review", in Monoclonal Antibodies '84: Biological and Clinical Applications, Pinchera et al. (eds.), pp. 475-506 (1985).
Tse, K.F. et al., "Inhibition of FLT3-mediated transformation by use of a tyrosine kinase inhibitor" Leukemia, Jul. 2001 15(7):1001-10.
Wustrow, et al, "Coupling of Arylboronic Acids with a Partially Reduced Pyridine Derivative" Synthesis, 993 (1991).

Yee, K.W.H. et al., "SU5416 and SU5614 inhibit kinase activity of wild-type and mutant FLT3 receptor tyrosine kinase" Blood, Sep. 2002; 100:2941-294.
Vippagunta et al., Crystalline solids, 2001, Advanced Drug Delivery Reviews, 48, pp. 3 and 18.
Abarbri et al., J. Org. Chem. (2000), 65, 4618-4634.
Barkenbus et al., Journal of Organic Chemistry (1951), 16, 232-8.
Beller et al., Applied Homogeneous Catalysis with Organometallic Compounds, Cornils, B. and Herrmann, W. A. (Eds.), 2, 1009-1024, VCH, Weinheim, Germany (1996).
Brown et al., J. Chem. Soc., Perkin Trans. 2, 1039-1051 (2002).
Byrn et al., Solid-State Chemistry of Drugs, Second Edition, 1999, pp. 233-247.
Crandall et al., J. Am. Chem. Soc. (1968), 90, 6251-6253.
Cummins et al., Tetrahedron (1988), 44(16), 5151.
Eastwood, P., Tetrahedron Lett. (2000), 41, 3705-8.
Ferrara et al., "Prognostic factors and therapeutic options for relapsed or refractory acute myeloid leukemia." Haematologica. Aug. 2004, vol. 89, No. 8, Aug. 2004; pp. 998-1008.
Gavezzotti, "Are Crystal Structures Predictable?" Accounts of Chemical Research, vol. 27, pp. 309-314 (1994).
Guillory (in Brittain ed.) Polymorphism, etc., NY: Marcel Dekker, Inc., 1999, 1-2, 183-226.
Harmata et al., Org. Lett. (2000), 2, 2703-2705.
Hess et al., J. Am. Chem. Soc. (1998), 120, 12310.
Hill et al., J. Am. Chem. Soc. (1973), 95, 1338.
Hogermeier et al., Chem. Eur. J., 2007, 13, 2410.
Johnson et al., J. Org. Chem. (1970), 35(3), 584-592.
Kim et al., European Journal of Organic Chemistry (2000), 12, 2195-2201.
Larock, R.C., Comprehensive Organic Transformations, $2^{nd}$ Ed., Wiley-VCH, NY, (1999), pp. 996-1003.
Lee, K. and Cha, J. K., J. Amer. Chem. Soc., 123: 5590-5591 (2001).
Lipshutz et al., Tetrahedron Lett. (1988), 29, 3411-3414.
McBee et al., Journal of the American Chemical Society (1957), 79, 2323-5.
Meltzer et al., Bioorganic & Medicinal Chemistry (2002), 10(11) and 3583-3591.
Noyori et al., Org. React., 1983, 29, 163.
Reinecke et al., Chemistry-A European Journal (1995), 1(6), 368-73.
Sasaki et al., Tett. Lett. (1982), 23, 1693.
Sato et al., Bulletin of the Chemical Society of Japan (1983), 56(9), 2680-99.
Sato et al., Bulletin of the Chemical Society of Japan (1984), 57(9), 2515-25.
Schmid et al., Helv. Chim. Acta. (1974), 57, 1883 [see English summary provided].
Sendelbach, et al, Journal of Organic Chemistry (1999), 64(10), 3398-3408.
Sundermeier, U., Doebler, C. and Beller, M., Modern Oxidation Methods, Baeckvall, J. (Ed.)., 1-20, Wiley-Verlag (2004) Weinheim, Germany (2004).
Takahashi, K., et al, Chem. Lett. (2000), 126-7.
Takaya et al., J Amer Chem Soc, (1978), 100(6), 1765-77.
Thompson et al., Journal of Industrial and Engineering Chemistry (Washington, D.C.) (1952), 44, 1659-62.
West et al., J. Org. Chem (1993), 58, 6795-6803.
Wroblewski et al., Journal of the American Chemical Society (1996), 118, 10168-10174.
Armstrong, S.A. et al., (2004) "FLT3 mutations in childhood acute lymphoblastic leukemia." Blood. 103: 3544-6.
Burnett, A. K. (2002). "Acute myeloid leukemia: treatment of adults under 60 years." Rev Clin Exp Hematol 6(1): 26-45.
Buchner T., W. Hiddemann, et al. (2002). "Acute myeloid leukemia: treatment over 60." Rev Clin Exp Hematol. 6(1):46-59.
Chou TC, Talalay P. (1984) "Quantitative analysis of dose-effect relationships: the combined effects of multiple drugs or enzyme inhibitors." Adv Enzyme Regul. 22:27-55.
Gotlib, J (2005) "Farnesyltransferase inhibitor therapy in acute myelogenous leukemia." Curr. Hematol. Rep.;4(1):77-84.
Haluska P., G.K. Dy, A.A. Adjei. (2002) "Farnesyl transferase inhibitors as anticancer agents." Eur J Cancer. 38(13):1685-700.

(56) References Cited

OTHER PUBLICATIONS

Hengartner, MO. (2000) "The biochemistry of apoptosis." Nature 407:770-76.
Lancet J.E., J.D. Rosenblatt, J.E. Karp. (2003) "Farnesyltransferase inhibitors and myeloid malignancies: phase I evidence of Zarnestra activity in high-risk leukemias." Semin Hematol. 39(3 Suppl 2):31-5.
Levis, M., et al. (2004) "In vitro studies of a FLT3 inhibitor combined with chemotherapy: sequence of administration is important to achieve synergistic cytotoxic effects." Blood. 104(4):1145-50.
Lovborg H, Gullbo J, Larsson R. (2005) "Screening for apoptosis-classical and emerging techniques." Anticancer Drugs 16:593-9.
Nunez G, Benedict MA, Hu Y, Inohara N. (1998) "Caspases: the proteases of the apoptotic pathway." Oncogene 17:3237-45.
Prendergast et al., (2001) "Farnesyl Transferase Inhibtors: Mechanism and Applications" Expert Opin Investig Drugs. 10(12):2105-16).
Shih L. Y. et al., (2004) "Internal tandem duplication of fms-like tyrosine kinase 3 is associated with poor outcome in patients with myelodysplastic syndrome." Cancer, 101; 989-98.
Takada, Y., et al. (2004). "Protein farnesyltransferase inhibitor (SCH 66336) abolishes NF-kappaB activation induced by various carcinogens and inflammatory stimuli leading to suppression of NF-kappaB-regulated gene expression and up-regulation of apoptosis."J Biol Chem 279, 26287-99.
van Engeland M., L.J. Nieland ,et al. (1998) "Annexin V-affinity assay: a review on an apoptosis detection system based on phosphatidylserine exposure." Cytometry. 31(1):1-9.
Yee KW, Schittenhelm M, O'Farrell AM, Town AR, McGreevey L, Bainbridge T, Cherrington JM, Heinrich MC. (2004) "Synergistic effect of SU11248 with cytarabine or daunorubicin on FLT3ITD-positive leukemic cells." Blood. 104(13):4202-9.
Pure Appl. Chem., 1976, 45:13-30.
Lyon et al. J. Med. Chem., 29: 630-4 (1986).
Romeo et al., J. Med. Chem., 46: 2877 (2003).
Coll. Czech. Chem. Commun.: 31(11), 4432-41, (1966).
International Search Report re: PCT/US2006/022412 dated Nov. 6, 2006.
Aboutaleb et al., International Sem in Surgical Oncol 6(17): 1-3, 2006.
Advani, A., Curr Hematologic Malignancy Reports 1:101-107,2006.
Auewarakul et al., Ann Hematol, 85:108-112, 2006.
Beletskaya et al., Chem. Rev., 100:3009 (2000).
Brase et al., *Angew. Chemie Int. Ed.*, 44(33), 5188-5240, (2005).
Brase et al., Metal-Catalyzed Cross-Coupling Reactions (2nd Edition), p. 217-315, A. de Meijere, F. Diederich, Eds., Wiley-VCH, Weinheim (2004).
Chemcats RN 93730-20-2, Nov. 28, 1988.
Chemcats RN 443895-82-7 Apr. 24, 2003.
Chemcats RN 701272-70-0, Jan. 1, 2004.
Chemcats RN 712290-43, Jan. 1, 2004.
Corey et al., *Tetrahedron Lett.*, 29, 995 (1988).
Couturier et al., *Organic Process Research & Development*, 2002, 6, 42-48.
Dirlam et al., *J. Heterocyclic Chem*, 17, 409, (1980).
Dolan, S., et al, *J. Chem., Soc., Chem. Commun.*, 1588-9 (1985).
Fohlisch et al, *Liebigs Annalen der Chemie*, (1), 1-5 (1987) [English Abstract provided].
Galemmo et al., *J. Med. Chem.*, 33(10), 2828-41; (1990).
Guanti et al., *Tetrahedron*, 46 (20), 7081, (1990).
Guanti et al., *Tetrahedron: Asymmetry* 8(13), 2175-2187, (1997).
Han, J., Advances in Characterization of Pharmaceutical Hydrates, Trends in Bio/PharmaceuticalIndustry, pp. 25-29. Mar. 2006.
Hayakawa et al., *Bioorg. Med. Chem. Lett.*, 14(2): 455-8 (2004).
Hulkenberg et al., *Tetrahedron Lett.*, 23(14), 1505-08; (1982).
Ishikubo et al (Jpn J Clin Oncol 36:494-498, 2006).
Itsuno et al., *Synthesis*, 12, 995-6, (1988).
Johnson et al., Brit J Cancer, 84:1424-1431 (2001).
Jonas, Nilsson W. et al., "Solid-Phase Synthesis of Libraries Generated from a 4-Phenyl-2-carboxy-piperazine Scaffold", J. Comb. Chem., 2001, 3, 546-553.
Khanapure et al, *J. Med. Chem.*, 48(11): 3930-34 (2005).
Koutek, et al, *Synth. Commun.*, 6 (4), 305-8 (1976).
Leonard et al., *J. Org. Chem.*, 28, 3021, (1963).
Liu et al., . *Am. Chem. Soc.* 2004, 126, 5182.
Martinez_Teipel et al., *QSAR & Combinatorial Science*, 23(10), 854-858 (2004).
Mock et al., *J. Phys. Org. Chem.*, 16(3), 175-182 (2003).
Moffett, Robert Bruce et al., "Antiulcer Agents. p-Aminobenzamido Aromatic Compounds", Journal of Medicinal Chemistry 1971, vol. 14, No. 10, pp. 963-968.
Myles et al., *J. Org. Chem.*, 55, 1636 (1990).
Nguyen et al., *Tetrahedron*, 62(4), 647-651; (2006).
Nilsson et al., J. Comb. Chem., vol. 3, pp. 546-553 (2001).
Nose et al., *Chem. Pharm. Bull.*, 38(8), 2097-101, (1990).
Quintard et al., *J. Org. Chem.*, 48: 1559-60 (1983).
Rastelli et al. J. Med. Chem., 2003, 46, 2834-2845.
Reed et al., *Synthetic Communications*, 20(4), 563-71, (1990).
Roush, W., *J. Am. Chem. Soc.* 102, 1390 (1980).
Suzuki, A., "Metal-Catalyzed Coupling Reactions" F. Deiderich, P. Stang, Eds., Wiley-VCH, Weinheim (1998).
Tohma et al., *Adv. Syn. Catalysis*, 346, 111-124 (2004).
Walker et al (Dermatol 212:70-72, 2006; (Abstract Only).
Wilson et al., Reducing Ion Channel Activity in a Series of 4-Heterocyclic Arylamide FMS Inhibitors, 20 Bioorg. & Med Chem. Letts. 3925-3929 (2010).
Wustrow et al., Tetrahedron Lett., 35, 61-4 (1994).
www.cancer.org (accessed online Mar. 2, 2010), "Can Acute Myeloid Luchemia (AML) Be Prevented?".

* cited by examiner

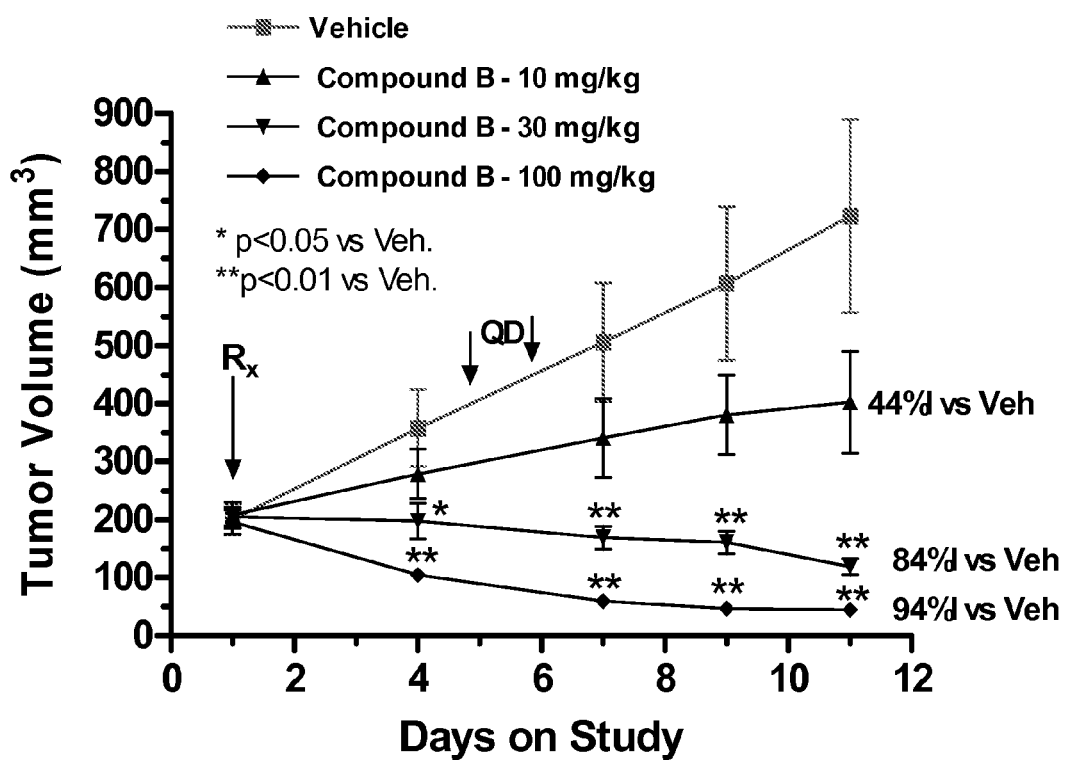
Figure 1. Effects of orally administered Compound B on the growth of MV4-11 tumor xenografts in nude mice.

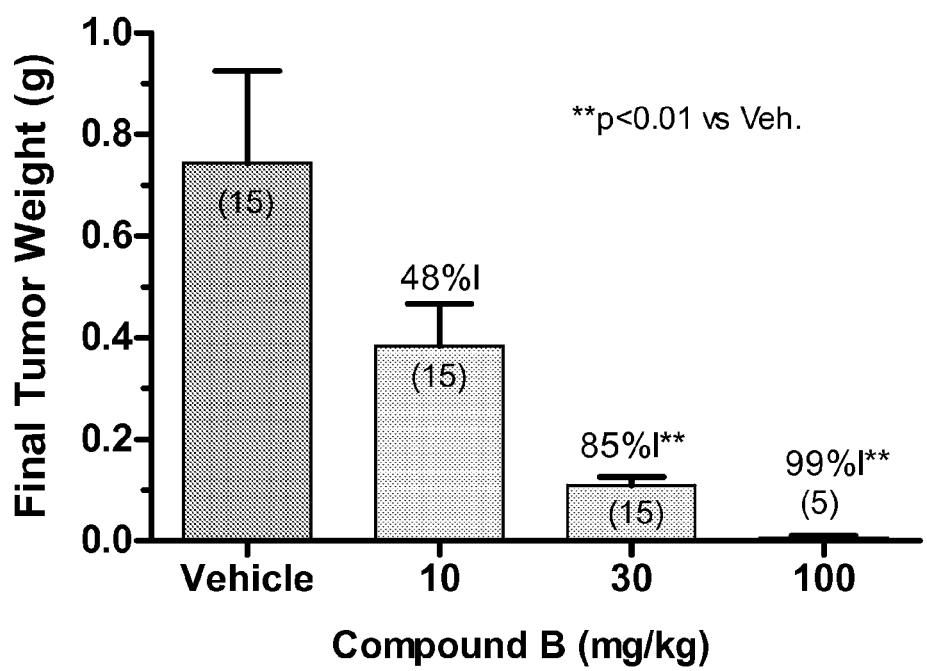
Figure 2. Effects of orally administered Compound B on the final weight of MV4-11 tumor xenografts in nude mice.

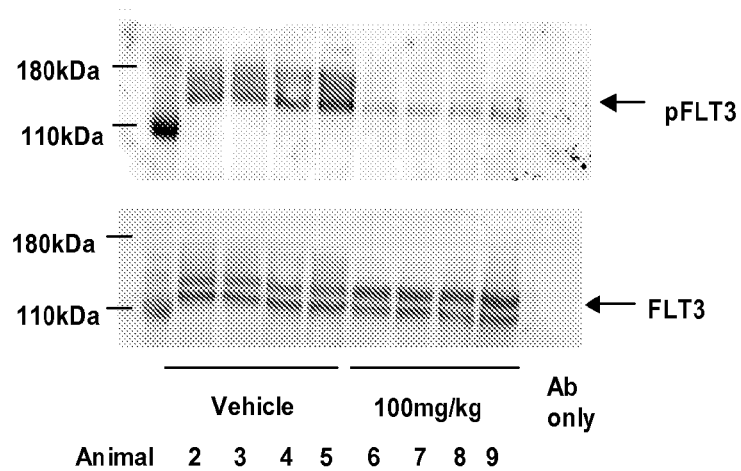
Figure 3. FLT3 phosphorylation in MV4-11 tumors obtained from vehicle- and Compound B treated mice.

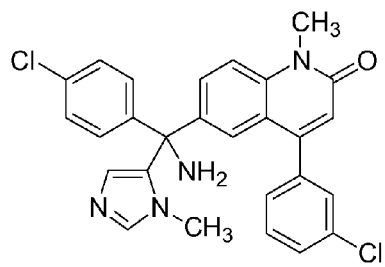
FTI - Tipifarnib
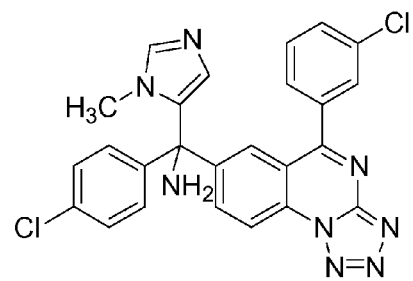
FTI - 176
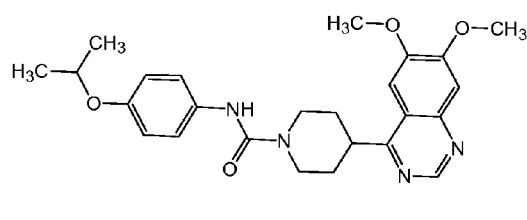
FLT3 Inhibitor
Compound A
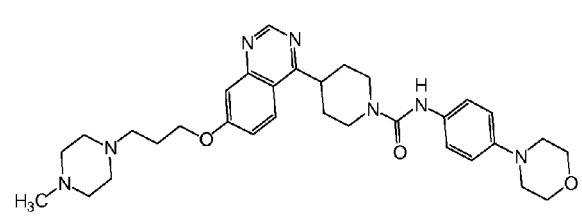
FLT3 Inhibitor
Compound B
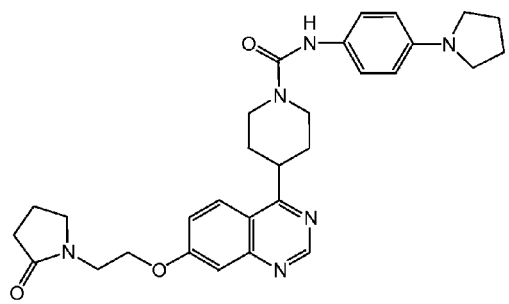
FLT3 Inhibitor
Compound C
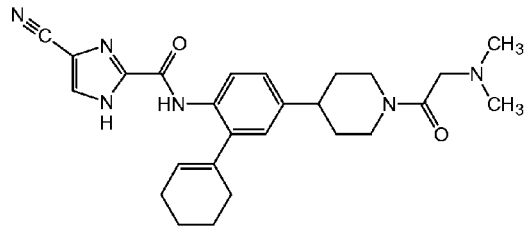
FLT3 Inhibitor
Compound D
Figure 4a. Compounds tested alone or in combination for inhibition of AML cell proliferation

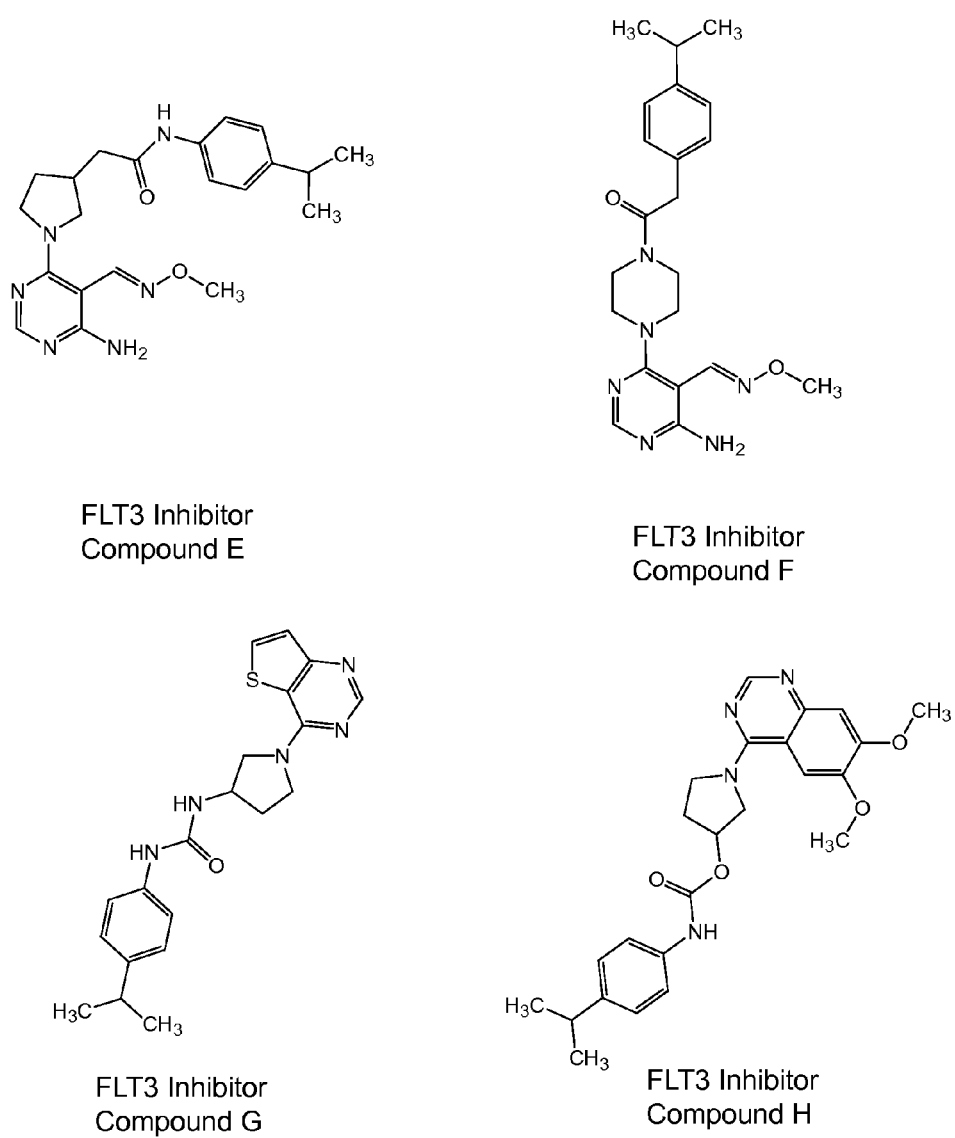
Figure 4b. Compounds tested alone or in combination for inhibition of AML cell proliferation

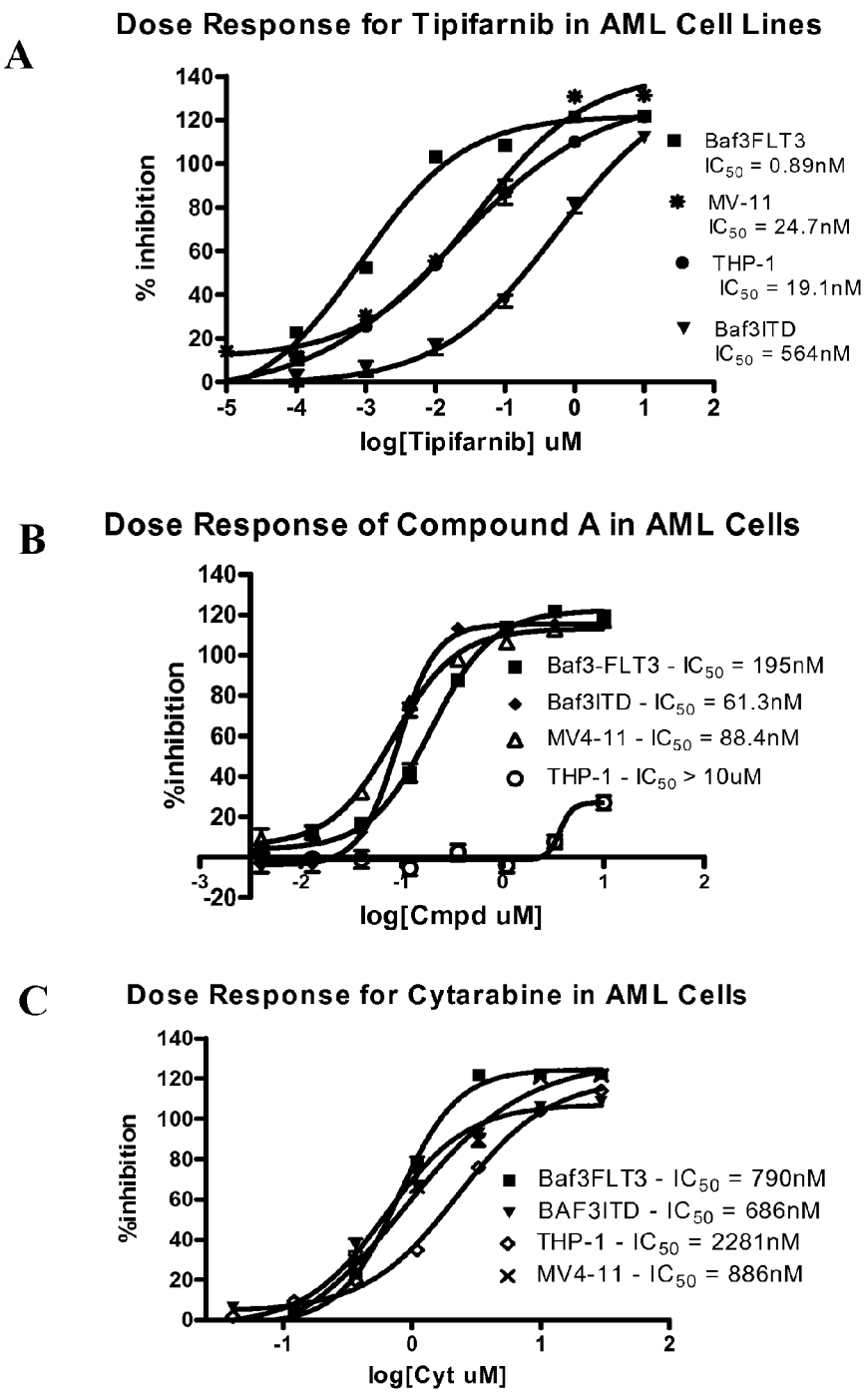
Figure 5.1 a-c. Dose responses of single agents on FLT3 dependent AML cell proliferation

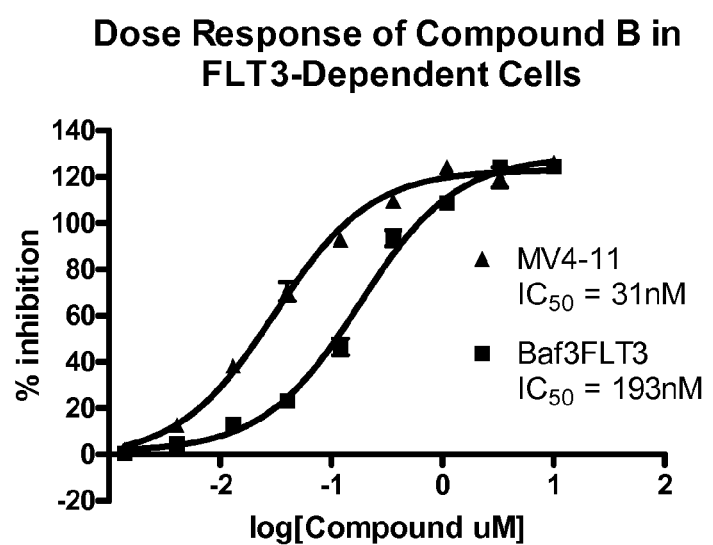
Figure 5.2. Dose responses of Compound B on FLT3-dependent AML cell proliferation

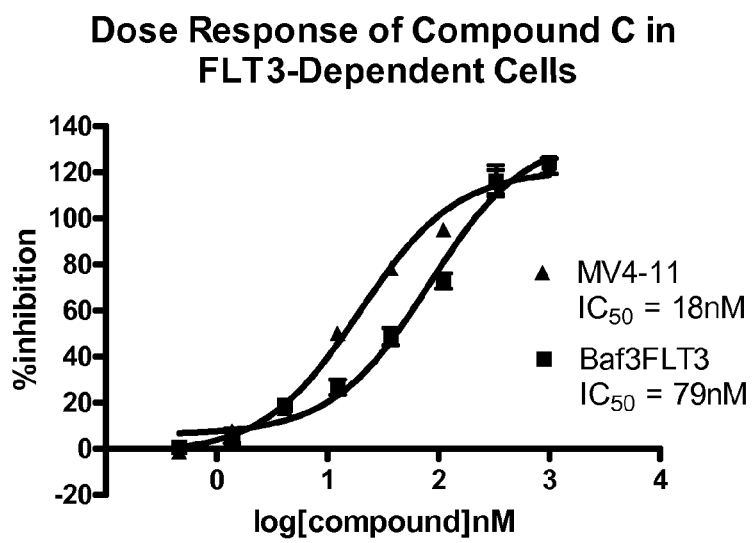
Figure 5.3. Dose responses of Compound C on FLT3-dependent AML cell proliferation

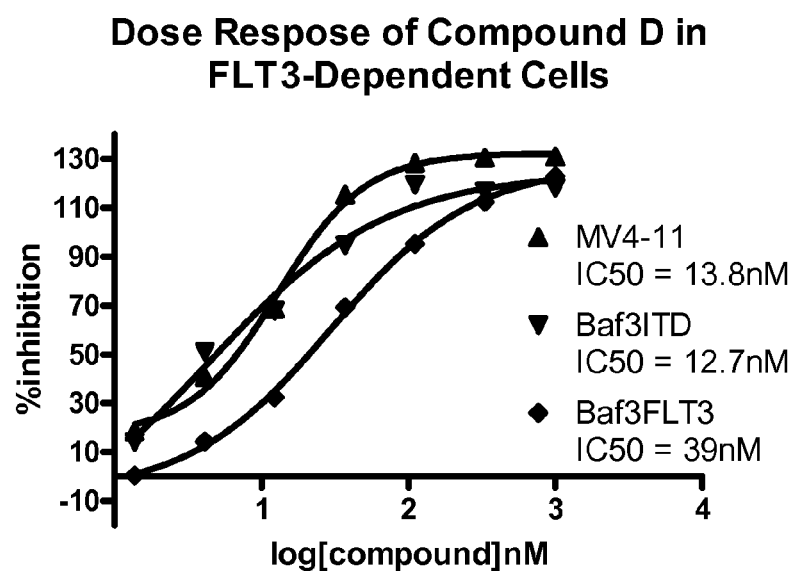
Figure 5.4. Dose responses of Compound D on FLT3-dependent AML cell proliferation

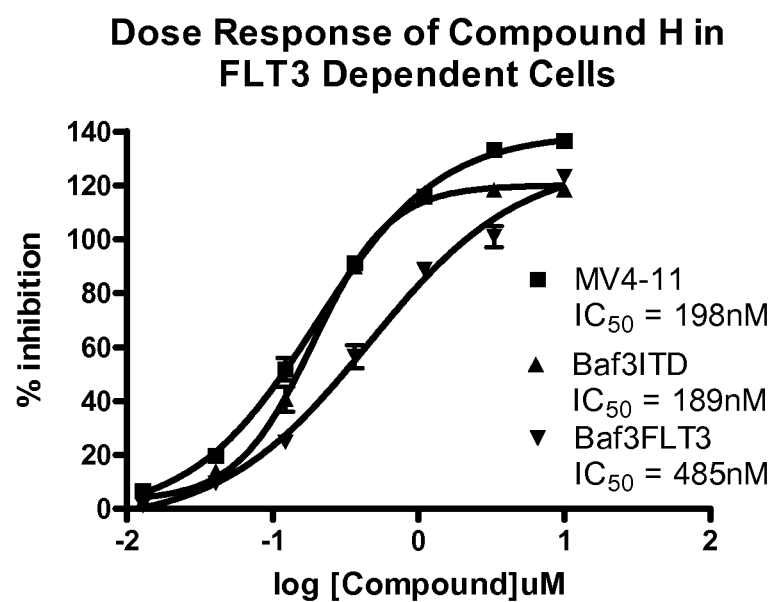
Figure 5.5. Dose responses of Compound H on FLT3 dependent AML cell proliferation

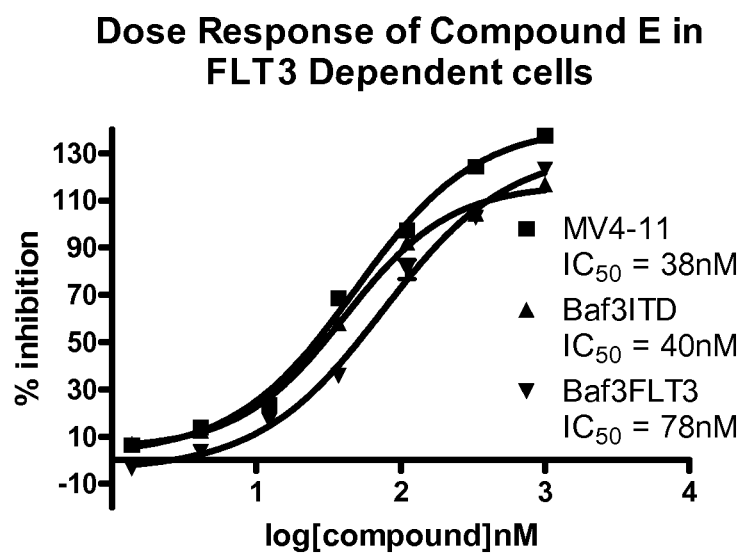
Figure 5.6. Dose responses of Compound E on FLT3-dependent AML cell proliferation

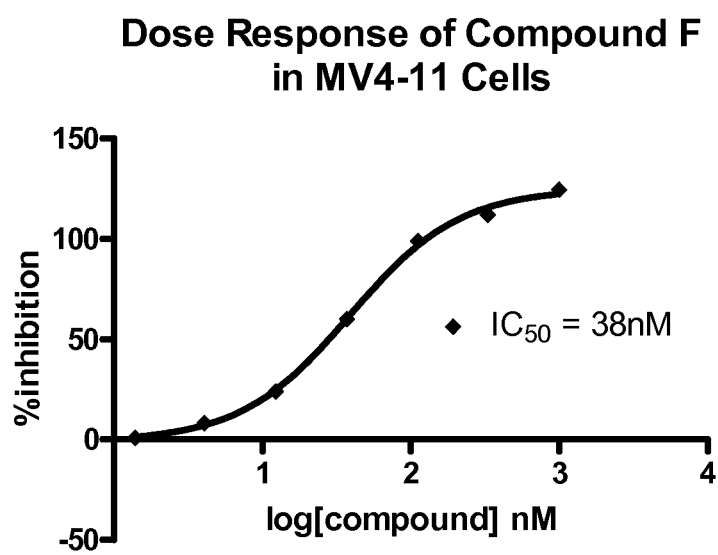
Figure 5.7. Dose responses of Compound F on MV4-11 cell proliferation

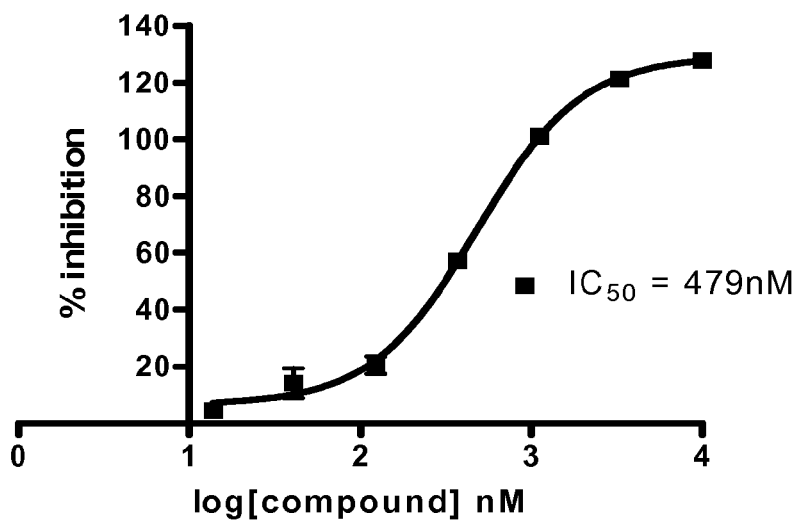
Figure 5.8. Dose responses of Compound G on MV4-11 cell proliferation

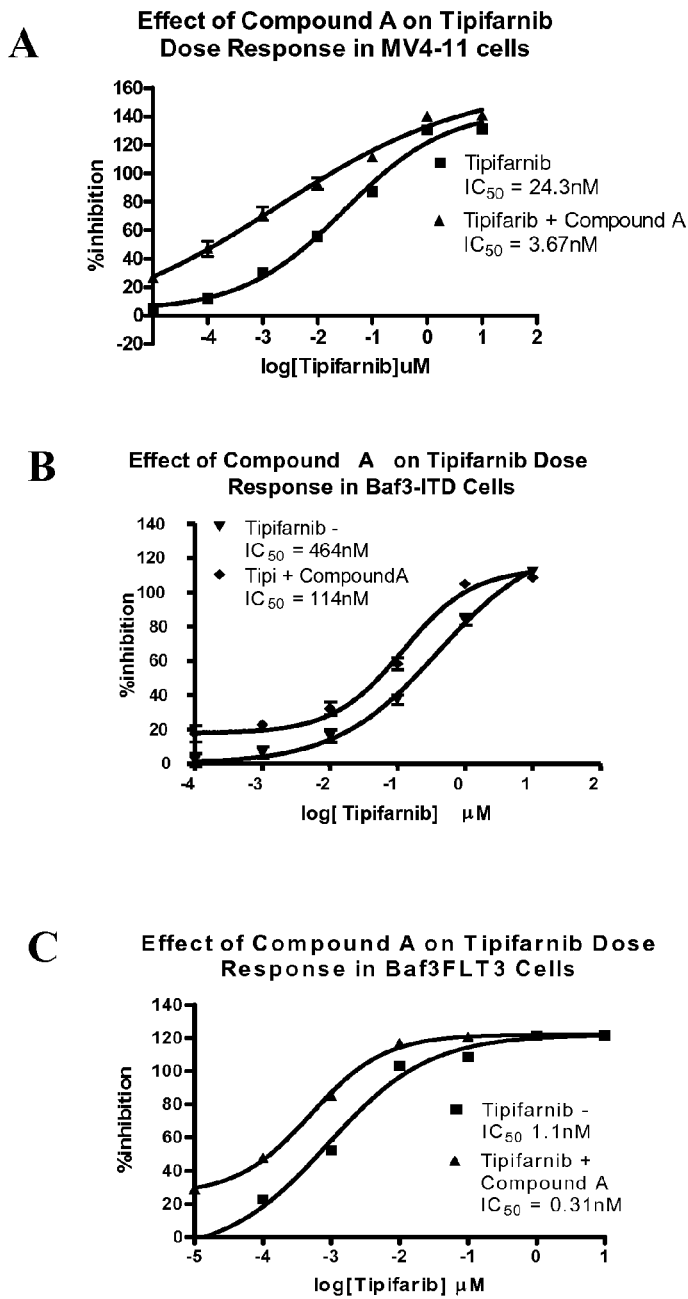
Figure 6a-c. A low dose of a FLT3 inhibitor significantly shifts the potency of Tipifarnib in FLT3 dependent cells

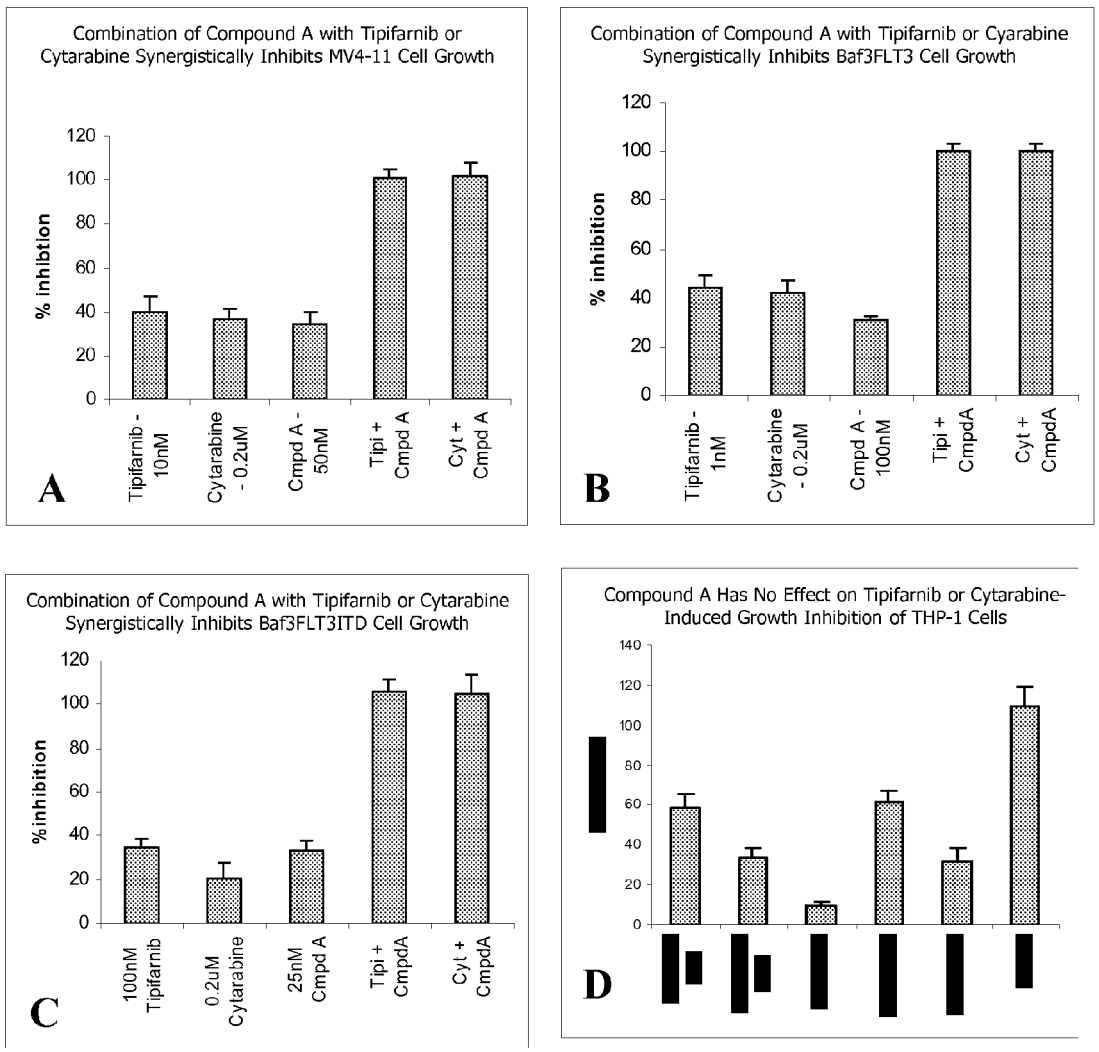
Figure 7a-d. Single dose combinations of a FLT3 inhibitor (Compound A) and Tipifarnib or Cytarabine synergistically inhibit FLT3-dependent cell line growth.

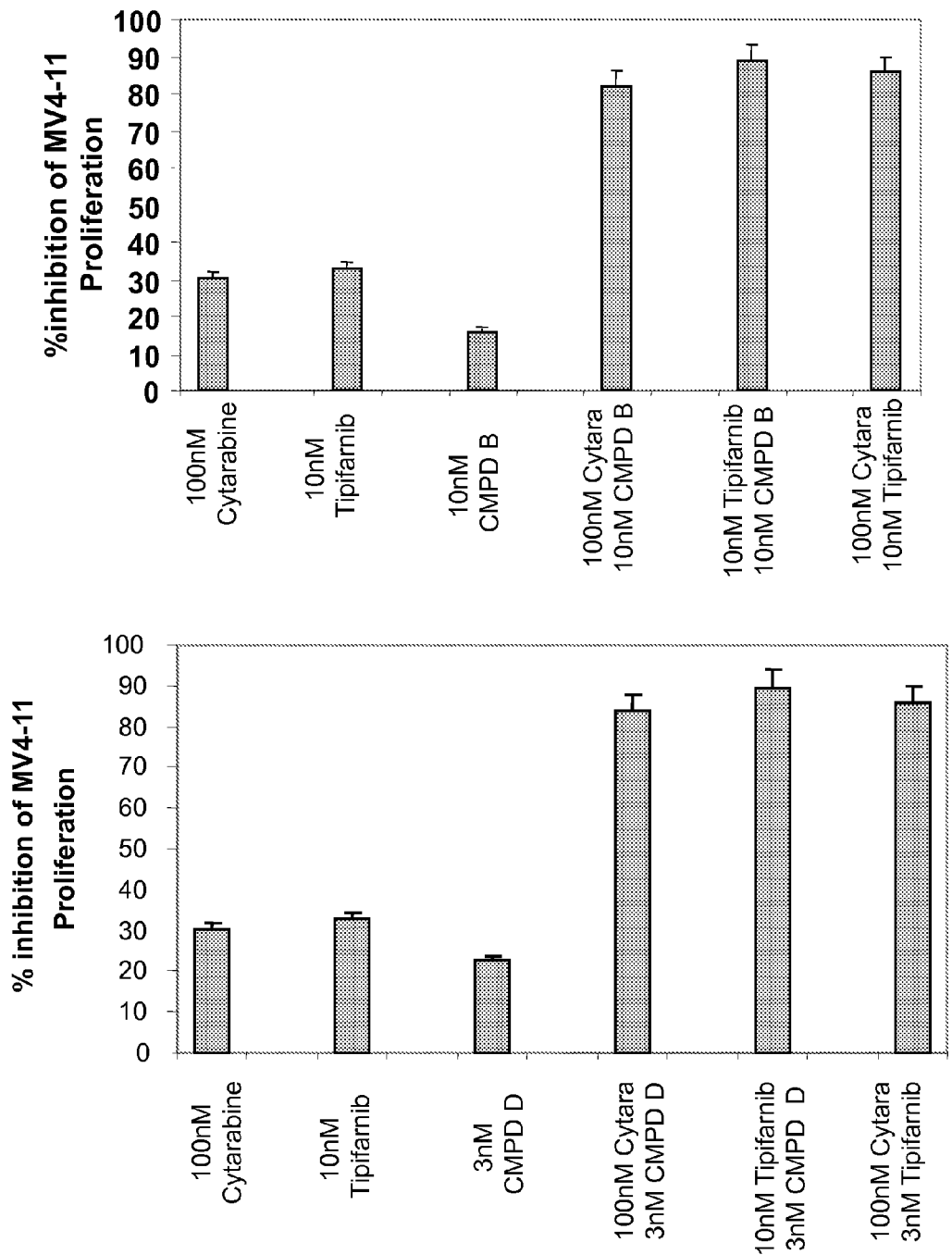
Figure 8a-b. Single dose combinations of a FLT3 inhibitor (Compound B and D) and Tipifarnib or Cytarabine synergistically inhibit FLT3-dependent AML cell line (MV4-11) growth.

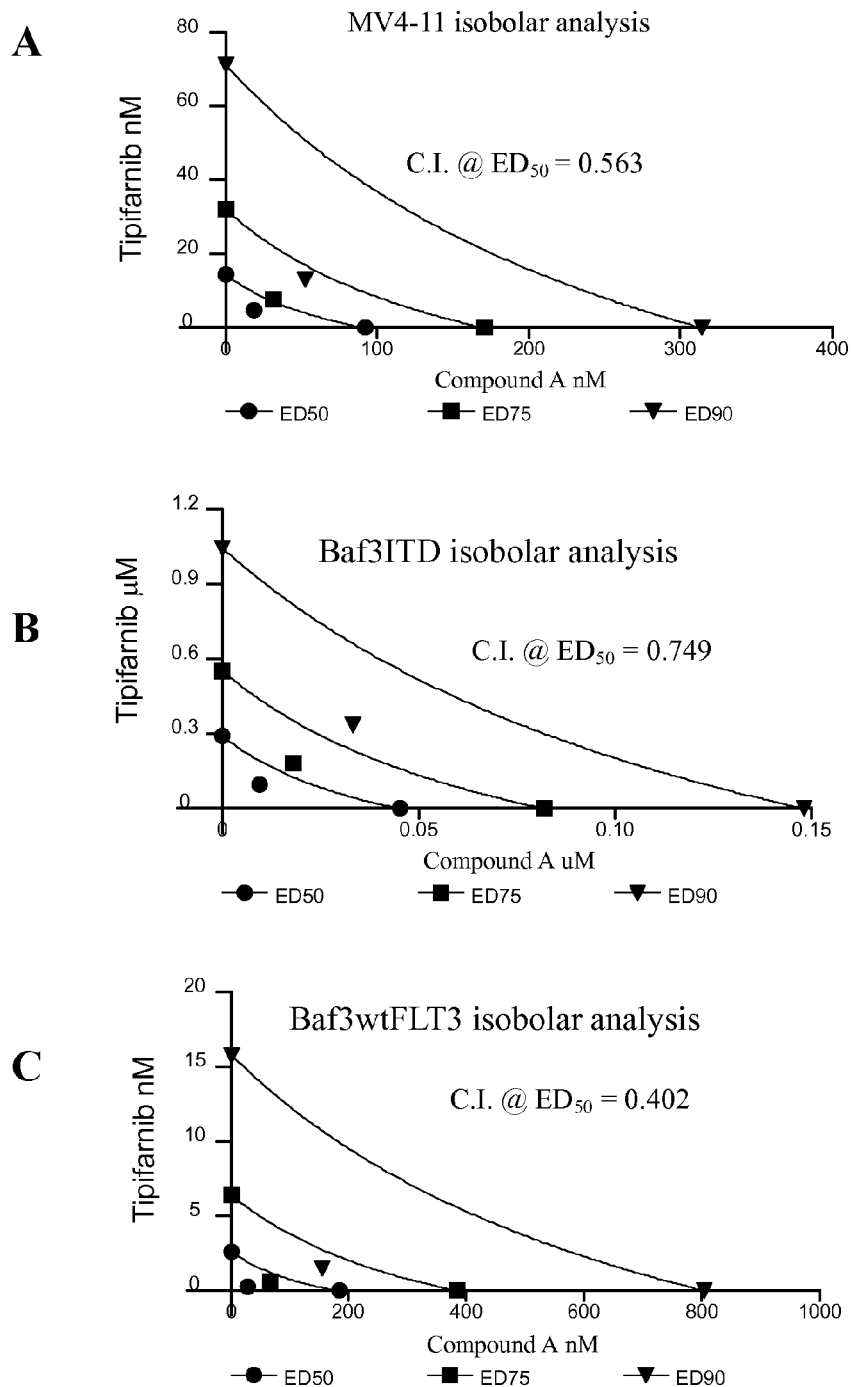
Figure 9.1. Compound A and Tipifarnib synergistically inhibit the proliferation of FLT3-dependent cells as measured by the method of Chou ad Talalay

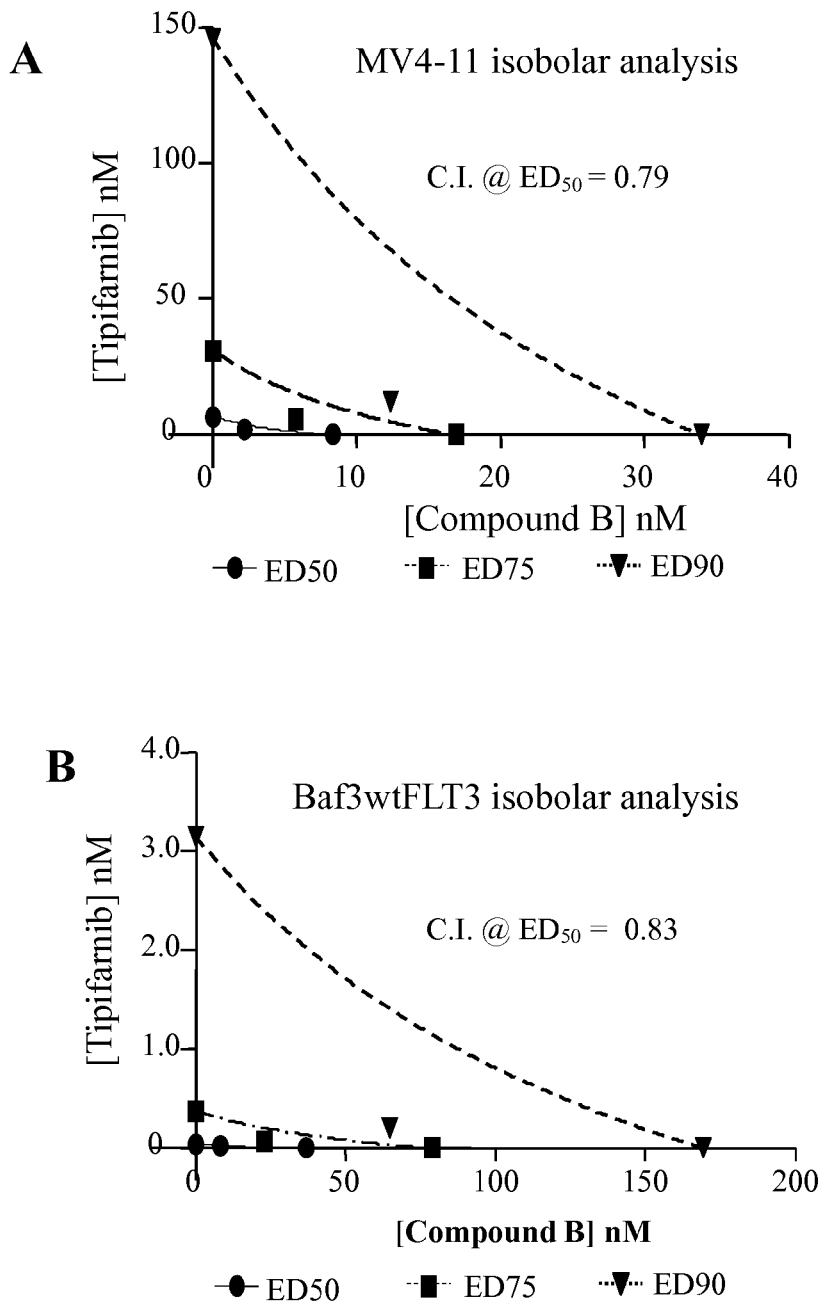
Figure 9.2. Compound B and Tipifarnib synergistically inhibit the proliferation of MV4-11 and Baf3-FLT3 cells as measured by the method of Chou and Talalay

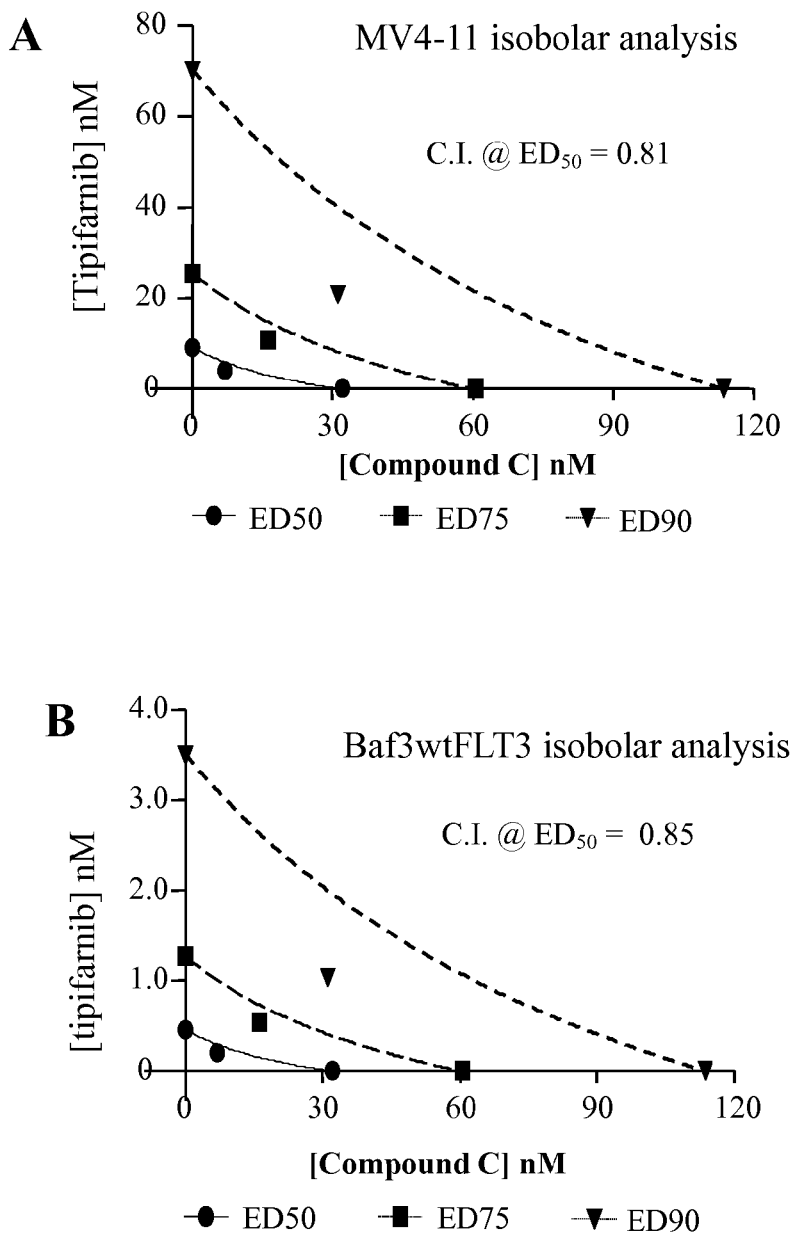
Figure 9.3. Compound C and Tipifarnib synergistically inhibit the proliferation of MV4-11and Baf3-FLT3 cells as measured by the method of Chou and Talalay

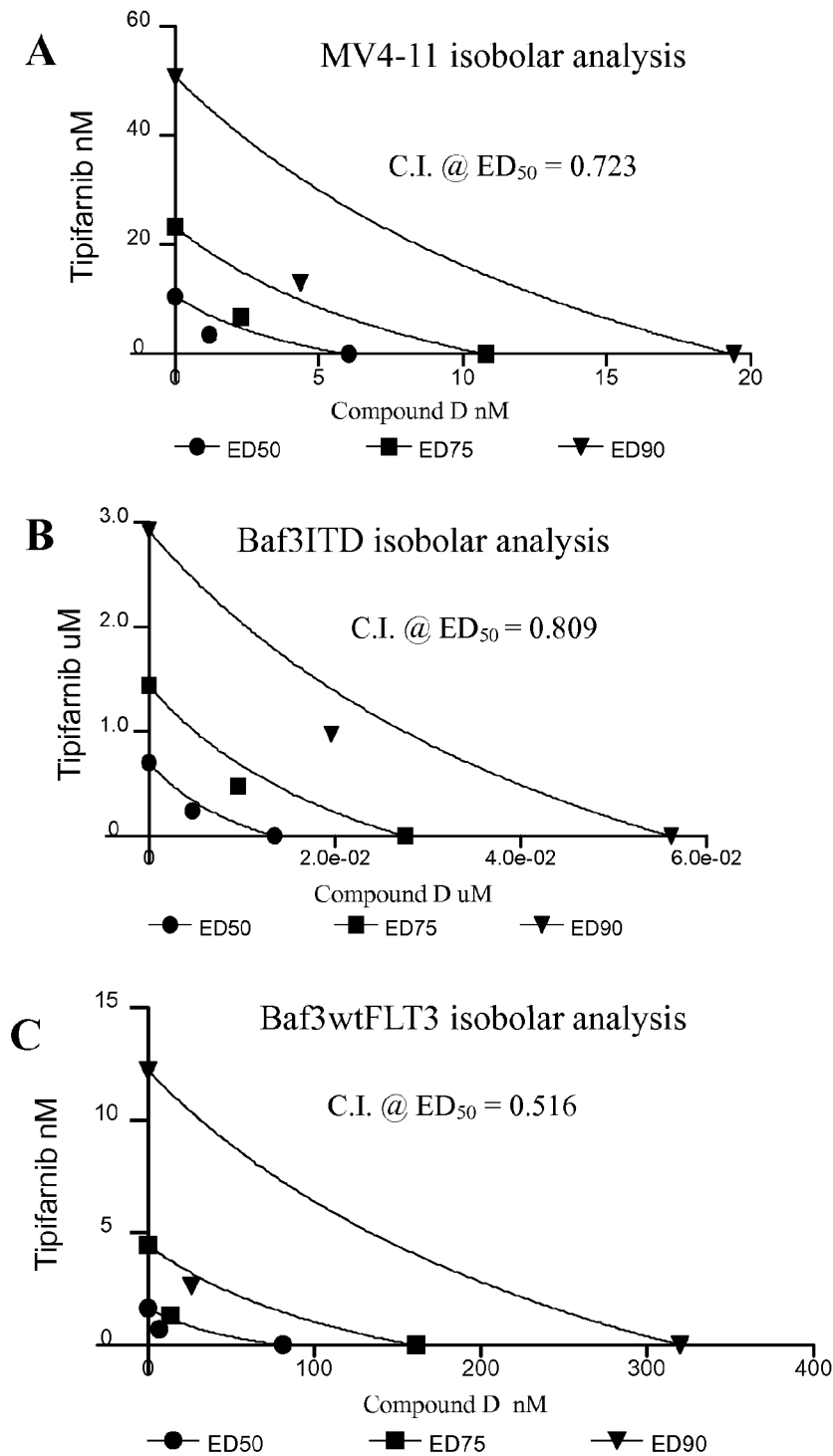
Figure 9.4. Compound D and Tipifarnib synergistically inhibit the proliferation of FLT3-dependent cells as measured by the method of Chou ad Talalay

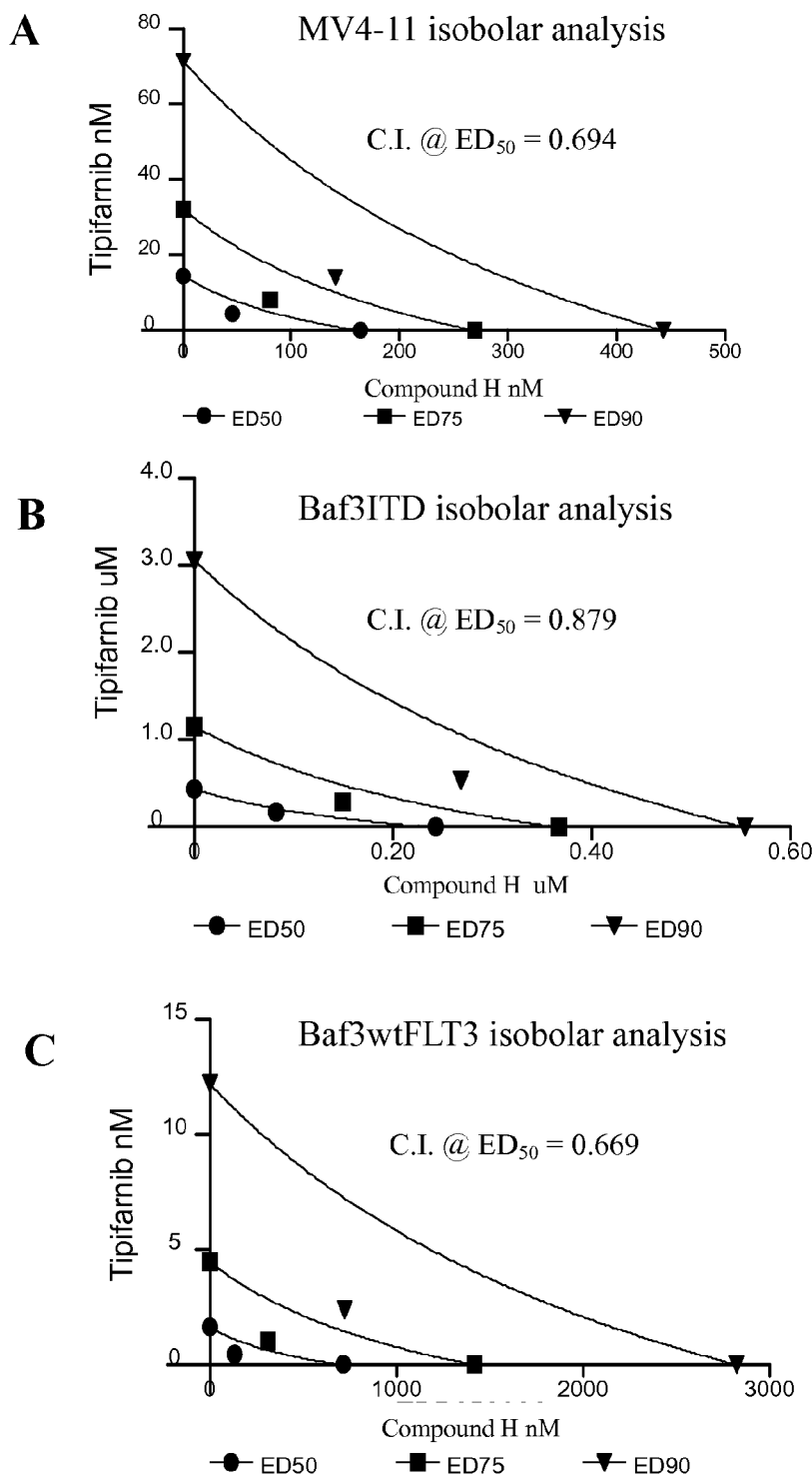
Figure 9.5. Compound H and Tipifarnib synergistically inhibit the proliferation of FLT3-dependent cells as measured by the method of Chou and Talalay A
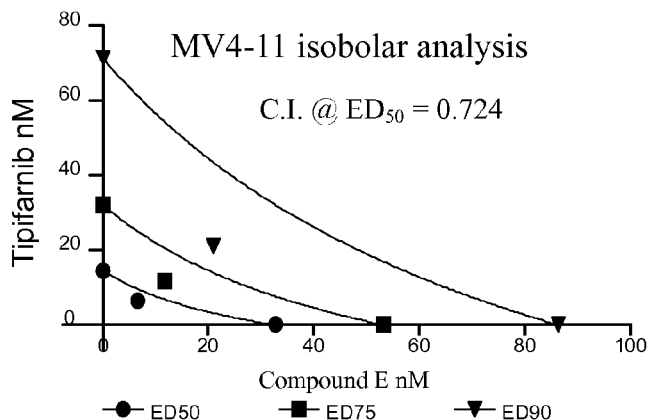
B
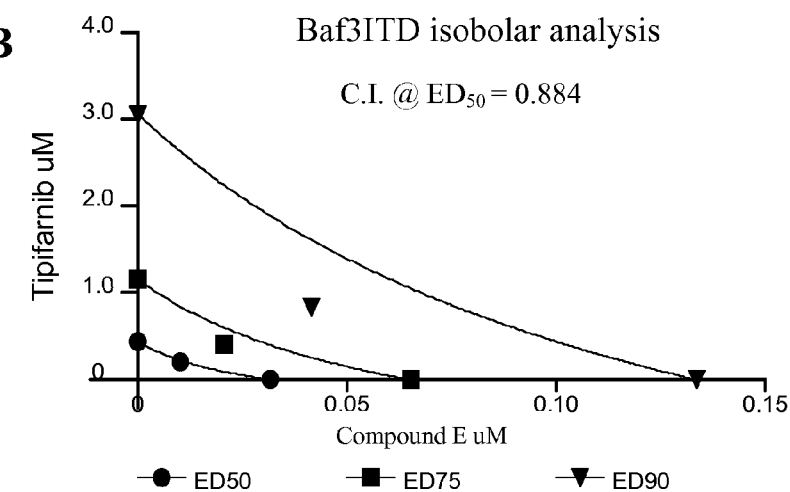
C
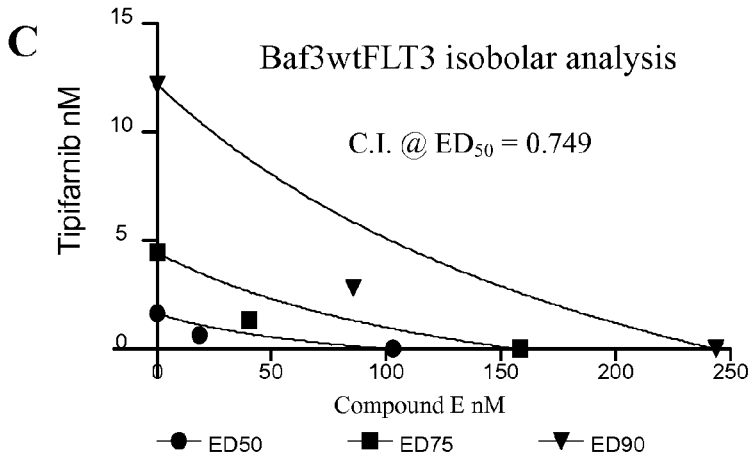
Figure 9.6. Compound E and Tipifarnib synergistically inhibit the proliferation of FLT3-dependent cells as measured by the method of Chou and Talalay

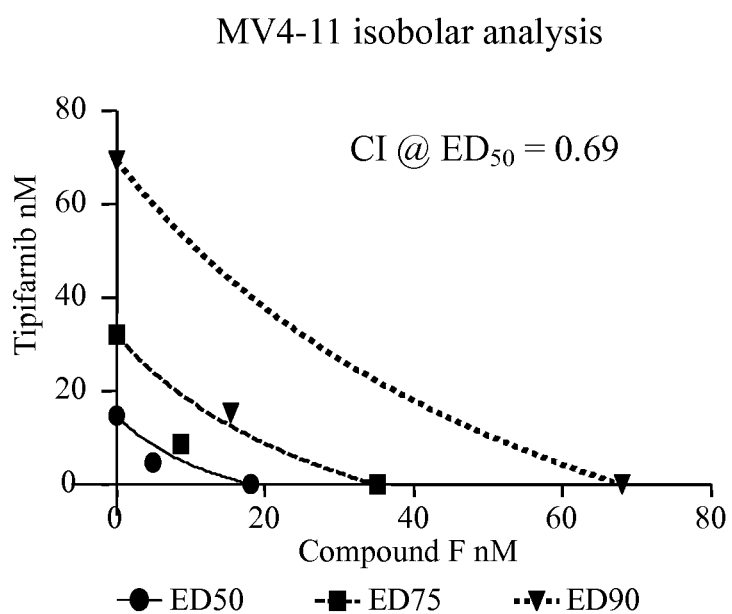
Figure 9.7. Compound F and Tipifarnib synergistically inhibit the proliferation of MV4-11 cells as measured by the method of Chou and Talalay

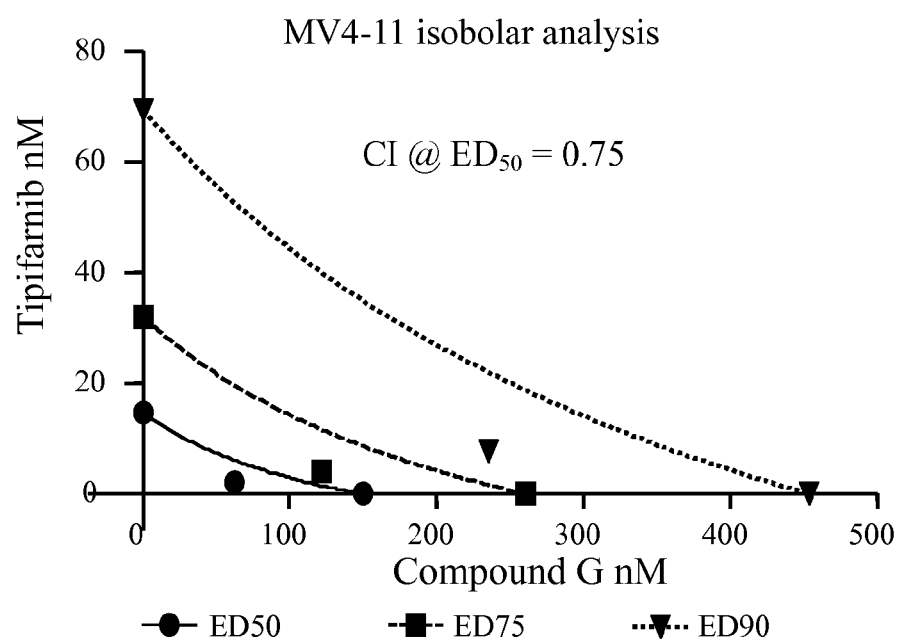
Figure 9.8. Compound G and Tipifarnib synergistically inhibit the proliferation of MV4-11 cells as measured by the method of Chou and Talalay

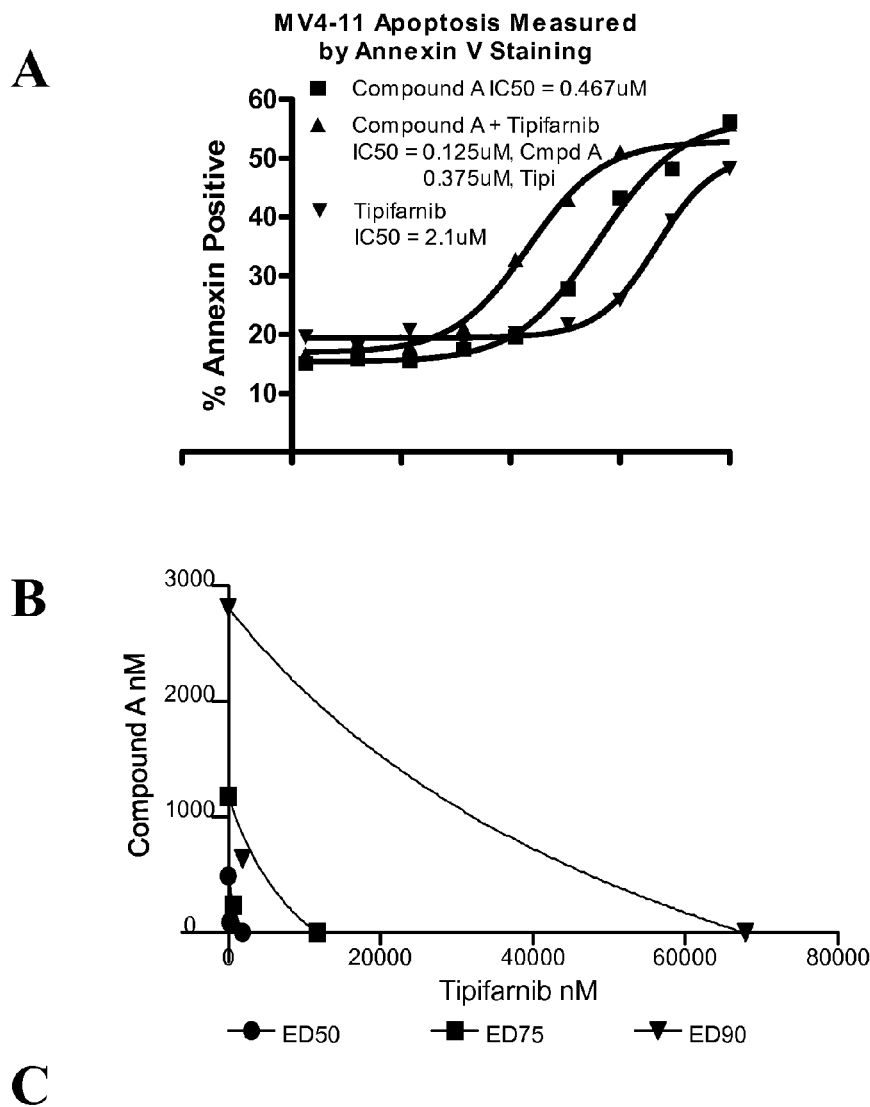
Figure 10a-c. The combination of a FLT3 inhibitor and an FTI synergistically induces annexin V staining and apoptosis of MV4-11 cells

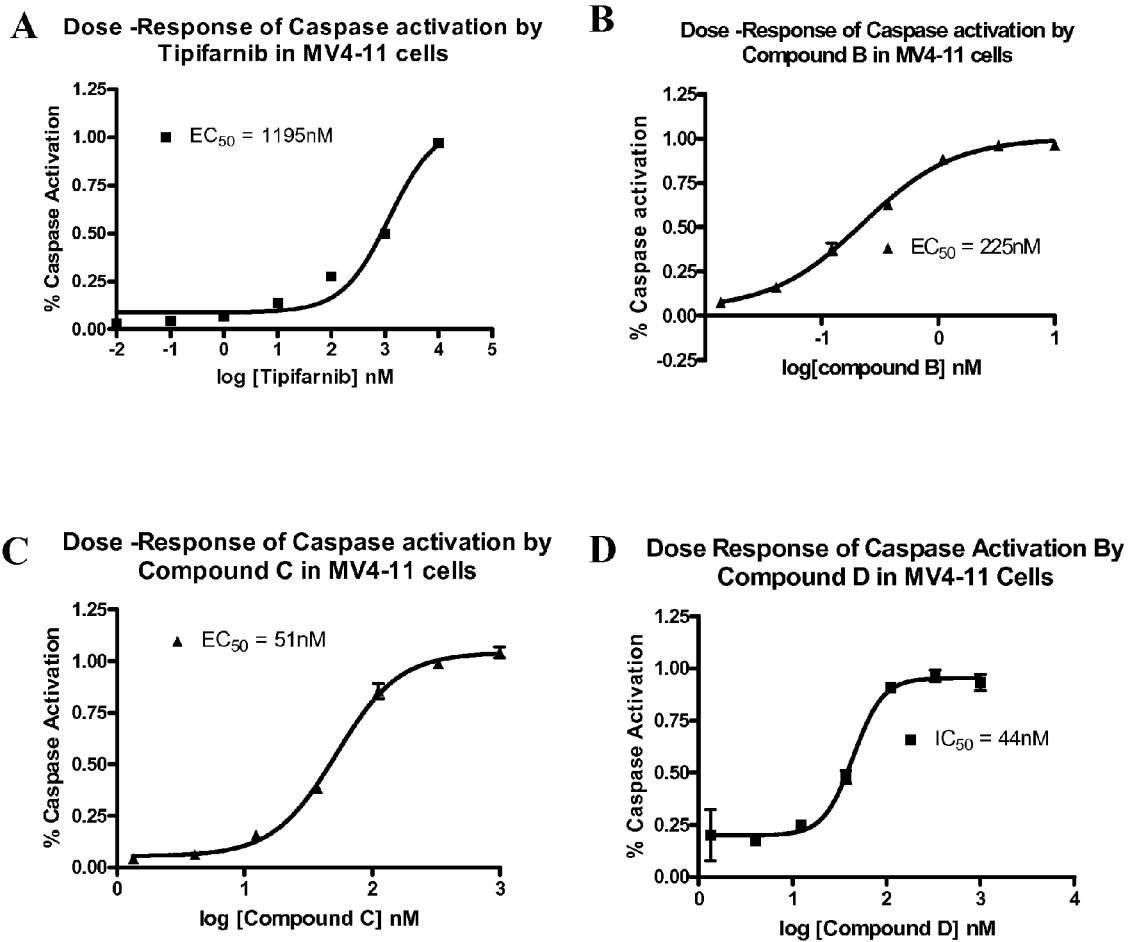
Figure 11a-d. Dose responses of single agent caspase activation in FLT3-ITD dependent MV4-11 cells.

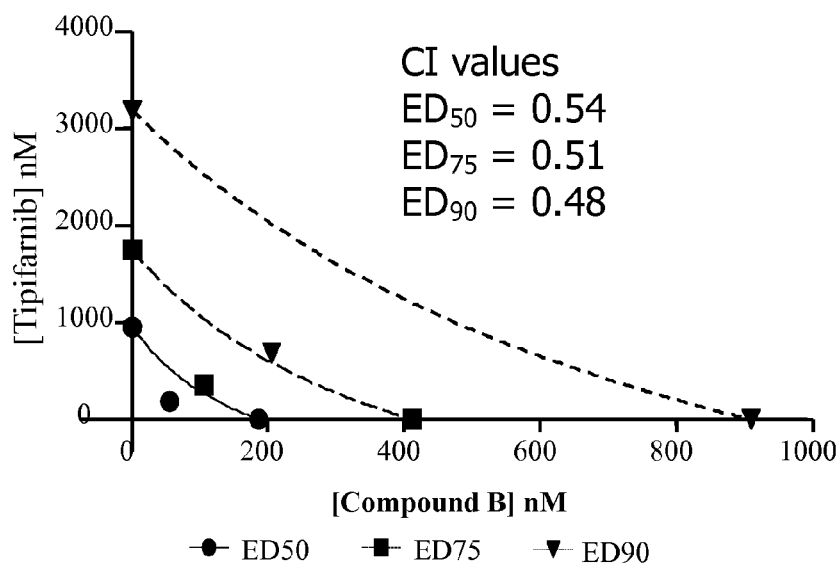
Figure 12.1. The combination of FLT3 inhibitor Compound B and Tipifarnib synergistically induces caspase activation and apoptosis of MV4-11 cells.

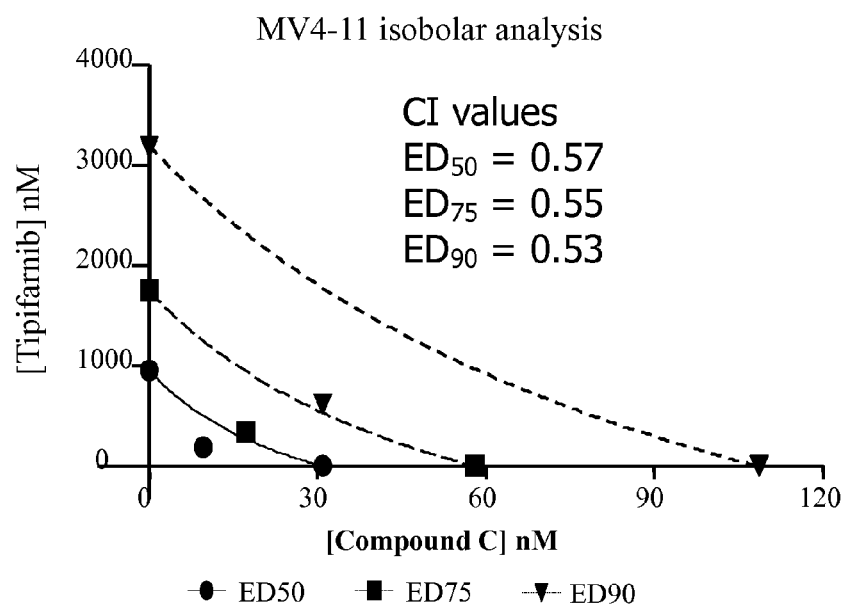
Figure 12.2. The combination of FLT3 inhibitor Compound C and Tipifarnib synergistically induces caspase activation and apoptosis of MV4-11 cells.

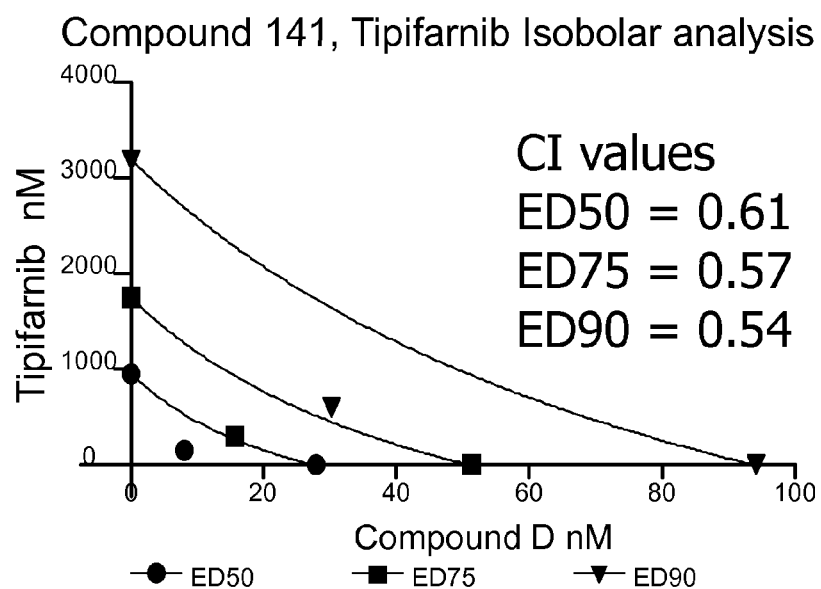
Figure 12.3. The combination of FLT3 inhibitor Compound D and Tipifarnib synergistically induces caspase activation and apoptosis of MV4-11 cells.

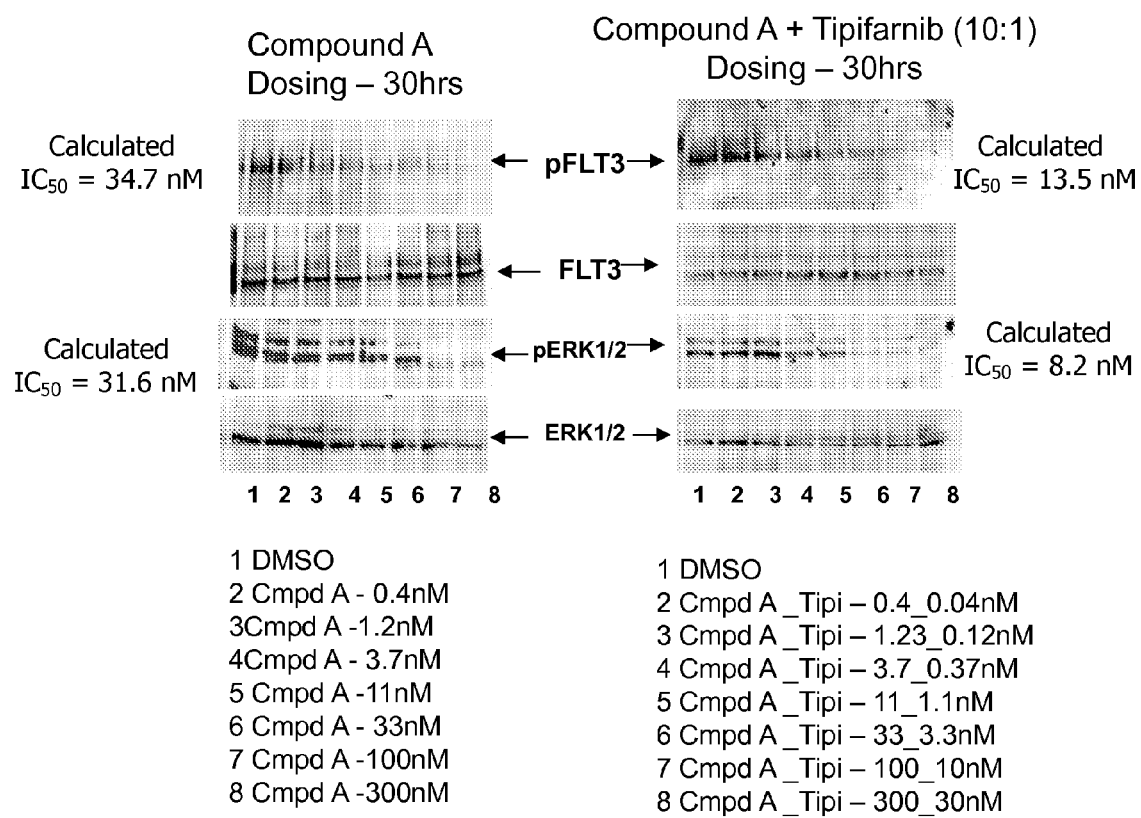
Figure 13. Tipifarnib increases the potency of Compound A inhibition of FLT3 and MapKinase phosphorylation in MV4-11 cells

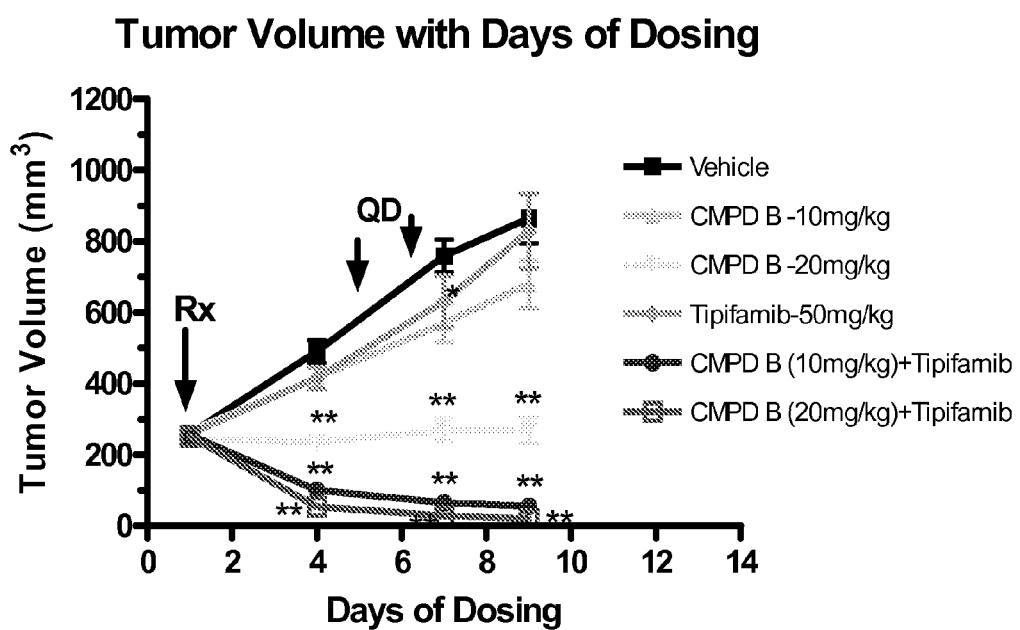
Figure 14. The combination of Compound B and Tipifarnib synergistically causes tumor growth regression in the MV4-11 xenograft tumor model.

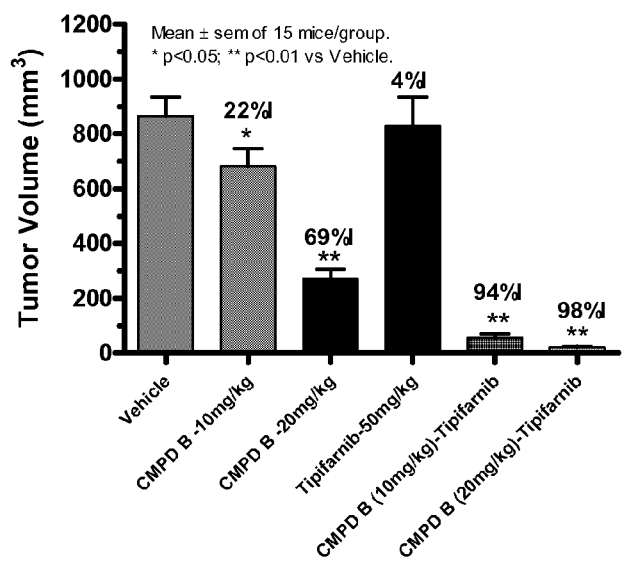
Figure 15. The combination of Compound B and Tipifarnib synergistically decreases tumor volume in the MV4-11 xenograft tumor model after 9days.

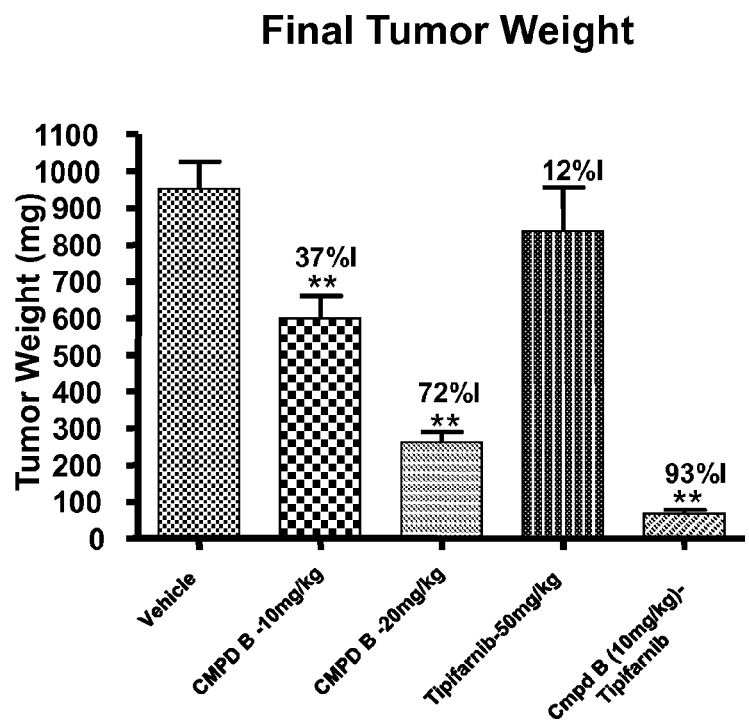
Note - Mice in 20 mpk Compound B + Tipifarnib combination group were taken off drug and kept alive to monitor tumor re-growth.
Figure 16. The combination of Compound B and Tipifarnib synergistically decreases tumor weight in the MV4-11 xenograft tumor model after 9days.

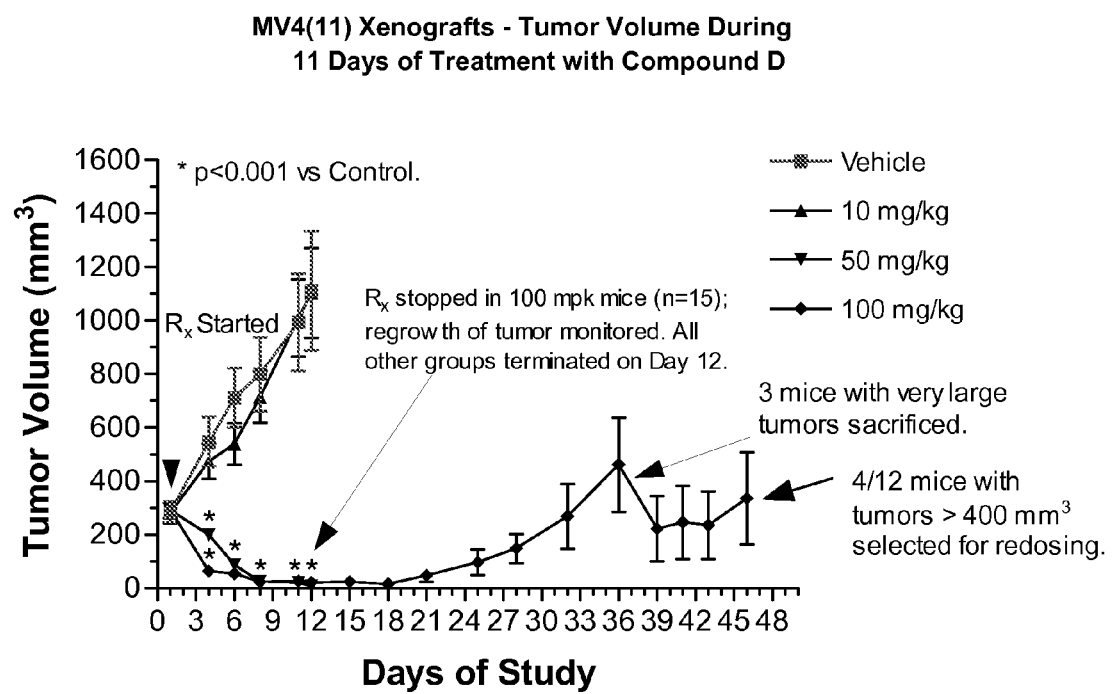
Figure 17. Effects of orally administered Compound D on the growth of MV4-11 tumor xenografts in nude mice.

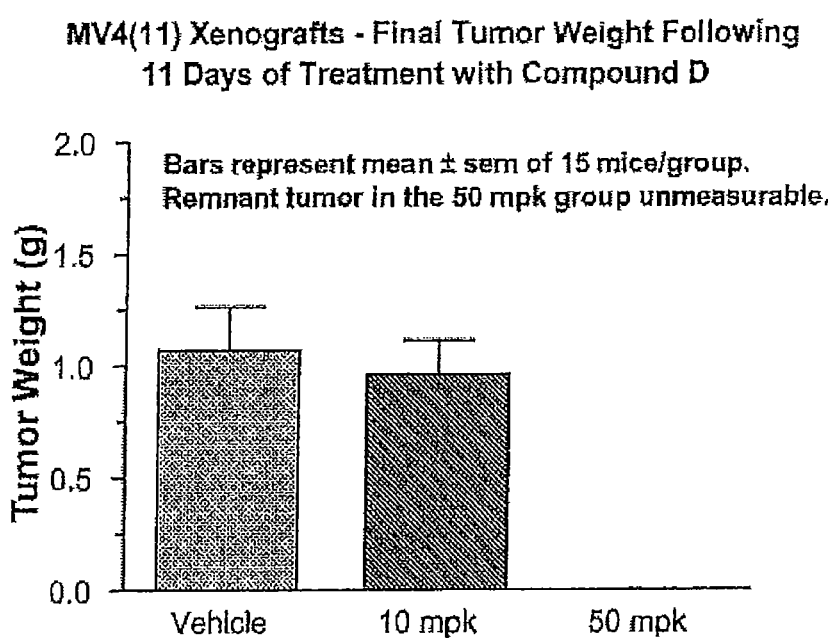
Figure 18. Effects of orally administered Compound D on the final weight of MV4-11 tumor xenografts in nude mice.

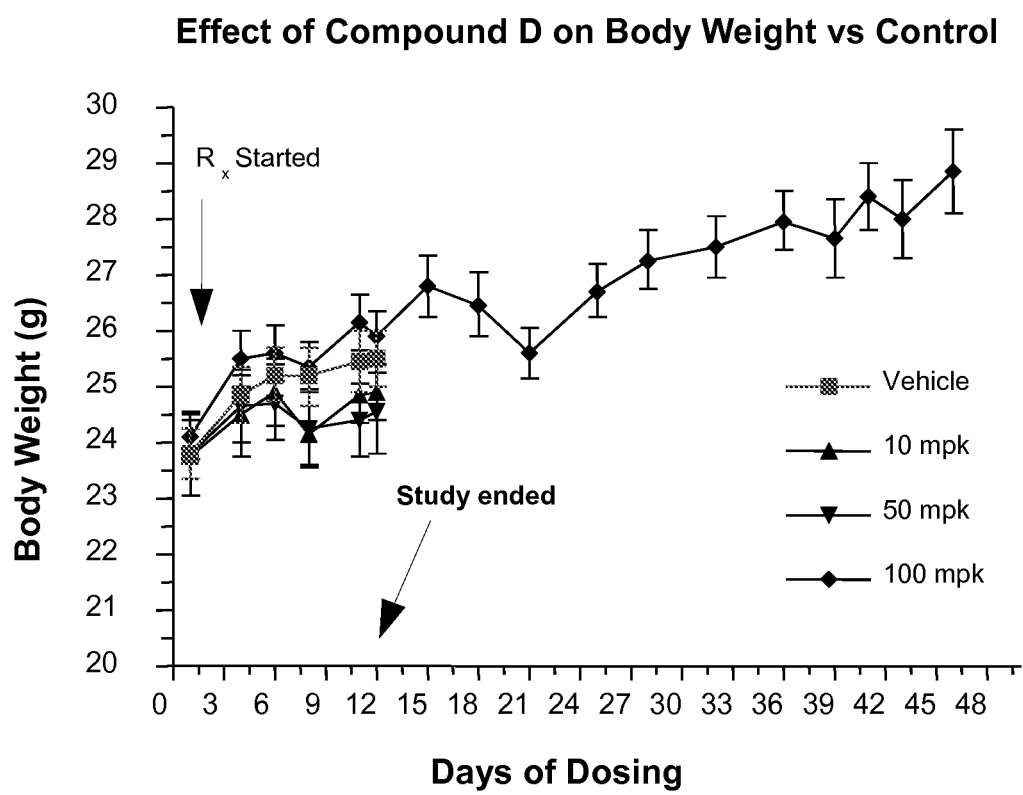
Figure 19. Effects of orally administered Compound D on the body weight of nude mice.

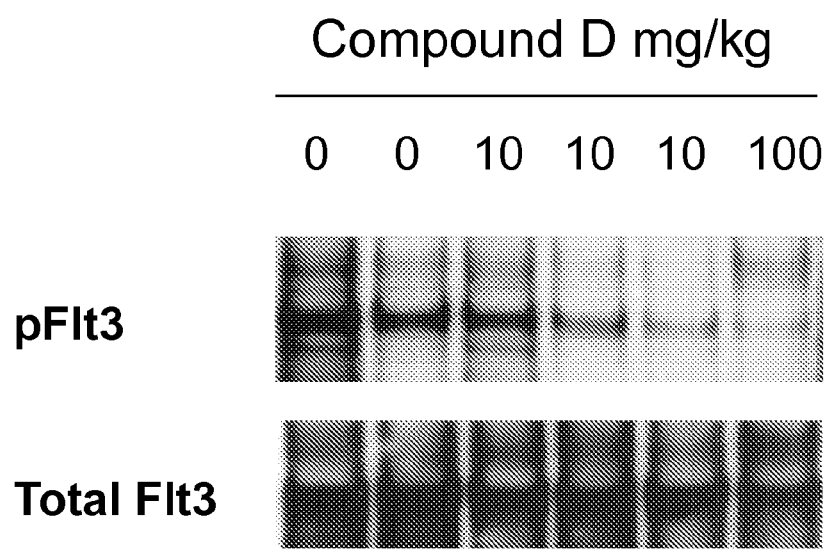
Figure 20. FLT3 phosphorylation in MV4-11 tumors obtained from vehicle- and Compound D-treated mice.

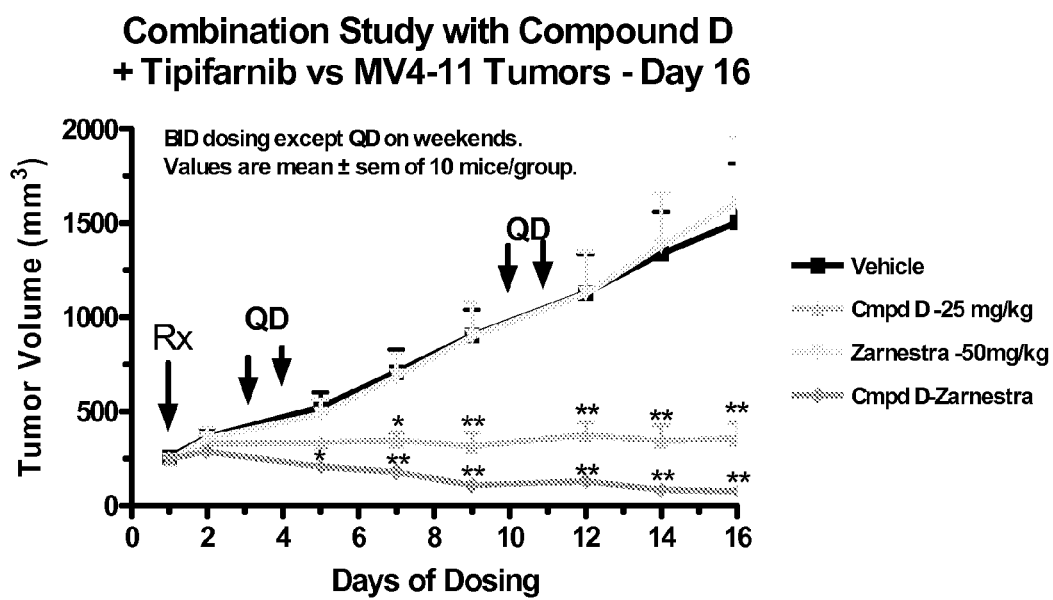
Figure 21. The combination of Compound D and Tipifarnib synergistically causes tumor growth regression in the MV4-11 xenograft tumor model.

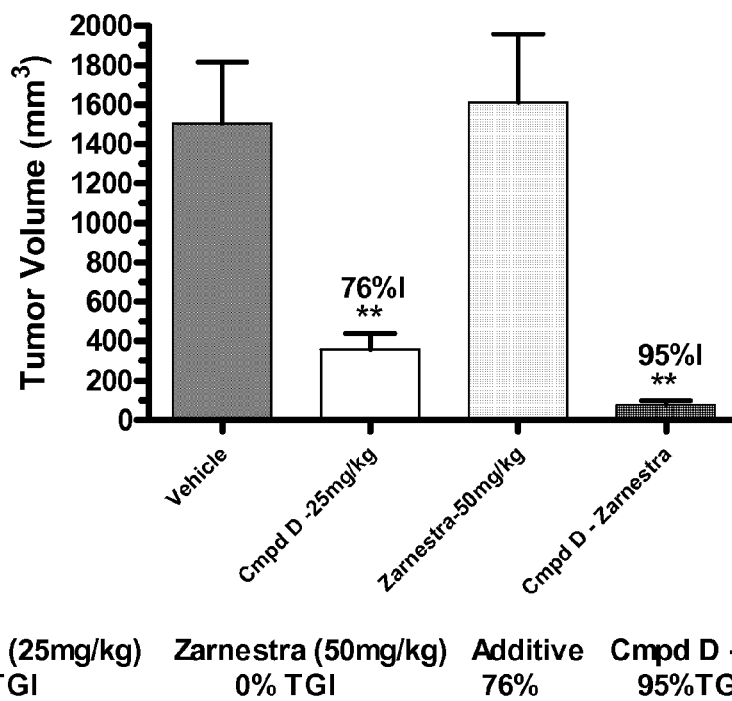
Figure 22. The combination of Compound D and Tipifarnib synergistically decreases tumor volume in the MV4-11 xenograft tumor model after 16 days.

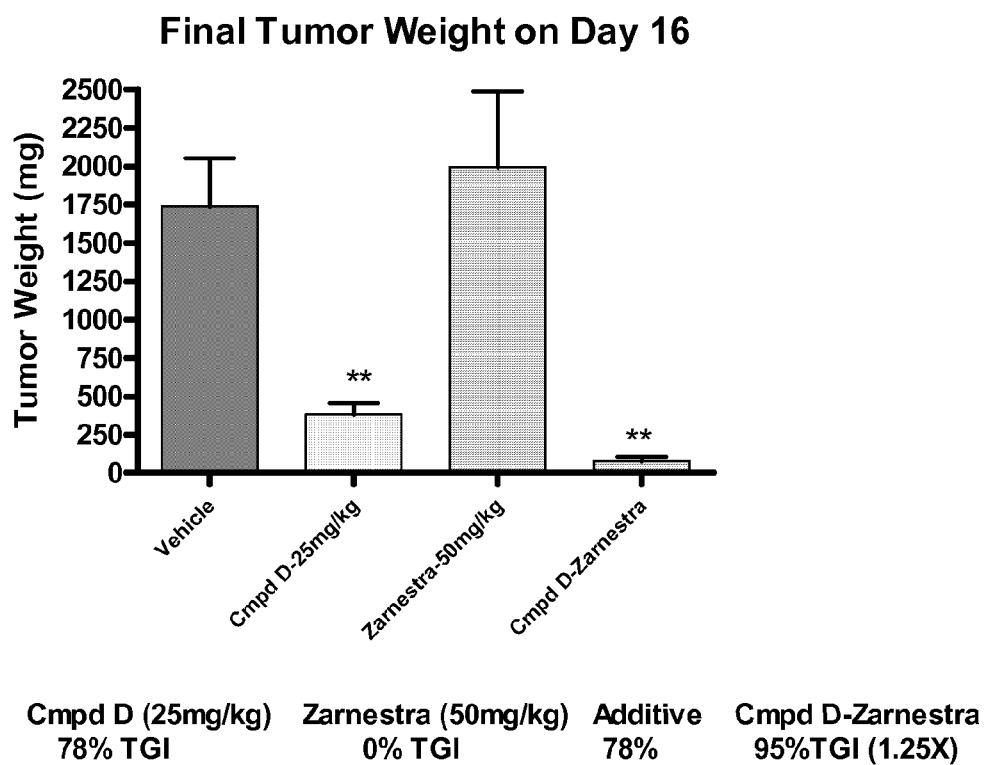
Figure 23. The combination of Compound D and Tipifarnib synergistically decreases tumor weight in the MV4-11 xenograft tumor model after 16 days.

SYNERGISTIC MODULATION OF FLT3 KINASE USING A FLT3 INHIBITOR AND A FARNESYL TRANSFERASE INHIBITOR

CROSS REFERENCE TO RELATED APPLICATIONS

This application is a continuation of U.S. application Ser. No. 11/422,413, filed Jun. 6, 2006 now abandonded, which claims priority to U.S. Provisional Application for Patent No. 60/793,320, filed Apr. 19, 2006 and U.S. Provisional Application for Patent No. 60/690,070, filed Jun. 10, 2005, the entire disclosures of which are hereby incorporated in their entirety.

FIELD OF THE INVENTION

The present invention relates to the treatment of a cell proliferative disorder or disorders related to FLT3 using a farnesyl transferase inhibitor in combination with an inhibitor of FLT3 tyrosine kinase.

BACKGROUND OF THE INVENTION

The fms-like tyrosine kinase 3 (FLT3) ligand (FLT3L) is one of the cytokines that affects the development of multiple hematopoietic lineages. These effects occur through the binding of FLT3L to the FLT3 receptor, also referred to as fetal liver kinase-2 (flk-2) and STK-1, a receptor tyrosine kinase (RTK) expressed on hematopoietic stem and progenitor cells. The FLT3 gene encodes a membrane-spanning class III RTK that plays an important role in proliferation, differentiation and apoptosis of cells during normal hematopoiesis. The FLT3 gene is mainly expressed by early myeloid and lymphoid progenitor cells. See McKenna, Hilary J. et al. Mice lacking flt3 ligand have deficient hematopoiesis affecting hematopoietic progenitor cells, dendritic cells, and natural killer cells. Blood. June 2000; 95: 3489-3497; Drexler, H. G. and H. (2004). "FLT3: receptor and ligand." Growth Factors 22(2): 71-3.

The ligand for FLT3 is expressed by the marrow stromal cells and other cells and synergizes with other growth factors to stimulate proliferation of stem cells, progenitor cells, dendritic cells, and natural killer cells.

Hematopoietic disorders are pre-malignant disorders of these systems and include, for instance, the myeloproliferative disorders, such as thrombocythemia, essential thrombocytosis (ET), angiogenic myeloid metaplasia, myelofibrosis (MF), myelofibrosis with myeloid metaplasia (MMM), chronic idiopathic myelofibrosis (IMF), polycythemia vera (PV), the cytopenias, and pre-malignant myelodysplastic syndromes. See Stirewalt, D. L. and J. P. Radich (2003). "The role of FLT3 in haematopoietic malignancies." Nat Rev Cancer 3(9): 650-65; Scheijen, B. and J. D. Griffin (2002). "Tyrosine kinase oncogenes in normal hematopoiesis and hematological disease." Oncogene 21(21): 3314-33.

Hematological malignancies are cancers of the body's blood forming and immune systems, the bone marrow and lymphatic tissues. Whereas in normal bone marrow, FLT3 expression is restricted to early progenitor cells, in hematological malignancies, FLT3 is expressed at high levels or FLT3 mutations cause an uncontrolled induction of the FLT3 receptor and downstream molecular pathway, possibly Ras activation. Hematological malignancies include leukemias, lymphomas (non-Hodgkin's lymphoma), Hodgkin's disease (also called Hodgkin's lymphoma), and myeloma—for instance, acute lymphocytic leukemia (ALL), acute myeloid leukemia (AML), acute promyelocytic leukemia (APL), chronic lymphocytic leukemia (CLL), chronic myeloid leukemia (CML), chronic neutrophilic leukemia (CNL), acute undifferentiated leukemia (AUL), anaplastic large-cell lymphoma (ALCL), prolymphocytic leukemia (PML), juvenile myelomonocytic leukemia (JMML), adult T-cell ALL, AML with trilineage myelodysplasia (AML/TMDS), mixed lineage leukemia (MLL), myelodysplastic syndromes (MDSs), myeloproliferative disorders (MPD), multiple myeloma, (MM) and myeloid sarcoma. See Kottaridis, P. D., R. E. Gale, et al. (2003). "Flt3 mutations and leukaemia." Br J Haematol 122(4): 523-38. Myeloid sarcoma is also associated with FLT3 mutations. See Ansari-Lari, Ali et al. FLT3 mutations in myeloid sarcoma. British Journal of Haematology. 2004 Sep. 126(6):785-91.

Acute Myelogenous Leukemia (AML) is the most prevalent form of adult leukemia and represents 15-20% of childhood leukemias. In 2002, in the United States, approximately 11,000 new cases of AML were diagnosed and an estimated 8,000 patients died from AML. See National Cancer Institute SEER database—http://seer.cancer.gov/. Although diagnosis for AML is traditionally based on histological techniques and blood leukocyte count, recent advances in cytogenetic and genetic analysis have revealed that AML is a mixture of distinct diseases that differ in their genetic abnormalities, clinical features and response to therapy. Recent efforts have begun to tailor chemotherapy to the different sub-types of AML (subtypes are based on cytogenetic analysis and immunohistochemical analysis for disease associated protein expression) with some success. Treatment of AML typically occurs in two phases: induction and post-induction therapy. Induction therapy typically consists of three doses of an anthracycline such as daunorubicin followed by i.v. bolus infusion of the cytotoxic cytarabine for 7-10 days. This regime is effective at inducing remission in 70-80% of patient <60 years of age and 50% of patients >60. See Burnett, A. K. (2002). "Acute myeloid leukemia: treatment of adults under 60 years." Rev Clin Exp Hematol 6(1): 26-45; Buchner T., W. Hiddemann, et al. (2002). "Acute myeloid leukemia: treatment over 60." Rev Clin Exp Hematol. 6(1):46-59. After remission induction there are several post-induction options including an additional cycle of chemotherapy or bone marrow transplantation. Post-induction treatment choice and success depends on the patient's age and AML sub-type. Despite the advances in diagnosis and treatment of AML over the last decade, the 5 year disease free survival for patients under 65 is only 40% and the 5 year disease free survival of patients over 65 is less than 10% percent. Thus, there remains a significant unmet clinical need for AML particularly in patients over 65. With the increased knowledge of the mechanisms of the different sub-types of AML new tailored treatments for the disease are beginning to immerge with some promising results.

One recent success in relapse and refractory AML treatment is the development and use of farnesyl transferase inhibitors (FTI) for post-induction treatment. Farnesyl transferase inhibitors are a potent and selective class of inhibitors of intracellular farnesyl protein transferase (FPT). FPT catalyses the lipid modification of a host of intracellular proteins, including the small GTPases of the Ras and Rho family and lamin proteins, to direct their localization to the plasma membrane or membrane compartments within the cell.

FTIs were originally developed to prevent post-translational farnesylation and activation of Ras oncoproteins (Prendergast G. C. and Rane, N. (2001) "Farnesyl Transferase Inhibitors: Mechanism and Applications" Expert Opin Investig Drugs. 10(12):2105-16). Recent studies also demonstrate FTI induced inhibition of Nf-κB activation leading to increased sensitivity to induction of apoptosis and downregulation of inflammatory gene expression through suppression of Ras-dependent Nf-κB activation. See Takada, Y., et al. (2004). "Protein farnesyltransferase inhibitor (SCH 66336) abolishes NF-kappaB activation induced by various carcinogens and inflammatory stimuli leading to suppression of NF-kappaB-regulated gene expression and up-regulation of apoptosis." J Biol Chem 279, 26287-99.

Of particular interest for oncology, FTI inhibition of the oncogenes of the Ras and Rho family leads to growth arrest and apoptosis of tumor cells both in vitro and in vivo. See Haluska P., G. K. Dy, A. A. Adjei. (2002) "Farnesyl transferase inhibitors as anticancer agents." Eur J Cancer. 38(13): 1685-700. From a clinical perspective, myeloid malignancies, particularly AML, represent a significant opportunity for FTI therapy.

As discussed earlier, AML is a disease with very low long-term survival and an elevated rate of chemotherapy-induced toxicity and resistance (particularly in patients >60 years of age). Additionally, the mechanism of proliferation of AML cells relies on the small GTPases of the Ras and Rho family. With the plethora of pre-clinical data supporting the efficacy of FTIs in AML treatment, several clinical trials were initiated with an FTI including; R115777 (Zarnestra, Johnson and Johnson), BMS-214662, CP-60974 (Pfizer) and Sch-6636 (Ionafarnib, Schering-Plough).

ZARNESTRA® (also known as R115777 or tipifarnib) is the most advanced and promising of the FTI class of compounds. In clinical studies of patients with relapsed and refractory AML, Zarnestra treatment resulted in a ~30% response rate with 2 patients achieving complete remission. See Lancet J. E., J. D. Rosenblatt, J. E. Karp. (2003) "Farnesyltransferase inhibitors and myeloid malignancies: phase I evidence of Zarnestra activity in high-risk leukemias." Semin Hematol. 39(3 Suppl 2):31-5. These responses occurred independently of the patients Ras mutational status, as none of the patients in the trial had the Ras mutations that are sometimes seen in AML patients. However, there was a direct correlation of patient responses to their level of MAPkinase activation (a downstream target of both Ras and Rho protein activity) at the onset of treatment, suggesting that the activity of the Ras/MAPkinase pathway, activated by other mechanisms may be a good predictor of patient responses. See Lancet J. E., J. D. Rosenblatt, J. E. Karp. (2003) "Farnesyltransferase inhibitors and myeloid malignancies: phase I evidence of Zarnestra activity in high-risk leukemias." Semin Hematol. 39(3 Suppl 2): 31-5. Additionally, a recent multicenter Phase II trial in patients with relapsed AML demonstrated complete responses (bone marrow blasts <5%) in 17 of 50 patients and a >50% reduction in bone marrow blasts in 31 of 50 patients. Reviewed in Gotlib, J (2005) "Farnesyltransferase inhibitor therapy in acute myelogenous leukemia." Curr. Hematol. Rep.; 4(1):77-84. Preliminary analysis of genes regulated by the FTI treatment in responders in that trial also demonstrated an effect on proteins in the MAPKinase pathway. This promising result has experts in the field anticipating the use of Zarnestra in the clinic in the near future.

Recently, another target for the treatment of AML, and a subset of patients with MDS and ALL, has emerged. The receptor tyrosine kinase, FLT3 and mutations of FLT3, have been identified as key player in the progression of AML. A summary of the many studies linking FLT3 activity to disease have been extensively reviewed by Gilliland, D. G. and J. D. Griffin (2002). "The roles of FLT3 in hematopoiesis and leukemia." Blood 100(5): 1532-42, and Stirewalt, D. L. and J. P. Radich (2003). "The role of FLT3 in haematopoietic malignancies." Nat Rev Cancer 3(9): 650-65. Greater than 90% of patients with AML have FLT3 expression in blast cells. It is now known that roughly 30-40% of patients with AML have an activating mutation of FLT3, making FLT3 mutations the most common mutation in patients with AML. There are two known types of activating mutations of FLT3. One is a duplication of 4-40 amino acids in the juxtamembrane region (ITD mutation) of the receptor (25-30% of patients) and the other is a point mutation in the kinase domain (5-7% of patients). These receptor mutations cause constitutive activation of multiple signal transduction pathways including Ras/MAPkinase, PI3kinase/AKT, and the STAT pathways. Additionally, the FLT3ITD mutation also has been shown to decrease the differentiation of early myeloid cells. More significantly, patients with the ITD mutation have decreased rates of remission induction, decreased remission times, and poorer overall prognosis. FLT3ITD mutations have also been found in ALL with the MLL gene rearrangement and in a sub-population of MDS patients. The presence of the FLT3ITD mutation in MDS and ALL is also correlated with accelerated disease progression and poorer prognosis in these patients. See Shih L. Y. et al., (2004) "Internal tandem duplication of fins-like tyrosine kinase 3 is associated with poor outcome in patients with myelodysplastic syndrome." Cancer, 101; 989-98; and Armstrong, S. A. et al., (2004) "FLT3 mutations in childhood acute lymphoblastic leukemia." Blood. 103: 3544-6. To date, there is no strong evidence that suggests either the kinase domain point mutations or the over expressed wild-type receptor is causative of disease, however, FLT3 expression may contribute to the progression of the disease. This building pre-clinical and clinical evidence has led to the development of a number of FLT3 inhibitors which are currently being evaluated in the pre-clinical and clinical setting.

An emerging strategy for the treatment of AML is the combination of target directed therapeutic agents together or with conventional cytotoxic agents during induction and/or post-induction therapy. Recent proof of concept data has been published that demonstrate the combination of the cytotoxic agents (such as cytarabine or daunorubicin) and FLT3 inhibitors inhibit the growth of AML cells expressing FLT3ITD. See Levis, M., R. Pham, et al. (2004). "In vitro studies of a FLT3 inhibitor combined with chemotherapy: sequence of administration is important to achieve synergistic cytotoxic effects." Blood 104(4): 1145-50, and Yee K W, Schittenhelm M, O'Farrell A M, Town A R, McGreevey L, Bainbridge T, Chemington J M, Heinrich M C. (2004) "Synergistic effect of SU11248 with cytarabine or daunorubicin on FLT3ITD-positive leukemic cells." Blood. 104(13):4202-9.

Accordingly, the present invention provides a synergistic method of treatment comprising co-administration (simultaneous or sequential) of a novel FLT3 kinase inhibitor described herein and a farnesyl transferase inhibitor for the treatment of FLT3 expressing cell proliferative disorders.

A variety of FTase inhibitors are currently known. FTIs appropriate for use in the present invention are the following: WO-97/21701 and U.S. Pat. No. 6,037,350, which are incorporated herein in their entirety, describe the preparation, formulation and pharmaceutical properties of certain farnesyl transferase inhibiting (imidazoly-5-yl)methyl-2-quinolinone derivatives of formulas (I), (II) and (III), as well as intermediates of formula (II) and (III) that are metabolized in vivo to the compounds of formula (I). The compounds of formulas (I), (II) and (III) are represented by

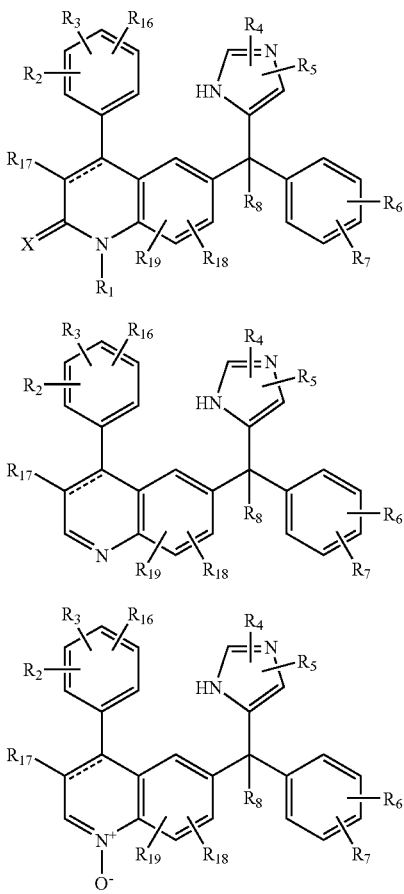

the pharmaceutically acceptable acid or base addition salts and the stereochemically isomeric forms thereof, wherein the dotted line represents an optional bond;

X is oxygen or sulfur;

$R^1$ is hydrogen, $C_{1-12}$alkyl, $Ar^1$, $Ar^2C_{1-6}$alkyl, quinolinyl$C_{1-6}$alkyl, pyridyl$C_{1-6}$alkyl, hydroxy$C_{1-6}$alkyl, $C_{1-6}$alkyloxy$C_{1-6}$alkyl, mono- or di($C_{1-6}$alkyl)amino$C_{1-6}$alkyl, amino$C_{1-6}$alkyl, or a radical of formula -Alk$^1$—C(=O)—R$^9$, -Alk$^1$-S(O)—R$^9$ or -Alk$^1$-S(O)$_2$—R$^9$, wherein Alk$^1$ is $C_{1-6}$alkanediyl, $R^9$ is hydroxy, $C_{1-6}$alkyl, $C_{1-6}$alkyloxy, amino, $C_{1-8}$alkylamino or $C_{1-8}$alkylamino substituted with $C_{1-6}$alkyloxycarbonyl;

$R^2$, $R^3$ and $R^{16}$ each independently are hydrogen, hydroxy, halo, cyano, $C_{1-6}$alkyl, $C_{1-6}$alkyloxy, hydroxy$C_{1-6}$alkyloxy, $C_{1-6}$alkyloxy$C_{1-6}$alkyloxy, amino$C_{1-6}$alkyloxy, mono- or di($C_{1-6}$alkyl)amino$C_{1-6}$alkyloxy, $Ar^1$, $Ar^2C_{1-6}$alkyl, $Ar^2$oxy, $Ar^2C_{1-6}$alkyloxy, hydroxycarbonyl, $C_{1-6}$alkyloxycarbonyl, trihalomethyl, trihalomethoxy, $C_{2-6}$alkenyl, 4,4-dimethyloxazolyl; or when on adjacent positions $R^2$ and $R^3$ taken together may form a bivalent radical of formula —O—CH$_2$—O— (a-1), —O—CH$_2$—CH$_2$—O— (a-2), —O—CH=CH— (a-3), —O—CH$_2$—CH$_2$— (a-4), —O—CH$_2$—CH$_2$—CH$_2$— (a-5), or —CH=CH—CH=CH— (a-6);

$R^4$ and $R^5$ each independently are hydrogen, halo, $Ar^1$, $C_{1-6}$alkyl, hydroxy$C_{1-6}$alkyl, $C_{1-6}$alkyloxy$C_{1-6}$alkyl, $C_{1-6}$alkyloxy, $C_{1-6}$alkylthio, amino, hydroxycarbonyl, $C_{1-6}$alkyloxycarbonyl, $C_{1-6}$alkylS(O)$C_{1-6}$alkyl or $C_{1-6}$alkylS(O)$_2C_{1-6}$alkyl;

$R^6$ and $R^7$ each independently are hydrogen, halo, cyano, $C_{1-6}$alkyl, $C_{1-6}$alkyloxy, $Ar^2$oxy, trihalomethyl, $C_{1-6}$alkylthio, di($C_{1-6}$alkyl)amino, or when on adjacent positions $R^6$ and $R^7$ taken together may form a bivalent radical of formula —O—CH$_2$—O— (c-1), or —CH=CH—CH=CH— (c-2);

$R^8$ is hydrogen, $C_{1-6}$alkyl, cyano, hydroxycarbonyl, $C_{1-6}$alkyloxycarbonyl, $C_{1-6}$alkylcarbonyl$C_{1-6}$alkyl, cyano$C_{1-6}$alkyl, $C_{1-6}$alkyloxycarbonyl$C_{1-6}$alkyl, carboxy$C_{1-6}$alkyl, hydroxy$C_{1-6}$alkyl, amino$C_{1-6}$alkyl, mono- or di($C_{1-6}$alkyl)amino$C_{1-6}$alkyl, imidazolyl, halo$C_{1-6}$alkyl, $C_{1-6}$alkyloxy$C_{1-6}$alkyl, aminocarbonyl$C_{1-6}$alkyl, or a radical of formula —O—R$^{10}$ (b-1), —S—R$^{10}$ (b-2), —N—R$^{11}$R$^{12}$ (b-3), wherein $R^{10}$ is hydrogen, $C_{1-6}$alkyl, $C_{1-6}$alkylcarbonyl, $Ar^1$, $Ar^2C_{1-6}$alkyl, $C_{1-6}$alkyloxycarbonyl$C_{1-6}$alkyl, or a radical of formula -Alk$^2$-OR$^{13}$ or -Alk$^2$-NR$^{14}$R$^{15}$;

$R^{11}$ is hydrogen, $C_{1-12}$alkyl, $Ar^1$ or $Ar^2C_{1-6}$alkyl;

$R^{12}$ is hydrogen, $C_{1-6}$alkyl, $C_{1-16}$alkylcarbonyl, $C_{1-6}$alkyloxycarbonyl, $C_{1-6}$alkylaminocarbonyl, $Ar^1$, $Ar^2C_{1-6}$alkyl, $C_{1-6}$alkylcarbonyl$C_{1-6}$alkyl, a natural amino acid, $Ar^1$carbonyl, $Ar^2C_{1-6}$alkylcarbonyl, aminocarbonylcarbonyl, $C_{1-6}$alkyloxy$C_{1-6}$alkylcarbonyl, hydroxy, $C_{1-6}$alkyloxy, aminocarbonyl, di($C_{1-6}$alkyl)amino$C_{1-6}$alkylcarbonyl, amino, $C_{1-6}$alkylamino, $C_{1-6}$alkylcarbonylamino, or a radical of formula -Alk$^2$-OR$^{13}$ or -Alk$^2$-NR$^{14}$R$^{15}$;

wherein Alk$^2$ is $C_{1-6}$alkanediyl;

$R^{13}$ is hydrogen, $C_{1-6}$alkyl, $C_{1-6}$alkylcarbonyl, hydroxy$C_{1-6}$alkyl, $Ar^1$ or $Ar^2C_{1-6}$alkyl;

$R^{14}$ is hydrogen, $C_{1-6}$alkyl, $Ar^1$ or $Ar^2C_{1-6}$alkyl;

$R^{15}$ is hydrogen, $C_{1-6}$alkyl, $C_{1-6}$alkylcarbonyl, $Ar^1$ or $Ar^2C_{1-6}$alkyl;

$R^{17}$ is hydrogen, halo, cyano, $C_{1-6}$alkyl, $C_{1-6}$alkyloxycarbonyl, $Ar^1$;

$R^{18}$ is hydrogen, $C_{1-6}$alkyl, $C_{1-6}$alkyloxy or halo;

$R^{19}$ is hydrogen or $C_{1-6}$alkyl;

$Ar^1$ is phenyl or phenyl substituted with $C_{1-6}$alkyl, hydroxy, amino, $C_{1-6}$alkyloxy or halo; and $Ar^2$ is phenyl or phenyl substituted with $C_{1-6}$alkyl, hydroxy, amino, $C_{1-6}$alkyloxy or halo.

WO-97/16443 and U.S. Pat. No. 5,968,952, which are incorporated herein in their entirety, describe the preparation, formulation and pharmaceutical properties of farnesyltransferase inhibiting compounds of formula (IV), as well as intermediates of formula (V) and (VI) that are metabolized in vivo to the compounds of formula (IV). The compounds of formulas (IV), (V) and (VI) are represented by

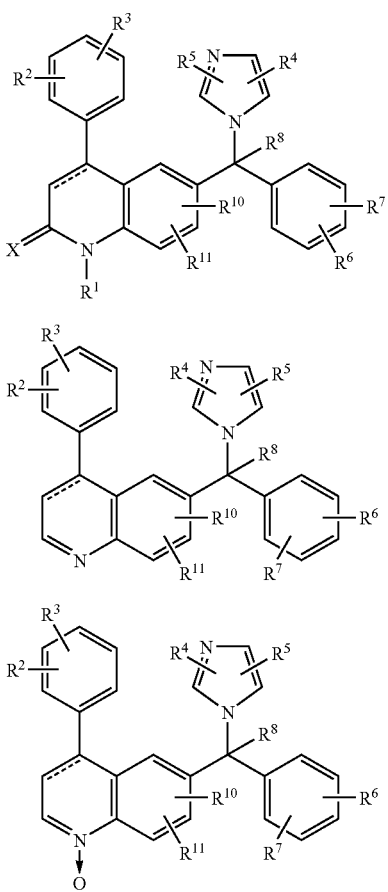

the pharmaceutically acceptable acid or base addition salts and the stereochemically isomeric forms thereof, wherein
the dotted line represents an optional bond;
X is oxygen or sulfur;
$R^1$ is hydrogen, $C_{1-12}$alkyl, $Ar^1$, $Ar^2C_{1-6}$alkyl, quinolinyl$C_{1-6}$alkyl, pyridyl$C_{1-6}$alkyl, hydroxy$C_{1-6}$alkyl, $C_{1-6}$alkyloxy$C_{1-6}$alkyl, mono- or di($C_{1-6}$alkyl)amino$C_{1-6}$alkyl, amino$C_{1-6}$alkyl,
or a radical of formula -Alk$^1$—C(=O)—R$^9$, -Alk$^1$-S(O)—R$^9$ or -Alk$^1$-S(O)$_2$—R$^9$,
wherein Alk$^1$ is $C_{1-6}$alkanediyl,
$R^9$ is hydroxy, $C_{1-6}$alkyl, $C_{1-6}$alkyloxy, amino, $C_{1-8}$alkylamino or $C_{1-8}$alkylamino substituted with $C_{1-6}$alkyloxycarbonyl;
$R^2$ and $R^3$ each independently are hydrogen, hydroxy, halo, cyano, $C_{1-6}$alkyl, $C_{1-6}$alkyloxy, hydroxy$C_{1-6}$alkyloxy, $C_{1-6}$alkyloxy$C_{1-6}$alkyloxy, amino$C_{1-6}$alkyloxy, mono- or di($C_{1-6}$alkyl)amino$C_{1-6}$alkyloxy, $Ar^1$, $Ar^2C_{1-6}$alkyl, $Ar^2$oxy, $Ar^2C_{1-6}$alkyloxy, hydroxycarbonyl, $C_{1-6}$alkyloxycarbonyl, trihalomethyl, trihalomethoxy, $C_{2-6}$alkenyl; or
when on adjacent positions $R^2$ and $R^3$ taken together may form a bivalent radical of formula —O—CH$_2$—O—      (a-1), —O—CH$_2$—CH$_2$—O—      (a-2), —O—CH=CH—      (a-3), —O—CH$_2$—CH$_2$—      (a-4), —O—CH$_2$—CH$_2$—CH$_2$—      (a-5), or —CH=CH—CH=CH—      (a-6);

$R^4$ and $R^5$ each independently are hydrogen, $Ar^1$, $C_{1-6}$alkyl, $C_{1-6}$alkyloxy$C_{1-6}$alkyl, $C_{1-6}$alkyloxy, $C_{1-6}$alkylthio, amino, hydroxycarbonyl, $C_{1-6}$alkyloxycarbonyl, $C_{1-6}$alkylS(O)$C_{1-6}$alkyl or $C_{1-6}$alkylS(O)$_2$$C_{1-6}$alkyl;

$R^6$ and $R^7$ each independently are hydrogen, halo, cyano, $C_{1-6}$alkyl, $C_{1-6}$alkyloxy or $Ar^2$oxy;

$R^8$ is hydrogen, $C_{1-6}$alkyl, cyano, hydroxycarbonyl, $C_{1-6}$alkyloxycarbonyl, $C_{1-6}$alkylcarbonyl$C_{1-6}$alkyl, cyano$C_{1-6}$alkyl, $C_{1-6}$alkyloxycarbonyl$C_{1-6}$alkyl, hydroxycarbonyl$C_{1-6}$alkyl, hydroxy$C_{1-6}$alkyl, amino$C_{1-6}$alkyl, mono- or di($C_{1-6}$alkyl)amino$C_{1-6}$alkyl, halo$C_{1-6}$alkyl, $C_{1-6}$alkyloxy$C_{1-6}$alkyl, aminocarbonyl$C_{1-6}$alkyl, $Ar^1$, $Ar^2C_{1-6}$alkyloxy$C_{1-6}$alkyl, $C_{1-6}$alkylthio$C_{1-6}$alkyl;

$R^{10}$ is hydrogen, $C_{1-6}$alkyl, $C_{1-6}$alkyloxy or halo;

$R^{11}$ is hydrogen or $C_{1-6}$alkyl;

$Ar^1$ is phenyl or phenyl substituted with $C_{1-6}$alkyl, hydroxy, amino, $C_{1-6}$alkyloxy or halo;

$Ar^2$ is phenyl or phenyl substituted with $C_{1-6}$alkyl, hydroxy, amino, $C_{1-6}$alkyloxy or halo.

WO-98/40383 and U.S. Pat. No. 6,187,786, which are incorporated herein in their entirety, disclose the preparation, formulation and pharmaceutical properties of farnesyltransferase inhibiting compounds of formula (VII)

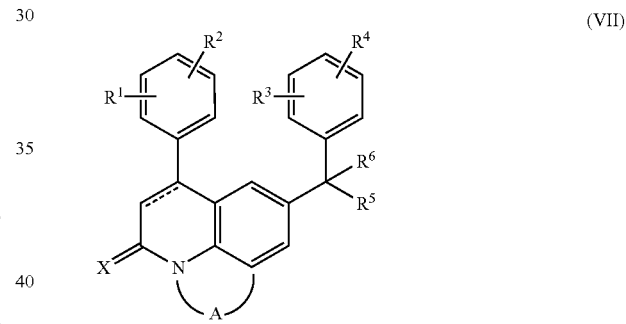

the pharmaceutically acceptable acid addition salts and the stereochemically isomeric forms thereof, wherein
the dotted line represents an optional bond;
X is oxygen or sulfur;
-A- is a bivalent radical of formula

| | |
|---|---|
| —CH=CH— | (a-1), |
| —CH$_2$—CH$_2$— | (a-2), |
| —CH$_2$—CH$_2$—CH$_2$— | (a-3), |
| —CH$_2$—O— | (a-4), |
| —CH$_2$—CH$_2$—O— | (a-5), |
| —CH$_2$—S— | (a-6), |
| —CH$_2$—CH$_2$—S— | (a-7), |
| —CH=N— | (a-8), |
| —N=N— | (a-9), or |
| —CO—NH— | (a-10); | wherein optionally one hydrogen atom may be replaced by $C_{1-4}$alkyl or $Ar^1$;
$R^1$ and $R^2$ each independently are hydrogen, hydroxy, halo, cyano, $C_{1-6}$alkyl, trihalomethyl, trihalomethoxy, $C_{2-6}$alkenyl, $C_{1-6}$alkyloxy, hydroxy$C_{1-6}$alkyloxy, $C_{1-6}$alkyloxy$C_{1-6}$alkyloxy, $C_{1-6}$alkyloxycarbonyl, amino$C_{1-6}$alkyloxy, mono- or di($C_{1-6}$alkyl)amino$C_{1-6}$alkyloxy, $Ar^2$, $Ar^2$—$C_{1-6}$ alkyl, Ar²-oxy, Ar²—C$_{1-6}$alkyloxy; or when on adjacent positions R¹ and R² taken together may form a bivalent radical of formula —O—CH$_2$—O— (b-1), —O—CH$_2$—CH$_2$—O— (b-2), —O—CH=CH— (b-3), —O—CH$_2$—CH$_2$— (b-4), —O—CH$_2$—CH$_2$—CH$_2$— (b-5), or —CH=CH—CH=CH— (b-6);

R³ and R⁴ each independently are hydrogen, halo, cyano, C$_{1-6}$alkyl, C$_{1-6}$alkyloxy, Ar³-oxy, C$_{1-6}$alkylthio, di(C$_{1-6}$alkyl)amino, trihalomethyl, trihalomethoxy, or when on adjacent positions R³ and R⁴ taken together may form a bivalent radical of formula —O—CH$_2$—O— (c-1), —O—CH$_2$—CH$_2$—O— (c-2), or —CH=CH—CH=CH— (c-3);

R⁵ is a radical of formula

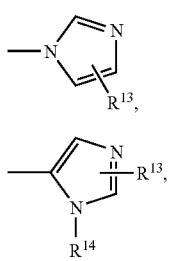

(d-1)

(d-2)

wherein R¹³ is hydrogen, halo, Ar⁴, C$_{1-6}$alkyl, hydroxyC$_{1-6}$alkyl, C$_{1-6}$alkyloxyC$_{1-6}$alkyl, C$_{1-6}$alkyloxy, C$_{1-6}$alkylthio, amino, C$_{1-6}$alkyloxycarbonyl, C$_{1-6}$alkylS(O)C$_{1-6}$alkyl or C$_{1-6}$alkylS(O)$_2$C$_{1-6}$alkyl;

R¹⁴ is hydrogen, C$_{1-6}$alkyl or di(C$_{1-4}$alkyl)aminosulfonyl;

R⁶ is hydrogen, hydroxy, halo, C$_{1-6}$alkyl, cyano, haloC$_{1-6}$alkyl, hydroxyC$_{1-6}$alkyl, cyanoC$_{1-6}$alkyl, aminoC$_{1-6}$alkyl, C$_{1-6}$alkyloxyC$_{1-6}$alkyl, C$_{1-6}$alkylthioC$_{1-6}$alkyl, aminocarbonylC$_{1-6}$alkyl, C$_{1-6}$alkyloxycarbonylC$_{1-6}$alkyl, C$_{1-6}$alkylcarbonyl-C$_{1-6}$alkyl, C$_{1-6}$alkyloxycarbonyl, mono- or di(C$_{1-6}$alkyl)aminoC$_{1-6}$alkyl, Ar⁵, Ar⁵—C$_{1-6}$alkyloxyC$_{1-6}$alkyl; or a radical of formula —O—R⁷ (e-1), —S—R⁷ (e-2), —N—R⁸R⁹ (e-3), wherein R⁷ is hydrogen, C$_{1-6}$alkyl, C$_{1-6}$alkylcarbonyl, Ar⁶, Ar⁶—C$_{1-6}$alkyl, C$_{1-6}$alkyloxycarbonylC$_{1-6}$alkyl, or a radical of formula -Alk-OR¹⁰ or -Alk-NR¹¹R¹²;

R⁸ is hydrogen, C$_{1-6}$alkyl, Ar⁷ or Ar⁷—C$_{1-6}$alkyl;

R⁹ is hydrogen, C$_{1-6}$alkyl, C$_{1-6}$alkylcarbonyl, C$_{1-6}$alkyloxycarbonyl, C$_{1-6}$alkylaminocarbonyl, Ar⁸, Ar⁸—C$_{1-6}$alkyl, C$_{1-6}$alkylcarbonyl-C$_{1-6}$alkyl, Ar⁸-carbonyl, Ar⁸—C$_{1-6}$alkylcarbonyl, aminocarbonylcarbonyl, C$_{1-6}$alkyloxyC$_{1-6}$alkylcarbonyl, hydroxy, C$_{1-6}$alkyloxy, aminocarbonyl, di (C$_{1-6}$alkyl)aminoC$_{1-6}$alkylcarbonyl, amino, C$_{1-6}$alkylamino, C$_{1-6}$alkylcarbonylamino, or a radical of formula -Alk-OR¹⁰ or -Alk-NR¹¹R¹²;

wherein Alk is C$_{1-6}$alkanediyl;

R¹⁰ is hydrogen, C$_{1-6}$alkyl, C$_{1-6}$alkylcarbonyl, hydroxyC$_{1-6}$alkyl, Ar⁹ or Ar⁹—C$_{1-6}$alkyl;

R¹¹ is hydrogen, C$_{1-6}$alkyl, C$_{1-6}$alkylcarbonyl, Ar¹⁰ or Ar¹⁰—C$_{1-6}$alkyl;

R¹² is hydrogen, C$_{1-6}$alkyl, Ar¹¹ or Ar¹¹—C$_{1-6}$alkyl; and

Ar¹ to Ar¹¹ are each independently selected from phenyl; or phenyl substituted with halo, C$_{1-6}$alkyl, C$_{1-6}$alkyloxy or trifluoromethyl.

WO-98/49157 and U.S. Pat. No. 6,117,432, which are incorporated herein in their entirety, concern the preparation, formulation and pharmaceutical properties of farnesyltransferase inhibiting compounds of formula (VIII)

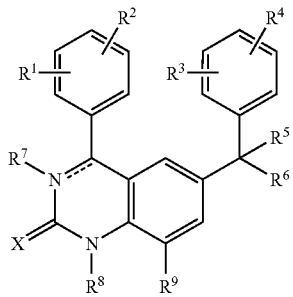

(VIII)

the pharmaceutically acceptable acid addition salts and the stereochemically isomeric forms thereof, wherein the dotted line represents an optional bond;

X is oxygen or sulfur;

R¹ and R² each independently are hydrogen, hydroxy, halo, cyano, C$_{1-6}$alkyl, trihalomethyl, trihalomethoxy, C$_{2-6}$alkenyl, C$_{1-6}$alkyloxy, hydroxyC$_{1-6}$alkyloxy, C$_{1-6}$alkyloxyC$_{1-6}$alkyloxy, C$_{1-6}$alkyloxycarbonyl, aminoC$_{1-6}$alkyloxy, mono- or di(C$_{1-6}$alkyl)aminoC$_{1-6}$alkyloxy, Ar¹, Ar¹C$_{1-6}$alkyl, Ar¹oxy or Ar¹C$_{1-6}$alkyloxy;

R³ and R⁴ each independently are hydrogen, halo, cyano, C$_{1-6}$alkyl, C$_{1-6}$alkyloxy, Ar¹ oxy, C$_{1-6}$alkylthio, di(C$_{1-6}$alkyl)amino, trihalomethyl or trihalomethoxy;

R⁵ is hydrogen, halo, C$_{1-6}$alkyl, cyano, haloC$_{1-6}$alkyl, hydroxyC$_{1-6}$alkyl, cyanoC$_{1-6}$alkyl, aminoC$_{1-6}$alkyl, C$_{1-6}$alkyloxyC$_{1-6}$alkyl, C$_{1-6}$alkylthioC$_{1-6}$alkyl, aminocarbonylC$_{1-6}$alkyl, C$_{1-6}$alkyloxycarbonylC$_{1-6}$alkyl, C$_{1-6}$alkylcarbonyl-C$_{1-6}$alkyl, C$_{1-6}$alkyloxycarbonyl, mono- or di(C$_{1-6}$alkyl)aminoC$_{1-6}$alkyl, Ar¹, Ar¹C$_{1-6}$alkyloxyC$_{1-6}$alkyl; or a radical of formula —O—R¹⁰ (a-1), —S—R¹⁰ (a-2), —N—R¹¹R¹² (a-3), wherein R¹⁰ is hydrogen, C$_{1-6}$alkyl, C$_{1-6}$alkylcarbonyl, Ar¹, Ar¹C$_{1-6}$alkyl, C$_{1-6}$alkyloxycarbonylC$_{1-6}$alkyl, or a radical of formula -Alk-OR¹³ or -Alk-NR¹⁴R¹⁵;

R¹¹ is hydrogen, C$_{1-6}$alkyl, Ar¹ or Ar¹C$_{1-6}$alkyl;

R¹² is hydrogen, C$_{1-6}$alkyl, C$_{1-6}$alkylcarbonyl, C$_{1-6}$alkyloxycarbonyl, C$_{1-6}$alkylaminocarbonyl, Ar¹, Ar¹C$_{1-6}$alkyl, C$_{1-6}$alkylcarbonyl-C$_{1-6}$alkyl, Ar¹carbonyl, Ar¹C$_{1-6}$alkylcarbonyl, aminocarbonylcarbonyl, C$_{1-6}$alkyloxyC$_{1-6}$alkylcarbonyl, hydroxy, C$_{1-6}$alkyloxy, aminocarbonyl, di(C$_{1-6}$alkyl)aminoC$_{1-6}$alkylcarbonyl, amino, $C_{1-6}$alkylamino, $C_{1-6}$alkylcarbonylamino, or a radical of formula -Alk-OR$^{13}$ or -Alk-NR$^{14}$R$^{15}$;

wherein Alk is $C_{1-6}$alkanediyl;

R$^{13}$ is hydrogen, $C_{1-6}$alkyl, $C_{1-6}$alkylcarbonyl, hydroxy$C_{1-6}$alkyl, Ar$^1$ or Ar$^1$C$_{1-6}$alkyl;

R$^{14}$ is hydrogen, $C_{1-6}$alkyl, Ar$^1$ or Ar$^1$C$_{1-6}$alkyl;

R$^{15}$ is hydrogen, $C_{1-6}$alkyl, $C_{1-6}$alkylcarbonyl, Ar$^1$ or ArC$_{1-6}$alkyl;

R$^6$ is a radical of formula

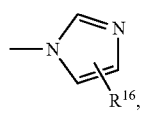 (b-1)

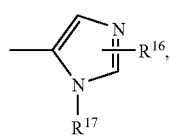 (b-2)

wherein R$^{16}$ is hydrogen, halo, Ar$^1$, $C_{1-6}$alkyl, hydroxy$C_{1-6}$alkyl, $C_{1-6}$alkyloxy$C_{1-6}$alkyl, $C_{1-6}$alkyloxy, $C_{1-6}$alkylthio, amino, $C_{1-6}$alkyloxycarbonyl, $C_{1-6}$alkylthio$C_{1-6}$alkyl, $C_{1-6}$alkylS(O)$C_{1-6}$alkyl or $C_{1-6}$alkylS(O)$_2$C$_{1-6}$alkyl;

R$^{17}$ is hydrogen, $C_{1-6}$alkyl or di($C_{1-4}$alkyl)aminosulfonyl;

R$^7$ is hydrogen or $C_{1-6}$alkyl provided that the dotted line does not represent a bond;

R$^8$ is hydrogen, $C_{1-6}$alkyl or Ar$^2$CH$_2$ or Het$^1$CH$_2$;

R$^9$ is hydrogen, $C_{1-6}$alkyl, $C_{1-6}$alkyloxy or halo; or

R$^8$ and R$^9$ taken together to form a bivalent radical of formula

—CH═CH— (c-1),

—CH$_2$—CH$_2$— (c-2),

—CH$_2$—CH$_2$—CH$_2$— (c-3),

—CH$_2$—O— (c-4), or

—CH$_2$—CH$_2$—O— (c-5);

Ar$^1$ is phenyl; or phenyl substituted with 1 or 2 substituents each independently selected from halo, $C_{1-6}$alkyl, $C_{1-6}$alkyloxy or trifluoromethyl;

Ar$^2$ is phenyl; or phenyl substituted with 1 or 2 substituents each independently selected from halo, $C_{1-6}$alkyl, $C_{1-6}$alkyloxy or trifluoromethyl; and Het$^1$ is pyridinyl; pyridinyl substituted with 1 or 2 substituents each independently selected from halo, $C_{1-6}$alkyl, $C_{1-6}$alkyloxy or trifluoromethyl.

WO-00/39082 and U.S. Pat. No. 6,458,800, which are incorporated herein in their entirety, describe the preparation, formulation and pharmaceutical properties of farnesyltransferase inhibiting compounds of formula (IX)

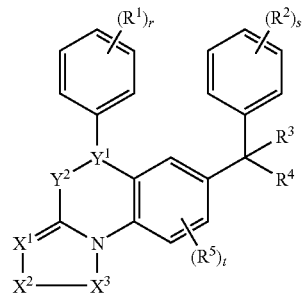 (IX)

or the pharmaceutically acceptable acid addition salts and the stereochemically isomeric forms thereof, wherein
═X$^1$—X$^2$—X$^3$- is a trivalent radical of formula

| | |
|---|---|
| ═N—CR$^6$═CR$^7$— | (x-1), |
| ═N—N═CR$^6$— | (x-2), |
| ═N—NH—C(═O)— | (x-3), |
| ═N—N═N— | (x-4), |
| ═N—CR$^6$═N— | (x-5), |
| ═CR$^6$—CR$^7$═CR$^8$— | (x-6), |
| ═CR$^6$—N═CR$^7$— | (x-7), |
| ═CR$^6$—NH—C(═O)— | (x-8), or |
| ═CR$^6$—N═N— | (x-9); | wherein each R$^6$, R$^7$ and R$^8$ are independently hydrogen, $C_{1-4}$alkyl, hydroxy, $C_{1-4}$alkyloxy, aryloxy, $C_{1-4}$alkyloxycarbonyl, hydroxy$C_{1-4}$alkyl, $C_{1-4}$alkyloxy$C_{1-4}$alkyl, mono- or di($C_{1-4}$alkyl)amino$C_{1-4}$alkyl, cyano, amino, thio, $C_{1-14}$alkylthio, arylthio or aryl;

>Y$^1$—Y$^2$- is a trivalent radical of formula

>CH—CHR$^9$— (y-1),

>C═N— (y-2),

>CH—NR$^9$— (y-3), or

>C═CR$^9$— (y-4);

wherein each R$^9$ independently is hydrogen, halo, halocarbonyl, aminocarbonyl, hydroxy$C_{1-4}$alkyl, cyano, carboxyl, $C_{1-4}$alkyl, $C_{1-4}$alkyloxy, $C_{1-4}$alkyloxy$C_{1-4}$alkyl, $C_{1-4}$alkyloxycarbonyl, mono- or di($C_{1-4}$alkyl)amino, mono- or di($C_{1-4}$alkyl)amino$C_{1-4}$alkyl, aryl;

r and s are each independently 0, 1, 2, 3, 4 or 5;

t is 0, 1, 2 or 3;

each R$^1$ and R$^2$ are independently hydroxy, halo, cyano, $C_{1-6}$alkyl, trihalomethyl, trihalomethoxy, $C_{2-6}$alkenyl, $C_{1-6}$alkyloxy, hydroxy$C_{1-6}$alkyloxy, $C_{1-6}$alkylthio, $C_{1-6}$alkyloxy$C_{1-6}$alkyloxy, $C_{1-6}$alkyloxycarbonyl, amino$C_{1-6}$alkyloxy, mono- or di($C_{1-6}$alkyl)amino, mono- or di($C_{1-6}$alkyl)amino$C_{1-6}$alkyloxy, aryl, aryl$C_{1-6}$alkyl, aryloxy or aryl$C_{1-6}$alkyloxy, hydroxycarbonyl, $C_{1-6}$alkyloxycarbonyl, aminocarbonyl, amino$C_{1-6}$alkyl, mono- or di($C_{1-6}$alkyl)aminocarbonyl, mono- or di($C_{1-6}$alkyl)amino$C_{1-6}$alkyl; or two R$^1$ or R$^2$ substituents adjacent to one another on the phenyl ring may independently form together a bivalent radical of formula —O—CH$_2$—O— (a-1), —O—CH$_2$—CH$_2$—O— (a-2), —O—CH═CH— (a-3), —O—CH$_2$—CH$_2$— (a-4), —O—CH$_2$—CH$_2$—CH$_2$— (a-5), or —CH=CH—CH=CH— (a-6);

R$^3$ is hydrogen, halo, C$_{1-6}$alkyl, cyano, haloC$_{1-6}$alkyl, hydroxyC$_{1-6}$alkyl, cyanoC$_{1-6}$alkyl, aminoC$_{1-6}$alkyl, C$_{1-6}$alkyloxyC$_{1-6}$alkyl, C$_{1-6}$alkylthioC$_{1-6}$alkyl, aminocarbonylC$_{1-6}$alkyl, hydroxycarbonyl, hydroxycarbonylC$_{1-6}$alkyl, C$_{1-6}$alkyloxycarbonylC$_{1-6}$alkyl, C$_{1-6}$alkylcarbonylC$_{1-6}$alkyl, C$_{1-6}$alkyloxycarbonyl, aryl, arylC$_{1-6}$alkyloxyC$_{1-6}$alkyl, mono- or di(C$_{1-6}$alkyl)aminoC$_{1-6}$alkyl;

or a radical of formula

—O—R$^{10}$ (b-1)

—S—R$^{10}$ (b-2),

—NR$^{11}$R$^{12}$ (b-3), wherein R$^{10}$ is hydrogen, C$_{1-6}$alkyl, C$_{1-6}$alkylcarbonyl, aryl, arylC$_{1-6}$alkyl, C$_{1-6}$alkyloxycarbonylC$_{1-6}$alkyl, or a radical of formula -Alk-OR$^{13}$ or -Alk-NR$^{14}$R$^{15}$;

R$^{11}$ is hydrogen, C$_{1-6}$alkyl, aryl or arylC$_{1-6}$alkyl;

R$^{12}$ is hydrogen, C$_{1-6}$alkyl, aryl, hydroxy, amino, C$_{1-6}$alkyloxy, C$_{1-6}$alkylcarbonylC$_{1-6}$alkyl, arylC$_{1-6}$alkyl, C$_{1-6}$alkylcarbonylamino, mono- or di(C$_{1-6}$alkyl)amino, C$_{1-6}$alkylcarbonyl, aminocarbonyl, arylcarbonyl, haloC$_{1-6}$alkylcarbonyl, arylC$_{1-6}$alkylcarbonyl, C$_{1-6}$alkyloxycarbonyl, C$_{1-6}$alkyloxyC$_{1-6}$alkylcarbonyl, mono- or di(C$_{1-6}$alkyl)aminocarbonyl wherein the alkyl moiety may optionally be substituted by one or more substituents independently selected from aryl or C$_{1-13}$alkyloxycarbonyl, aminocarbonylcarbonyl, mono- or di(C$_{1-6}$alkyl)aminoC$_{1-6}$alkylcarbonyl, or a radical of formula -Alk-OR$^{13}$ or -Alk-NR$^{14}$R$^{15}$;

wherein Alk is C$_{1-6}$alkanediyl;

R$^{13}$ is hydrogen, C$_{1-6}$alkyl, C$_{1-6}$alkylcarbonyl, hydroxyC$_{1-6}$alkyl, aryl or arylC$_{1-6}$alkyl;

R$^{14}$ is hydrogen, C$_{1-6}$alkyl, aryl or arylC$_{1-6}$alkyl;

R$^{15}$ is hydrogen, C$_{1-6}$alkyl, C$_{1-6}$alkylcarbonyl, aryl or arylC$_{1-6}$alkyl;

R$^4$ is a radical of formula

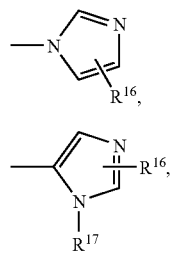

wherein R$^{16}$ is hydrogen, halo, aryl, C$_{1-6}$alkyl, hydroxyC$_{1-6}$alkyl, C$_{1-6}$alkyloxyC$_{1-6}$alkyl, C$_{1-6}$alkyloxy, C$_{1-6}$alkylthio, amino, mono- or di(C$_{1-4}$alkyl)amino, hydroxycarbonyl, C$_{1-6}$alkyloxycarbonyl, C$_{1-6}$alkylthioC$_{1-6}$alkyl, C$_{1-6}$alkylS(O)C$_{1-6}$alkyl or C$_{1-6}$alkylS(O)$_2$C$_{1-6}$alkyl;

R$^{16}$ may also be bound to one of the nitrogen atoms in the imidazole ring of formula (c-1) or (c-2), in which case the meaning of R$^{16}$ when bound to the nitrogen is limited to hydrogen, aryl, C$_{1-6}$alkyl, hydroxyC$_{1-6}$alkyl, C$_{1-6}$alkyloxyC$_{1-6}$alkyl, C$_{1-6}$alkyloxycarbonyl, C$_{1-6}$alkylS(O)C$_{1-6}$alkyl or C$_{1-6}$alkylS(O)$_2$C$_{1-6}$alkyl;

R$^{17}$ is hydrogen, C$_{1-6}$alkyl, C$_{1-6}$alkyloxyC$_{1-6}$alkyl, aryl C$_{1-6}$alkyl, trifluoromethyl or di(C$_{1-4}$alkyl)aminosulfonyl;

R$^5$ is C$_{1-6}$alkyl, C$_{1-6}$alkyloxy or halo;

aryl is phenyl, naphthalenyl or phenyl substituted with 1 or more substituents each independently selected from halo, C$_{1-6}$alkyl, C$_{1-6}$alkyloxy or trifluoromethyl.

In addition to the farnesyltransferase inhibitors of formula (I), (II), (III), (IV), (V), (VI), (VII), (VIII) or (IX) above, other farnesyltransferase inhibitors known in the art include: Argiabin (i.e. 1(R)-10-epoxy-5(S),7(S)-guaia-3(4),11(13)-dien-6,12-olide described in WO-98/28303 (NuOncology Labs); perrilyl alcohol described in WO-99/45912 (Wisconsin Genetics); SCH-66336, i.e. (+)-(R)-4-[2-[4-(3,10-dibromo-8-chloro-5,6-dihydro-11H-benzo[5,6]cyclohepta[1,2-b]pyridin-11-yl)piperidin-1-yl]-2-oxoethyl]piperidine-1-carboxamide, described in U.S. Pat. No. 5,874,442 (Schering); L778123, i.e. 1-(3-chlorophenyl)-4-[1-(4-cyanobenzyl)-5-imidazolylmethyl]-2-piperazinone, described in WO-00/01691 (Merck); compound 2(S)-[2(S)-[2(R)-amino-3-mercapto]propylamino-3(S)-methyl]-pentyloxy-3-phenylpropionyl-methionine sulfone described in WO-94/10138 (Merck); and BMS 214662, i.e. (R)-2,3,4,5-tetrahydro-1-(1H-imidazol-4-ylmethyl)-3-(phenylmethyl)-4-(2-thienylsulphonyl)-1H-1,4-benzodiazapine-7-carbonitrile, described in WO 97/30992 (Bristol Myers Squibb); and Pfizer compounds (A) and (B) described in WO-00/12498 and WO-00/12499:

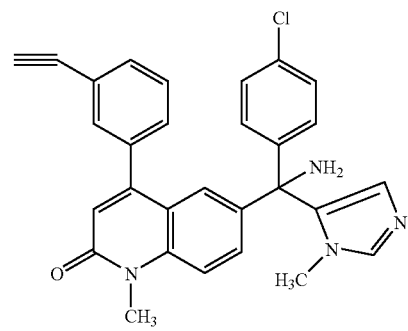

(A)

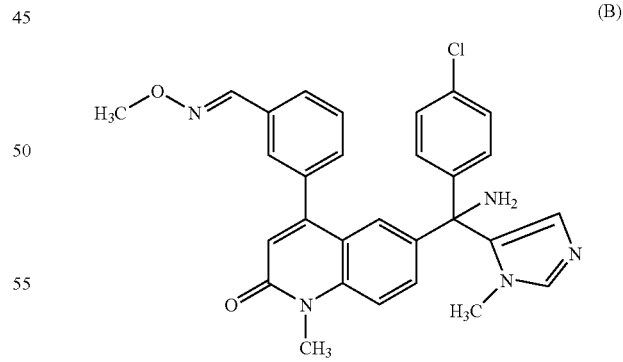

(B)

FLT3 kinase inhibitors known in the art include: AG1295 and AG1296; Lestaurtinib (also known as CEP 701, formerly KT-5555, Kyowa Hakko, licensed to Cephalon); CEP-5214 and CEP-7055 (Cephalon); CHIR-258 (Chiron Corp.); EB-10 and IMC-EB10 (ImClone Systems Inc.); GTP 14564 (Merk Biosciences UK). Midostaurin (also known as PKC 412 Novartis AG); MLN 608 (Millennium USA); MLN-518 (formerly CT53518, COR Therapeutics Inc., licensed to Millennium Pharmaceuticals Inc.); MLN-608 (Millennium Pharmaceuticals Inc.); SU-11248 (Pfizer USA); SU-11657 (Pfizer USA); SU-5416 and SU 5614; THRX-165724 (Theravance Inc.); AMI-10706 (Theravance Inc.); VX-528 and VX-680 (Vertex Pharmaceuticals USA, licensed to Novartis (Switzerland), Merck & Co USA); and XL 999 (Exelixis USA).

See also Levis, M., K. F. Tse, et al. (2001) "A FLT3 tyrosine kinase inhibitor is selectively cytotoxic to acute myeloid leukemia blasts harboring FLT3 internal tandem duplication mutations." Blood 98(3): 885-7; Tse K F, et al. (2001) Inhibition of FLT3-mediated transformation by use of a tyrosine kinase inhibitor. Leukemia. Jul.; 15(7):1001-10; Smith, B. Douglas et al. Single-agent CEP-701, a novel FLT3 inhibitor, shows biologic and clinical activity in patients with relapsed or refractory acute myeloid leukemia Blood, May 2004; 103: 3669-3676; Griswold, Ian J. et al. Effects of MLN518, A Dual FLT3 and KIT Inhibitor, on Normal and Malignant Hematopoiesis. Blood, July 2004; [Epub ahead of print]; Yee, Kevin W. H. et al. SU5416 and SU5614 inhibit kinase activity of wild-type and mutant FLT3 receptor tyrosine kinase. Blood, September 2002; 100: 2941-294; O'Farrell, Anne-Marie et al. SUI 1248 is a novel FLT3 tyrosine kinase inhibitor with potent activity in vitro and in vivo. Blood, May 2003; 101: 3597-3605; Stone, R. M. et al. PKC 412 FLT3 inhibitor therapy in AML: results of a phase II trial. Ann Hematol. 2004; 83 Suppl 1:S89-90; and Murata, K. et al. Selective cytotoxic mechanism of GTP-14564, a novel tyrosine kinase inhibitor in leukemia cells expressing a constitutively active Fms-like tyrosine kinase 3 (FLT3). J Biol. Chem. 2003 Aug. 29; 278(35):32892-8; Levis, Mark et al. Novel FLT3 tyrosine kinase inhibitors. Expert Opin. Investing. Drugs (2003) 12(12) 1951-1962; Levis, Mark et al. Small Molecule FLT3 Tyrosine Kinase Inhibitors. Current Pharmaceutical Design, 2004, 10, 1183-1193.

SUMMARY OF THE INVENTION

The present invention comprises a method of inhibiting FLT3 tyrosine kinase activity or expression or reducing FLT3 kinase activity or expression in a cell or a subject comprising the administration of a FLT3 kinase inhibitor and a farnesyl transferase inhibitor. Included within the present invention is both prophylactic and therapeutic methods for treating a subject at risk of (or susceptible to) developing a cell proliferative disorder or a disorder related to FLT3, the methods comprising generally administering to the subject a prophylactically effective amount of a FLT3 kinase inhibitor and a farnesyl transferase inhibitor. The FLT3 kinase inhibitor and farnesyl transferase inhibitor can be administered as a unitary pharmaceutical composition comprising a FLT3 kinase inhibitor, a farnesyl transferase inhibitor and a pharmaceutically acceptable carrier, or as separate pharmaceutical compositions: (1) a first pharmaceutical composition comprising a FLT3 kinase inhibitor and a pharmaceutically acceptable carrier, and (2) a second pharmaceutical composition comprising a farnesyl transferase inhibitor and a pharmaceutically acceptable carrier. The invention further encompasses a multiple component therapy for treating or inhibiting onset of a cell proliferative disorder or a disorder related to FLT3 in a subject comprising administering to the subject a therapeutically or prophylactically effective amount of a FLT3 kinase inhibitor, a farnesyl transferase inhibitor and one or more other anti-cell proliferation therapy(ies) including chemotherapy, radiation therapy, gene therapy and immunotherapy.

Other embodiments, features, advantages, and aspects of the invention will become apparent from the detailed description below in reference to the drawing figures.

DESCRIPTION OF THE DRAWINGS

FIG. 1. Effects of oral administration of compounds of the present invention on the growth of MV4-11 tumor xenografts in nude mice.

FIG. 2. Effects of oral administration of compounds of the present invention on the final weight of MV4-11 tumor xenografts in nude mice.

FIG. 3. FLT3 phosphorylation in MV4-11 tumors obtained from mice treated with compounds of the present invention.

FIG. 4. Compounds tested for inhibition of FLT3-dependent proliferation.

FIGS. 5.1-5.8. Dose responses of single agents on FLT3 dependent AML cell proliferation.

FIG. 6a-c. A low dose of a FLT3 inhibitor significantly shifts the potency of Tipifarnib in FLT3 dependent cells.

FIG. 7a-d. Single dose combinations of a FLT3 inhibitor Compound (A) and Tipifarnib or Cytarabine synergistically inhibit FLT3-dependent cell line growth.

FIG. 8a-b. Single dose combination of FLT3 inhibitor Compounds B and D with either Tipifarnib or Cytarabine synergistically inhibits MV4-11 cell growth.

FIG. 9.1. FLT3 inhibitor Compound A and Tipifarnib synergistically inhibit the proliferation of FLT3 dependent cells as measured by the method of Chou ad Talalay.

FIG. 9.2. FLT3 inhibitor Compound B and Tipifarnib synergistically inhibit the proliferation of FLT3 dependent cells as measured by the method of Chou ad Talalay.

FIG. 9.3. FLT3 inhibitor Compound C and Tipifarnib synergistically inhibit the proliferation of FLT3 dependent cells as measured by the method of Chou ad Talalay.

FIG. 9.4. FLT3 inhibitor Compound D and Tipifarnib synergistically inhibit the proliferation of FLT3 dependent cells as measured by the method of Chou ad Talalay.

FIG. 9.5. FLT3 inhibitor Compound H and Tipifarnib synergistically inhibit the proliferation of MV4-11 cells as measured by the method of Chou and Talalay.

FIG. 9.6. FLT3 inhibitor Compound E and Zarnestra synergistically inhibit the proliferation of MV4-11 cells as measured by the method of Chou and Talalay.

FIG. 9.7. FLT3 inhibitor Compound F and Tipifarnib synergistically inhibit the proliferation of FLT3 dependent MV4-11 cells as measured by the method of Chou ad Talalay.

FIG. 9.8. FLT3 inhibitor Compound G and Tipifarnib synergistically inhibit the proliferation of FLT3 dependent MV4-11 cells as measured by the method of Chou ad Talalay.

FIG. 10a-c. The combination of a FLT3 inhibitor and an FTI synergistically induces apoptosis of MV4-11 cells.

FIG. 11 a-d. Dose responses of single agent induction of caspase 3/7 activation and apoptosis of FLT3 dependent MV4-11 cells.

FIG. 12.1. FLT3 inhibitor Compound B and Tipifarnib synergistically induce the activation of caspase 3/7 in FLT3 dependent MV4-11 cells as measured by the method of Chou ad Talalay.

FIG. 12.2. FLT3 inhibitor Compound C and Tipifarnib synergistically induce the activation of caspase 3/7 in FLT3 dependent MV4-11 cells as measured by the method of Chou ad Talalay.

FIG. 12.3. FLT3 inhibitor Compound D and Tipifarnib synergistically induce the activation of caspase 3/7 in FLT3 dependent MV4-11 cells as measured by the method of Chou ad Talalay.

FIG. 13. Tipifarnib increases the potency of FLT3 inhibitor Compound A inhibition of FLT3 and MapKinase phosphorylation in MV4-11 cells.

FIG. 14. Effects over time on tumor volume of orally administered FLT3 inhibitor Compound B and Tipifarnib, alone and in combination, on the growth of MV-4-11 tumor xenografts in nude mice.

FIG. 15. Effects on tumor volume of orally administered FLT3 inhibitor Compound B and Tipifarnib alone or in combination on the growth of MV-4-11 tumor xenografts in nude mice at the terminal study day.

FIG. 16. Effects on tumor weight of orally administered FLT3 inhibitor Compound B and Tipifarnib alone or in combination on the growth of MV-4-11 tumor xenografts in nude mice at the terminal study day.

FIG. 17. Effects of oral administration of FLT3 inhibitor Compound D of the present invention on the growth of MV4-11 tumor xenografts in nude mice.

FIG. 18. Effects of oral administration of FLT3 inhibitor Compound D of the present invention on the final weight of MV4-11 tumor xenografts in nude mice.

FIG. 19. Effects of oral administration of FLT3 inhibitor Compound D of the present invention on mouse body weight.

FIG. 20. FLT3 phosphorylation in MV4-11 tumors obtained from mice treated with FLT3 inhibitor Compound D of the present invention.

FIG. 21. Effects over time on tumor volume of orally administered FLT3 inhibitor Compound D and Tipifarnib, alone and in combination, on the growth of MV-4-11 tumor xenografts in nude mice.

FIG. 22. Effects on tumor volume of orally administered FLT3 inhibitor Compound D and Tipifarnib alone or in combination on the growth of MV-4-11 tumor xenografts in nude mice.

FIG. 23. Effects of orally administered FLT3 inhibitor Compound D and Tipifarnib alone or in combination on the final weight of MV-4-11 tumor xenografts in nude mice.

DETAILED DESCRIPTION OF THE INVENTION AND PREFERRED EMBODIMENTS

The terms "comprising", "including", and "containing" are used herein in their open, non-limited sense.

The present invention comprises a method of inhibiting FLT3 tyrosine kinase activity or expression or reducing FLT3 kinase activity or expression in a cell or a subject comprising the administration of a FLT3 kinase inhibitor and a farnesyl transferase inhibitor.

An embodiment of the present invention comprises a method for reducing or inhibiting FLT3 tyrosine kinase activity in a subject comprising the administration of a FLT3 kinase inhibitor and a farnesyl transferase inhibitor to the subject.

An embodiment of the present invention comprises a method of treating disorders related to FLT3 tyrosine kinase activity or expression in a subject comprising the administration of a FLT3 kinase inhibitor and a farnesyl transferase inhibitor to the subject.

An embodiment of the present invention comprises a method for reducing or inhibiting the activity of FLT3 tyrosine kinase in a cell comprising the step of contacting the cell with a FLT3 kinase inhibitor and a farnesyl transferase inhibitor.

The present invention also provides a method for reducing or inhibiting the expression of FLT3 tyrosine kinase in a subject comprising the step of administering a FLT3 kinase inhibitor and a farnesyl transferase inhibitor to the subject.

The present invention further provides a method of inhibiting cell proliferation in a cell comprising the step of contacting the cell with a FLT3 kinase inhibitor and a farnesyl transferase inhibitor.

The kinase activity of FLT3 in a cell or a subject can be determined by procedures well known in the art, such as the FLT3 kinase assay described herein.

The term "subject" as used herein, refers to an animal, preferably a mammal, most preferably a human, who has been the object of treatment, observation or experiment.

The term "contacting" as used herein, refers to the addition of compound to cells such that compound is taken up by the cell.

In other embodiments to this aspect, the present invention provides both prophylactic and therapeutic methods for treating a subject at risk of (or susceptible to) developing a cell proliferative disorder or a disorder related to FLT3.

In one example, the invention provides methods for preventing in a subject a cell proliferative disorder or a disorder related to FLT3, comprising administering to the subject a prophylactically effective amount of (1) a first pharmaceutical composition comprising a FLT3 kinase inhibitor and a pharmaceutically acceptable carrier, and (2) a second pharmaceutical composition comprising a farnesyl transferase inhibitor and a pharmaceutically acceptable carrier.

In one example, the invention provides methods for preventing in a subject a cell proliferative disorder or a disorder related to FLT3, comprising administering to the subject a prophylactically effective amount of a pharmaceutical composition comprising a FLT3 kinase inhibitor, a farnesyl transferase inhibitor and a pharmaceutically acceptable carrier.

Administration of said prophylactic agent(s) can occur prior to the manifestation of symptoms characteristic of the cell proliferative disorder or disorder related to FLT3, such that a disease or disorder is prevented or, alternatively, delayed in its progression.

In another example, the invention pertains to methods of treating in a subject a cell proliferative disorder or a disorder related to FLT3 comprising administering to the subject a therapeutically effective amount of (1) a first pharmaceutical composition comprising a FLT3 kinase inhibitor and a pharmaceutically acceptable carrier, and (2) a second pharmaceutical composition comprising a farnesyl transferase inhibitor and a pharmaceutically acceptable carrier.

In another example, the invention pertains to methods of treating in a subject a cell proliferative disorder or a disorder related to FLT3 comprising administering to the subject a therapeutically effective amount of a pharmaceutical composition comprising a FLT3 kinase inhibitor, a farnesyl transferase inhibitor and a pharmaceutically acceptable carrier.

Administration of said therapeutic agent(s) can occur concurrently with the manifestation of symptoms characteristic of the disorder, such that said therapeutic agent serves as a therapy to compensate for the cell proliferative disorder or disorders related to FLT3.

The FLT3 kinase inhibitor and farnesyl transferase inhibitor can be administered as a unitary pharmaceutical composition comprising a FLT3 kinase inhibitor, a farnesyl transferase inhibitor and a pharmaceutically acceptable carrier, or as separate pharmaceutical compositions: (1) a first pharmaceutical composition comprising a FLT3 kinase inhibitor and a pharmaceutically acceptable carrier, and (2) a second pharmaceutical composition comprising a farnesyl transferase inhibitor and a pharmaceutically acceptable carrier. In the latter case, the two pharmaceutical compositions may be administered simultaneously (albeit in separate compositions), sequentially in either order, at approximately the same time, or on separate dosing schedules. On separate dosing schedules, the two compositions are administered within a period and in an amount and manner that is sufficient to ensure that an advantageous or synergistic effect is achieved.

It will be appreciated that the preferred method and order of administration and the respective dosage amounts and regimes for each component of the combination will depend on the agent being administered, their route of administration, the particular tumor being treated and the particular host being treated.

As will be understood by those of ordinary skill in the art, the optimum method and order of administration and the dosage amounts and regime of the FLT3 kinase inhibitor and farnesyl transferase inhibitor can be readily determined by those skilled in the art using conventional methods and in view of the information set out herein.

Generally, the dosage amounts and regime of the FLT3 kinase inhibitor and farnesyl transferase inhibitor will be similar to or less than those already employed in clinical therapies where these agents are administered alone, or in combination with other chemotherapeutics.

The term "prophylactically effective amount" refers to an amount of an active compound or pharmaceutical agent that inhibits or delays in a subject the onset of a disorder as being sought by a researcher, veterinarian, medical doctor or other clinician.

The term "therapeutically effective amount" as used herein, refers to an amount of active compound or pharmaceutical agent that elicits the biological or medicinal response in a subject that is being sought by a researcher, veterinarian, medical doctor or other clinician, which includes alleviation of the symptoms of the disease or disorder being treated.

Methods are known in the art for determining therapeutically and prophylactically effective doses for the instant pharmaceutical composition(s).

As used herein, the term "composition" is intended to encompass a product comprising the specified ingredients in the specified amounts, as well as any product which results, directly or indirectly, from combinations of the specified ingredients in the specified amounts.

As used herein, the terms "disorders related to FLT3", or "disorders related to FLT3 receptor", or "disorders related to FLT3 receptor tyrosine kinase" shall include diseases associated with or implicating FLT3 activity, for example, the overactivity of FLT3, and conditions that accompany with these diseases. The term "overactivity of FLT3" refers to either 1) FLT3 expression in cells which normally do not express FLT3; 2) FLT3 expression by cells which normally do not express FLT3; 3) increased FLT3 expression leading to unwanted cell proliferation; or 4) mutations leading to constitutive activation of FLT3. Examples of "disorders related to FLT3" include disorders resulting from over stimulation of FLT3 due to abnormally high amount of FLT3 or mutations in FLT3, or disorders resulting from abnormally high amount of FLT3 activity due to abnormally high amount of FLT3 or mutations in FLT3. It is known that overactivity of FLT3 has been implicated in the pathogenesis of a number of diseases, including the cell proliferative disorders, neoplastic disorders and cancers listed below.

The term "cell proliferative disorders" refers to unwanted cell proliferation of one or more subset of cells in a multicellular organism resulting in harm (i.e., discomfort or decreased life expectancy) to the multicellular organisms. Cell proliferative disorders can occur in different types of animals and humans. For example, as used herein "cell proliferative disorders" include neoplastic disorders and other cell proliferative disorders. As used herein, a "neoplastic disorder" refers to a tumor resulting from abnormal or uncontrolled cellular growth. Examples of neoplastic disorders include, but are not limited to, hematopoietic disorders such as, for instance, the myeloproliferative disorders, such as thrombocythemia, essential thrombocytosis (ET), angiogenic myeloid metaplasia, myelofibrosis (MF), myelofibrosis with myeloid metaplasia (MMM), chronic idiopathic myelofibrosis (IMF), polycythemia vera (PV), the cytopenias, and pre-malignant myelodysplastic syndromes; cancers such as glioma cancers, lung cancers, breast cancers, colorectal cancers, prostate cancers, gastric cancers, esophageal cancers, colon cancers, pancreatic cancers, ovarian cancers, and hematoglogical malignancies, including myelodysplasia, multiple myeloma, leukemias and lymphomas. Examples of hematological malignancies include, for instance, leukemias, lymphomas (non-Hodgkin's lymphoma), Hodgkin's disease (also called Hodgkin's lymphoma), and myeloma—for instance, acute lymphocytic leukemia (ALL), acute myeloid leukemia (AML), acute promyelocytic leukemia (APL), chronic lymphocytic leukemia (CLL), chronic myeloid leukemia (CML), chronic neutrophilic leukemia (CNL), acute undifferentiated leukemia (AUL), anaplastic large-cell lymphoma (ALCL), prolymphocytic leukemia (PML), juvenile myelomonocyctic leukemia (JMML), adult T-cell ALL, AML with trilineage myelodysplasia (AML/TMDS), mixed lineage leukemia (MLL), myelodysplastic syndromes (MDSs), myeloproliferative disorders (MPD), and multiple myeloma, (MM).

In a further embodiment to this aspect, the invention encompasses a multiple component therapy for treating or inhibiting onset of a cell proliferative disorder or a disorder related to FLT3 in a subject comprising administering to the subject a therapeutically or prophylactically effective amount of a FLT3 kinase inhibitor, a farnesyl transferase inhibitor and one or more other anti-cell proliferation therapy(ies) including chemotherapy, radiation therapy, gene therapy and immunotherapy.

As used herein, "chemotherapy" refers to a therapy involving a chemotherapeutic agent. A variety of chemotherapeutic agents may be used in the multiple component treatment methods disclosed herein. Chemotherapeutic agents contemplated as exemplary, include, but are not limited to: platinum compounds (e.g., cisplatin, carboplatin, oxaliplatin); taxane compounds (e.g., paclitaxcel, docetaxol); campotothecin compounds (irinotecan, topotecan); vinca alkaloids (e.g., vincristine, vinblastine, vinorelbine); anti-tumor nucleoside derivatives (e.g., 5-fluorouracil, leucovorin, gemcitabine, capecitabine) alkylating agents (e.g., cyclophosphamide, carmustine, lomustine, thiotepa); epipodophyllotoxins/podophyllotoxins (e.g. etoposide, teniposide); aromatase inhibitors (e.g., anastrozole, letrozole, exemestane); anti-estrogen compounds (e.g., tamoxifen, fulvestrant), antifolates (e.g., premetrexed disodium); hypomethylating agents (e.g., azacitidine); biologics (e.g., gemtuzamab, cetuximab, rituximab, pertuzumab, trastuzumab, bevacizumab, erlotinib); antibiotics/anthracyclines (e.g. idarubicin, actinomycin D, bleomycin, daunorubicin, doxorubicin, mitomycin C, dactinomycin, caminomycin, daunomycin); antimetabolites (e.g., aminopterin, clofarabine, cytosine arabinoside, methotrexate); tubulin-binding agents (e.g. combretastatin, colchicine, nocodazole); topoisomerase inhibitors (e.g., camptothecin). Further useful agents include verapamil, a calcium antagonist found to be useful in combination with antineoplastic agents to establish chemosensitivity in tumor cells resistant to accepted chemotherapeutic agents and to potentiate the efficacy of such compounds in drug-sensitive malignancies. See Simpson W G, The calcium channel blocker verapamil and cancer chemotherapy. Cell Calcium. 1985 December; 6(6):449-67.

Additionally, yet to emerge chemotherapeutic agents are contemplated as being useful in combination with the compound of the present invention.

In another embodiment of the present invention, the FLT3 kinase inhibitor and farnesyl transferase inhibitor may be administered in combination with radiation therapy. As used herein, "radiation therapy" refers to a therapy that comprises exposing the subject in need thereof to radiation. Such therapy is known to those skilled in the art. The appropriate scheme of radiation therapy will be similar to those already employed in clinical therapies wherein the radiation therapy is used alone or in combination with other chemotherapeutics.

In another embodiment of the present invention, the FLT3 kinase inhibitor and farnesyl transferase inhibitor may be administered in combination with gene therapy. As used herein, "gene therapy" refers to a therapy targeting on particular genes involved in tumor development. Possible gene therapy strategies include the restoration of defective cancer-inhibitory genes, cell transduction or transfection with antisense DNA corresponding to genes coding for growth factors and their receptors, RNA-based strategies such as ribozymes, RNA decoys, antisense messenger RNAs and small interfering RNA (siRNA) molecules and the so-called 'suicide genes'.

In other embodiments of this invention, the FLT3 kinase inhibitor and farnesyl transferase inhibitor may be administered in combination with immunotherapy. As used herein, "immunotherapy" refers to a therapy targeting particular protein involved in tumor development via antibodies specific to such protein. For example, monoclonal antibodies against vascular endothelial growth factor have been used in treating cancers.

Where one or more additional chemotherapeutic agent(s) are used in conjunction with the FLT3 kinase inhibitor and farnesyl transferase inhibitor, the additional chemotherapeutic agent(s), the FLT3 kinase inhibitor and the farnesyl transferase inhibitor may be administered simultaneously (e.g. in separate or unitary compositions) sequentially in any order, at approximately the same time, or on separate dosing schedules. In the latter case, the pharmaceuticals will be administered within a period and in an amount and manner that is sufficient to ensure that an advantageous and synergistic effect is achieved. It will be appreciated that the preferred method and order of administration and the respective dosage amounts and regimes for the additional chemotherapeutic agent(s) will depend on the particular chemotherapeutic agent(s) being administered in conjunction with the FLT3 kinase inhibitor and farnesyl transferase inhibitor, their route of administration, the particular tumor being treated and the particular host being treated. As will be understood by those of ordinary skill in the art, the appropriate doses of the additional chemotherapeutic agent(s) will be generally similar to or less than those already employed in clinical therapies wherein the chemotherapeutics are administered alone or in combination with other chemotherapeutics.

The optimum method and order of administration and the dosage amounts and regime can be readily determined by those skilled in the art using conventional methods and in view of the information set out herein.

By way of example only, platinum compounds are advantageously administered in a dosage of 1 to 500 mg per square meter ($mg/m^2$) of body surface area, for example 50 to 400 $mg/m^2$, particularly for cisplatin in a dosage of about 75 $mg/m^2$ and for carboplatin in about 30 $mg/m^2$ per course of treatment. Cisplatin is not absorbed orally and must therefore be delivered via injection intravenously, subcutaneously, intratumorally or intraperitoneally.

By way of example only, taxane compounds are advantageously administered in a dosage of 50 to 400 mg per square meter ($mg/m^2$) of body surface area, for example 75 to 250 $mg/m^2$, particularly for paclitaxel in a dosage of about 175 to 250 $mg/m^2$ and for docetaxel in about 75 to 150 $mg/m^2$ per course of treatment.

By way of example only, camptothecin compounds are advantageously administered in a dosage of 0.1 to 400 mg per square meter ($mg/m^2$) of body surface area, for example 1 to 300 $mg/m^2$, particularly for irinotecan in a dosage of about 100 to 350 $mg/m^2$ and for topotecan in about 1 to 2 $mg/m^2$ per course of treatment.

By way of example only, vinca alkaloids may be advantageously administered in a dosage of 2 to 30 mg per square meter ($mg/m^2$) of body surface area, particularly for vinblastine in a dosage of about 3 to 12 $mg/m^2$, for vincristine in a dosage of about 1 to 2 $mg/m^2$, and for vinorelbine in dosage of about 10 to 30 $mg/m^2$ per course of treatment.

By way of example only, anti-tumor nucleoside derivatives may be advantageously administered in a dosage of 200 to 2500 mg per square meter ($mg/m^2$) of body surface area, for example 700 to 1500 $mg/m^2$. 5-fluorouracil (5-FU) is commonly used via intravenous administration with doses ranging from 200 to 500 $mg/m^2$ (preferably from 3 to 15 mg/kg/day). Gemcitabine is advantageously administered in a dosage of about 800 to 1200 $mg/m^2$ and capecitabine is advantageously administered in about 1000 to 2500 $mg/m^2$ per course of treatment.

By way of example only, alkylating agents may be advantageously administered in a dosage of 100 to 500 mg per square meter ($mg/m^2$) of body surface area, for example 120 to 200 $mg/m^2$, particularly for cyclophosphamide in a dosage of about 100 to 500 $mg/m^2$, for chlorambucil in a dosage of about 0.1 to 0.2 mg/kg of body weight, for carmustine in a dosage of about 150 to 200 $mg/m^2$, and for lomustine in a dosage of about 100 to 150 $mg/m^2$ per course of treatment.

By way of example only, podophyllotoxin derivatives may be advantageously administered in a dosage of 30 to 300 mg per square meter (mg/m2) of body surface area, for example 50 to 250 $mg/m^2$, particularly for etoposide in a dosage of about 35 to 100 $mg/m^2$ and for teniposide in about 50 to 250 $mg/m^2$ per course of treatment.

By way of example only, anthracycline derivatives may be advantageously administered in a dosage of 10 to 75 mg per square meter ($mg/m^2$) of body surface area, for example 15 to 60 $mg/m^2$, particularly for doxorubicin in a dosage of about 40 to 75 $mg/m^2$, for daunorubicin in a dosage of about 25 to 45 $mg/m^2$, and for idarubicin in a dosage of about 10 to 15 $mg/m^2$ per course of treatment.

By way of example only, anti-estrogen compounds may be advantageously administered in a dosage of about 1 to 100 mg daily depending on the particular agent and the condition being treated. Tamoxifen is advantageously administered orally in a dosage of 5 to 50 mg, preferably 10 to 20 mg twice a day, continuing the therapy for sufficient time to achieve and maintain a therapeutic effect. Toremifene is advantageously administered orally in a dosage of about 60 mg once a day, continuing the therapy for sufficient time to achieve and maintain a therapeutic effect. Anastrozole is advantageously administered orally in a dosage of about 1 mg once a day. Droloxifene is advantageously administered orally in a dosage of about 20-100 mg once a day. Raloxifene is advantageously administered orally in a dosage of about 60 mg once a day. Exemestane is advantageously administered orally in a dosage of about 25 mg once a day.

By way of example only, biologics may be advantageously administered in a dosage of about 1 to 5 mg per square meter (mg/m$^2$) of body surface area, or as known in the art, if different. For example, trastuzumab is advantageously administered in a dosage of 1 to 5 mg/m$^2$ particularly 2 to 4 mg/m$^2$ per course of treatment.

Dosages may be administered, for example once, twice or more per course of treatment, which may be repeated for example every 7, 14, 21 or 28 days.

The FLT3 kinase inhibitor and farnesyl transferase inhibitor can be administered to a subject systemically, for example, intravenously, orally, subcutaneously, intramuscular, intradermal, or parenterally. The FLT3 kinase inhibitor and farnesyl transferase inhibitor can also be administered to a subject locally. Non-limiting examples of local delivery systems include the use of intraluminal medical devices that include intravascular drug delivery catheters, wires, pharmacological stents and endoluminal paving. The FLT3 kinase inhibitor and farnesyl transferase inhibitor can further be administered to a subject in combination with a targeting agent to achieve high local concentration of the FLT3 kinase inhibitor and farnesyl transferase inhibitor at the target site. In addition, the FLT3 kinase inhibitor and farnesyl transferase inhibitor may be formulated for fast-release or slow-release with the objective of maintaining the drugs or agents in contact with target tissues for a period ranging from hours to weeks.

The separate pharmaceutical compositions comprising the FLT3 kinase inhibitor in association with a pharmaceutically acceptable carrier, and the farnesyl transferase inhibitor in association with a pharmaceutically acceptable carrier may contain between about 0.1 mg and 1000 mg, preferably about 100 to 500 mg, of the individual agents compound, and may be constituted into any form suitable for the mode of administration selected.

The unitary pharmaceutical composition comprising the FLT3 kinase inhibitor and farnesyl transferase inhibitor in association with a pharmaceutically acceptable carrier may contain between about 0.1 mg and 1000 mg, preferably about 100 to 500 mg, of the compound, and may be constituted into any form suitable for the mode of administration selected.

The phrases "pharmaceutically acceptable" refer to molecular entities and compositions that do not produce an adverse, allergic or other untoward reaction when administered to an animal, or a human, as appropriate. Veterinary uses are equally included within the invention and "pharmaceutically acceptable" formulations include formulations for both clinical and/or veterinary use.

Carriers include necessary and inert pharmaceutical excipients, including, but not limited to, binders, suspending agents, lubricants, flavorants, sweeteners, preservatives, dyes, and coatings. Compositions suitable for oral administration include solid forms, such as pills, tablets, caplets, capsules (each including immediate release, timed release and sustained release formulations), granules, and powders, and liquid forms, such as solutions, syrups, elixirs, emulsions, and suspensions. Forms useful for parenteral administration include sterile solutions, emulsions and suspensions.

The pharmaceutical compositions of the present invention, whether unitary or separate, may be formulated for slow release of the FLT3 kinase inhibitor and farnesyl transferase inhibitor. Such a composition, unitary or separate, includes a slow release carrier (typically, a polymeric carrier) and one, or in the case of the unitary composition, both, of the FLT3 kinase inhibitor and farnesyl transferase inhibitor.

Slow release biodegradable carriers are well known in the art. These are materials that may form particles that capture therein an active compound(s) and slowly degrade/dissolve under a suitable environment (e.g., aqueous, acidic, basic, etc) and thereby degrade/dissolve in body fluids and release the active compound(s) therein. The particles are preferably nanoparticles (i.e., in the range of about 1 to 500 nm in diameter, preferably about 50-200 nm in diameter, and most preferably about 100 nm in diameter).

Farnesyltransferase Inhibitors

Examples of farnesyltransferase inhibitors which may be employed in the methods or treatments in accordance with the present invention include the farnesyltransferase inhibitors ("FTIs") of formula (I), (II), (III), (IV), (V), (VI), (VII), (VIII) or (IX) above.

Preferred FTIs include compounds of formula (I), (II) or (III):

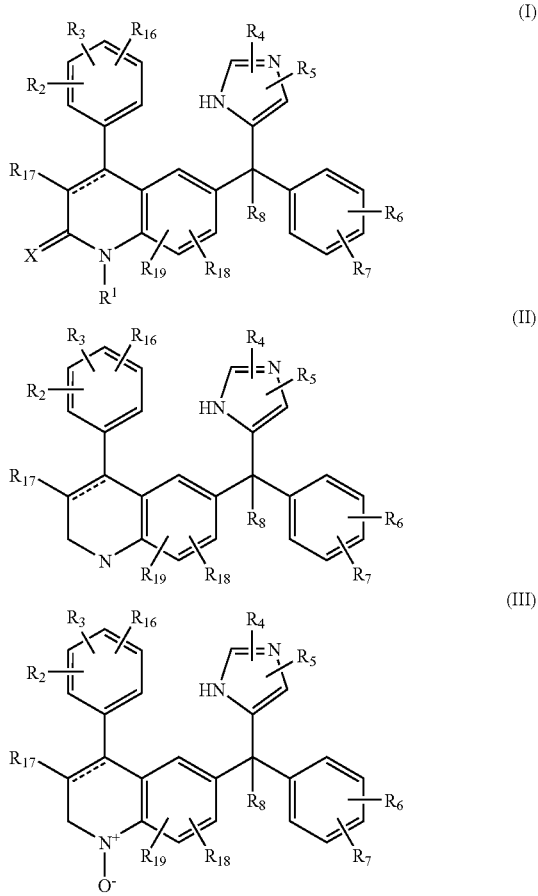

the pharmaceutically acceptable acid or base addition salts and the stereochemically isomeric forms thereof, wherein
the dotted line represents an optional bond;
X is oxygen or sulfur;
R$^1$ is hydrogen, C$_{1-12}$alkyl, Ar$^1$, Ar$^2$C$_{1-6}$alkyl, quinolinylC$_{1-6}$alkyl, pyridylC$_{1-6}$alkyl, hydroxyC$_{1-6}$alkyl, C$_{1-6}$alkyloxyC$_{1-6}$alkyl, mono- or di(C$_{1-6}$alkyl)aminoC$_{1-6}$alkyl, aminoC$_{1-6}$alkyl,
  or a radical of formula -Alk$^1$—C(=O)—R$^9$, -Alk$^1$-S(O)—R$^9$ or -Alk$^1$-S(O)$_2$—R$^9$,
    wherein Alk$^1$ is C$_{1-6}$alkanediyl,
      R$^9$ is hydroxy, C$_{1-6}$alkyl, C$_{1-6}$alkyloxy, amino, C$_{1-6}$alkylamino or C$_{1-8}$alkylamino substituted with C$_{1-6}$alkyloxycarbonyl;
R$^2$, R$^3$ and R$^{16}$ each independently are hydrogen, hydroxy, halo, cyano, C$_{1-6}$alkyl, C$_{1-6}$alkyloxy, hydroxyC$_{1-6}$alkyloxy, $C_{1-6}$alkyloxy$C_{1-6}$alkyloxy, amino$C_{1-6}$alkyloxy, mono- or di($C_{1-6}$alkyl)amino$C_{1-6}$alkyloxy, $Ar^1$, $Ar^2C_{1-6}$alkyl, $Ar^2$oxy, $Ar^2C_{1-6}$alkyloxy, hydroxycarbonyl, $C_{1-6}$alkyloxycarbonyl, trihalomethyl, trihalomethoxy, $C_{2-6}$alkenyl, 4,4-dimethyloxazolyl; or when on adjacent positions $R^2$ and $R^3$ taken together may form a bivalent radical of formula

  (a-1),

  (a-2),

  (a-3),

  (a-4),

  (a-5), or

  (a-6);

$R^4$ and $R^5$ each independently are hydrogen, halo, $Ar^1$, $C_{1-6}$alkyl, hydroxy$C_{1-6}$alkyl, $C_{1-6}$alkyloxy$C_{1-6}$alkyl, $C_{1-6}$alkyloxy, $C_{1-6}$alkylthio, amino, hydroxycarbonyl, $C_{1-6}$alkyloxycarbonyl, $C_{1-6}$alkylS(O)$C_{1-6}$alkyl or $C_{1-6}$alkylS(O)$_2C_{1-6}$alkyl;

$R^6$ and $R^7$ each independently are hydrogen, halo, cyano, $C_{1-6}$alkyl, $C_{1-6}$alkyloxy, $Ar^2$oxy, trihalomethyl, $C_{1-6}$alkylthio, di($C_{1-6}$alkyl)amino, or when on adjacent positions $R^6$ and $R^7$ taken together may form a bivalent radical of formula

  (c-1), or

  (c-2);

$R^8$ is hydrogen, $C_{1-6}$alkyl, cyano, hydroxycarbonyl, $C_{1-6}$alkyloxycarbonyl, $C_{1-6}$alkylcarbonyl$C_{1-6}$alkyl, cyano$C_{1-6}$alkyl, $C_{1-6}$alkyloxycarbonyl$C_{1-6}$alkyl, carboxy$C_{1-6}$alkyl, hydroxy$C_{1-6}$alkyl, amino$C_{1-6}$alkyl, mono- or di($C_{1-6}$alkyl)amino$C_{1-6}$alkyl, imidazolyl, halo$C_{1-6}$alkyl, $C_{1-6}$alkyloxy$C_{1-6}$alkyl, aminocarbonyl$C_{1-6}$alkyl, or a radical of formula

  (b-1),

  (b-2),

  (b-3), wherein $R^{10}$ is hydrogen, $C_{1-6}$alkyl, $C_{1-6}$alkylcarbonyl, $Ar^1$, $Ar^2C_{1-6}$alkyl, $C_{1-6}$alkyloxycarbonyl$C_{1-6}$alkyl, or a radical of formula -Alk$^2$-OR$^{13}$ or -Alk$^2$-NR$^{14}$R$^{15}$;

$R^{11}$ is hydrogen, $C_{1-12}$alkyl, $Ar^1$ or $Ar^2C_{1-6}$alkyl;

$R^{12}$ is hydrogen, $C_{1-6}$alkyl, $C_{1-16}$alkylcarbonyl, $C_{1-6}$alkyloxycarbonyl, $C_{1-6}$alkylaminocarbonyl, $Ar^1$, $Ar^2C_{1-6}$alkyl, $C_{1-6}$alkylcarbonyl$C_{1-6}$alkyl, a natural amino acid, $Ar^1$carbonyl, $Ar^2C_{1-6}$alkylcarbonyl, aminocarbonylcarbonyl, $C_{1-6}$alkyloxy$C_{1-6}$alkylcarbonyl, hydroxy, $C_{1-6}$alkyloxy, aminocarbonyl, di($C_{1-6}$alkyl)amino$C_{1-6}$alkylcarbonyl, amino, $C_{1-6}$alkylamino, $C_{1-6}$alkylcarbonylamino, or a radical of formula -Alk$^2$-OR$^{13}$ or -Alk$^2$-NR$^{14}$R$^{15}$;

wherein Alk$^2$ is $C_{1-6}$alkanediyl;

$R^{13}$ is hydrogen, $C_{1-6}$alkyl, $C_{1-6}$alkylcarbonyl, hydroxy$C_{1-6}$alkyl, $Ar^1$ or $Ar^2C_{1-6}$alkyl;

$R^{14}$ is hydrogen, $C_{1-6}$alkyl, $Ar^1$ or $Ar^2C_{1-6}$alkyl;

$R^{15}$ is hydrogen, $C_{1-6}$alkyl, $C_{1-6}$alkylcarbonyl, $Ar^1$ or $Ar^2C_{1-6}$alkyl;

$R^{17}$ is hydrogen, halo, cyano, $C_{1-6}$alkyl, $C_{1-6}$alkyloxycarbonyl, $Ar^1$;

$R^{18}$ is hydrogen, $C_{1-6}$alkyl, $C_{1-6}$alkyloxy or halo;

$R^{19}$ is hydrogen or $C_{1-6}$alkyl;

$Ar^1$ is phenyl or phenyl substituted with $C_{1-6}$alkyl, hydroxy, amino, $C_{1-6}$alkyloxy or halo; and $Ar^2$ is phenyl or phenyl substituted with $C_{1-6}$alkyl, hydroxy, amino, $C_{1-6}$alkyloxy or halo.

In Formulas (I), (II) and (III), $R^4$ or $R^5$ may also be bound to one of the nitrogen atoms in the imidazole ring. In that case the hydrogen on the nitrogen is replaced by $R^4$ or $R^5$ and the meaning of $R^4$ and $R^5$ when bound to the nitrogen is limited to hydrogen, $Ar^1$, $C_{1-6}$alkyl, hydroxy$C_{1-6}$alkyl, $C_{1-6}$alkyloxy$C_{1-6}$alkyl, $C_{1-6}$alkyloxycarbonyl, $C_{1-6}$alkylS(O)$C_{1-6}$alkyl, $C_{1-6}$alkylS(O)$_2C_{1-6}$alkyl.

Preferably the substituent $R^{18}$ in Formulas (I), (II) and (III) is situated on the 5 or 7 position of the quinolinone moiety and substituent $R^{19}$ is situated on the 8 position when $R^{18}$ is on the 7-position.

Preferred examples of FTIs are those compounds of formula (I) wherein X is oxygen.

Also, examples of preferred FTIs are those compounds of formula (I) wherein the dotted line represents a bond, so as to form a double bond.

Another group of preferred FTIs are those compounds of formula (I) wherein $R^1$ is hydrogen, $C_{1-6}$alkyl, $C_{1-6}$alkyloxy$C_{1-6}$alkyl, di($C_{1-6}$alkyl)amino$C_{1-6}$alkyl, or a radical of formula -Alk$^1$—C(=O)—R$^9$, wherein Alk$^1$ is methylene and $R^9$ is $C_{1-8}$alkylamino substituted with $C_{1-6}$alkyloxycarbonyl.

Still another group of preferred FTIs are those compounds of formula (I) wherein $R^3$ is hydrogen or halo; and $R^2$ is halo, $C_{1-6}$alkyl, $C_{2-6}$alkenyl, $C_{1-6}$alkyloxy, trihalomethoxy or hydroxy$C_{1-6}$alkyloxy.

A further group of preferred FTIs are those compounds of formula (I) wherein $R^2$ and $R^3$ are on adjacent positions and taken together to form a bivalent radical of formula (a-1), (a-2) or (a-3).

A still further group of preferred FTIs are those compounds of formula (I) wherein $R^5$ is hydrogen and $R^4$ is hydrogen or $C_{1-6}$alkyl.

Yet another group of preferred FTIs are those compounds of formula (I) wherein $R^7$ is hydrogen; and $R^6$ is $C_{1-6}$alkyl or halo, preferably chloro, especially 4-chloro.

Another exemplary group of preferred FTIs are those compounds of formula (I) wherein $R^8$ is hydrogen, hydroxy, halo$C_{1-6}$alkyl, hydroxy$C_{1-6}$alkyl, cyano$C_{1-6}$alkyl, $C_{1-6}$alkyloxycarbonyl$C_{1-6}$alkyl, imidazolyl, or a radical of formula —NR$^{11}$R$^{12}$ wherein $R^{11}$ is hydrogen or $C_{1-12}$alkyl and $R^{12}$ is hydrogen, $C_{1-6}$alkyl, $C_{1-6}$alkyloxy, hydroxy, $C_{1-6}$alkyloxy$C_{1-6}$alkylcarbonyl, or a radical of formula -Alk$^2$-OR$^{13}$ wherein $R^{13}$ is hydrogen or $C_{1-6}$alkyl.

Preferred compounds are also those compounds of formula (I) wherein $R^1$ is hydrogen, $C_{1-6}$alkyl, $C_{1-6}$alkyloxy$C_{1-6}$alkyl, di($C_{1-6}$alkyl)amino$C_{1-6}$alkyl, or a radical of formula -Alk$^1$—C(=O)—R$^9$, wherein Alk$^1$ is methylene and $R^9$ is $C_{1-8}$alkylamino substituted with $C_{1-6}$alkyloxycarbonyl; $R^2$ is halo, $C_{1-6}$alkyl, $C_{2-6}$alkenyl, $C_{1-6}$alkyloxy, trihalomethoxy, hydroxy$C_{1-6}$alkyloxy or $Ar^1$; $R^3$ is hydrogen; $R^4$ is methyl bound to the nitrogen in 3-position of the imidazole; $R^5$ is hydrogen; $R^6$ is chloro; $R^7$ is hydrogen; $R^8$ is hydrogen, hydroxy, halo$C_{1-6}$alkyl, hydroxy$C_{1-6}$alkyl, cyano$C_{1-6}$alkyl, $C_{1-6}$alkyloxycarbonyl$C_{1-6}$alkyl, imidazolyl, or a radical of formula —NR$^{11}$R$^{12}$ wherein $R^{11}$ is hydrogen or $C_{1-12}$alkyl and $R^{12}$ is hydrogen, $C_{1-6}$alkyl, $C_{1-6}$alkyloxy, $C_{1-6}$alkyloxy$C_{1-6}$alkylcarbonyl, or a radical of formula -Alk$^2$-OR$^{13}$ wherein $R^{13}$ is $C_{1-6}$alkyl; $R^{17}$ is hydrogen and $R^{18}$ is hydrogen.

Especially preferred FTIs are:
4-(3-chlorophenyl)-6-[(4-chlorophenyl)hydroxy(1-methyl-1H-imidazol-5-yl)methyl]-1-methyl-2(1H)-quinolinone;

6-[amino(4-chlorophenyl)-1-methyl-1H-imidazol-5-ylmethyl]-4-(3-chlorophenyl)-1-methyl-2(1H)-quinolinone;
6-[(4-chlorophenyl)hydroxy(1-methyl-1H-imidazol-5-yl)methyl]-4-(3-ethoxyphenyl)-1-methyl-2(1H)-quinolinone;
6-[(4-chlorophenyl)(1-methyl-1H-imidazol-5-yl)methyl]-4-(3-ethoxyphenyl)-1-methyl-2(1H)-quinolinone monohydrochloride.monohydrate;
6-[amino(4-chlorophenyl)(1-methyl-1H-imidazol-5-yl)methyl]-4-(3-ethoxyphenyl)-1-methyl-2(1H)-quinolinone;
6-amino(4-chlorophenyl)(1-methyl-1H-imidazol-5-yl)methyl]-1-methyl-4-(3-propylphenyl)-2(1H)-quinolinone; a stereoisomeric form thereof or a pharmaceutically acceptable acid or base addition salt; and
(+)-6-[amino(4-chlorophenyl)(1-methyl-1H-imidazol-5-yl)methyl]-4-(3-chlorophenyl)-1-methyl-2(1H)-quinolinone (tipifarnib; Compound 75 in Table 1 of WO 97/21701); and the pharmaceutically acceptable acid addition salts and the stereochemically isomeric forms thereof.

Tipifarnib or ZARNESTRA® is an especially preferred FTI.

Further preferred FTIs include compounds of formula (IX) wherein one or more of the following apply:
=$X^1$—$X^2$—$X^3$ is a trivalent radical of formula (x-1), (x-2), (x-3), (x-4) or (x-9) wherein each $R^6$ independently is hydrogen, $C_{1-4}$alkyl, $C_{1-4}$alkyloxycarbonyl, amino or aryl and $R^7$ is hydrogen;
>$Y^1$—$Y^2$ is a trivalent radical of formula (y-1), (y-2), (y-3), or (y-4) wherein each $R^9$ independently is hydrogen, halo, carboxyl, $C_{1-4}$alkyl or $C_{1-4}$alkyloxycarbonyl;
r is 0, 1 or 2;
s is 0 or 1;
t is 0;
$R^1$ is halo, $C_{1-6}$alkyl or two $R^1$ substituents ortho to one another on the phenyl ring may independently form together a bivalent radical of formula (a-1);
$R^2$ is halo;
$R^3$ is halo or a radical of formula (b-1) or (b-3) wherein $R^{10}$ is hydrogen or a radical of formula -Alk-$OR^{13}$.
$R^{11}$ is hydrogen;
$R^{12}$ is hydrogen, $C_{1-6}$alkyl, $C_{1-6}$alkylcarbonyl, hydroxy, $C_{1-6}$alkyloxy or mono- or di($C_{1-6}$alkyl)amino$C_{1-6}$alkylcarbonyl;
Alk is $C_{1-6}$alkanediyl and $R^{13}$ is hydrogen;
$R^4$ is a radical of formula (c-1) or (c-2) wherein
$R^{16}$ is hydrogen, halo or mono- or di($C_{1-4}$alkyl)amino;
$R^{17}$ is hydrogen or $C_{1-6}$alkyl;
aryl is phenyl.

Another group of preferred FTIs are compounds of formula (IX) wherein =$X^1$—$X^2$—$X^3$ is a trivalent radical of formula (x-1), (x-2), (x-3), (x-4) or (x-9), >$Y1$—$Y2$ is a trivalent radical of formula (y-2), (y-3) or (y-4), r is 0 or 1, s is 1, t is 0, $R^1$ is halo, $C_{(1-4)}$alkyl or forms a bivalent radical of formula (a-1), $R^2$ is halo or $C_{1-4}$alkyl, $R^3$ is hydrogen or a radical of formula (b-1) or (b-3), $R^4$ is a radical of formula (c-1) or (c-2), $R^6$ is hydrogen, $C_{1-4}$alkyl or phenyl, $R^7$ is hydrogen, $R^9$ is hydrogen or $C_{1-4}$alkyl, $R^{10}$ is hydrogen or -Alk-$OR^{13}$, $R^{11}$ is hydrogen and $R^{12}$ is hydrogen or $C_{1-6}$alkylcarbonyl and $R^{13}$ is hydrogen;

Preferred FTIs are those compounds of formula (IX) wherein =$X^1$—$X^2$—$X^3$ is a trivalent radical of formula (x-1) or (x-4), >$Y1$—$Y2$ is a trivalent radical of formula (y-4), r is 0 or 1, s is 1, t is 0, $R^1$ is halo, preferably chloro and most preferably 3-chloro, $R^2$ is halo, preferably 4-chloro or 4-fluoro, $R^3$ is hydrogen or a radical of formula (b-1) or (b-3), $R^4$ is a radical of formula (c-1) or (c-2), $R^6$ is hydrogen, $R^7$ is hydrogen, $R^9$ is hydrogen, $R^{10}$ is hydrogen, $R^{11}$ is hydrogen and $R^{12}$ is hydrogen.

Other preferred FTIs are those compounds of formula (IX) wherein =$X^1$—$X^2$—$X^3$ is a trivalent radical of formula (x-2), (x-3) or (x-4), >$Y1$—$Y2$ is a trivalent radical of formula (y-2), (y-3) or (y-4), r and s are 1, t is 0, $R^1$ is halo, preferably chloro, and most preferably 3-chloro or $R^1$ is $C_{1-4}$alkyl, preferably 3-methyl, $R^2$ is halo, preferably chloro, and most preferably 4-chloro, $R^3$ is a radical of formula (b-1) or (b-3), $R^4$ is a radical of formula (c-2), $R^6$ is $C_{1-4}$alkyl, $R^9$ is hydrogen, $R^{10}$ and $R^{11}$ are hydrogen and $R^{12}$ is hydrogen or hydroxy.

Especially preferred FTI compounds of formula (IX) are:
7-[(4-fluorophenyl)(1H-imidazol-1-yl)methyl]-5-phenylimidazo[1,2-a]quinoline;
α-(4-chlorophenyl)-α-(1-methyl-1H-imidazol-5-yl)-5-phenylimidazo[1,2-a]quinoline-7-methanol;
5-(3-chlorophenyl)-α-(4-chlorophenyl)-α-(1-methyl-1H-imidazol-5-yl)-imidazo[1,2-a]quinoline-7-methanol;
5-(3-chlorophenyl)-α-(4-chlorophenyl)-α-(1-methyl-1H-imidazol-5-yl)imidazo[1,2-a]quinoline-7-methanamine;
5-(3-chlorophenyl)-α-(4-chlorophenyl)-α-(1-methyl-1H-imidazol-5-yl)tetrazolo[1,5-a]quinoline-7-methanamine;
5-(3-chlorophenyl)-α-(4-chlorophenyl)-1-methyl-α-(1-methyl-1H-imidazol-5-yl)-1,2,4-triazolo[4,3-a]quinoline-7-methanol;
5-(3-chlorophenyl)-α-(4-chlorophenyl)-α-(1-methyl-1H-imidazol-5-yl)tetrazolo[1,5-a]quinoline-7-methanamine;
5-(3-chlorophenyl)-α-(4-chlorophenyl)-α-(1-methyl-1H-imidazol-5-yl)tetrazolo[1,5-a]quinazoline-7-methanol;
5-(3-chlorophenyl)-α-(4-chlorophenyl)-4,5-dihydro-α-(1-methyl-1H-imidazol-5-yl)tetrazolo[1,5-a]quinazoline-7-methanol;
5-(3-chlorophenyl)-α-(4-chlorophenyl)-α-(1-methyl-1H-imidazol-5-yl)tetrazolo[1,5-a]quinazoline-7-methanamine;
5-(3-chlorophenyl)-α-(4-chlorophenyl)-N-hydroxy-α-(1-methyl-1H-imidazol-5-yl)tetrahydro[1,5-a]quinoline-7-methanamine; and
α-(4-chlorophenyl)-α-(1-methyl-1H-imidazol-5-yl)-5-(3-methylphenyl)tetrazolo[1,5-a]quinoline-7-methanamine; and the pharmaceutically acceptable acid addition salts and the stereochemically isomeric forms thereof.

5-(3-chlorophenyl)-α-(4-chlorophenyl)-α-(1-methyl-1H-imidazol-5-yl)tetrazolo[1,5-a]quinazoline-7-methanamine, especially the (−) enantiomer, and its pharmaceutically acceptable acid addition salts is an especially preferred FTI.

The pharmaceutically acceptable acid or base addition salts as mentioned hereinabove are meant to comprise the therapeutically active non-toxic acid and non-toxic base addition salt forms which the FTI compounds of formulas (I), (II), (III), (IV), (V), (VI), (VII), (VIII) or (IX) are able to form. The FTI compounds of formulas (I), (II), (III), (IV), (V), (VI), (VII), (VIII) or (IX) which have basic properties can be converted in their pharmaceutically acceptable acid addition salts by treating the base form with an appropriate acid. Appropriate acids include, for example, inorganic acids such as hydrohalic acids, e.g. hydrochloric or hydrobromic acid; sulfuric; nitric; phosphoric and the like acids; or organic acids, such as acetic, propanoic, hydroxyacetic, lactic, pyruvic, oxalic, malonic, succinic (i.e. butanedioic acid), maleic, fumaric, malic, tartaric, citric, methanesulfonic, ethanesulfonic, benzenesulfonic, p-toluenesulfonic, cyclamic, salicylic, p-aminosalicylic, pamoic and the like acids.

The FTI compounds of formulae (I), (II), (III), (IV), (V), (VI), (VII), (VIII) or (IX) which have acidic properties may be converted in their pharmaceutically acceptable base addition salts by treating the acid form with a suitable organic or inorganic base. Appropriate base salt forms comprise, for example, the ammonium salts, the alkali and earth alkaline metal salts, e.g. the lithium, sodium, potassium, magnesium, calcium salts and the like, salts with organic bases, e.g. the benzathine, N-methyl-D-glucamine, hydrabamine salts, and salts with amino acids, for example, arginine, lysine and the like.

Acid and base addition salts also comprise the hydrates and the solvent addition forms which the preferred FTI compounds of formulae (I), (II), (III), (IV), (V), (VI), (VII), (VIII) or (IX) are able to form. Examples of such forms are e.g. hydrates, alcoholates and the like.

The FTI compounds of formulae (I), (II), (III), (IV), (V), (VI), (VII), (VIII) or (IX), as used hereinbefore, encompass all stereochemically isomeric forms of the depicted structural formulae (all possible compounds made up of the same atoms bonded by the same sequence of bonds but having different three-dimensional structures that are not interchangeable). Unless otherwise mentioned or indicated, the chemical designation of an FTI compound should be understood as encompassing the mixture of all possible stereochemically isomeric forms which the compound may possess. Such mixture may contain all diastereomers and/or enantiomers of the basic molecular structure of the compound. All stereochemically isomeric forms of the FTI compounds of formulae (I), (II), (III), (IV), (V), (VI), (VII), (VIII) or (IX) both in pure form or in admixture with each other are intended to be embraced within the scope of the depicted formulae.

Some of the FTI compounds of formulae (I), (II), (III), (IV), (V), (VI), (VII), (VIII) or (IX) may also exist in their tautomeric forms. Such forms, although not explicitly shown in the above formulae, are intended to be included within the scope thereof.

Thus, unless indicated otherwise hereinafter, the terms "compounds of formulae (I), (II), (III), (IV), (V), (VI), (VII), (VIII) or (IX)" and "farnesyltransferase inhibitors of formulae (I), (II), (III), (IV), (V), (VI), (VII), (VIII) or (IX)" are meant to include also the pharmaceutically acceptable acid or base addition salts and all stereoisomeric and tautomeric forms.

Other farnesyltransferase inhibitors which can be employed in accordance with the present invention include: Arglabin, perrilyl alcohol, SCH-66336, 2(S)-[2(S)-[2(R)-amino-3-mercapto]propylamino-3 (S)-methyl]-pentyloxy-3-phenylpropionyl-methionine sulfone (Merck); L778123, BMS 214662, Pfizer compounds A and B described above. Suitable dosages or therapeutically effective amounts for the compounds Arglabin (WO98/28303), perrilyl alcohol (WO 99/45712), SCH-66336 (U.S. Pat. No. 5,874,442), L778123 (WO 00/01691), 2(S)-[2(S)-[2(R)-amino-3-mercapto]propylamino-3(S)-methyl]-pentyloxy-3-phenylpropionyl-methionine sulfone (WO94/10138), BMS 214662 (WO 97/30992), Pfizer compounds A and B (WO 00/12499 and WO 00/12498) are given in the published patent specifications or are known to or can be readily determined by a person skilled in the art.

FLT3 Kinase Inhibitors

The FLT3 kinase inhibitors of the present invention comprise compounds of Formula I':

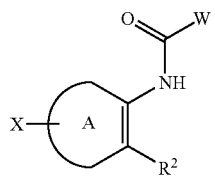

I or a solvate, hydrate, tautomer or pharmaceutically acceptable salt thereof, wherein:

A is
  phenyl or pyridyl, either of which may be substituted with one of chloro, fluoro, methyl, —$N_3$, —$NH_2$, —NH (alkyl), —N(alkyl)$_2$, —S(alkyl), —O(alkyl), or 4-aminophenyl;

W is
  pyrrolyl (including 1H-pyrrol-2-yl), imidazolyl, (including 1H-imidazol-2-yl), isoxazolyl, oxazolyl, 1,2,4 triazolyl, or furanyl (including furan-2-yl), any of which may be connected through any carbon atom, wherein the pyrrolyl, imidazolyl, isoxazolyl, oxazolyl, 1,2,4 triazolyl, or furanyl may contain one —Cl, —CN, —$NO_2$, —OMe, or —$CF_3$ substitution, connected to any other carbon;

$R^2$ is
  cycloalkyl (including cyclohexenyl, cyclopentenyl), thiophenyl, dihydrosulfonopyranyl, phenyl, furanyl, tetrahydropyridyl, or dihydropyranyl, any of which may be independently substituted with one or two of each of the following: chloro, fluoro, and $C_{(1-3)}$alkyl (including 4,4-dimethyl cyclohexenyl, 4-methyl cyclohexenyl, 2-methyl thiophenyl, 3-methyl thiophenyl), with the proviso that tetrahydropyridyl is connected to the ring A through a carbon-carbon bond;

X is

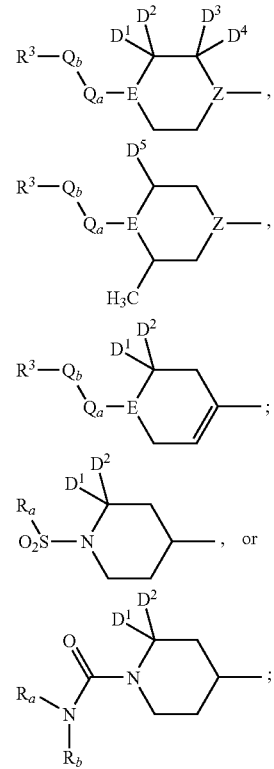

Z is
  CH or N;
$D^1$ and $D^2$ are
  each hydrogen or taken together form a double bond to an oxygen;
$D^3$ and $D^4$ are
  each hydrogen or taken together form a double bond to an oxygen;
$D^5$ is
  hydrogen or —$CH_3$, wherein said —$CH_3$ may be relatively oriented syn or anti;
$R_a$ and $R_b$ are independently
hydrogen, cycloalkyl, haloalkyl, aryl, aralkyl, heteroaryl, or heteroaralkyl;

E is
    N, S, O, SO or $SO_2$, with the proviso that E may not be N if the following three conditions are simultaneously met: $Q_a$ is absent, $Q_b$ is absent, and $R^3$ is an amino group or cyclic amino radical wherein the point of attachment to E is N;
$Q_a$ is
    absent, —$CH_2$—, —$CH_2CH_2$—, or C(O);
$Q_b$ is
    absent, —NH—, —$CH_2$—, —$CH_2CH_2$—, or C(O), with the proviso that $Q_b$ may not be C(O) if $Q_a$ is C(O), and further provided that $Q_b$ may not be —NH— if E is N and $Q_a$ is absent, further provided that $Q_b$ may not be —NH— if $R^3$ is an amino group or cyclic amino radical wherein the point of attachment to $Q_b$ is N;
$R^3$ is
    hydrogen, phenyl, hydroxyalkylamino (including 2-hydroxy ethylamino), (hydroxyalkyl)$_2$-amino, hydroxyalkyl(alkyl)amino (including 1-hydroxyeth-2-yl(methyl)amino), alkylamino (including methylamino), aminoalkyl (including 2-amino isopropyl), dihydroxyalkyl (including 1,3-dihydroxy isopropyl, 1,2-dihydroxy ethyl), alkoxy (including methoxy), dialkylamino (including dimethylamino), hydroxyalkyl (including 1-hydroxyeth-2-yl), —COOH, —$CONH_2$, —CN, —$SO_2$-alkyl-$R^4$ (including —$SO_2CH_3$), —$NH_2$, or a 5 or six membered ring which contains at least one heteroatom N and may optionally contain an additional heteromoiety selected from S, $SO_2$, N, and O, and the 5 or 6 membered ring may be saturated, partially unsaturated or aromatic (including piperidinyl, morpholinyl, imidazolyl, and pyridyl) wherein aromatic nitrogen in the 5 or 6 membered ring may be present as N-oxide (including pyridyl N-oxide), and the 5 or 6 membered ring may be optionally substituted with methyl, halogen, alkylamino, or alkoxy (including 1 methyl imidazolyl);
    $R^3$ may also be absent, with the proviso that $R^3$ is not absent when E is nitrogen;
$R^4$ is
    hydrogen, —OH, alkoxy, carboxy, carboxamido, or carbamoyl.

As used hereafter, the term "compounds of Formula I'" is meant to include also the solvates, hydrates, tautomers and pharmaceutically acceptable salts thereof.

Embodiments of FLT3 Inhibitors of Formula I'

Embodiments of the FLT3 inhibitors of the present invention include compounds of Formula I' wherein:
a) A is
    phenyl or pyridyl, either of which may be substituted with one of chloro, fluoro, methyl, —$N_3$, —$NH_2$, —NH(alkyl), —N(alkyl)$_2$, —S(alkyl), —O(alkyl), or 4-aminophenyl;
b) A is
    phenyl;
c) W is
    pyrrolyl (including 1H-pyrrol-2-yl), imidazolyl, (including 1H-imidazol-2-yl), isoxazolyl, oxazolyl, 1,2,4 triazolyl, or furanyl (including furan-2-yl), any of which may be connected through any carbon atom, wherein the pyrrolyl, imidazolyl, isoxazolyl, oxazolyl, 1,2,4 triazolyl, or furanyl may contain one —Cl, —CN, —$NO_2$, —OMe, or —$CF_3$ substitution, connected to any other carbon;
d) W is
    furan-2-yl, 1H-pyrrol-2-yl, or 1H-imidazol-2-yl, any of which may be substituted at the 4 or 5 carbons with —CN;
e) W is
    3H-2-imidazolyl-4-carbonitrile or 5-cyano-1H-pyrrol-2-yl;
f) W is
    3H-2-imidazolyl-4-carbonitrile;
g) $R^2$ is
    cycloalkyl (including cyclohexenyl, cyclopentenyl), thiophenyl, dihydrosulfonopyranyl, phenyl, furanyl, tetrahydropyridyl, or dihydropyranyl, any of which may be independently substituted with one or two of each of the following: chloro, fluoro, and $C_{(1-3)}$alkyl (including 4,4-dimethyl cyclohexenyl, 4-methyl cyclohexenyl, 2-methyl thiophenyl, 3-methyl thiophenyl), with the proviso that tetrahydropyridyl is connected to the ring A through a carbon-carbon bond;
h) $R^2$ is
    cycloalkyl (including cyclohexenyl, cyclopentenyl), which may substituted with one or two $C_{(1-3)}$alkyl (including 4,4-dimethyl cyclohexenyl, 4-methyl cyclohexenyl);
i) $R^2$ is
    cyclohexenyl, which may substituted with one or two $C_{(1-3)}$ alkyl:
j) $R^2$ is
    cyclohexenyl, 4,4-dimethyl cyclohexenyl, or 4-methyl cyclohexenyl;
k) $R^2$ is
    cyclohexenyl;
l) X is

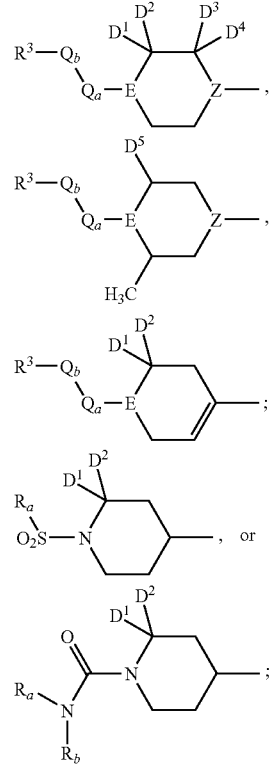

m) X is

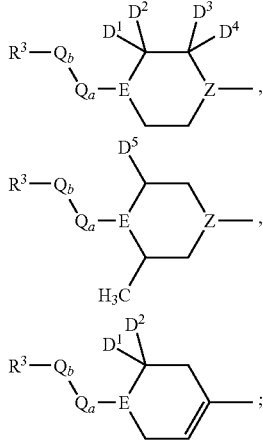

n) X is

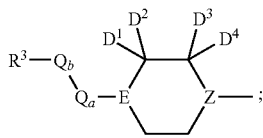

o) Z is
CH or N;
p) Z is
CH;
q) $D^1$ and $D^2$ are
each hydrogen or taken together form a double bond to an oxygen;
r) $D^1$ and $D^2$ are
each hydrogen;
s) $D^3$ and $D^4$ are
each hydrogen or taken together form a double bond to an oxygen;
t) $D^3$ and $D^4$ are
each hydrogen;
u) $D^5$ is
hydrogen or —$CH_3$, wherein said —$CH_3$ may be relatively oriented syn or anti;
v) $R_a$ and $R_b$ are independently
hydrogen, cycloalkyl, haloalkyl, aryl, aralkyl, heteroaryl, or heteroaralkyl;
w) E is
N, S, O, SO or $SO_2$, with the proviso that E may not be N if the following three conditions are simultaneously met: $Q_a$ is absent, $Q_b$ is absent, and $R^3$ is an amino group or cyclic amino radical wherein the point of attachment to E is N;
x) E is
N, with the proviso that E may not be N if the following three conditions are simultaneously met: $Q_a$ is absent, $Q_b$ is absent, and $R^3$ is an amino group or cyclic amino radical wherein the point of attachment to E is N;
y) $Q_a$ is
absent, —$CH_2$—, —$CH_2CH_2$—, or C(O);
z) $Q_a$ is
absent, —$CH_2CH_2$—, or C(O);
aa) $Q_a$ is
absent, or C(O);
bb) $Q_a$ is
C(O);
cc) $Q_b$ is
absent, —NH—, —$CH_2$—, —$CH_2CH_2$—, or C(O), with the proviso that $Q_b$ may not be C(O) if $Q_a$ is C(O), and further provided that $Q_b$ may not be —NH— if E is N and $Q_a$ is absent, further provided that $Q_b$ may not be —NH— if $R^3$ is an amino group or cyclic amino radical wherein the point of attachment to $Q_b$ is N;
dd) $Q_b$ is
absent, —$CH_2CH_2$—, or C(O), with the proviso that $Q_b$ may not be C(O) if $Q_a$ is C(O);
ee) $Q_b$ is
absent, or C(O), with the proviso that $Q_b$ may not be C(O) if $Q_a$ is C(O);
ff) $R^3$ is
hydrogen, phenyl, hydroxyalkylamino (including 2-hydroxy ethylamino), (hydroxyalkyl)$_2$amino, hydroxyalkyl(alkyl)amino (including 1-hydroxyeth-2-yl(methyl)amino), alkylamino (including methylamino), aminoalkyl (including 2-amino isopropyl), dihydroxyalkyl (including 1,3-dihydroxy isopropyl, 1,2-dihydroxy ethyl), alkoxy (including methoxy), dialkylamino (including dimethylamino), hydroxyalkyl (including 1-hydroxyeth-2-yl), —COOH, —$CONH_2$, —CN, —$SO_2$-alkyl-$R^4$ (including —$SO_2CH_3$), —$NH_2$, or a 5 or six membered ring which contains at least one heteroatom N and may optionally contain an additional heteromoiety selected from S, $SO_2$, N, and O, and the 5 or 6 membered ring may be saturated, partially unsaturated or aromatic (including piperidinyl, morpholinyl, imidazolyl, and pyridyl) wherein aromatic nitrogen in the 5 or 6 membered ring may be present as N-oxide (including pyridyl N-oxide), and the 5 or 6 membered ring may be optionally substituted with methyl, halogen, alkylamino, or alkoxy (including 1 methyl imidazolyl); $R^3$ may also be absent, with the proviso that $R^3$ is not absent when E is nitrogen;
gg) $R^3$ is
hydrogen, phenyl, 2-hydroxy ethylamino, 1-hydroxyeth-2-yl(methyl)amino, methylamino, 2-amino isopropyl, 1,3-dihydroxy isopropyl, 1,2-dihydroxy ethyl, methoxy, dimethylamino, 1-hydroxyeth-2-yl, —COOH, —$CONH_2$, —CN, —$SO_2$—, —$SO_2CH_3$), —$NH_2$, piperidinyl, morpholinyl, imidazolyl, pyridyl, pyridyl N-oxide), or 1 methyl imidazolyl;
hh) $R^3$ is
alkylamino (including methylamino), dialkylamino (including dimethylamino), or —$SO_2$-alkyl-$R^4$ (including —$SO_2CH_3$);
ii) $R^3$ is
methylamino, dimethylamino, or —$SO_2CH_3$;
jj) $R^3$ is
dimethylamino;
kk) $R^4$ is
hydrogen, —OH, alkoxy, carboxy, carboxamido, or carbamoyl; and
ll) $R^4$ is
hydrogen;
and all combinations of a) to ll), inclusive, herein above.

Preferred FLT3 inhibitors of the present invention include compounds of Formula I' wherein W is substituted with one —CN.

Other preferred FLT3 inhibitors of the present invention include compounds of Formula I' wherein:

A is
  pyridyl, which may be substituted with one of chloro, fluoro, methyl, —$N_3$, —$NH_2$, —NH(alkyl), —N(alkyl)$_2$, —S(alkyl), —O(alkyl), or 4-aminophenyl;
W is
  imidazolyl, (including 1H-imidazol-2-yl), which may contain one —CN; and
$R^2$ is
  cycloalkyl.

Still other preferred FLT3 inhibitor compounds of Formula I' are those wherein:

A is
  phenyl which may be substituted with one of chloro, fluoro, or methyl;
X is

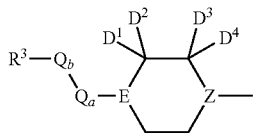

and is attached to the phenyl A ring para to the nitrogen substituent, as depicted in formula II;

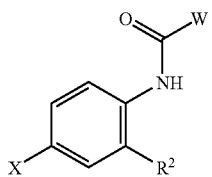

$D^3$ and $D^4$ are hydrogen;
E is
  N or $SO_2$, with the proviso that E may not be N if the following three conditions are simultaneously met: $Q_a$ is absent, $Q_b$ is absent, and $R^3$ is an amino group or cyclic amino radical wherein the point of attachment to E is N; and
$R^3$ is
  hydrogen, piperidinyl, alkylamino, dialkylamino, hydroxyalkylamino, (hydroxyalkyl)$_2$amino, imidazolyl, 1-methyl imidazolyl, pyridyl, pyridyl N-oxide, hydroxyalkyl, —COOH, —$CONH_2$, —CN, —$SO_2CH_3$, —$NH_2$, morpholinyl; $R^3$ may also be absent, with the proviso that $R^3$ is not absent when E is nitrogen.

More preferred FLT3 inhibitor compounds of Formula I' are those wherein:

A is
  phenyl;
W is
  furan-2-yl, 1H-pyrrol-2-yl, or 1H-imidazol-2-yl, any of which may be substituted at the 4 or 5 carbons with —CN; and
$R^2$ is
  cycloalkyl, dihydrosulfonopyranyl, phenyl, furanyl, tetrahydropyridyl, or dihydropyranyl, any of which may be independently substituted with one or two of each of the substituents selected from the group consisting of chloro, fluoro, and $C_{(1-3)}$alkyl, with the proviso that tetrahydropyridyl must be connected to the ring A through a carbon-carbon bond.

Even more preferred FLT3 inhibitor compounds of Formula I' are those wherein:

W is
  3H-2-imidazolyl-4-carbonitrile or 5-cyano-1H-pyrrol-2-yl;
$R^2$ is
  cyclohexenyl, or cyclopentenyl, either of which may be substituted with chloro, fluoro or one two $C_{(1-3)}$alkyl groups;
E is
  N, with the proviso that E may not be N if the following three conditions are simultaneously met: $Q_a$ is absent, $Q_b$ is absent, and $R^3$ is an amino group or cyclic amino radical wherein the point of attachment to E is N; and
Z is CH.

Especially preferred FLT3 inhibitor compounds of Formula I' are those wherein:

W is imidazolyl, (including 1H-imidazol-2-yl), 1,2,4 triazolyl, or furanyl (including furan-2-yl), any of which may be connected through any carbon atom, wherein the imidazolyl, 1,2,4 triazolyl, or furanyl may contain one —Cl or —CN, connected to any other carbon;
$R^2$ is
  cycloalkyl (including $C_{(1-3)}$alkyl substituted cycloalkyl, further including $C_{(1-3)}$alkyl substituted cyclopentenyl, and $C_{(1-3)}$alkyl substituted cyclohexenyl, further including 4-methyl cyclohexenyl), $C_{(1-3)}$dialkyl substituted cycloalkyl (including 4,4-dimethyl cyclohexenyl), thiophenyl (including $C_{(1-3)}$alkyl substituted thiophenyl, further including 2-methyl thiophenyl and 3-methyl thiophenyl), $C_{(1-3)}$alkyl substituted phenyl (including methyl phenyl), dihydropyranyl, and 1,1-dioxo-tetrahydrothiopyranyl;
X is

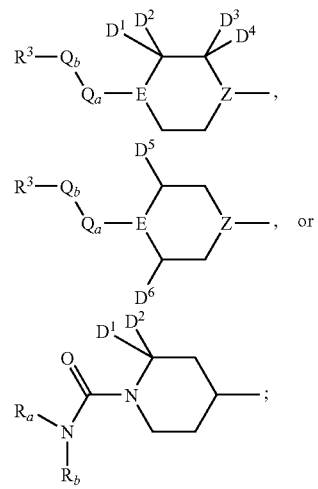

E is
  N or $SO_2$, with the proviso that E may not be N if the following three conditions are simultaneously met: $Q_a$ is absent, $Q_b$ is absent, and $R^3$ is an amino group or cyclic amino radical wherein the point of attachment to E is N; and R³ is
hydrogen, phenyl, hydroxyalkylamino (including 2-hydroxy ethylamino), hydroxyalkyl(alkyl)amino (including 1-hydroxyeth-2-yl(methyl)amino, alkylamino (including methylamino), aminoalkyl (including 2-amino isopropyl), dihydroxyalkyl (including 1,3-dihydroxy isopropyl, 1,2-dihydroxy ethyl), alkoxy (including methoxy), dialkylamino (including dimethylamino), hydroxyalkyl (including 1-hydroxyeth-2-yl), —COOH, —CONH₂, —CN, —SO₂CH₃, —NH₂, or a 5 or six membered ring selected from the group consisting of: piperidinyl, morpholinyl, imidazolyl, and pyridyl, wherein the 5 or 6 membered ring may be optionally substituted with methyl, halogen, alkylamino, or alkoxy (including 1 methyl imidazolyl), R³ may also be absent, with the proviso that R³ is not absent when E is nitrogen.

Most preferred FLT3 inhibitor compounds of Formula I' are those wherein:

W is
3H-2-imidazolyl-4-carbonitrile;

$Q_a$ is CO; and

R³ is
hydrogen, piperidinyl, hydroxyalkylamino, (hydroxyalkyl)₂amino, alkylamino, dialkylamino, imidazolyl, 1-methyl imidazolyl, pyridyl, pyridyl N-oxide, hydroxyalkyl, —COOH, —CONH₂, —CN, —SO₂CH₃, —NH₂, morpholinyl.

Examples of FLT3 inhibitor compounds of Formula I' include:

5-cyano-furan-2-carboxylic acid [4-(4-methyl-piperazin-1-yl)-2-(3-methyl-thiophen-2-yl)-phenyl]-amide, and 5-cyano-furan-2-carboxylic acid [4-(4-methyl-piperazin-1-yl)-2-(2-methyl-thiophen-3-yl)-phenyl]-amide, and solvates, hydrates, tautomers and pharmaceutically acceptable salts thereof.

Additional examples of FLT3 inhibitor compounds of Formula I' include:

4-cyano-1H-imidazole-2-carboxylic acid [4-(1-acetyl-piperidin-4-yl)-2-(1,2,5,6-tetrahydro-pyridin-3-yl)-phenyl]-amide, 4-cyano-1H-imidazole-2-carboxylic acid [2-cyclohex-1-enyl-4-(1,1-dioxo-hexahydro-1λ⁶-thiopyran-4-yl)-phenyl]-amide, 5-cyano-furan-2-carboxylic acid [2-cyclohex-1-enyl-4-(4-methyl-piperazin-1-yl)-phenyl]-amide, 5-cyano-furan-2-carboxylic acid [2-(3,6-dihydro-2H-pyran-4-yl)-4-(4-methyl-piperazin-1-yl)-phenyl]-amide, 4-cyano-1H-imidazole-2-carboxylic acid [2-(1,1-dioxo-1,2,3,6-tetrahydro-1λ⁶-thiopyran-4-yl)-4-piperidin-4-yl-phenyl]-amide, 4-cyano-1H-imidazole-2-carboxylic acid [4-(1-acetyl-piperidin-4-yl)-2-(1,1-dioxo-1,2,3,6-tetrahydro-1λ⁶-thiopyran-4-yl)-phenyl]-amide, 5-cyano-furan-2-carboxylic acid [2'-methyl-5-(4-methyl-piperazin-1-yl)-biphenyl-2-yl]-amide, and 5-cyano-furan-2-carboxylic acid [2'-fluoro-5-(4-methyl-piperazin-1-yl)-biphenyl-2-yl]-amide, and solvates, hydrates, tautomers and pharmaceutically acceptable salts thereof.

Further examples of FLT3 inhibitor compounds of Formula I' are:

(4-{4-[(4-cyano-1H-imidazole-2-carbonyl)-amino]-3-cyclohex-1-enyl-phenyl}-piperidin-1-yl)-acetic acid, 4-cyano-1H-imidazole-2-carboxylic acid [4-(1-carbamoylmethyl-piperidin-4-yl)-2-cyclohex-1-enyl-phenyl]-amide, 4-cyano-1H-imidazole-2-carboxylic acid [2-(4-methyl-cyclohex-1-enyl)-4-piperidin-4-yl-phenyl]-amide, 4-cyano-1H-imidazole-2-carboxylic acid {2-cyclohex-1-enyl-4-[1-(2-hydroxy-ethyl)-piperidin-4-yl]-phenyl}-amide, 4-cyano-1H-imidazole-2-carboxylic acid [2-(4-methyl-cyclohex-1-enyl)-4-(1-pyridin-2-ylmethyl-piperidin-4-yl)-phenyl]-amide, 4-cyano-1H-imidazole-2-carboxylic acid {2-cyclohex-1-enyl-4-[1-(2-hydroxy-1-hydroxymethyl-ethyl)-piperidin-4-yl]-phenyl}-amide, 4-cyano-1H-imidazole-2-carboxylic acid {4-[1-(2-cyano-ethyl)-piperidin-4-yl]-2-cyclohex-1-enyl-phenyl}-amide, 4-cyano-1H-imidazole-2-carboxylic acid {2-cyclohex-1-enyl-4-[1-(2-morpholin-4-yl-ethyl)-piperidin-4-yl]-phenyl}-amide, 4-cyano-1H-imidazole-2-carboxylic acid (2-cyclohex-1-enyl-4-piperidin-4-yl-phenyl)-amide, 4-cyano-1H-imidazole-2-carboxylic acid {2-cyclohex-1-enyl-4-[1-(2-methanesulfonyl-ethyl)-piperidin-4-yl]-phenyl}-amide, 4-cyano-1H-imidazole-2-carboxylic acid [2-cyclohex-1-enyl-4-(1-pyridin-2-ylmethyl-piperidin-4-yl)-phenyl]-amide, 4-cyano-1H-imidazole-2-carboxylic acid {2-cyclopent-1-enyl-4-[1-(1-methyl-1H-imidazol-2-ylmethyl)-piperidin-4-yl]-phenyl}-amide, 4-cyano-1H-imidazole-2-carboxylic acid (2-cyclopent-1-enyl-4-piperidin-4-yl-phenyl)-amide, 4-cyano-1H-pyrrole-2-carboxylic acid (2-cyclohex-1-enyl-4-piperidin-4-yl-phenyl)-amide, 4-cyano-1H-imidazole-2-carboxylic acid [2-cyclohex-1-enyl-4-(3,4,5,6-tetrahydro-2H-[1,2']bipyridinyl-4-yl)-phenyl]-amide, and 4-cyano-1H-pyrrole-2-carboxylic acid [4-(1-acetyl-piperidin-4-yl)-2-cyclohex-1-enyl-phenyl]-amide, and solvates, hydrates, tautomers and pharmaceutically acceptable salts thereof.

Other examples of FLT3 inhibitor compounds of Formula I' are:

4-cyano-1H-imidazole-2-carboxylic acid {2-cyclohex-1-enyl-4-[1-(1-oxy-pyridine-3-carbonyl)-piperidin-4-yl]-phenyl}-amide, 4-cyano-1H-imidazole-2-carboxylic acid {2-cyclohex-1-enyl-4-[1-(1-oxy-pyridine-4-carbonyl)-piperidin-4-yl]-phenyl}-amide, 4-cyano-1H-imidazole-2-carboxylic acid {2-cyclohex-1-enyl-4-[1-(3-morpholin-4-yl-propionyl)-piperidin-4-yl]-phenyl}-amide, 4-{4-[(4-cyano-1H-imidazole-2-carbonyl)-amino]-3-cyclohex-1-enyl-phenyl}-piperidine-1-carboxylic acid amide, 4-cyano-1H-imidazole-2-carboxylic acid {2-cyclohex-1-enyl-4-[1-(pyridine-3-carbonyl)-piperidin-4-yl]-phenyl}-amide, 4-{4-[(4-cyano-1H-imidazole-2-carbonyl)-amino]-3-cyclohex-1-enyl-phenyl}-piperidine-1-carboxylic acid (2-hydroxy-ethyl)-amide, 4-cyano-1H-imidazole-2-carboxylic acid {2-cyclohex-1-enyl-4-[1-(2-3H-imidazol-4-yl-acetyl)-piperidin-4-yl]-phenyl}-amide, 4-cyano-1H-imidazole-2-carboxylic acid {2-cyclohex-1-enyl-4-[1-(2-pyridin-4-yl-acetyl)-piperidin-4-yl]-phenyl}-amide, 4-cyano-1H-imidazole-2-carboxylic acid (2-cyclohex-1-enyl-4-{1-[2-(1-methyl-1H-imidazol-4-yl)-acetyl]-piperidin-4-yl}-phenyl)-amide, 4-cyano-1H-imidazole-2-carboxylic acid {2-cyclohex-1-enyl-4-[1-(2-pyridin-3-yl-acetyl)-piperidin-4-yl]-phenyl}-amide,
4-cyano-1H-imidazole-2-carboxylic acid {2-cyclohex-1-enyl-4-[1-(2-methanesulfonyl-acetyl)-piperidin-4-yl]-phenyl}-amide,
4-cyano-1H-imidazole-2-carboxylic acid {2-cyclohex-1-enyl-4-[1-(2-pyridin-2-yl-acetyl)-piperidin-4-yl]-phenyl}-amide, and
4-cyano-1H-imidazole-2-carboxylic acid [4-(1-acetyl-piperidin-4-yl)-2-cyclohex-1-enyl-phenyl]-amide,
and solvates, hydrates, tautomers and pharmaceutically acceptable salts thereof.

Another example FLT3 inhibitor compound of Formula I' is:
4-cyano-1H-imidazole-2-carboxylic acid [2-cyclohex-1-enyl-4-(1-{2-[(2-hydroxy-ethyl)-methyl-amino]-acetyl}-piperidin-4-yl)-phenyl]-amide,
and solvates, hydrates, tautomers and pharmaceutically acceptable salts thereof.

Another FLT3 inhibitor compound of Formula I' is:
4-cyano-1H-imidazole-2-carboxylic acid {2-cyclohex-1-enyl-4-[1-(2-dimethylamino-acetyl)-piperidin-4-yl]-phenyl}-amide,
and solvates, hydrates, tautomers and pharmaceutically acceptable salts thereof.

Another FLT3 inhibitor compound of Formula I' is:
4-cyano-1H-imidazole-2-carboxylic acid {2-cyclohex-1-enyl-4-[1-(2-morpholin-4-yl-acetyl)-piperidin-4-yl]-phenyl}-amide,
and solvates, hydrates, tautomers and pharmaceutically acceptable salts thereof.

Still other FLT3 inhibitor compounds of Formula I' are:
4-Cyano-1H-imidazole-2-carboxylic acid {4-[1-(3-amino-3-methyl-butyryl)-piperidin-4-yl]-2-cyclohex-1-enyl-phenyl}-amide trifluoroacetic acid salt,
4H-[1,2,4]-triazole-3-carboxylic acid (2-cyclohex-1-enyl-4-piperidin-4-yl-phenyl)-amide bis trifluoroacetic acid salt,
5-Chloro-4H-[1,2,4]-triazole-3-carboxylic acid (2-cyclohex-1-enyl-4-piperidin-4-yl-phenyl)-amide trifluoroacetic acid salt,
5-Cyano-1H-imidazole-2-carboxylic acid [2-cyclohex-1-enyl-4-(cis-2,6-dimethyl-piperidin-4-yl)-phenyl]-amide bis trifluoroacetic acid salt,
5-cyano-1H-imidazole-2-carboxylic acid [2-cyclohex-1-enyl-4-(trans-2,6-dimethyl-piperidin-4-yl)-phenyl]-amide bis trifluoroacetic acid salt,
5-Cyano-1H-imidazole-2-carboxylic acid {2-cyclohex-1-enyl-4-[1-(R)-(+)-(2,3-dihydroxy-propionyl)-piperidin-4-yl]-phenyl}-amide,
5-Cyano-1H-imidazole-2-carboxylic acid [2-cyclohex-1-enyl-4-(1-methoxy-piperidin-4-yl)-phenyl]-amide trifluoroacetic acid salt,
4-Cyano-1H-imidazole-2-carboxylic acid [6-(4,4-dimethyl-cyclohex-1-enyl)-1',2',3',4',5',6'-hexahydro-[2,4']bipyridinyl-5-yl]-amide trifluoroacetic acid salt,
5-Cyano-1H-imidazole-2-carboxylic acid {4-[1-(2-amino-2-methyl-propionyl)-piperidin-4-yl]-2-cyclohex-1-enyl-phenyl}-amide trifluoroacetic acid salt, and
5-Cyano-1H-imidazole-2-carboxylic acid [6-cyclohex-1-enyl-1'-(2-methanesulfonyl-ethyl)-1',2',3',4',5',6'-hexahydro-[2,4']bipyridinyl-5-yl]-amide,
and solvates, hydrates, tautomers and pharmaceutically acceptable salts thereof.

Additional FLT3 inhibitor compound of Formula I'are:
4-Cyano-1H-imidazole-2-carboxylic acid {2-cyclohex-1-enyl-4-[1-(2-methylamino-acetyl)-piperidin-4-yl]-phenyl}-amide,
4-Cyano-1H-imidazole-2-carboxylic acid [1'-(2-dimethylamino-acetyl)-6-(4,4-dimethyl-cyclohex-1-enyl)-1',2',3',4',5',6'-hexahydro-[2,4']bipyridinyl-5-yl]-amide trifluoroacetic acid salt, and
4-Cyano-1H-imidazole-2-carboxylic acid [6-(4,4-dimethyl-cyclohex-1-enyl)-1'-(2-methanesulfonyl-ethyl)-1',2',3',4',5',6'-hexhydro-[2,4']bipyridinyl-5-yl]-amide trifluoroacetic acid salt,
and solvates, hydrates, tautomers and pharmaceutically acceptable salts thereof.

Definitions & Abbreviations
As used in regards to the FLT3 inhibitors of Formula I' only, the following terms are intended to have the following meanings:
ATP adenosine triphosphate
Boc or BOC tert-butoxycarbonyl
DCM dichloromethane
DMF dimethylformamide
DMSO dimethylsulfoxide
DIEA diisopropylethylamine
EDCI 1-(3-dimethylaminopropyl)-3-ethylcarbodiimide hydrochloride
EDTA ethylenediaminetetraaceticacid
EtOAc ethyl acetate
FBS fetal bovine serum
FP fluorescence polarization
GM-CSF granulocyte and macrophage colony stimulating factor
HOBT or HOBt 1-hydroxybenzotriazole hydrate
HPβCD hydroxypropyl β-cyclodextrin
HRP horse radish peroxidase
LC/MS (ESI) Liquid chromatography/mass spectrum (electrospray ionization)
MeOH Methyl alcohol
NMR nuclear magnetic resonance
PBS phosphatebufferedsaline
RPMI Rosewell Park Memorial Institute
RT room temperature
RTK receptor tyrosine kinase
SDS-PAGE sodium dodecyl sulfate polyacrylamide gel electrophoresis
TFA trifluoroacetic acid
THF tetrahydrofuran
TLC thin layer chromatography
(Additional Abbreviations are Provided where Needed Throughout the Specification.)
Definitions
The term "alkyl" refers to both linear and branched chain radicals of up to 12 carbon atoms, preferably up to 6 carbon atoms, unless otherwise indicated, and includes, but is not limited to, methyl, ethyl, propyl, isopropyl, butyl, isobutyl, sec-butyl, tert-butyl, pentyl, isopentyl, hexyl, isohexyl, heptyl, octyl, 2,2,4-trimethylpentyl, nonyl, decyl, undecyl and dodecyl.

The term "hydroxyalkyl" refers to both linear and branched chain radicals of up to 6 carbon atoms, in which one hydrogen atom has been replaced with an OH group.

The term "hydroxyalkylamino" refers to an hydroxyalkyl group in which one hydrogen atom from the carbon chain has been replaced with an amino group, wherein the nitrogen is the point of attachment to the rest of the molecule.

The term "cycloalkyl" refers to a saturated or partially unsaturated ring composed of from 3 to 8 carbon atoms. Up to four alkyl substituents may optionally be present on the ring. Examples include cyclopropyl, 1,1-dimethyl cyclobutyl, 1,2,3-trimethylcyclopentyl, cyclohexyl, cyclopentenyl, cyclohexenyl, and 4,4-dimethyl cyclohexenyl.

The term "dihydrosulfonopyranyl" refers to the following radical:

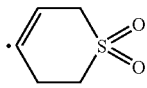

The term "hydroxyalkyl" refers to at least one hydroxyl group bonded to any carbon atom along an alkyl chain.

The term "aminoalkyl" refers to at least one primary or secondary amino group bonded to any carbon atom along an alkyl chain, wherein an alkyl group is the point of attachment to the rest of the molecule.

The term "alkylamino" refers to an amino with one alkyl substituent, wherein the amino group is the point of attachment to the rest of the molecule.

The term "dialkylamino" refers to an amino with two alkyl substituents, wherein the amino group is the point of attachment to the rest of the molecule.

The term "heteroaromatic" or "heteroaryl" refers to 5- to 7-membered mono- or 8- to 10-membered bicyclic aromatic ring systems, any ring of which may consist of from one to four heteroatoms selected from N, O or S where the nitrogen and sulfur atoms can exist in any allowed oxidation state. Examples include benzimidazolyl, benzothiazolyl, benzothienyl, benzoxazolyl, furyl, imidazolyl, isothiazolyl, isoxazolyl, oxazolyl, pyrazinyl, pyrazolyl, pyridyl, pyrimidinyl, pyrrolyl, quinolinyl, thiazolyl and thienyl.

The term "heteroatom" refers to a nitrogen atom, an oxygen atom or a sulfur atom wherein the nitrogen and sulfur atoms can exist in any allowed oxidation states.

The term "alkoxy" refers to straight or branched chain radicals of up to 12 carbon atoms, unless otherwise indicated, bonded to an oxygen atom. Examples include methoxy, ethoxy, propoxy, isopropoxy and butoxy.

The term "aryl" refers to monocyclic or bicyclic aromatic ring systems containing from 6 to 12 carbons in the ring. Alkyl substituents may optionally be present on the ring. Examples include benzene, biphenyl and napththalene.

The term "aralkyl" refers to a $C_{1-6}$ alkyl group containing an aryl substituent. Examples include benzyl, phenylethyl or 2-naphthylmethyl.

The term "sulfonyl" refers to the group —$S(O)_2R_a$, where $R_a$ is hydrogen, alkyl, cycloalkyl, haloalkyl, aryl, aralkyl, heteroaryl and heteroaralkyl. A "sulfonylating agent" adds the —$S(O)_2R_a$ group to a molecule.

The FLT3 inhibitors of Formula I' may also be present in the form of pharmaceutically acceptable salts.

For use in medicines, the salts of the compounds of the FLT3 inhibitors of Formula I' refer to non-toxic "pharmaceutically acceptable salts." FDA approved pharmaceutically acceptable salt forms (Ref. International J. Pharm. 1986, 33, 201-217; J. Pharm. Sci., 1977, January, 66(1), p 1) include pharmaceutically acceptable acidic/anionic or basic/cationic salts.

Pharmaceutically acceptable acidic/anionic salts include, and are not limited to acetate, benzenesulfonate, benzoate, bicarbonate, bitartrate, bromide, calcium edetate, camsylate, carbonate, chloride, citrate, dihydrochloride, edetate, edisylate, estolate, esylate, fumarate, glyceptate, gluconate, glutamate, glycollylarsanilate, hexylresorcinate, hydrabamine, hydrobromide, hydrochloride, hydroxynaphthoate, iodide, isethionate, lactate, lactobionate, malate, maleate, mandelate, mesylate, methylbromide, methylnitrate, methylsulfate, mucate, napsylate, nitrate, pamoate, pantothenate, phosphate/diphosphate, polygalacturonate, salicylate, stearate, subacetate, succinate, sulfate, tannate, tartrate, teoclate, tosylate and triethiodide. Organic or inorganic acids also include, and are not limited to, hydriodic, perchloric, sulfuric, phosphoric, propionic, glycolic, methanesulfonic, hydroxyethanesulfonic, oxalic, 2-naphthalenesulfonic, p-toluenesulfonic, cyclohexanesulfamic, saccharinic or trifluoroacetic acid.

Pharmaceutically acceptable basic/cationic salts include, and are not limited to aluminum, 2-amino-2-hydroxymethylpropane-1,3-diol (also known as tris(hydroxymethyl)aminomethane, tromethane or "TRIS"), ammonia, benzathine, t-butylamine, calcium, calcium gluconate, calcium hydroxide, chloroprocaine, choline, choline bicarbonate, choline chloride, cyclohexylamine, diethanolamine, ethylenediamine, lithium, LiOMe, L-lysine, magnesium, meglumine, $NH_3$, $NH_4OH$, N-methyl-D-glucamine, piperidine, potassium, potassium-t-butoxide, potassium hydroxide (aqueous), procaine, quinine, sodium, sodium carbonate, sodium-2-ethylhexanoate (SEH), sodium hydroxide, triethanolamine (TEA) or zinc.

The FLT3 inhibitors of the present invention includes within its scope prodrugs of the compounds of Formula I'. In general, such prodrugs will be functional derivatives of the compounds which are readily convertible in vivo into an active compound. Thus, in the methods of treatment of the present invention, the term "administering" shall encompass the means for treating, ameliorating or preventing a syndrome, disorder or disease described herein with a compound specifically disclosed or a compound, or prodrug thereof, which would obviously be included within the scope of the invention albeit not specifically disclosed for certain of the instant compounds. Conventional procedures for the selection and preparation of suitable prodrug derivatives are described in, for example, "Design of Prodrugs", ed. H. Bundgaard, Elsevier, 1985.

One skilled in the art will recognize that the FLT3 inhibitors of Formula I' may have one or more asymmetric carbon atoms in their structure. It is intended that the present invention include within its scope single enantiomer forms of the compounds, racemic mixtures, and mixtures of enantiomers in which an enantiomeric excess is present.

The term "single enantiomer" as used herein defines all the possible homochiral forms which the compounds of Formula I' and their N-oxides, addition salts, quaternary amines or physiologically functional derivatives may possess.

Stereochemically pure isomeric forms may be obtained by the application of art known principles. Diastereoisomers may be separated by physical separation methods such as fractional crystallization and chromatographic techniques, and enantiomers may be separated from each other by the selective crystallization of the diastereomeric salts with optically active acids or bases or by chiral chromatography. Pure stereoisomers may also be prepared synthetically from appropriate stereochemically pure starting materials, or by using stereoselective reactions.

The term "isomer" refers to compounds that have the same composition and molecular weight but differ in physical and/or chemical properties. Such substances have the same number and kind of atoms but differ in structure. The structural difference may be in constitution (geometric isomers) or in an ability to rotate the plane of polarized light (enantiomers).

The term "stereoisomer" refers to isomers of identical constitution that differ in the arrangement of their atoms in space. Enantiomers and diastereomers are examples of stereoisomers.

The term "chiral" refers to the structural characteristic of a molecule that makes it impossible to superimpose it on its mirror image.

The term "enantiomer" refers to one of a pair of molecular species that are mirror images of each other and are not superimposable.

The term "diastereomer" refers to stereoisomers that are not mirror images.

The symbols "R" and "S" represent the configuration of substituents around a chiral carbon atom(s).

The term "racemate" or "racemic mixture" refers to a composition composed of equimolar quantities of two enantiomeric species, wherein the composition is devoid of optical activity.

The term "homochiral" refers to a state of enantiomeric purity.

The term "optical activity" refers to the degree to which a homochiral molecule or nonracemic mixture of chiral molecules rotates a plane of polarized light.

The term "geometric isomer" refers to isomers that differ in the orientation of substituent atoms in relationship to a carbon-carbon double bond, to a cycloalkyl ring or to a bridged bicyclic system. Substituent atoms (other than H) on each side of a carbon-carbon double bond may be in an E or Z configuration. In the "E" (opposite sided) configuration, the substituents are on opposite sides in relationship to the carbon-carbon double bond; in the "Z" (same sided) configuration, the substituents are oriented on the same side in relationship to the carbon-carbon double bond. Substituent atoms (other than hydrogen) attached to a carbocyclic ring may be in a cis or trans configuration. In the "cis" configuration, the substituents are on the same side in relationship to the plane of the ring; in the "trans" configuration, the substituents are on opposite sides in relationship to the plane of the ring. Compounds having a mixture of "cis" and "trans" species are designated "cis/trans".

It is to be understood that the various substituent stereoisomers, geometric isomers and mixtures thereof used to prepare compounds of the present invention are either commercially available, can be prepared synthetically from commercially available starting materials or can be prepared as isomeric mixtures and then obtained as resolved isomers using techniques well-known to those of ordinary skill in the art.

The isomeric descriptors "R," "S," "E," "Z," "cis," and "trans" are used as described herein for indicating atom configuration(s) relative to a core molecule and are intended to be used as defined in the literature (IUPAC Recommendations for Fundamental Stereochemistry (Section E), *Pure Appl. Chem.*, 1976, 45:13-30). The FLT3 inhibitors of Formula I' may be prepared as individual isomers by either isomer-specific synthesis or resolved from an isomeric mixture. Conventional resolution techniques include forming the free base of each isomer of an isomeric pair using an optically active salt (followed by fractional crystallization and regeneration of the free base), forming an ester or amide of each of the isomers of an isomeric pair (followed by chromatographic separation and removal of the chiral auxiliary) or resolving an isomeric mixture of either a starting material or a final product using preparative TLC (thin layer chromatography) or a chiral HPLC column.

Furthermore, the FLT3 inhibitors of Formula I' may have one or more polymorph or amorphous crystalline forms and as such are intended to be included in the scope of the invention. In addition, some of the compounds may form solvates with water (i.e., hydrates) or common organic solvents, and such are also intended to be encompassed within the scope of this invention.

The FLT3 inhibitors of Formula I' may be converted to the corresponding N-oxide forms following art-known procedures for converting a trivalent nitrogen into its N-oxide form. Said N-oxidation reaction may generally be carried out by reacting the starting material of Formula I' with an appropriate organic or inorganic peroxide. Appropriate inorganic peroxides comprise, for example, hydrogen peroxide, alkali metal or earth alkaline metal peroxides, e.g. sodium peroxide, potassium peroxide; appropriate organic peroxides may comprise peroxy acids such as, for example, benzenecarboperoxoic acid or halo substituted benzenecarboperoxoic acid, e.g. 3-chlorobenzenecarboperoxoic acid, peroxoalkanoic acids, e.g. peroxoacetic acid, alkylhydroperoxides, e.g. t-butyl hydroperoxide. Suitable solvents are, for example, water, lower alcohols, e.g. ethanol and the like, hydrocarbons, e.g. toluene, ketones, e.g. 2-butanone, halogenated hydrocarbons, e.g. dichloromethane, and mixtures of such solvents.

Some of FLT3 inhibitors of Formula I' may also exist in their tautomeric forms. Such forms although not explicitly indicated in the present application are intended to be included within the scope of the present invention.

Preparation of FLT3 Inhibitors of Formula I'

During any of the processes for preparation of the FLT3 inhibitors of Formula I', it may be necessary and/or desirable to protect sensitive or reactive groups on any of the molecules concerned. This may be achieved by means of conventional protecting groups, such as those described in *Protecting Groups*, P. Kocienski, Thieme Medical Publishers, 2000; and T. W. Greene & P. G. M. Wuts, *Protective Groups in Organic Synthesis*, 3$^{rd}$ ed. Wiley Interscience, 1999. The protecting groups may be removed at a convenient subsequent stage using methods known in the art.

Methods of Preparation

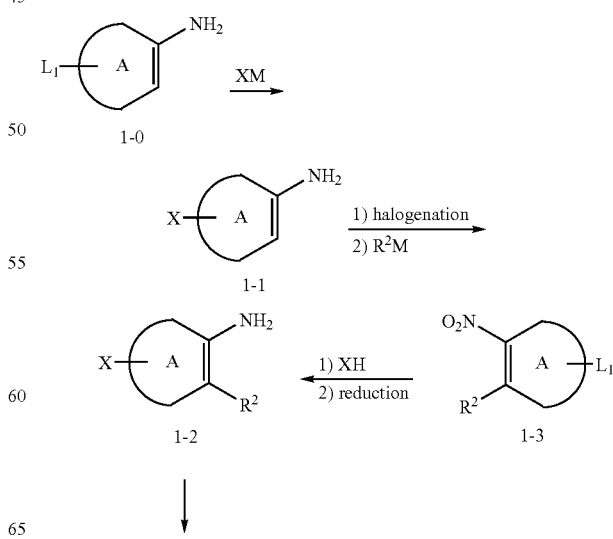

-continued

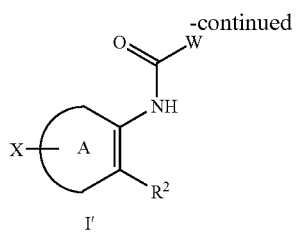

I'

Scheme 1 illustrates general methodology for the preparation of the FLT3 inhibitor compounds of Formula I'. Compounds of Formula 1-2 can be obtained by ortho-halogenation, preferably bromination, of amino compounds of Formula 1-1 followed by metal-catalyzed coupling reactions with boronic acids or boronate esters (Suzuki reactions, where $R^2M$ is $R^2B(OH)_2$ or a boronic ester) or tin reagents (Stille reactions, where $R^2M$ is $R^2Sn(alkyl)_3$) (for reviews, see N. Miyaura, A. Suzuki, *Chem. Rev.*, 95:2457 (1995), J. K. Stille, *Angew. Chem., Int. Ed. Engl.*, 25: 508024 (1986) and A. Suzuki in Metal-Catalyzed Coupling Reactions, F. Deiderich, P. Stang, Eds., Wiley-VCH, Weinheim (1988)). Compounds of formula 1-1 may be commercially available, or the above palladium mediated cross-coupling reactions described above may be used to generate compounds of Formula 1-1 from starting material 1-0.

Preferred conditions for the bromination of 1-1 are N-bromosuccinimide (NBS) in a suitable solvent such as N,N-dimethylformamide (DMF), dichloromethane (DCM) or acetonitrile. Metal-catalyzed couplings, preferably Suzuki reactions, can be performed according to standard methodology, preferably in the presence of a palladium catalyst such as tetrakis(triphenylphosphine)palladium(0) (Pd(PPh$_3$)$_4$), an aqueous base such aq. Na$_2$CO$_3$, and a suitable solvent such as toluene, ethanol, dimethoxyethane (DME), or DMF.

The FLT3 inhibitor compounds of Formula I' can be prepared by reaction of compounds of Formula 1-2 with carboxylic acids WCOOH according to standard procedures for amide bond formation (for a review, see: M. Bodansky and A. Bodansky, The Practice of Peptide Synthesis, Springer-Verlag, NY (1984)) or by reaction with acid chlorides WCOCl or activated esters WCO$_2$Rq (where Rq is a leaving group such as pentafluorophenyl or N-succinimide). The preferred reaction conditions for coupling with WCOOH are: when W is a furan, oxalyl chloride in DCM with DMF as a catalyst to form the acid chloride WCOCl and then coupling in the presence of a trialkylamine such as DIEA; when W is a pyrrole, 1-(3-dimethylaminopropyl)-3-ethylcarbodiimide hydrochloride (EDCI) and 1-hydroxybenzotriazole-6-sulfonamidomethyl hydrochloride (HOBt); and when W is an imidazole, the preferred conditions are bromotripyrrolidinophosphonium hexafluorophosphate (PyBrOP) and diisopropylethylamine (DIEA) in DCM.

It is understood that the optional substitution present on ring A in the FLT3 inhibitor compounds of Formula I' may be present in the starting materials 1-1 or 1-3 and, in such cases, would be carried through the synthesis outlined in Scheme 1. Alternatively various substituents on compounds of Formula I' may be introduced in a number of ways described below to provide the optional substitution listed for the FLT3 inhibitor compounds of Formula I'. The leaving group "L$_1$" present on ring A in Formula 1-0 or 1-3, can be substituted before or at any step during Scheme 1. When such leaving groups (preferably fluoro or chloro) are activated by the nitro group of Formula 1-3 for nucleophilic attack, they can undergo direct nucleophilic aromatic substitution by ammonia and azide anion or by amines, alcohols, thiols and other nucleophiles in the presence of a suitable base such as K$_2$CO$_3$, N,N-diisopropylethylamine (DIEA) or NEt$_3$. When the leaving group is suitable for metal-catalyzed couplings (preferably bromo or trifluoromethane-sulfonyloxy), a number of cross-coupling reactions (such as Suzuki or Stille reactions as discussed above for the introduction of $R^2$) may be performed. Other metal-catalyzed coupling reactions that can be employed include aromatic and heteroaromatic amination and amidation. For reviews, see, S. L. Buchwald, et al, *Top. Curr. Chem.*, 219:131-209 (2001) and J. F. Hartwig in "*Organopalladium Chemistry for Organic Synthesis*," Wiley Interscience, NY (2002). Additional metal catalyzed cross coupling reactions with 2,4,6-trimethyl-cyclotriboroxane may be employed if L$_1$ is bromo, iodo, or chloro activated by nitro to generate optional methyl substitution. See M. Gray, et al, Tetrahedron Lett., 41: 6237-40 (2000).

In some cases, the initial substituents can be further derivatized as described below to provide the final substitution of the FLT3 inhibitor compounds of Formula I'.

An alternative method for the introduction of nitrogen-containing heterocyclic substituents onto ring A is to form the heterocycle from an amino group on ring A. The amino group may be originally present in the starting material in a protected or unprotected form or may result from the reduction of a nitro group which also can be either originally present in the starting material or attached by a nitration reaction. In addition, the amino group may be formed by reduction of an azide group which can be present in the starting material or may result from nucleophilic aromatic substitution of an activated halide by azide anion as mentioned above. The amino group may also result from nucleophilic aromatic substitution of an activated halide (m, for example a nitrohalo compound) by ammonia or by the anion of a protected ammonia equivalent, for example, t-butyl carbamate. If introduced in protected form, the amine can be deprotected according to standard literature methods. For examples of amine protecting groups and deprotection methods. see Theodora W. Greene and Peter G. M. Wuts, John Wiley and Sons, Inc., NY (1991). The ring-forming reaction involves treatment of the aniline amino group with a suitable optionally substituted di-electrophile, preferably a dihalide or dicarbonyl compound, which results in two substitutions on the amino group to form an optionally substituted heterocycle. In the case of dihalides, any of a number of suitable bases can be added as an acid scavenger such as potassium carbonate, sodium hydroxide, or, a trialkylamine such as triethylamine. Thus, treatment with a bis(2-haloethyl)amine such as bis(2-chloroethyl)amine or bis(2-bromoethyl)amine would afford a piperazine ring (see, e.g., *J. Med. Chem.*, 29: 640-4 (1986) and *J. Med. Chem.*, 46: 2837 (2003)). Optional substitution on the amine nitrogen of the reagent would incorporate optional substitution on the terminal amine of the piperazine. For example, treatment with N,N-bis(2-chloroethyl)aniline would give an N-phenylpiperazino group. Treatment with a bis(2-haloethyl)ether or bis(2-haloethyl)thioether would afford a morpholine or thiomorpholine ring, respectively.

Another alternative method to direct substitution to introduce heterocyclic substituents onto ring A is to form the heterocycle from an aldehyde (i.e. from a formyl group on ring A). The formyl group may be originally present in the starting material in a protected or unprotected form or may result from any of a number of formylation reactions known in the literature including a Vilsmeier-Haack reaction For a review of formylation chemistry, see, G. A. Olah, et al, Chem.

Rev., 87: (1987), or by para-formylation of nitroaromatics, see, e.g., A. Katritsky and L. Xie, *Tetrahedron Lett.,* 37:347-50 (1996).

Finally it is understood that the FLT3 inhibitor compounds of Formula I' may be further derivatized. Protecting groups on the FLT3 inhibitor compounds of Formula I' can be removed according to standard synthetic methodologies (see, e.g., Theodora W. Greene and Peter G. M. Wuts, John Wiley and Sons, Inc., NY (1991)) and can be then subjected to further derivatization. Examples of further derivatization of the FLT3 inhibitor compounds of Formula I' include, but are not limited to: when compounds of Formula I' contain a primary or secondary amine, the amine may be reacted with aldehydes or ketones in the presence of a reducing agent such as sodium triacetoxyborohydride (see, Abdel-Magid *J. Org. Chem.* 61, pp. 3849-3862, (1996)) to reductively alkylate; with acid chlorides or carboxylic acids and an amide bond forming reagent as described above to form amides; with sulfonyl chlorides to form sulfonamides; with isocyanates to form ureas; with aryl- or heteroaryl-halides in the presence of a palladium catalyst as described above (see, Buchwald and Hartwig references above) to form aryl and heteroarylamines. In addition, when the FLT3 inhibitor compounds of Formula I' contain an aryl halide or heteroaryl halide, these compounds may be subjected to metal-catalyzed reactions with boronic acids (for example, Suzuki or Stille couplings as described above), or, amines or alcohols (Buchwald- or Hartwig-type couplings, see Buchwald and Hartwig references above). When the FLT3 inhibitor compounds of Formula I' contain a cyano group, this group may be hydrolyzed to amides or acids under acid or basic conditions. Basic amines may be oxidized to N-oxides and conversely N-oxides may be reduced to basic amines. When compounds of Formula I' contain a sulfide, either acyclic or cyclic, the sulfide can be further oxidized to the corresponding sulfoxides or sulfones. Sulfoxides can be obtained by oxidation using an appropriate oxidant such as one equivalent of (meta-chloroperbenzoicacid) MCPBA or by treatment with $NaIO_4$ (see, e.g., J. Regan, et al, *J. Med. Chem.,* 46: 4676-86 (2003)) and sulfones can be obtained using two equivalents of MCPBA or by treatment with 4-methylmorpholine N-oxide and catalytic osmium tetroxide (see, e.g., PCT application WO 01/47919).

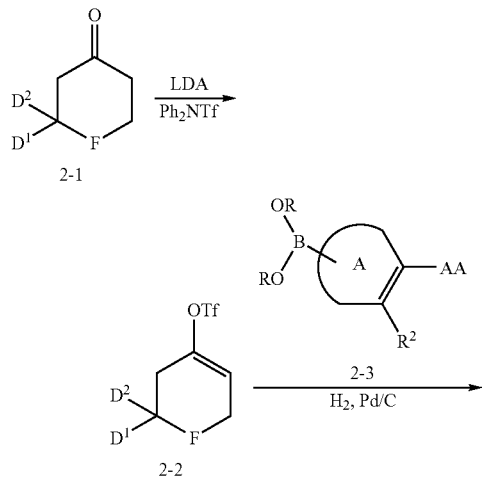

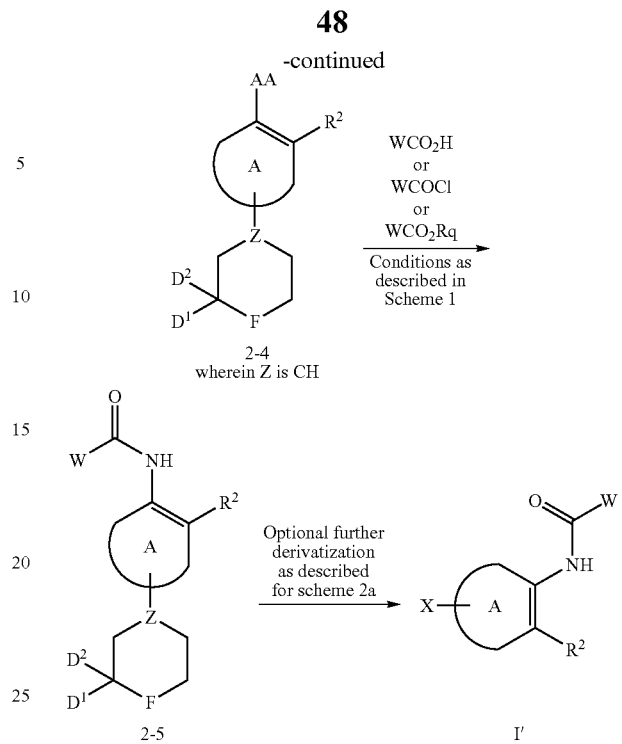

Scheme 2a illustrates a route to FLT3 inhibitor compounds of Formula I'. F represents $—NQ_aQ_bR^3—$, $—O—$, S, SO, or $SO_2$, and AA represents $—NH_2$ or $—NO_2$. $D^1$ and $D^2$ are shown for illustrative purposes only; it is recognized by those skilled in art that $D^5 D^6 D^7 D^8$ may also be present. Ketones of formula 2-1 can be converted to a vinyl triflate of formula 2-2 by treatment with a non-nucleophilic base such as LDA and then trapping of the resulting enolate with a triflating reagent such as trifluoromethanesulfonic anhydride or preferably N-phenyltrifluoromethanesulfonimide. Suzuki coupling of boronic acids or boronate esters of formula 2-3 to vinyl triflates of formula 2-2 can provide compounds of formula 2-4 where Z is C (*Synthesis,* 993 (1991)).

For compounds of formula 2-4 treatment with Pd/C can reduce both the olefin (and the nitro if AA is $NO_2$) to give Z is CH, AA is $NH_2$. Compounds of formula 2-4 where F represents $—SO_2$ can be prepared from compounds of formula 2-4 where AA is $—NO_2$ and F is a sulfide (F is $—S—$) by oxidation with MCPBA or other methods described in Scheme 1. The nitro group may then be reduced with Pd/C to reduce both the nitro and the olefin.

Compounds of formula 2-4 (AA is $NH_2$) are then converted to compounds of Formula 2-5 (which also represent FLT3 inhibitor compounds of Formula I' if no further modifications are required) as described in Scheme 1.

Compounds of formula 2-5 may be further modified to provide additional FLT3 inhibitor compounds of Formula I'. For example, in cases where F is $—NQ_3Q_bR^3—$, $Q_aQ_b$ is a direct bond, and $R_3$ represents a BOC protecting group ($CO_2tBu$), the BOC group may be removed according to standard methodology such as trifluoroactic acid (TFA) in DCM (Greene and Wuts, ibid.) to provide a secondary amine that can then be further derivatized to provide FLT3 inhibitor compounds of Formula I'. Further derivatization includes, but is not limited to: reactions with aldehydes or ketones in the presence of a reducing agent such as sodium triacetoxyborohydride to provide FLT3 inhibitor compounds of Formula II' where F is —NCH$_2$R$^3$ (A. F. Abdel-Magid, ibid.); with acid chlorides or with carboxylic acids and an amide bond forming reagent (as described in Scheme 1) to provide FLT3 inhibitor compounds of Formula II' where F is —NCOR$^3$; with sulfonyl chlorides (as described in Scheme 1) to provide FLT3 inhibitor compounds of Formula I' where F is —NSO$_2$R$_a$; with isocyanates (as described in Scheme 1) to provide FLT3 inhibitor compounds of Formula II' where F is —NCONR$_a$R$_b$; or subjected to metal-catalyzed substitution reactions as outlined in Scheme 1 to provide FLT3 inhibitor compounds of Formula I' where F is —NR$^3$ (S. L. Buchwald, et al, ibid.; J. H. Hartwig, ibid.) For the above example, R$_a$ and R$_b$ are independently hydrogen, alkyl, cycloalkyl, haloalkyl, aryl, aralkyl, heteroaryl and heteroaralkyl.

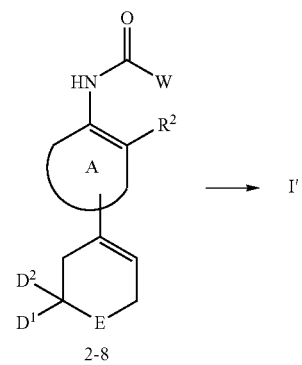

Scheme 2b illustrates a modification of Scheme 2a to synthesize partially unsaturated FLT3 inhibitor compounds of Formula I'. E represents —NQ$_a$Q$_b$R$^3$—, —O— (D$^1$ and D$^2$ are H), —S— (D$^1$ and D$^2$ are H), -(D$^1$ and D$^2$ are H), or —SO$_2$— (D$^1$ and D$^2$ are H), and R$_{AA}$ represents —NH$_2$ or —NO$_2$. Compounds of formula 2-4 are prepared as shown in Scheme 2. If R$_{AA}$ is —NO$_2$, the nitro group must be reduced by a method that does not reduce olefins, such as iron and ammonium chloride. If R$_{AA}$ of formula 2-4 is an amino group then no step is necessary and compounds of formula 2-4 are also compounds of formula 2-7. To prepared compounds of formula 2-7 where E is —SO$_2$— or —SO—, the oxidation of the sulfide must be performed on compound 2-4 where R$_{AA}$ is —NO$_2$ as described above, followed by nitro reduction.

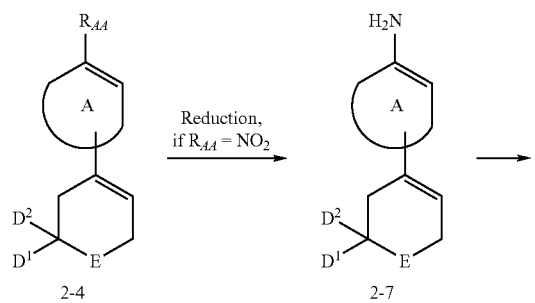

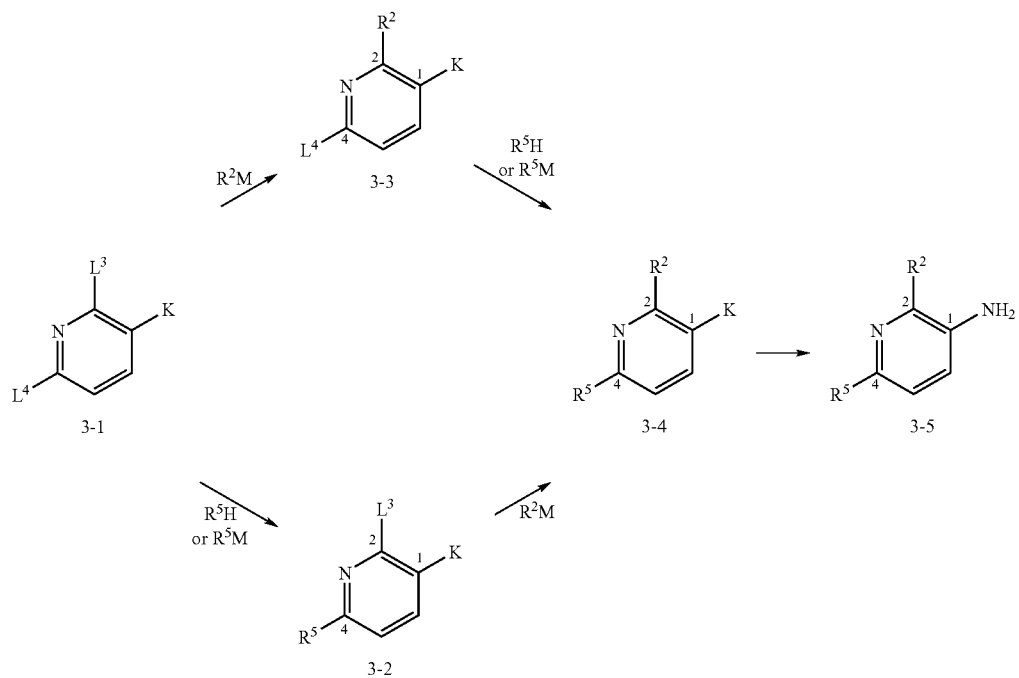

Scheme 3 illustrates the preparation of intermediates for the synthesis of FLT3 inhibitor compounds of Formula I', where ring A is pyridyl, and $R^5$ is the optional substitution on ring A or one of the heterocyclic substituents as defined in Formula I'. K is $NH_2$ or other functional groups such as $NO_2$, COOH or COOR which can eventually be converted to amino group by known literature methods such as reductions for $NO_2$ (as discussed for Scheme 1) or Curtius rearrangement for COOH (for a review, see *Organic Reactions*, 3: 337 (1947)). $L^3$ and $L^4$ are halogens. (K is COOH can also be formed from K is COOR by simple base- or acid-catalyzed hydrolysis.)

In general, the selectivity and order in introducing $R^2$ and $R^5$ can be achieved by the relative reactivity of the halogens $L^3$ and $L^4$ chosen in compound (3-1), the intrinsic selectivity of the heterocycle and/or the reaction conditions employed. An example of using the relative reactivity of the halogens $L^3$ and $L^4$ in selectively introducing $R^2$ and $R^5$ would include the situation where, in compounds of Formula 3-1 where $L^3$ is a fluoro group and $L^4$ is a bromo group, selective displacement of the fluoro group by a nucleophile can be achieved followed by substitution of the remaining bromo group by metal-catalyzed substitution chemistry (such as Suzuki or Stille cross-coupling reactions as further outlined below). Similarly in compounds of Formula 3-1 where one of $L^3$ and $L^4$ is an iodo group and the other is a bromo or chloro group, selective metal-catalyzed substitution chemistry (such as Suzuki or Stille cross-coupling reactions or Buchwald/Hartwig aminations as further discussed below) on the iodo group can be achieved followed by replacement of the remaining bromo or chloro group by another metal-catalyzed substitution reaction.

As illustrated in Scheme 3, leaving group $L^3$ in Formula 3-1 can be first substituted to obtain compounds of Formula 3-3 or leaving group $L^4$ can be first substituted to obtain compound of Formula 3-2. Compounds 3-2 or 3-3 can then be reacted to displace $L^3$ or $L^4$ to furnish the compound of Formula 3-4.

Thus, a direct nucleophilic displacement or metal-catalyzed amination of compound of Formula 3-1 with a secondary amine, ammonia or a protected amine such as tert-butyl carbamate (for review, see Modern Amination Methods: Ricci, A., Ed.; Wiley-VCH: Weinheim, 2000), can be used to introduce $R^5$ in Formulae 3-2 or 3-3 where $R^5$ is a primary or secondary amine, amino group ($NH_2$), and amine equivalent or a protected amino group. Metal-catalyzed coupling of compound 3-1 with boronic acids or boronates esters (Suzuki reaction, M is boronic acid group or boronate ester group) or with organotin compounds (Stille reaction, M is $SnR_3$, where R is alkyl and the other substituents as defined above, as described in Scheme 1 can provide compounds of Formulae 3-2 or 3-3.

Compound 3-2 can be further converted to compound 3-4 by a metal-catalyzed Suzuki or Stille coupling as described above. $L^4$ in compound 3-3 also subsequently can be substituted with $R^5$ to obtain compounds of Formula 3-4, again, by a direct nucleophilic substitution or metal-catalyzed reaction with a nucleophile or by the same metal-catalyzed cross-coupling reaction as described above. When $R^5$ in the formulae (3-2, 3-3 or 3-4) is a protected amine and K not an amino group, it can be deprotected to unmask the amino functionality. This amino functionality can then be further derivatized as described in Scheme 1. When the K group in Formula 3-4 is not an amino group (such as functionality described above), it can be converted to an amino group according to known literature methods (see, for example Comprehensive Organic Transformations: Larock, R. S.; Wiley and Sons Inc., USA, 1999) and the resulting amine 3-5 can be employed in amide bond formation reactions as described in Scheme (1) to obtain the FLT3 inhibitor compounds of Formula I'. When K in Formula 3-4 is an amino group it can be directly used in amide coupling as described above.

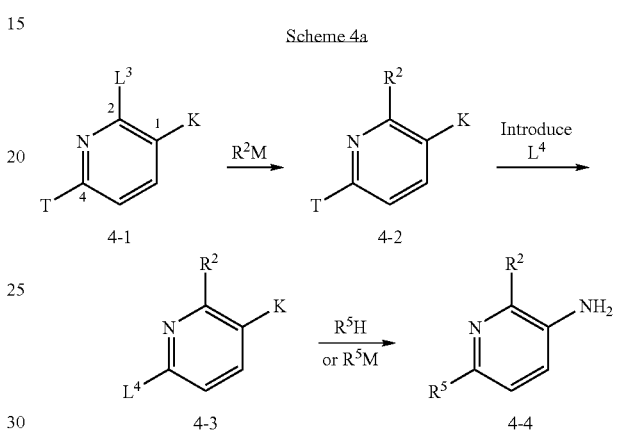

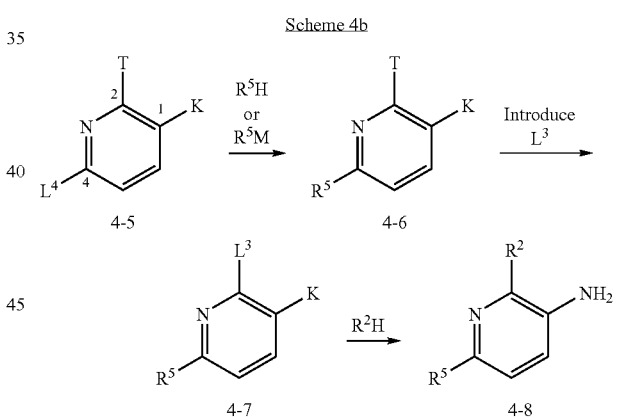

Schemes 4a and 4b illustrate the preparation of intermediates to be further modified according to Scheme 3 starting from a monohalo-substituted compound of Formulae 4-1 and 4-5 by introducing the second leaving group after the replacement of the first one has been completed. These can also be used for the synthesis of FLT3 inhibitor compounds of Formula I' where ring A is a pyridine and $R^5$ is either the optional substitution on Ring A or one of the heterocyclic substituents. As in Scheme 3, the remaining positions on the pyridine ring can be substituted as described in Formula I'. K is $NH_2$ or other functional groups such as $NO_2$, COOH or COOR which can eventually be converted to amino group by known literature methods such as reductions or Curtius rearrangement as described in Scheme 3. $L^3$ and $L^4$ are halogens. In these compounds, T is either H or is a functional group such as OH that can be converted to leaving groups $L^3$ or $L^4$ such as halogen, triflate or mesylate by known literature methods (see, for example, Nicolai, E., et al., *J. Heterocyclic Chemistry*, 31, (73), (1994)). Displacement of $L^3$ in compound of Formula 4-1 or $L^4$ in Formula 4-5 by methods described in Scheme 3, can yield compounds of Formulae 4-2 and 4-6. At this point, the substituent T of compounds 4-2 or 4-6 can be converted to a leaving group $L^4$ or $L^3$ (preferably a halogen) by standard methods to provide compounds of Formulae 4-3 and 4-5. For example, when T is OH, the preferred reagents to effect this transformation are thionyl chloride, $PCl_5$, $POCl_3$ or $PBr_3$ (see, for examples, Kolder, den Hertog., *Recl. Trav. Chim. Pays-Bas*; 285, (1953), and Iddon, B, et. al., *J. Chem. Soc. Perkin Trans. I.*, 1370, (1980)). When T is H, it can be directly halogenated (preferably brominated) to provide compounds of Formulae 4-3 or 4-7 (see, for example, Canibano, V. et al., *Synthesis*, 14, 2175, (2001)). The preferred conditions for bromination are NBS in a suitable solvent such as DCM or acetonitrile.

The compounds of Formulae 4-3 or 4-7 can be converted to compounds of Formulae 4-4 or 4-8 by introduction of the remaining groups $R^2$ or $R^5$, respectively, by the methods described above and then on to FLT3 inhibitor compounds of Formula I', by the methods described in Scheme 3 for conversion of compounds of Formulae 3-4 and 3-5 to FLT3 inhibitor compounds of Formula I'

Representative FLT3 Inhibitors of Formula I'

Representative FLT3 inhibitors of Formula I' synthesized by the aforementioned methods are in the following chart and examples thereafter. The following are for exemplary purposes only and are in no way meant to limit the invention. Preferred compounds of the present invention are Examples 5, 17, 23, 34, 38, and 51.

| | Name | Structure |
|---|---|---|
| 4 | 5-Cyano-furan-2-carboxylic acid [4-(4-methyl-piperazin-1-yl)-2-(3-methyl-thiophen-2-yl)-phenyl]-amide | 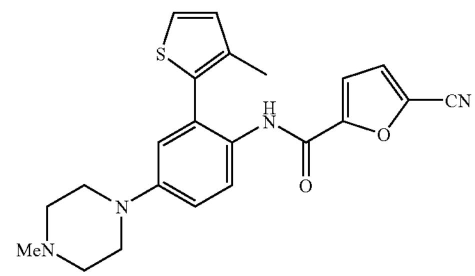 [SMILES: Cc1ccsc1-c1cc(N2CCN(C)CC2)ccc1NC(=O)c1ccc(C#N)o1] |
| 5 | 5-Cyano-furan-2-carboxylic acid [4-(4-methyl-piperazin-1-yl)-2-(4-methyl-thiophen-3-yl)-phenyl]-amide | 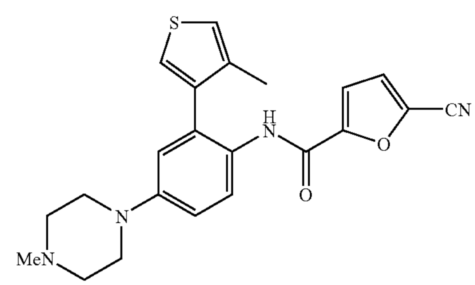 [SMILES: Cc1cscc1-c1cc(N2CCN(C)CC2)ccc1NC(=O)c1ccc(C#N)o1] |
| 6 | 4-Cyano-1H-imidazole-2-carboxylic acid {2-cyclohex-1-enyl-4-[1-(2-hydroxy-1-hydroxymethyl-ethyl)-piperidin-4-yl]-phenyl}-amide trifluoroacetic acid salt | 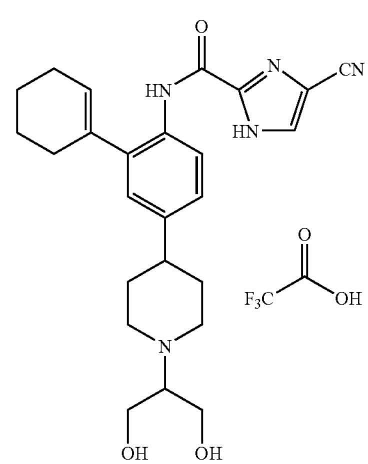 [SMILES: N#Cc1c[nH]c(C(=O)Nc2ccc(C3CCN(C(CO)CO)CC3)cc2C2=CCCCC2)n1 ; O=C(O)C(F)(F)F] |

| | Name | Structure |
|---|---|---|
| 7 | 4-Cyano-1H-imidazole-2-carboxylic acid {2-cyclohex-1-enyl-4-[1-(2-morpholin-4-yl-acetyl)-piperidin-4-yl]-phenyl}-amide | 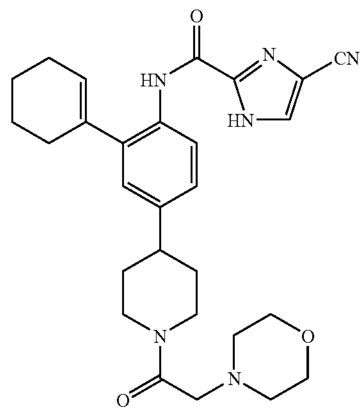 [SMILES: N#Cc1c[nH]c(C(=O)Nc2ccc(C3CCN(C(=O)CN4CCOCC4)CC3)cc2C2=CCCCC2)n1] |
| 8 | 4-Cyano-1H-imidazole-2-carboxylic acid {2-cyclohex-1-enyl-4-[1-(3-morpholin-4-yl-propionyl)-piperidin-4-yl]-phenyl}-amide | 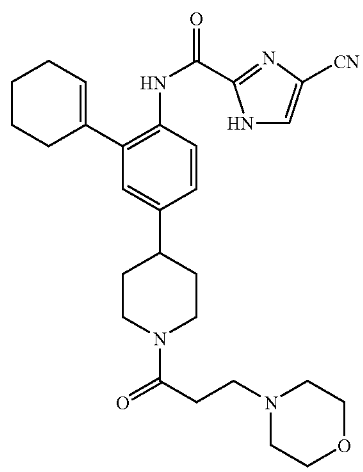 [SMILES: N#Cc1c[nH]c(C(=O)Nc2ccc(C3CCN(C(=O)CCN4CCOCC4)CC3)cc2C2=CCCCC2)n1] |
| 9 | 5-Cyano-furan-2-carboxylic acid [2'-methyl-5-(4-methyl-piperazin-1-yl)-biphenyl-2-yl]-amide | 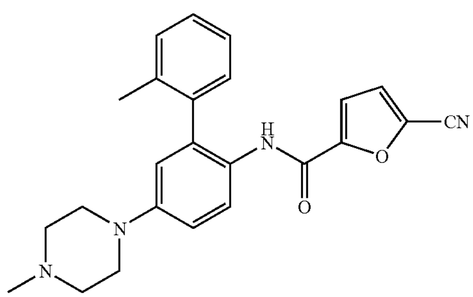 [SMILES: Cc1ccccc1-c1cc(N2CCN(C)CC2)ccc1NC(=O)c1ccc(C#N)o1] |
| 10 | 5-Cyano-furan-2-carboxylic acid [2'-fluoro-5-(4-methyl-piperazin-1-yl)-biphenyl-2-yl]-amide | 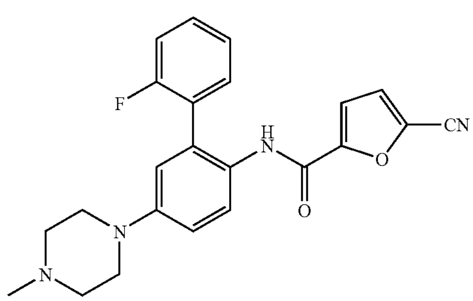 |

-continued

| | Name | Structure |
|---|---|---|
| 11 | 5-Cyano-furan-2-carboxylic acid [2-cyclohex-1-enyl-4-(4-methyl-piperazin-1-yl)-phenyl]-amide | 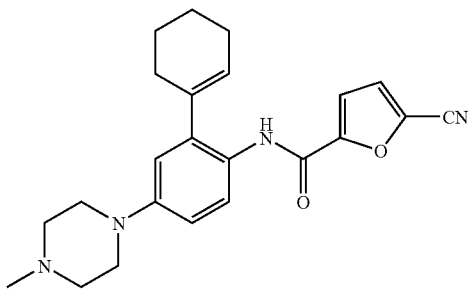 [SMILES: CN1CCN(c2ccc(NC(=O)c3ccc(C#N)o3)c(C3=CCCCC3)c2)CC1] |
| 12 | 5-Cyano-furan-2-carboxylic acid[2-(3,6-dihydro-2H-pyran-4-yl)-4-(4-methyl-piperazin-1-yl)-phenyl-amide | 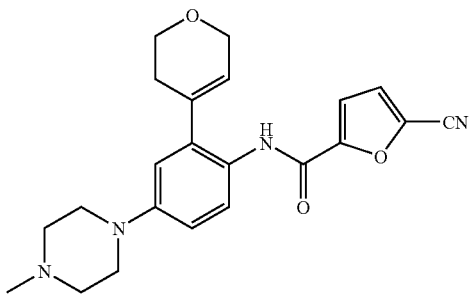 [SMILES: CN1CCN(c2ccc(NC(=O)c3ccc(C#N)o3)c(C3=CCOCC3)c2)CC1] |
| 13 | 4-Cyano-1H-pyrrole-2-carboxylic acid (2-cyclohex-1-enyl-4-piperidin-4-yl-phenyl)-amide trifluoroacetic acid salt | 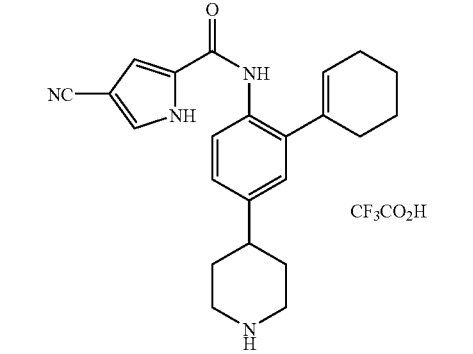 |
| 14 | 4-Cyano-1H-imidazole-2-carboxylic acid (2-cyclohex-1-enyl-4-piperidin-4-yl-phenyl)-amide trifluoroacetic acid salt | 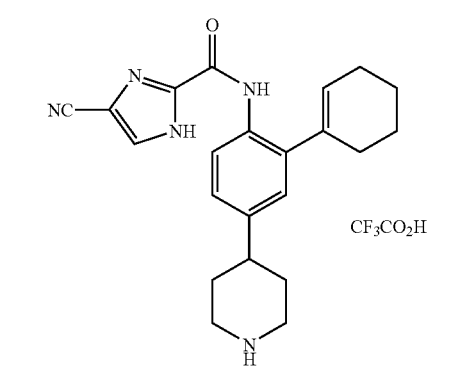 |

| | Name | Structure |
|---|---|---|
| 15 | 4-Cyano-1H-pyrrole-2-carboxylic acid [4-(1-acetyl-piperidin-4-yl)-2-cyclohex-1-enyl-phenyl]-amide | 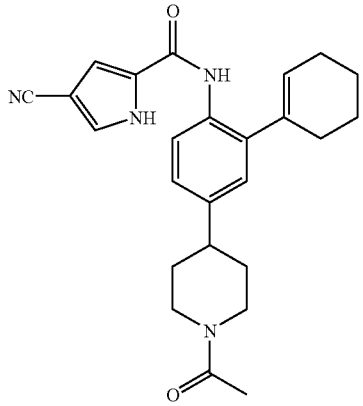 |
| 16 | 4-Cyano-1H-imidazole-2-carboxylic acid [4-(1-acetyl-piperidin-4-yl)-2-cyclohex-1-enyl-phenyl]-amide | 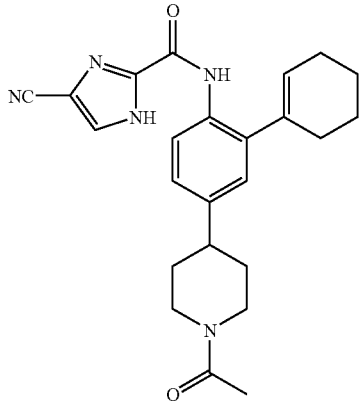 |
| 17 | 4-Cyano-1H-imidazole-2-carboxylic acid [2-(4-methyl-cyclohex-1-enyl)-4-piperidin-4-yl-phenyl]-amide trifluoroacetic acid salt | 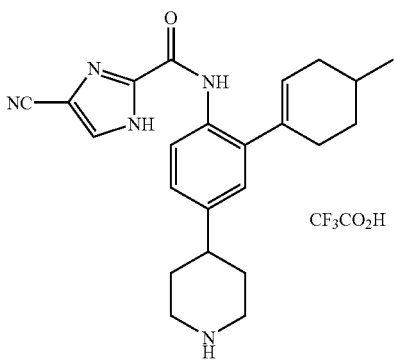 |
| 18 | 4-Cyano-1H-imidazole-2-carboxylic acid (2-cyclopent-1-enyl-4-piperidin-4-yl-phenyl)-amide trifluoroacetic acid salt | 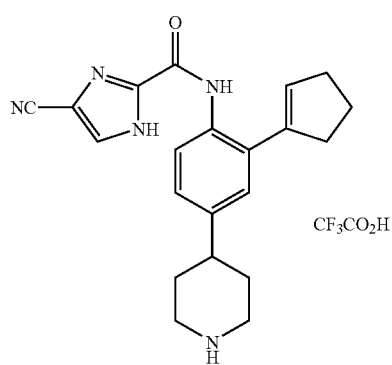 |

-continued

| | Name | Structure |
|---|---|---|
| 20 | 4-Cyano-1H-imidazole-2-carboxylic acid {2-cyclohex-1-enyl-4-[1-(2-methanesulfonyl-acetyl)-piperidin-4-yl]-phenyl}-amide | 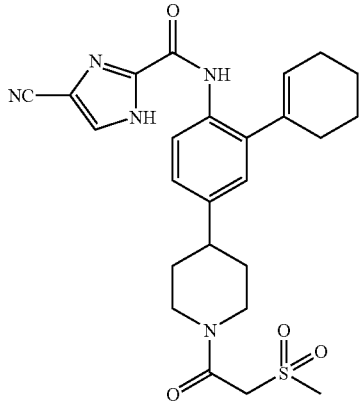 |
| 21 | 4-Cyano-1H-imidazole-2-carboxylic acid [2-cyclohex-1-enyl-4-(1-pyridin-2-ylmethyl-piperidin-4-yl)-phenyl]-amide trifluoroacetic acid salt | 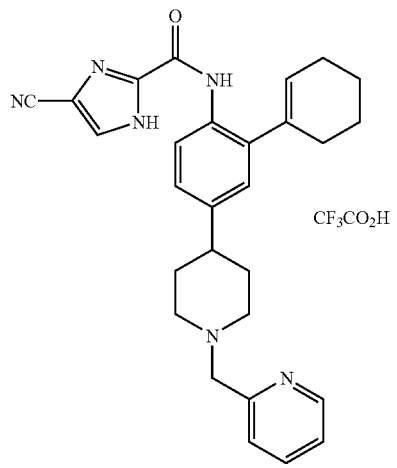 |
| 22 | 4-Cyano-1H-imidazole-2-carboxylic acid [2-(4-methyl-cyclohex-1-enyl)-4-(1-pyridin-2-ylmethyl-piperidin-4-yl)-phenyl]-amide trifluoroacetic acid salt | 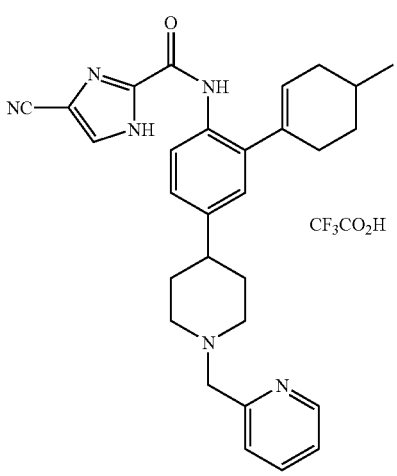 |

-continued

| | Name | Structure |
|---|---|---|
| 23 | 4-Cyano-1H-imidazole-2-carboxylic acid {2-cyclopent-1-enyl-4-[1-(1-methyl-1H-imidazol-2-ylmethyl)-piperidin-4-yl]-phenyl}-amide trifluoroacetic acid salt | 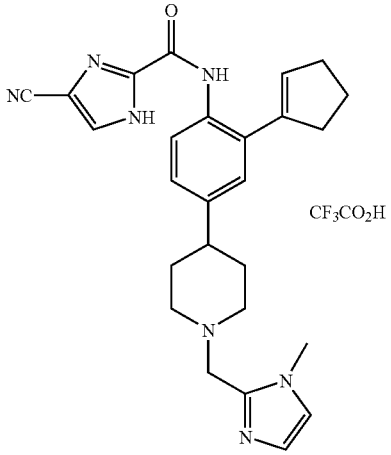 |
| 24 | 4-{4-[(4-Cyano-1H-imidazole-2-carbonyl)-amino]-3-cyclohex-1-enyl-phenyl}-piperidine-1-carboxylic acid amide | 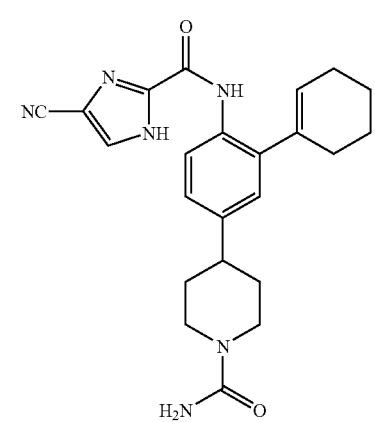 |
| 25 | 4-Cyano-1H-imidazole-2-carboxylic acid [2-cyclohex-1-enyl-4-(3,4,5,6-tetrahydro-2H-[1,2']bipyridinyl-4-yl)-phenyl]-amide trifluoroacetic acid salt | 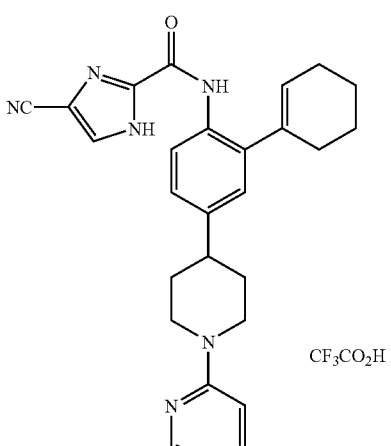 |

| | Name | Structure |
|---|---|---|
| 26 | 4-Cyano-1H-imidazole-2-carboxylic acid {2-cyclohex-1-enyl-4-[1-(2-hydroxy-ethyl)-piperidin-4-yl]-phenyl}-amide trifluoroacetic acid salt | 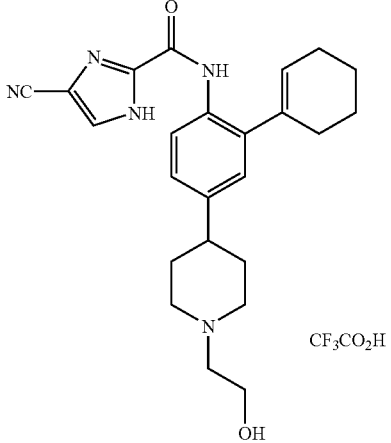 |
| 27 | 4-Cyano-1H-imidazole-2-carboxylic acid {4-[1-(2-cyano-ethyl)-piperidin-4-yl]-2-cyclohex-1-enyl-phenyl}-amide trifluoroacetic acid salt | 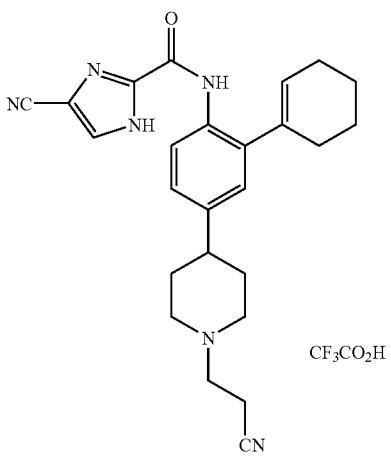 |
| 28 | 4-Cyano-1H-imidazole-2-carboxylic acid [4-(1-carbamoylmethyl-piperidin-4-yl)-2-cyclohex-1-enyl-phenyl]-amide trifluoroacetic acid salt | 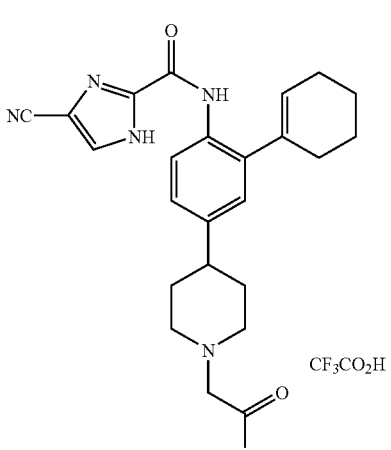 |

-continued

| Name | Structure |
|---|---|
| 29 4-Cyano-1H-imidazole-2-carboxylic acid {2-cyclohex-1-enyl-4-[1-(2-pyridin-2-yl-acetyl)-piperidin-4-yl]-phenyl}-amide trifluoroacetic acid salt | 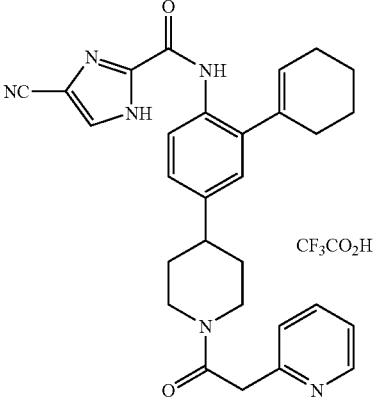 |
| 30 4-Cyano-1H-imidazole-2-carboxylic acid {2-cyclohex-1-enyl-4-[1-(2-pyridin-3-yl-acetyl)-piperidin-4-yl]-phenyl}-amide trifluoroacetic acid salt | 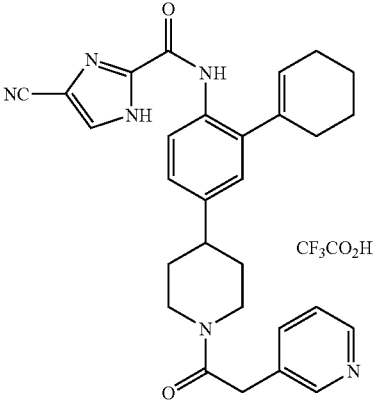 |
| 31 4-Cyano-1H-imidazole-2-carboxylic acid {2-cyclohex-1-enyl-4-[1-(2-pyridin-4-yl-acetyl)-piperidin-4-yl]-phenyl}-amide trifluoroacetic acid salt | 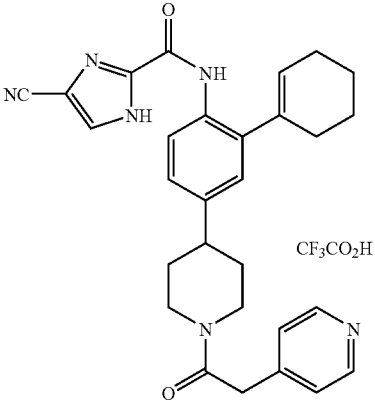 |

| | Name | Structure |
|---|---|---|
| 32 | 4-Cyano-1H-imidazole-2-carboxylic acid (2-cyclohex-1-enyl-4-{1-[2-(1-methyl-1H-imidazol-4-yl)-acetyl]-piperidin-4-yl}-phenyl)-amide trifluoroacetic acid salt | 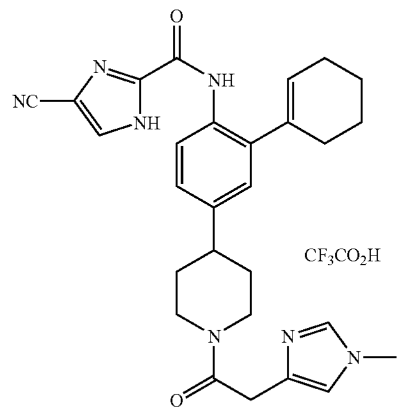 |
| 33 | 4-Cyano-1H-imidazole-2-carboxylic acid {2-cyclohex-1-enyl-4-[1-(2-1H-imidazol-4-yl-acetyl)-piperidin-4-yl]-phenyl}-amide trifluoroacetic acid salt | 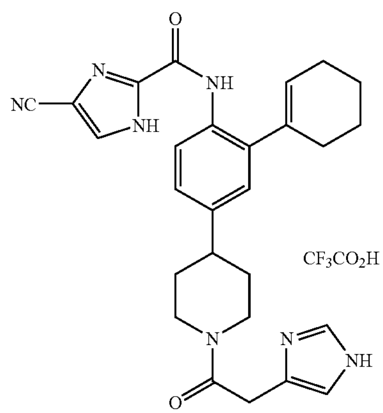 |
| 34 | 4-Cyano-1H-imidazole-2-carboxylic acid {2-cyclohex-1-enyl-4-[1-(2-morpholin-4-yl-ethyl)-piperidin-4-yl]-phenyl}-amide di-trifluoroacetic acid salt | 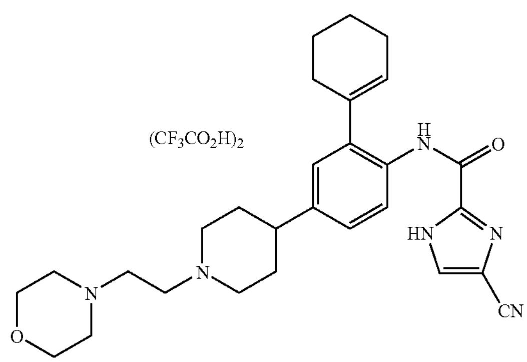 [SMILES: N#Cc1c[nH]c(C(=O)Nc2ccc(C3CCN(CCN4CCOCC4)CC3)cc2C2=CCCCC2)n1 ; "(CF3CO2H)2"] |
| 35 | 4-Cyano-1H-imidazole-2-carboxylic acid [2-(1,1-dioxo-1,2,3,6-tetrahydro-1$\lambda^6$-thiopyran-4-yl)-4-piperidin-4-yl-phenyl]-amide | 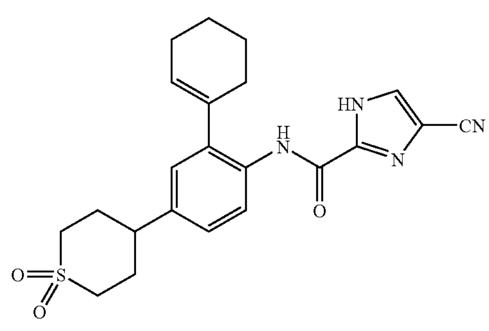 [SMILES: N#Cc1c[nH]c(C(=O)Nc2ccc(C3CCS(=O)(=O)CC3)cc2C2=CCCCC2)n1] |

| Name | Structure |
|---|---|
| 36 4-Cyano-1H-imidazole-2-carboxylic acid [2-(1,1-dioxo-1,2,3,6-tetrahydro-1λ⁶-thiopyran-4-yl)-4-piperidin-4-yl-phenyl]-amide trifluoroacetic acid salt | 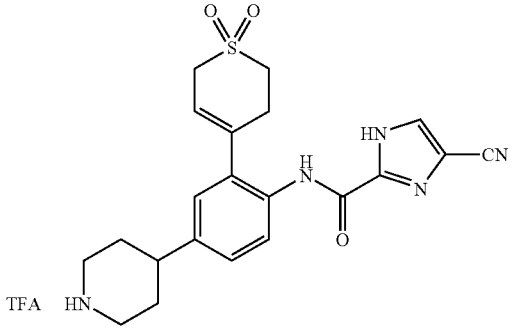 [SMILES: "TFA" ; N#Cc1c[nH]c(C(=O)Nc2ccc(C3CCNCC3)cc2C2=CCS(=O)(=O)CC2)n1] |
| 37 4-Cyano-1H-imidazole-2-carboxylic acid [4-(1-acetyl-piperidin-4-yl)-2-(1,1-dioxo-1,2,3,6-tetrahydro-1λ⁶-thiopyran-4-yl)-phenyl]-amide | 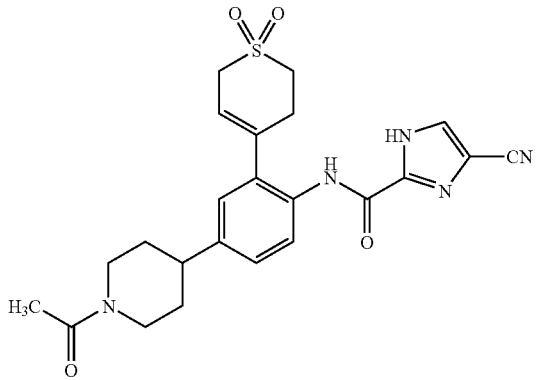 [SMILES: CC(=O)N1CCC(c2ccc(NC(=O)c3nc(C#N)c[nH]3)c(C3=CCS(=O)(=O)CC3)c2)CC1] |
| 38 4-Cyano-1H-imidazole-2-carboxylic acid {2-cyclohex-1-enyl-4-[1-(2-dimethylamino-acetyl)-piperidin-4-yl]-phenyl}-amide | 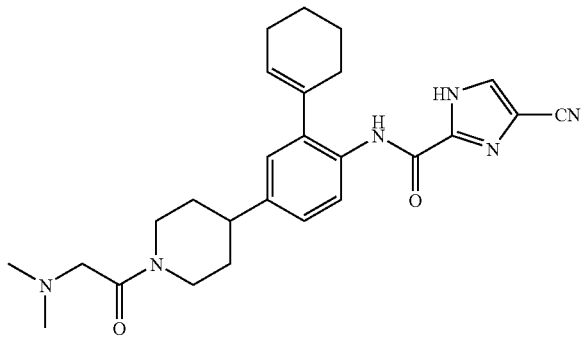 [SMILES: CN(C)CC(=O)N1CCC(c2ccc(NC(=O)c3nc(C#N)c[nH]3)c(C3=CCCCC3)c2)CC1] |
| 38b 4-Cyano-1H-imidazole-2-carboxylic acid {2-cyclohex-1-enyl-4-[1-(2-methylamino-acetyl)-piperidin-4-yl]-phenyl}-amide | 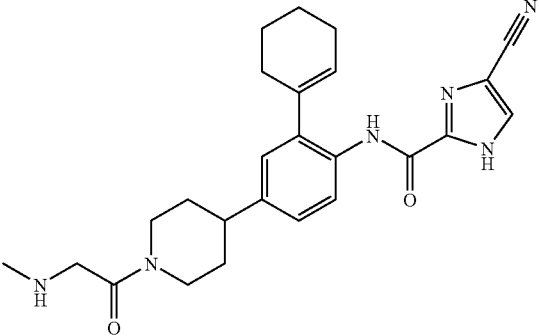 [SMILES: CNCC(=O)N1CCC(c2ccc(NC(=O)c3nc(C#N)c[nH]3)c(C3=CCCCC3)c2)CC1] |

| Name | Structure |
|---|---|
| 39 | 4-{4-[(4-Cyano-1H-imidazole-2-carbonyl)-amino]-3-cyclohex-1-enyl-phenyl}-piperidine-1-carboxylic acid (2-hydroxy-ethyl)-amide |
| 40 | 4-Cyano-1H-imidazole-2-carboxylic acid {2-cyclohex-1-enyl-4-[1-(2-methanesulfonyl-ethyl)-piperidin-4-yl]-phenyl}-amide |
| 41 | 4-Cyano-1H-imidazole-2-carboxylic acid {2-cyclohex-1-enyl-4-[1-(1-oxy-pyridine-4-carbonyl)-piperidin-4-yl]-phenyl}-amide |
| 42 | 4-Cyano-1H-imidazole-2-carboxylic acid {2-cyclohex-1-enyl-4-[1-(1-oxy-pyridine-3-carbonyl)-piperidin-4-yl]-phenyl}-amide |

| | Name | Structure |
|---|---|---|
| 43 | 4-Cyano-1H-imidazole-2-carboxylic acid {2-cyclohex-1-enyl-4-[1-(pyridine-3-carbonyl)-piperidin-4-yl]-phenyl}-amide | 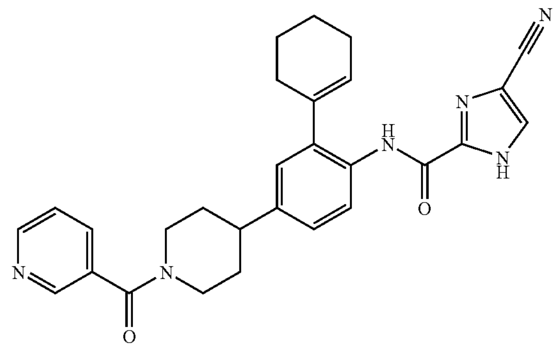 [SMILES: N#Cc1c[nH]c(C(=O)Nc2ccc(C3CCN(C(=O)c4cccnc4)CC3)cc2C2=CCCCC2)n1] |
| 44 | 4-Cyano-1H-imidazole-2-carboxylic acid (2-cyclohex-1-enyl-4-{1-[2-(2-hydroxy-ethylamino)-acetyl]-piperidin-4-yl}-phenyl)-amide trifluoroacetic acid salt | 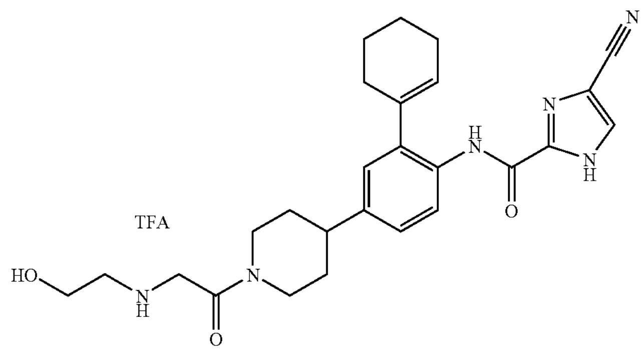 [SMILES: N#Cc1c[nH]c(C(=O)Nc2ccc(C3CCN(C(=O)CNCCO)CC3)cc2C2=CCCCC2)n1] |
| 45 | 4-Cyano-1H-imidazole-2-carboxylic acid (2-cyclohex-1-enyl-4-{1-[2-(2-hydroxy-ethyl)-methyl-amino-acetyl]-piperidin-4-yl}-phenyl)-amide trifluoroacetic acid salt | 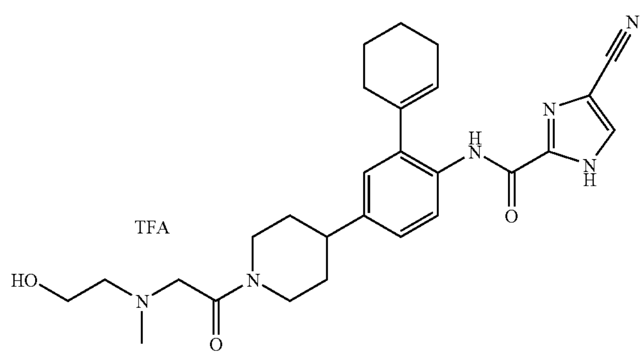 [SMILES: CN(CCO)CC(=O)N1CCC(c2ccc(NC(=O)c3nc(C#N)c[nH]3)c(C3=CCCCC3)c2)CC1] |
| 46 | 4-Cyano-1H-imidazole-2-carboxylic acid [4-(1-acetyl-piperidin-4-yl)-2-(1,2,5,6-tetrahydro-pyridin-3-yl)-phenyl]-amide trifluoroacetic acid salt | 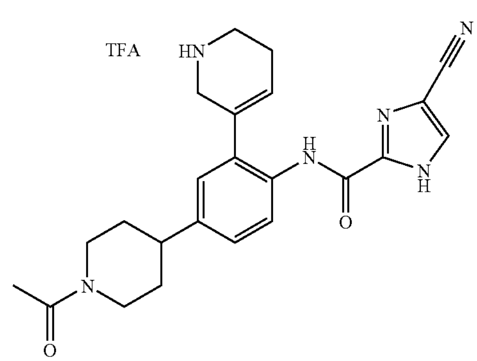 [SMILES: CC(=O)N1CCC(c2ccc(NC(=O)c3nc(C#N)c[nH]3)c(C3=CCCNC3)c2)CC1] |

| Name | Structure |
|---|---|
| 47 (4-{4-[(4-Cyano-1H-imidazole-2-carbonyl)-amino]-3-cyclohex-1-enyl-phenyl}-piperidin-1-yl)-acetic acid trifluoroacetic acid salt | 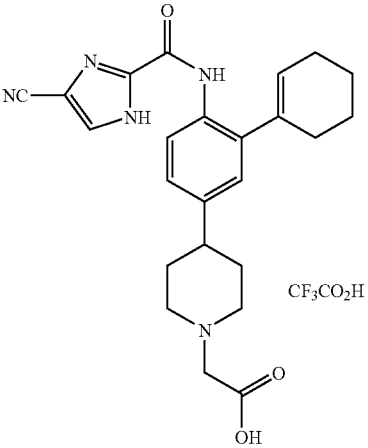 |
| 48 4-Cyano-1H-imidazole-2-carboxylic acid {4-[1-(3-amino-3-methyl-butyryl)-piperidin-4-yl]-2-cyclohex-1-enyl-phenyl}-amide trifluoroacetic acid salt | 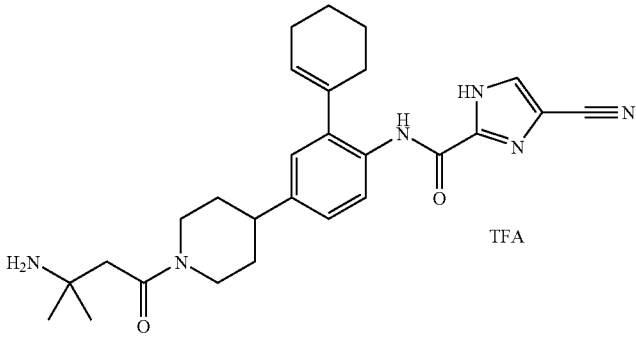 [SMILES: CC(C)(N)CC(=O)N1CCC(c2ccc(NC(=O)c3nc(C#N)c[nH]3)c(C3=CCCCC3)c2)CC1] |
| 49 4H-[1,2,4]-triazole-3-carboxylic acid (2-cyclohex-1-enyl-4-piperidin-4-yl-phenyl)-amide bis trifluoroacetic acid salt | 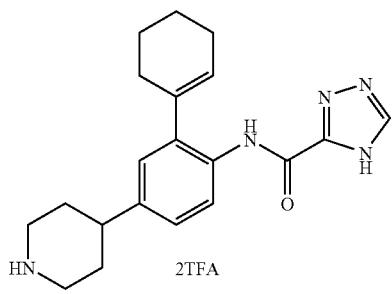 [SMILES: O=C(Nc1ccc(C2CCNCC2)cc1C1=CCCCC1)c1nnc[nH]1 ; "2TFA"] |
| 50 5-Chloro-4H-[1,2,4]-triazole-3-carboxylic acid (2-cyclohex-1-enyl-4-piperidin-4-yl-phenyl)-amide trifluoroacetic acid salt | 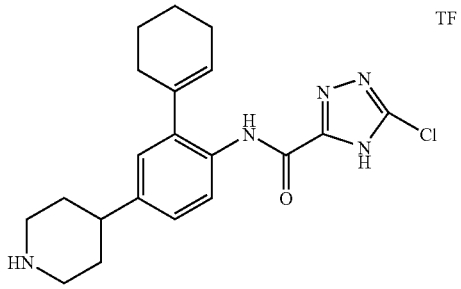 [SMILES: "TF" ; O=C(Nc1ccc(C2CCNCC2)cc1C1=CCCCC1)c1nnc(Cl)[nH]1] |

| Name | | Structure |
|---|---|---|
| 51a | 5-Cyano-1H-imidazole-2-carboxylic acid [2-cyclohex-1-enyl-4-(cis-2,6-dimethyl-piperidin-4-yl)-phenyl]-amide bis trifluoroacetic acid salt | 2 TFA |
| 51b | 5-cyano-1H-imidazole-2-carboxylic acid [2-cyclohex-1-enyl-4-(trans-2,6-dimethyl-piperidin-4-yl)-phenyl]-amide bis trifluoroacetic acid salt | 2TFA |
| 52 | 5-Cyano-1H-imidazole-2-carboxylic acid {2-cyclohex-1-enyl-4-[1-(R)-(+)-(2,3-dihydroxy-propionyl)-piperidin-4-yl]-phenyl}-amide | 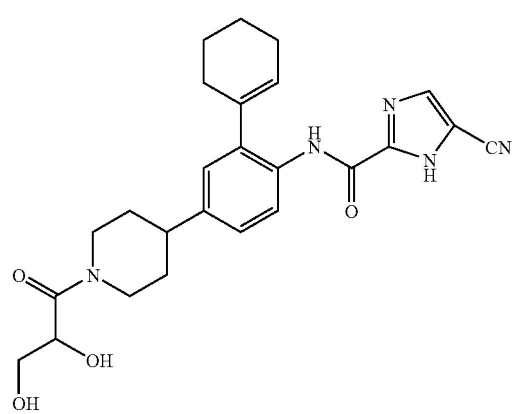 [SMILES: N#Cc1cnc(C(=O)Nc2ccc(C3CCN(C(=O)C(O)CO)CC3)cc2C2=CCCCC2)[nH]1] |
| 53 | 5-Cyano-1H-imidazole-2-carboxylic acid [2-cyclohex-1-enyl-4-(1-methoxy-piperidin-4-yl)-phenyl]-amide trifluoroacetic acid salt | TFA |

-continued

| | Name | Structure |
|---|---|---|
| 54 | 4-Cyano-1H-imidazole-2-carboxylic acid [6-(4,4-dimethyl-cyclohex-1-enyl)-1',2',3',4',5',6'-hexahydro-[2,4']bipyridinyl-5-yl]-amide trifluoroacetic acid salt | 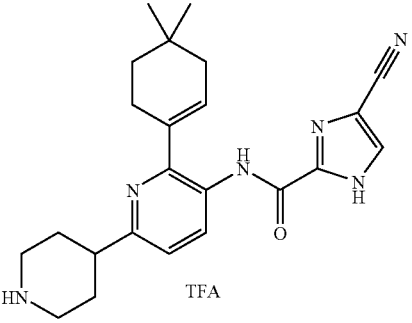 [SMILES: "TFA" ; CC1(C)CC=C(c2nc(C3CCNCC3)ccc2NC(=O)c2nc(C#N)c[nH]2)CC1] |
| 55 | 4-Cyano-1H-imidazole-2-carboxylic acid [1'-(2-dimethylamino-acetyl)-6-(4,4-dimethyl-cyclohex-1-enyl)-1',2',3',4',5',6'-hexahydro-[2,4']bipyridinyl-5-yl]-amide trifluoroacetic acid salt | 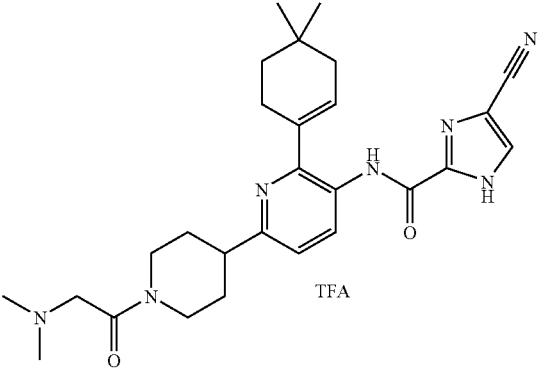 [SMILES: "TFA" ; CN(C)CC(=O)N1CCC(c2ccc(NC(=O)c3nc(C#N)c[nH]3)c(C3=CCC(C)(C)CC3)n2)CC1] |
| 56 | 4-Cyano-1H-imidazole-2-carboxylic acid [6-(4,4-dimethyl-cyclohex-1-enyl)-1'-(2-methanesulfonyl-ethyl)-1',2',3',4',5',6'-hexhydro-[2,4']bipyridinyl-5-yl]-amide trifluoroacetic acid salt | 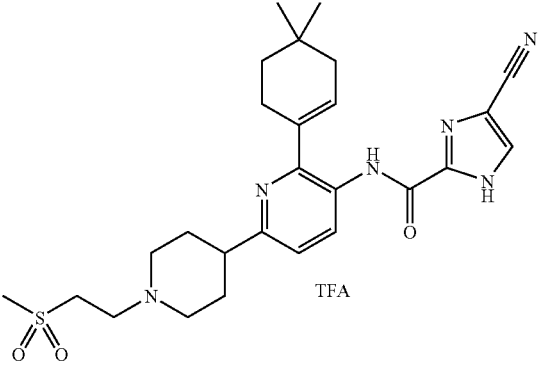 [SMILES: "TFA" ; CC1(C)CC=C(c2nc(C3CCN(CCS(C)(=O)=O)CC3)ccc2NC(=O)c2nc(C#N)c[nH]2)CC1] |
| 57 | 5-Cyano-1H-imidazole-2-carboxylic acid {4-[1-(2-amino-2-methyl-propionyl)-piperidin-4-yl]-2-cyclohex-1-enyl-phenyl}-amide trifluoroacetic acid salt | 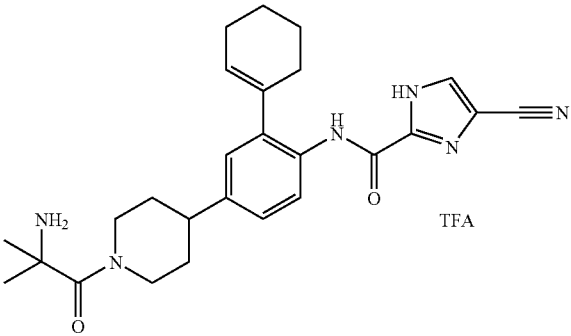 [SMILES: "TFA" ; CC(C)(N)C(=O)N1CCC(c2ccc(NC(=O)c3nc(C#N)c[nH]3)c(C3=CCCCC3)c2)CC1] |

| | Name | Structure |
|---|---|---|
| 58 | 5-Cyano-1H-imidazole-2-carboxylic acid [6-cyclohex-1-enyl-1'-(2-methanesulfonyl-ethyl)-1',2',3',4',5',6'-hexahydro-[2,4']bipyridinyl-5-yl]-amide | 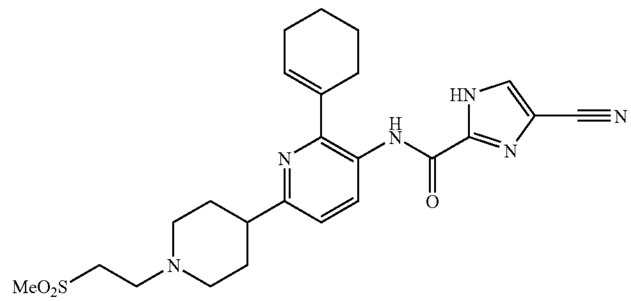 [SMILES: CS(=O)(=O)CCN1CCC(c2ccc(NC(=O)c3nc(C#N)c[nH]3)c(C3=CCCCC3)n2)CC1] |

EXAMPLE 1

5-Cyano-furan-2-carboxylic acid

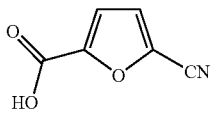

To a flask with a stir bar and Vigreaux column under Ar was added 2-formyl-5-furancarboxylic acid (2.8 g, 20 mmol), hydroxylamine hydrochloride (2.7 g, 40 mmol), and dry pyridine (50 mL). The mixture was heated to 85° C., acetic anhydride (40 mL) was added and the mixture was stirred for 3 h. After cooling to 60° C., water (250 mL) was added and the mixture was stirred at RT for 70 h. The mixture was acidified to pH 2 with concentrated hydrochloric acid and extracted with 3:1 dichloromethane-isopropanol (8×100 mL). The combined organic layers were washed with water (100 mL), brine (100 mL), dried over anh sodium sulfate and concentrated in vacuo to afford the title compound as a tan solid (1.26 g, 46%). $^1$H-NMR (CD$_3$OD; 400 MHz): δ 14.05 (br s, 1H), 7.74 (d, 1H, J=3.8 Hz), 7.42 (d, 1H, J=3.8 Hz).

EXAMPLE 2

4-Cyano-1H-pyrrole-2-carboxylic acid

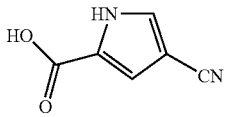

The title compound was prepared by the literature procedure (Loader and Anderson, Canadian J. Chem. 59: 2673 (1981)). $^1$H-NMR (CDCl$_3$; 400 MHz): δ 12.70 (br s, 1H), 7.78 (s, 1H), 7.13 (s, 1H).

EXAMPLE 3

4-Cyano-1-(2-trimethylsilanyl-ethoxymethyl)-1H-imidazole-2-carboxylate potassium salt

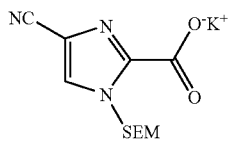

a) 1-(2-Trimethylsilanyl-ethoxymethyl)-1H-imidazole-4-carbonitrile

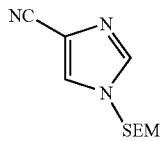

A flask charged with imidazole-4-carbonitrile (0.5 g, 5.2 mmol) (Synthesis, 677, 2003), 2-(trimethylsilyl)ethoxymethyl chloride (SEMCl) (0.95 mL, 5.3 mmol), K$_2$CO$_3$ (1.40 g, 10.4 mmol), and acetone (5 mL) was stirred for 10 h at RT. The mixture was diluted with EtOAc (20 mL) and washed with water (20 mL) and brine (20 mL) and the organic layer dried over MgSO$_4$. The crude product was eluted from a 20-g SPE cartridge (silica) with 30% EtOAc/hexane to give 0.80 g (70%) of the title compound as a colorless oil. Mass spectrum (CT (CH$_4$), m/z) Calcd. for C$_{10}$H$_{17}$N$_3$OSi, 224.1 (M+H). found 224.1.

b) 2-Bromo-1-(2-trimethylsilanyl-ethoxymethyl)-1H-imidazole-4-carbonitrile

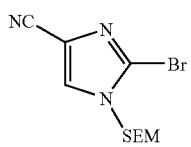

To a solution of 1-(2-trimethylsilanyl-ethoxymethyl)-1H-imidazole-4-carbonitrile (0.70 g, 3.1 mmol) (as prepared in the previous step) in CCl$_4$ (10 mL) was added NBS (0.61 g, 3.4 mmol) and AIBN (cat), and the mixture heated at 60° C. for 4 h. The reaction was diluted with EtOAc (30 mL) and washed with NaHCO$_3$ (2×30 mL) and brine (30 mL) and the organic layer was dried over Na$_2$SO$_4$ and then concentrated. The title compound was eluted from a 20-g SPE cartridge (silica) with 30% EtOAc/hexane to give 0.73 g (77%) of a yellow solid. Mass spectrum (CI (CH$_4$), m/z) Calcd. for C$_{10}$H$_{16}$BrN$_3$OSi, 302.0/304.0 (M+H). found 302.1/304.1.

c) 4-Cyano-1-(2-trimethylsilanyl-ethoxymethyl)-1H-imidazole-2-carboxylic acid ethyl ester

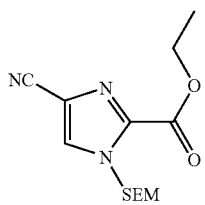

To a solution of 2-bromo-1-(2-trimethylsilanyl-ethoxymethyl)-1H-imidazole-4-carbonitrile (0.55 g, 1.8 mmol) (as prepared in the previous step) in THF (6 mL) at −40° C. was added drop wise a solution of 2M i-PrMgCl in THF (1 mL). The reaction was allowed to stir for 10 min at −40° C. and then cooled to −78° C., and ethyl cyanoformate (0.3 g, 3.0 mmol) was added. The reaction allowed to attain RT and stirred for 1 h. The reaction was quenched with satd aq NH$_4$Cl, diluted with EtOAc (20 mL) and washed with brine (2×20 mL), and the organic layer was dried over Na$_2$SO$_4$ and then concentrated. The title compound was eluted from a 20-g SPE cartridge (silica) with 30% EtOAc/hexane to give 0.4 g (74%) of a colorless oil. Mass spectrum (ESI, m/z): Calcd. for C$_{13}$H$_{21}$N$_3$O$_3$Si, 296.1 (M+H). found 296.1.

d) 4-Cyano-1-(2-trimethylsilanyl-ethoxymethyl)-1H-imidazole-2-carboxylate potassium salt

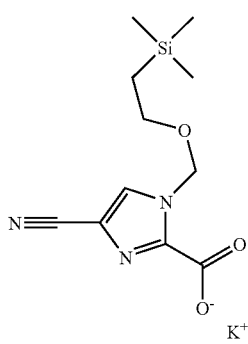 [SMILES: C[Si](C)(C)CCOCn1cc(C#N)nc1C(=O)[O-] ; [K+]]

To a solution of 4-cyano-1-(2-trimethylsilanyl-ethoxymethyl)-1H-imidazole-2-carboxylic acid ethyl ester (0.4 g, 1.3 mmol) (as prepared in the previous step) in ethanol (3 mL) was added a solution of 6M KOH (0.2 mL) and the reaction was stirred for 10 min and then concentrated to give 0.40 g (100%) of the title compound as a yellow solid. $^1$H-NMR (400 MHz, CD$_3$OD) δ 7.98 (s, 1H), 5.92 (s, 2H), 3.62 (m, 2H), 0.94 (m, 2H), 0.00 (s, 9H). Mass spectrum (ESI-neg, m/z) Calcd. for C$_{11}$H$_{17}$N$_3$O$_3$Si, 266.1 (M−H). found 266.0.

EXAMPLE 4

5-Cyano-furan-2-carboxylic acid [4-(4-methyl-piperazin-1-yl)-2-(3-methyl-thiophen-2-yl)-phenyl]-amide

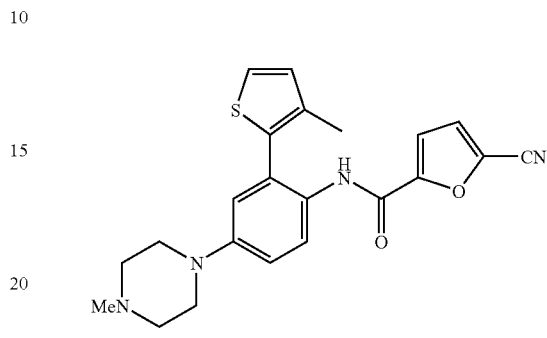

a) 1-(3-Bromo-4-nitro-phenyl)-4-methyl-piperazine

2-Bromo-4-fluoronitrobenzene (949 mg, 4.31 mmol) was added in two portions to neat N-methypiperazine (8 mL) at 0° C. and allowed to warm to room temperature. The reaction was heated to 60° C. for 1 h, and then it was diluted with 50 mL of EtOAc and poured into H$_2$O (50 mL). The layers were separated and the organic layer was washed with satd aq NaHCO$_3$, dried (Na$_2$SO$_4$), and concentrated in vacuo to afford 580 mg (45%) of the title compound as a yellow solid: Mass spectrum (ESI, m/z): Calcd. for C$_{11}$H$_{14}$BrN$_3$O$_2$, 300.0 (M+H). found 300.1.

b) 4,4,5,5-Tetramethyl-2-(3-methyl-thiophen-2-yl)-[1,3,2]dioxaborolane

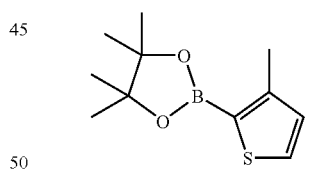

To a stirred solution of 2-bromo-3-methylthiophene (337 mg, 1.9 mmol) in 8 mL of THF at −40° C. was added n-BuLi (0.8 mL, 2.5 M/hexanes), and the reaction was allowed to stir for 30 min. At this time 2-isopropoxy-4,4,5,5-tetramethyl-[1,3,2]dioxaborolane (775 μL, 3.8 mmol) was added, and the reaction was allowed to warm to ambient temperature, and stirring was continued for 1 h. The reaction was then cooled to 0° C. and quenched with satd aq NaHCO$_3$ (10 mL). The mixture was poured into EtOAc (100 mL), washed with H$_2$O (2×50 mL), dried (Na$_2$SO$_4$) and concentrated in vacuo. Purification of the residue by silica gel preparative thin layer chromatography (20% EtOAc-hexanes) afforded 224 mg (53%) of the title compound as an oil. $^1$H-NMR (CDCl$_3$; 400 MHz): δ 1.36 (s, 12H), 2.5 (s, 3H), 6.99 (d, 1H, J=4.8 Hz), 7.50 (d, 1H, J=4.8 Hz).

c) 1-Methyl-4-[3-(3-methyl-thiophen-2-yl)-4-nitro-phenyl]-piperazine

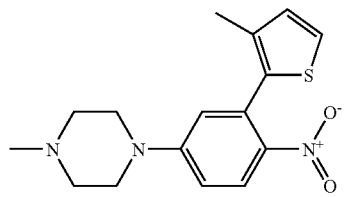 [SMILES: Cc1ccsc1-c1cc(N2CCN(C)CC2)ccc1[N+](=O)[O-]]

To a flask containing 1-(3-bromo-4-nitro-phenyl)-4-methyl-piperazine (68 mg, 0.2 mmol, as prepared in Example 4, step (a)), 4,4,5,5-tetramethyl-2-(3-methyl-thiophen-2-yl)-[1,3,2]dioxaborolane (61 mg, 0.27 mmol, as prepared in the previous step) and Pd(PPh$_3$)$_4$ (14 mg, 6 mol %) was charged toluene (3 mL), ethanol (3 mL) and 2M Na$_2$CO$_3$ (4 mL). The resultant mixture was heated at 80° C. for 2 h and then poured into EtOAc (25 mL). The organic layer was separated, dried (Na$_2$SO$_4$) and concentrated in vacuo. Purification by silica gel preparative thin layer chromatography (EtOAc) afforded 40 mg (63%) of the title compound as a light yellow solid. Mass spectrum (ESI, m/z): Calcd. for C$_{16}$H$_{19}$N$_3$O$_2$S, 318.1 (M+H). found 318.2.

d) 5-Cyano-furan-2-carboxylic acid [4-(4-methyl-piperazin-1-yl)-2-(3-methyl-thiophen-2-yl)-phenyl]-amide

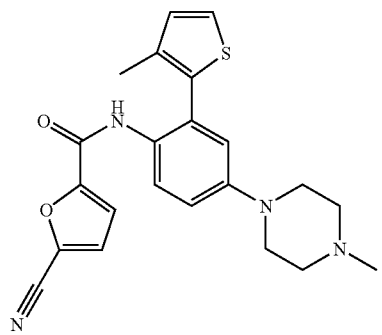 [SMILES: Cc1ccsc1-c1cc(N2CCN(C)CC2)ccc1NC(=O)c1ccc(C#N)o1]

1-Methyl-4-[3-(3-methyl-thiophen-2-yl)-4-nitro-phenyl]-piperazine (60 mg, 0.18 mmol, as prepared in the previous step) was stirred with 40 mg 5% Pd—C in MeOH (5 mL) under H$_2$ (1 atm) for 2 h. The reaction was filtered through Celite and concentrated in vacuo to afford 40 mg (72%) of 4-(4-methyl-piperazin-1-yl)-2-(3-methyl-thiophen-2-yl)-phenylamine as a brown solid, which was used immediately without further purification. Using a procedure similar to Example 9, step (c), 4-(4-methyl-piperazin-1-yl)-2-(3-methyl-thiophen-2-yl)-phenylamine (40 mg, 0.13 mmol) was allowed to react with 5-cyano-furan-2-carbonyl chloride (30 mg, 0.19 mmol, as prepared in Example 9, step (c)) in the presence of DIEA (61 µL, 0.34 mmol) to afford 18.9 mg (36%) of the title compound as a yellow solid. $^1$H-NMR (CDCl$_3$; 400 MHz): δ 2.13 (s, 3H), 2.38 (s, 3H), 2.59-2.62 (m, 4H), 3.24-3.27 (m, 4H), 6.92 (d, 1H, J=2.8 Hz), 7.06 (d, 1H, J=5.1 Hz), 7.15 (d, 1H, J=3.7 Hz), 7.19 (d, 1H, J=3.7 Hz), 7.02 (dd, 1H, J=2.8, 9.0 Hz), 7.42 (d, 1H, J=5.1 Hz), 8.11 (s, 1H), 8.34 (d, 1H, J=9.0 Hz); Mass spectrum (ESI, m/z): Calcd. for C$_{22}$H$_{22}$N$_4$O$_2$S, 407.1 (M+H). found 407.1.

EXAMPLE 5

5-Cyano-furan-2-carboxylic acid [4-(4-methyl-piperazin-1-yl)-2-(4-methyl-thiophen-3-yl)-phenyl]-amide

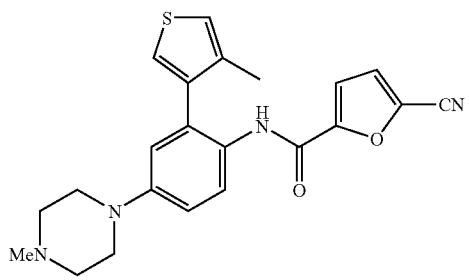 [SMILES: Cc1cscc1-c1cc(N2CCN(C)CC2)ccc1NC(=O)c1ccc(C#N)o1]

a) 4,4,5,5-Tetramethyl-2-(2-methyl-thiophen-3-yl)-[1,3,2]dioxaborolane

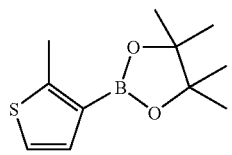

Using a procedure similar to Example 4, step (b), 3-bromo-4-methylthiophene (571 mg, 3.2 mmol) was treated with n-BuLi (1.41 mL, 2.5M/hexanes) and then allowed to react with 2-isopropoxy-4,4,5,5-tetramethyl-[1,3,2]dioxaborolane (775 µL, 3.8 mmol) to afford 189 mg (26%) of the title compound as a colorless oil. $^1$H-NMR (CDCl$_3$; 400 MHz): δ 1.32 (s, 12H), 2.42 (s, 3H), 6.90-6.91 (m, 1H), 7.84 (d, 1H, J=2.9 Hz).

b) 1-Methyl-4-[3-(4-methyl-thiophen-3-yl)-4-nitro-phenyl]-piperazine

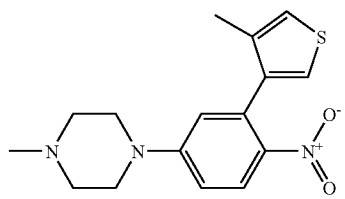 [SMILES: Cc1cscc1-c1cc(N2CCN(C)CC2)ccc1[N+](=O)[O-]]

Using a procedure similar to Example 4, step (c), 1-(3-bromo-4-nitro-phenyl)-4-methyl-piperazine (162 mg, 0.54 mmol), 4,4,5,5-tetramethyl-2-(2-methyl-thiophen-3-yl)-[1,3,2]dioxaborolane (145 mg, 0.64 mmol) and Pd(PPh$_3$)$_4$ (37 mg, 6 mol %) were allowed to react to afford 108 mg (71%) of the title compound as a yellow solid. $^1$H-NMR (CDCl$_3$; 400 MHz): δ 2.02 (s, 3H), 2.37 (s, 3H), 2.55-2.57 (m, 4H), 3.42-3.45 (m, 4H), 6.66 (d, 1H, J=2.8 Hz), 6.87 (s, 1H), 6.99-7.00 (m, 1H), 7.09 (d, 1H, J=3.2 Hz), 8.13 (d, 1H, J=9.2 Hz).

c) 4-(4-Methyl-piperazin-1-yl)-2-(4-methyl-thiophen-3-yl)-phenylamine

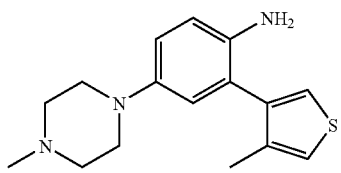 [SMILES: Cc1cscc1-c1cc(N2CCN(C)CC2)ccc1N]

Using a procedure similar to Example 4, step (d), 1-methyl-4-[3-(4-methyl-thiophen-3-yl)-4-nitro-phenyl]-piperazine (100 mg, 0.32 mmol) was stirred with 80 mg 5% Pd—C under H$_2$ to afford 82 mg (89%) of the title compound as a dark oil, which was used immediately without further purification spectrum (ESI, m/z): Calcd. for C$_{16}$H$_{21}$N$_3$S, 288.15 (M+H). found 288.1.

d) 5-Cyano-furan-2-carboxylic acid [4-(4-methyl-piperazin-1-yl)-2-(4-methyl-thiophen-3-yl)-phenyl]-amide

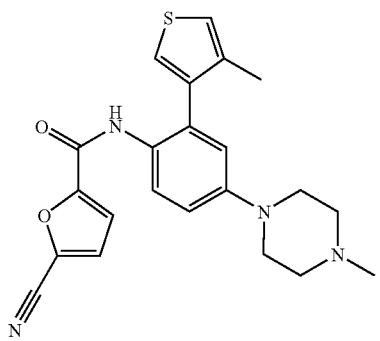 [SMILES: Cc1cscc1-c1cc(N2CCN(C)CC2)ccc1NC(=O)c1ccc(C#N)o1]

Using a procedure similar to Example 9, step (c), 5-cyano-furan-2-carbonyl chloride (64 mg, 0.41 mmol, as prepared in Example 9, step (c)) was allowed to react with 4-(4-methyl-piperazin-1-yl)-2-(4-methyl-thiophen-3-yl)-phenylamine (80 mg, 0.27 mmol, as prepared in the previous step) in the presence of DIEA (0.10 mL, 0.59 mmol) to afford 25.8 mg (24%) of the title compound as a yellow solid. $^1$H-NMR (CDCl$_3$; 400 MHz): δ 2.09 (s, 3H), 2.37 (s, 3H), 2.59-2.60 (m, 4H), 3.24-3.26 (m, 4H), 6.83 (d, 1H, J=2.9 Hz), 6.98-7.06 (m, 2H), 7.14-7.21 (m, 3H), 7.96 (s, 1H), 8.32 (d, 1H, J=9.0 Hz). Mass spectrum (ESI, m/z): Calcd. for C$_{22}$H$_{22}$N$_4$O$_2$S, 407.1 (M+H). found 407.1.

EXAMPLE 6

4-Cyano-1H-imidazole-2-carboxylic acid {2-cyclohex-1-enyl-4-[1-(2-hydroxy-1-hydroxymethyl-ethyl)-piperidin-4-yl]-phenyl}-amide trifluoroacetic acid salt

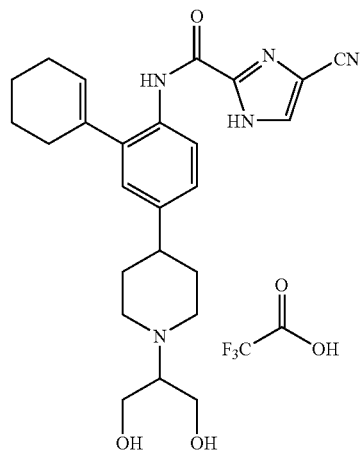

a) 4-Cyano-1H-imidazole-2-carboxylic acid {2-cyclohex-1-enyl-4-[1-(2,2-dimethyl-[1,3]dioxan-5-yl)-piperidin-4-yl]-phenyl}-amide To a slurry of 4-cyano-1H-imidazole-2-carboxylic acid (2-cyclohex-1-enyl-4-piperidin-4-yl-phenyl)-amide trifluoroacetic acid salt (81 mg, 0.16 mmol, as prepared in Example 14, step (b)) in CH$_2$Cl$_2$ (3 mL) was added NEt$_3$ (33µ, 0.24 mmol). The solution was then treated with 2,2-dimethyl-[1,3]dioxan-5-one (31 mg, 0.24 mmol) and the reaction was allowed to stir for 3 h. At this time NaBH(OAc)$_3$ (51 mg, 0.24 mmol) was added in one portion, and the reaction was allowed to stir for an additional 4 h. The reaction was diluted with H$_2$O (10 mL) and extracted with EtOAc (2×25 mL). The organic extracts were dried (Na$_2$SO$_4$) and concentrated in vacuo. Purification by silica gel preparative thin layer chromatography (10% MeOH—CHCl$_3$) afforded 22 mg (28%) of the title compound as an off-white semi-solid. Mass spectrum (ESI, m/z): Calcd. for C$_{28}$H$_{35}$N$_5$O$_3$, 490.2 (M+H). found 490.6.

b) 4-Cyano-1H-imidazole-2-carboxylic acid {2-cyclohex-1-enyl-4-[1-(2-hydroxy-1-hydroxymethyl-ethyl)-piperidin-4-yl]-phenyl}-amide trifluoro-acetic acid To a solution of 4-cyano-1H-imidazole-2-carboxylic acid {2-cyclohex-1-enyl-4-[1-(2,2-dimethyl-[1,3]dioxan-5-yl)-piperidin-4-yl]-phenyl}-amide (22 mg, 0.04 mmol, as prepared in the previous step) in THF—H$_2$O (1 mL, 4:1 v/v) was added TFA (0.4 mL), and the reaction was allowed to stir for 1 h. Removal of the solvent under vacuum afforded 14 mg (60%) of the title compound as an amber foam. $^1$H-NMR (CD$_3$OD, 400 MHz): δ 1.78-1.90 (m, 4H), 2.03-2.16 (m, 3H), 2.29 (br s, 4H), 2.88-2.96 (m, 1H), 3.37-3.40 (m, 1H), 3.46-3.53 (m, 2H), 3.74-3.78 (m, 3H), 5.83 (s, 1H), 7.13 (d, 1H, J=2.0 Hz), 7.22 (dd, 1H, J=2.0, 8.4 Hz), 8.03 (s, 1H), 8.17 (d, 1H, J=8.4 Hz); Mass spectrum (ESI, m/z): Calcd. for C$_{25}$H$_{31}$N$_5$O$_3$, 450.2 (M+H). found 450.2.

EXAMPLE 7

4-Cyano-1H-imidazole-2-carboxylic acid {2-cyclohex-1-enyl-4-[1-(2-morpholin-4-yl-acetyl)-piperidin-4-yl]-phenyl}-amide

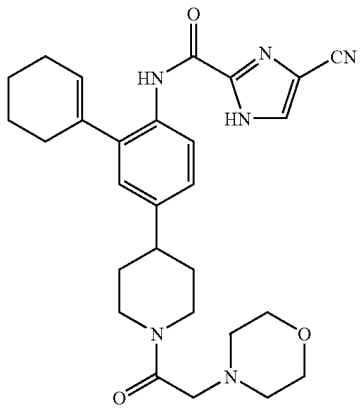 [SMILES: N#Cc1c[nH]c(C(=O)Nc2ccc(C3CCN(C(=O)CN4CCOCC4)CC3)cc2C2=CCCCC2)n1]

To a solution of morpholin-4-yl-acetic acid ethyl ester (117 mg, 0.67 mmol) in ethanol (4 mL) was added 6N KOH (110 μL, 0.67 mmol) via syringe and stirring was continued for 3 h. Concentration in vacuo afforded 122 mg (100%) of morpholin-4-yl-acetic acid potassium salt. To a mixture of morpholin-4-yl-acetic acid potassium salt (29 mg, 0.15 mmol), 4-cyano-1H-imidazole-2-carboxylic acid (2-cyclohex-1-enyl-4-piperidin-4-yl-phenyl)-amide trifluoroacetic acid salt (65.1 mg, 0.13 mmol, as prepared in Example 14, step (b)) and PyBroP (93 mg, 0.19 mmol) in CH$_2$Cl$_2$ (4 mL) was added DIEA (51 μL, 0.29 mmol) and the reaction was allowed to stir overnight. The reaction was diluted with CH$_2$Cl$_2$ (50 mL), washed with H$_2$O (2×25 mL), dried (Na$_2$SO$_4$) and concentrated in vacuo. Purification of the crude product by silica gel preparative TLC afforded 8.1 mg (12%) of the title compound as a white solid. $^1$H-NMR (CDCl$_3$; 400 MHz): δ 1.68-2.04 (m, 5H), 2.20-2.29 (m, 4H), 2.53-2.78 (m, 5H), 3.09-3.23 (m, 6H), 3.35-3.40 (m, 1H), 3.72 (br s, 4H), 4.16-4.22 (m, 1H), 4.73-4.77 (m, 1H), 5.82 (s, 1H), 7.00 (s, 1H), 7.12 (dd, 1H, J=0.6, 8.0 Hz), 7.73 (s, 1H), 8.27 (d, 1H, J=8.1 Hz), 9.48 (s, 1H); Mass spectrum (ESI, m/z): Calcd. for C$_{28}$H$_{34}$N$_6$O$_3$, 503.27 (M+H). found 503.1.

EXAMPLE 8

4-Cyano-1H-imidazole-2-carboxylic acid {2-cyclohex-1-enyl-4-[1-(3-morpholin-4-yl-propionyl)-piperidin-4-yl]-phenyl}-amide

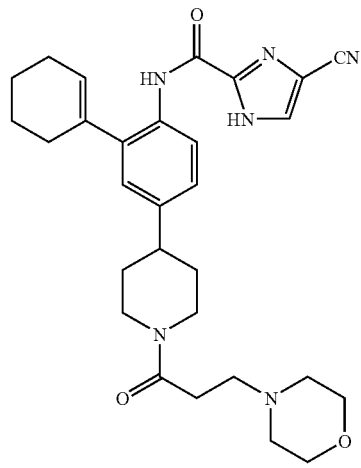 [SMILES: N#Cc1c[nH]c(C(=O)Nc2ccc(C3CCN(C(=O)CCN4CCOCC4)CC3)cc2C2=CCCCC2)n1]

To a flask containing 3-morpholin-4-yl-propionic acid potassium salt (94 mg, 0.47 mmol, prepared from 3-morpholin-4-yl-propionic acid ethyl ester exactly as described in Example 7, 4-cyano-1H-imidazole-2-carboxylic acid (2-cyclohex-1-enyl-4-piperidin-4-yl-phenyl)-amide trifluoroacetic acid salt (179 mg, 0.36 mmol, as prepared in Example 14 (b)), EDCI (83 mg, 0.43 mmol), and HOBT (68 mg, 0.5 mmol) was added DMF (4 mL). To the stirred slurry was added DIEA (157 μL, 0.9 mmol) and the reaction was allowed to stir overnight. The reaction was diluted with H$_2$O (10 mL) and extracted with EtOAc (2×25 mL). The combined organic extracts were dried (Na$_2$SO$_4$), concentrated in vacuo and the crude product was purified by silica gel preparative TLC to afford 10.4 mg (6%) of the title compound as a white solid. $^1$H-NMR (CDCl$_3$; 400 MHz): δ 1.49-1.93 (m, 5H), 2.22-2.31 (m, 3H), 2.52 (br s, 4H), 2.58-2.63 (m, 3H), 2.74-2.76 (m, 4H), 3.10-3.17 (m, 2H), 3.72 (br s, 4H), 3.97-4.02 (m, 2H), 4.76-4.81 (m, 2H), 5.81-5.82 (m, 1H), 6.81-6.82 (m, 1H), 6.99-7.00 (m, 1H), 7.09-7.13 (m, 1H), 7.70 (s, 1H), 8.26 (d, 1H, J=8.2 Hz), 9.51 (s, 1H); Mass spectrum (ESI, m/z): Calcd. for C$_{29}$H$_{36}$N$_6$O$_3$, 517.28 M+H). found 517.3.

EXAMPLE 9

5-Cyano-furan-2-carboxylic acid [2'-methyl-5-(4-methyl-piperazin-1-yl)-biphenyl-2-yl]-amide

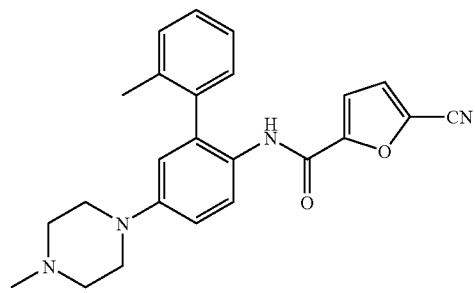 [SMILES: Cc1ccccc1-c1cc(N2CCN(C)CC2)ccc1NC(=O)c1ccc(C#N)o1]

a) 1-(3-Bromo-4-nitro-phenyl)-4-methyl-piperazine

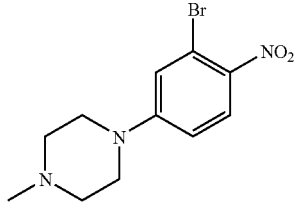 [SMILES: CN1CCN(c2ccc([N+](=O)[O-])c(Br)c2)CC1]

To a cooled (0° C.) solution of 1.00 g (4.55 mmol) of 2-bromo-4-fluoronitrobenzene (Oakwood) in 12 mL of EtOH was added 1.52 mL (13.7 mmol) of piperidine. The solution was stirred at 0° C. for 0.5 h and then at 60° C. for 4 h. The mixture was concentrated in vacuo, dissolved in EtOAc (60 mL), washed with water (3×100 mL) and brine (100 mL), and dried ($Na_2SO_4$). Concentration in vacuo and chromatography on a 50-g silica SPE column with 1-3% MeOH— dichloromethane afforded 1.06 g (77%) of the title compound as a tannish yellow solid. Mass spectrum (ESI, m/z): Calcd. for $C_1H_{14}BrN_3O_2$, 300.0 (M+H, $^{79}Br$). found 300.1.

b) 1-Methyl-4-(2'-methyl-6-nitro-biphenyl-3-yl)-piperazine

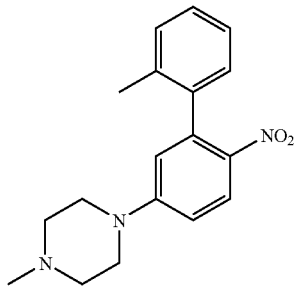 [SMILES: Cc1ccccc1-c1cc(N2CCN(C)CC2)ccc1[N+](=O)[O-]]

A mixture of 200 mg (0.666 mmol) 1-(3-bromo-4-nitro-phenyl)-4-methyl-piperazine (as prepared in the previous step), 136 mg (0.999 mmol) and 77.0 mg (0.0666 mmol) of tetrakis(triphenylphosphine)palladium (0) under Ar was added 4.0 mL of degassed dimethoxyethane (DME) and 400 µL (0.799 mmol) of 2.0 M aq $Na_2CO_3$. The mixture was heated with stirring under Ar at 80° C. for 14 h. The cooled (RT) mixture was concentrated and chromatographed on a 10-g silica SPE column with 1-5% MeOH in dichloromethane-hexane (1:1). The product fractions were treated with 80 mg of decolorizing carbon, filtered, concentrated, and then rechromatographed on a similar column with 1-3% EtOH-dichloromethane to afford 265 mg of the title compound as a yellow resin (75% purity by $^1H$-NMR as a mixture with triphenylphosphine) that was used in the following reaction without further purification: Mass spectrum (ESI, m/z): Calcd. for $C_{11}H_{21}N_3O_3$, 312.2 (M+H). found 312.2.

c) 5-Cyano-furan-2-carboxylic acid [2'-methyl-5-(4-methyl-piperazin-1-yl)-biphenyl-2-yl]-amide

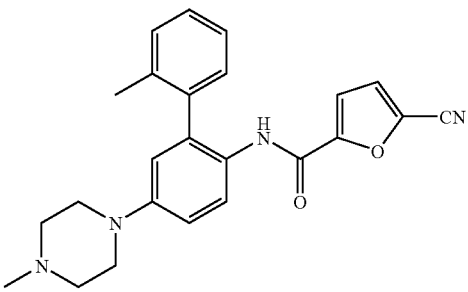

A mixture of 140 mg (0.337 mmol based on 75% purity) of 1-methyl-4-(2'-methyl-6-nitro-biphenyl-3-yl)-piperazine (as prepared in the previous step) and 70 mg of 10% palladium on carbon (Degussa type E101-NE/W, Aldrich, 50% by weight water) in 5 mL of THF was stirred vigorously under a balloon of hydrogen for 1 h. The mixture was filtered (Celite), washed with dichloromethane (2×2 mL), and the solution of the resulting aniline was placed under Ar and used immediately in the following reaction.

Simultaneously to the above reduction, 55.4 mg (0.404 mmol) of 5-cyanofuran-2-carboxylic acid (as prepared in Example 1) in 2.5 mL of anh dichloromethane under a $CaSO_4$ drying tube was treated with 52.9 µL (0.606 mmol) of oxalyl chloride followed by 10 µL of anh DMF. The solution was stirred for 25 min and quickly concentrated in vacuo at 20-25° C. The resulting 5-cyano-furan-2-carbonyl chloride was placed under high vacuum for 2-3 min and then immediately placed under Ar, cooled to 0° C. in an ice bath, and treated with the aniline solution produced above followed by 141 µL (0.808 mmol) of N,N-diisopropylethylamine (DIEA). After stirring for 30 min at RT, the mixture was concentrated in vacuo, and the resulting residue was chromatographed on a 20-g silica SPE column with 2-10% EtOH— dichloromethane to give a yellow resin (which was crystallized from EtOAc-hexane) to afford 17.2 mg (13%) of the pure title compound as a yellow solid along with 70.3 mg of impure title compound. The impure fraction was dissolved in 50 mL of EtOAc, washed with satd aq $NaHCO_3$-1M $K_2CO_3$ (1:1, 2×20 mL) and brine (20 mL), dried ($Na_2SO_4$) and concentrated to afford 43.4 mg (32%) additional title compound as a crystalline yellow solid (total yield 45%). $^1$H-NMR ($CDCl_3$; 400 MHz): δ 8.32 (d, 1H, J=9.0 Hz), 7.73 (br s, 1H), 7.34-7.54 (m, 3H), 7.25 (d, 1H, J=7.7 Hz), 7.12, 7.14 (AB q, 2H, J=3.7 Hz), 7.01 (dd, 1H, J=9.0, 2.8 Hz), 3.25-3.27 (m, 4H), 2.59-2.62 (m, 4H), 2.38 (s, 3H), and 2.15 (s, 3H). Mass spectrum (ESI, m/z): Calcd. for $C_{21}H_{24}N_4O_3$, 401.2 (M+H). found 401.1.

EXAMPLE 10

5-Cyano-furan-2-carboxylic acid [2'-fluoro-5-(4-methyl-piperazin-1-yl)-biphenyl-2-yl]-amide

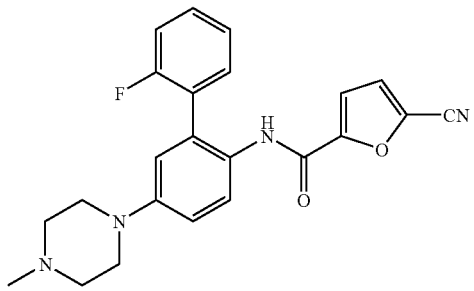

a) 1-(2'-Fluoro-6-nitro-biphenyl-3-yl)-4-methyl-piperazine

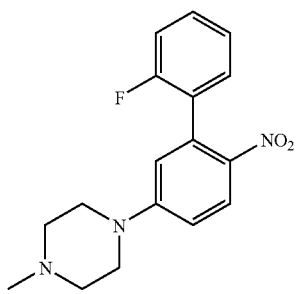

The procedure of Example 9, step (b) was followed using 75.0 mg (0.250 mmol) 1-(3-bromo-4-nitro-phenyl)-4-methyl-piperazine (as prepared in Example 9, step (a)), 136 mg (0.999 mmol) 2-fluorophenylboronic acid, 26.8 mg (0.0232 mmol) of tetrakis(triphenylphosphine)palladium (0) and 400 µL (0.799 mmol) of 2.0 M aq $Na_2CO_3$ in DME except the mixture was heated for 22 h. Chromatography on a 5-g silica SPE column with 1-5% MeOH in dichloromethane-hexane (1:1) afforded 95.0 mg of the title compound (76% purity by $^1$H-NMR as a mixture with triphenylphosphine) as a yellow resin that was used in the following reaction without further purification. Mass spectrum (ESI, m/z): Calcd. for $C_{17}H_{18}FN_3O_3$, 316.1 (M+H). found 316.2.

b) 5-Cyano-furan-2-carboxylic acid [2'-fluoro-5-(4-methyl-piperazin-1-yl)-biphenyl-2-yl]-amide

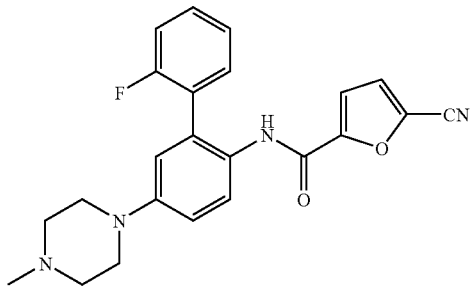

The procedure of Example 9, step (c) was followed using 93.2 mg (0.225 mmol based on 76% purity) of 1-(2'-fluoro-6-nitro-biphenyl-3-yl)-4-methyl-piperazine (as prepared in the previous step), 46 mg of 10% palladium on carbon, 37.0 mg (0.270 mmol) of 5-cyanofuran-2-carboxylic acid (as prepared in Example 1), 35.3 µL (0.405 mmol) of oxalyl chloride, 5.0 µL of anh DMF, and 94.1 µL (0.540 mmol) of DIEA. Chromatography on a 5-g silica SPE column with 1-4% MeOH— dichloromethane afforded 69.8 mg (77%) of the title compound as a yellow resin. $^1$H-NMR (CDCl$_3$; 400 MHz): δ 8.04 (d, 1H, J=9.0 Hz), 7.93 (br s, 1H), 7.434-7.48 (m, 1H), 7.37 (td, 1H, J=7.5, 1.8 Hz), 7.22-7.31 (m, 2H), 7.13, 7.18 (AB q, 2H, J=3.7 Hz), 7.02 (dd, 1H, J=9.0, 2.9 Hz), 6.88 (d, 1H, J=2.9 Hz), 3.24-3.27 (m, 4H), 2.57-2.60 (m, 4H), and 2.36 (s, 3H). Mass spectrum (ESI, m/z): Calcd. for $C_{23}H_{21}FN_4O_2$, 405.2 (M+H). found 405.2.

EXAMPLE 11

5-Cyano-furan-2-carboxylic acid [2-cyclohex-1-enyl-4-(4-methyl-piperazin-1-yl)-phenyl]-amide

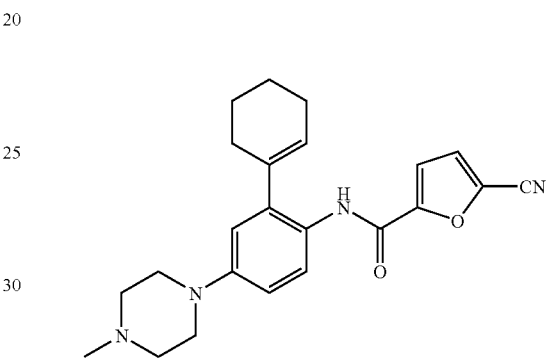

a) 1-(3-Cyclohex-1-enyl-4-nitro-phenyl)-4-methyl-piperazine

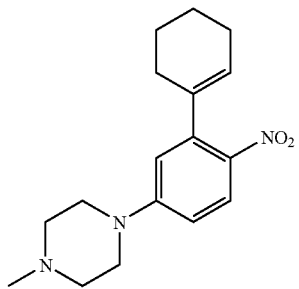 [SMILES: CN1CCN(c2ccc([N+](=O)[O-])c(C3=CCCCC3)c2)CC1]

A mixture of 102 mg (0.340 mmol) 1-(3-bromo-4-nitro-phenyl)-4-methyl-piperazine (as prepared in Example 9, step (a)), 59.7 mg (0.474 mmol) cyclohexen-1-ylboronic acid, 43.8 mg (0.0379 mmol) of tetrakis(triphenylphosphine)palladium (0) under Ar was treated with 206 µL (0.412 mmol) of 2.0 M degassed aq $Na_2CO_3$, 0.6 mL degassed anh toluene and 0.2 mL degassed anh EtOH and the mixture was heated at 100° C. for 21 h. After cooling to RT, the mixture was poured into EtOAc (10 mL), washed with brine (10 mL), dried ($Na_2SO_4$) and concentrated in vacuo. Chromatography on a 5-g silica SPE column with 1-3% EtOH in dichloromethane afforded 126 mg of the title compound (74% purity by RP-HPLC (C18 column) as a mixture with triphenylphosphine) as a yellow oil that was used in the following reaction without further purification. Mass spectrum (ESI, m/z): Calcd. for $C_{17}H_{23}N_3O_3$, 302.2 (M+H). found 302.2.

b) 5-Cyano-furan-2-carboxylic acid [2-cyclohex-1-enyl-4-(4-methyl-piperazin-1-yl)-phenyl]-amide

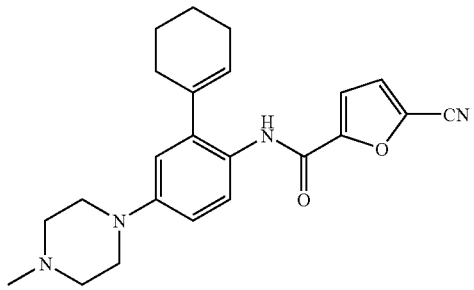 [SMILES: CN1CCN(c2ccc(NC(=O)c3ccc(C#N)o3)c(C3=CCCCC3)c2)CC1]

To 122 mg (0.299 mmol based on 74% purity) of 1-(3-cyclohex-1-enyl-4-nitro-phenyl)-4-methyl-piperazine (as prepared in the previous step) in 5.0 mL of EtOH-water (2:1) was added 83.8 mg (1.50 mmol) of iron powder and 160 mg (2.99 mmol) of NH$_4$Cl and the mixture refluxed under Ar for 12 h. An additional 83.8 mg (1.50 mmol) of iron powder was added, and the mixture was refluxed for 1 h. The mixture was poured into EtOAc (12 mL), filtered (Celite), washed with EtOAc (2×4 mL), concentrated in vacuo and dissolved in anh THF (4.0 mL). The resulting aniline solution was placed under Ar and used immediately in the following reaction.

61.6 mg (0.449 mmol) of 5-cyanofuran-2-carboxylic acid (as prepared in Example 1) in 2.5 mL of anh dichloromethane under a CaSO$_4$ drying tube was treated with 60.0 µL (0.688 mmol) of oxalyl chloride followed by 10 µL of anh DMF. The solution was stirred for 25 min and quickly concentrated in vacuo at 20-25° C. The residue was placed under high vacuum for 2-3 min and then immediately placed under Ar, cooled to 0° C. in an ice bath and treated with the aniline solution produced above followed by 104 µL (0.598 mmol) of DIEA. After stirring 30 min at RT, the mixture was concentrated in vacuo, dissolved in EtOAc (20 mL), washed with 1M K$_2$CO$_3$ (2×10 mL) and brine (10 mL), dried (Na$_2$SO$_4$) and concentrated in vacuo. The resulting residue was chromatographed on a 10-g silica SPE column with 1-4% MeOH-dichloromethane to give a yellow resin which was then crystallized from Et$_2$O-hexane to afford 84.7 mg (72%) of the title compound as a crystalline yellow solid. $^1$H-NMR (CDCl$_3$; 400 MHz): δ 8.57 (br s, 1H), 8.26 (d, 1H, J=9.0 Hz), 7.20, 7.23 (AB q, 2H, J=3.7 Hz), 6.86 (dd, 1H, J=9.0, 2.9 Hz), 6.74 (d, 1H, J=2.9 Hz), 5.84-5.85 (m, 1H), 3.20-3.22 (m, 4H), 2.57-2.59 (m, 4H), 2.36 (s, 3H), 2.23-2.30 (m, 4H) and 1.79-1.84 (m, 4H). Mass spectrum (ESI, m/z): Calcd. for C$_{23}$H$_{26}$N$_4$O$_2$, 391.2 (M+H). found 391.2.

EXAMPLE 12

5-Cyano-furan-2-carboxylic acid [2-(3,6-dihydro-2H-pyran-4-yl)-4-(4-methyl-piperazin-1-yl)-phenyl-amide

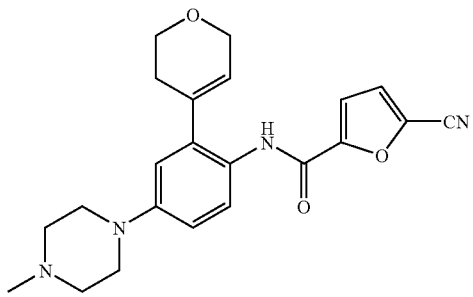 [SMILES: CN1CCN(c2ccc(NC(=O)c3ccc(C#N)o3)c(C3=CCOCC3)c2)CC1]

a) 1-[3-(3,6-Dihydro-2H-pyran-4-yl)-4-nitro-phenyl]-4-methyl-piperazine

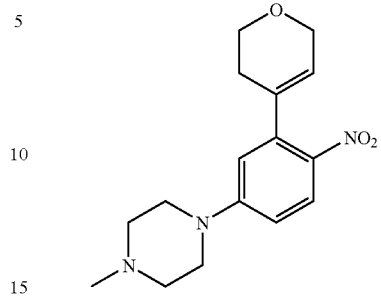

1-(3-Bromo-4-nitro-phenyl)-4-methyl-piperazine (as prepared in Example 9, step (a)) (225.1 mg, 0.79 mmol), K$_2$CO$_3$ (310.9 mg, 2.25 mmol) and 4-(4,4,5,5-tetramethyl-[1,3,2]dioxaborolan-2-yl)-3,6-dihydro-2H-pyran (Murata, M., et al, Synthesis, 778, (2000)) (157 mg, 0.75 mmol) in dioxane (5 mL) was heated at 80° C. overnight under Ar. The reaction mixture was allowed to cool to RT, concentrated, and the resulting residue was chromatographed on silica (10% EtOAc/hexane-20% MeOH/EtOAc) to obtain the title compound (82 mg, 36%). $^1$H-NMR (CDCl$_3$; 400 MHz): δ 8.04 (d, 1H, J=9.4 Hz), 6.78 (dd, 1H, J=9.4, 2.6 Hz), 6.58 (m, 1H, J=2.6 Hz), 5.58 (m, 1H), 4.34 (m, 2H), 3.95 (t, 2H, J=5.3 Hz), 3.46 (m, 4H), 2.57 (m, 4H), 2.38 (s, 3H), 2.30 (m, 2H).

b) 5-Cyano-furan-2-carboxylic acid [2-(3,6-dihydro-2H-pyran-4-yl)-4-(4-methyl-piperazin-1-yl)-phenyl-amide

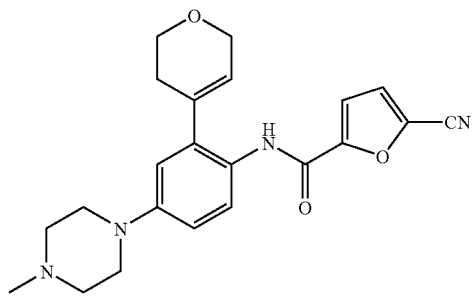 [SMILES: CN1CCN(c2ccc(NC(=O)c3ccc(C#N)o3)c(C3=CCOCC3)c2)CC1]

1-[3-(3,6-Dihydro-2H-pyran-4-yl)-4-nitro-phenyl]-4-methyl-piperazine (as prepared in previous step) (80 mg, 0.26 mmol) was converted to the corresponding amine using a procedure similar to Example 4, step (d), and coupled with 5-cyano-furan-2-carbonyl chloride as prepared in Example 9, step (c) (obtained from 137 mg, 1.00 mmol of 5-cyano-furan-2-carboxylic acid as prepared in Example 1) in CH$_2$Cl$_2$ (2 mL) at 0° C. The product was isolated by flash chromatography on silica (50% EtOAc/hexane-10% MeOH/EtOAc) to obtain the title compound (62.2 mg, 60%). $^1$H-NMR (CDCl$_3$; 400 MHz): δ 8.35 (br s, 1H), 8.12 (d, 1H each, J=8.76 Hz), 7.24 (d, 1H, J=5.08 Hz), 7.19 (d, 1H, J=5.08 Hz), 6.88 (dd, 1H, J=8.76, 2.7 Hz), 6.73 (d, 1H, J=2.7 Hz), 5.88 (br s, 1H), 4.34 (m, 2H), 3.94 (t, 2H, J=5.3 Hz), 3.23 (m, 4H), 2.59 (m, 4H), 2.38 (br s, 5H). LC-MS (ESI, m/z): Calcd. for C$_{22}$H$_{24}$N$_4$O$_3$, 393.1 (M+H). found 393.2.

EXAMPLE 13

4-Cyano-1H-pyrrole-2-carboxylic acid (2-cyclohex-1-enyl-4-piperidin-4-yl-phenyl)-amide trifluoroacetic acid salt

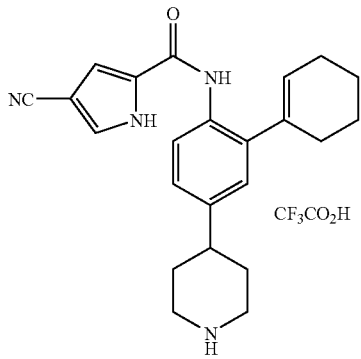

a) 4-(4-Amino-phenyl)-3,6-dihydro-2H-pyridine-1-carboxylic acid tert-butyl ester

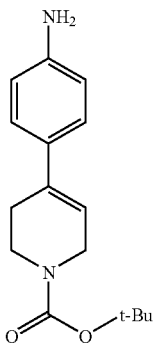 [SMILES: CC(C)(C)OC(=O)N1CC=C(c2ccc(N)cc2)CC1]

The title compound was prepared by Suzuki coupling of 4-(4,4,5,5-tetramethyl-[1,3,2]dioxaborolan-2-yl)-phenylamine with 4-trifluoromethanesulfonyloxy-3,6-dihydro-2H-pyridine-1-carboxylic acid tert-butyl ester (Synthesis, 993, (1991)) according to the procedure in Example 35, step (b). Mass spectrum (ESI, m/z): Calcd. for $C_{16}H_{22}N_2O_2$, 275.2 (M+H). found 275.1.

b) 4-(4-Amino-phenyl)-piperidine-1-carboxylic acid tert-butyl ester

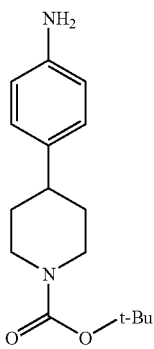 [SMILES: CC(C)(C)OC(=O)N1CCC(c2ccc(N)cc2)CC1]

A solution of 4-(4-amino-phenyl)-3,6-dihydro-2H-pyridine-1-carboxylic acid tert-butyl ester (0.35 g, 1.2 mmol) (as prepared in the previous step) in methanol was hydrogenated over 10% Pd/C at 20 psi for 1 h. The solution was filtered and concentrated to give 0.35 g (100%) of the title compound as a yellow solid: Mass spectrum (ESI, m/z): Calcd. for $C_{16}H_{24}N_2O_2$, 277.2 (M+H). found 277.1.

c) 4-(4-Amino-3-bromo-phenyl)-piperidine-1-carboxylic acid tert-butyl ester

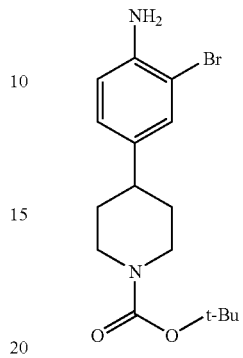

To a solution of 4-(4-amino-phenyl)-piperidine-1-carboxylic acid tert-butyl ester (0.20 g, 0.71 mmol) (as prepared in the previous step) in DCM (3 mL) was added N-bromosuccinimide (NBS) (0.13 g, 0.71 mmol), and the reaction stirred at RT for 10 h. The reaction was diluted with EtOAc (10 mL) and washed with NaHCO$_3$ (2×10 mL) and brine (10 mL). Concentration of the organic layer gave 0.26 g (100%) of the title compound as a yellow foam. Mass spectrum (ESI, m/z): Calcd. for $C_{16}H_{23}BrN_2O_2$, 355.1 (M+H). found 355.1.

d) 4-(4-Amino-3-cyclohex-1-enyl-phenyl)-piperidine-1-carboxylic acid tert-butyl ester

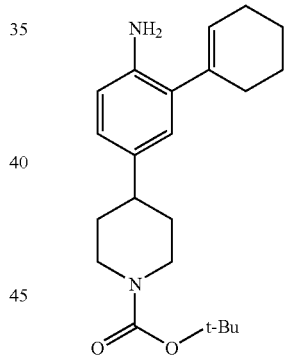

A flask was charged with 4-(4-amino-3-bromo-phenyl)-piperidine-1-carboxylic acid tert-butyl ester (0.13 g, 0.36 mmol) (as prepared in the previous step), cyclohex-1-enyl boronic acid (0.060 g, 0.48 mmol), Pd(PPh$_3$)$_4$ (0.04 g, 10 mol %), aqueous 2M Na$_2$CO$_3$ (1.5 mL), ethanol (1.5 mL), and toluene (3 mL), and heated at 80° C. for 3 h. The reaction was diluted EtOAc (10 mL), washed with NaHCO$_3$ (2×10 mL) and brine (10 mL), and the organic layer was dried over Na$_2$SO$_4$ and then concentrated. The title compound was eluted from a 20-g SPE cartridge (silica) with 30% EtOAc/hexane to give 0.010 g (85%) of the title compound as a yellow oil. Mass spectrum (ESI, m/z): Calcd. for $C_{22}H_{32}N_2O_2$, 357.2 (M+H). found 357.1.

e) 4-Cyano-1H-pyrrole-2-carboxylic acid (2-cyclohex-1-enyl-4-piperidin-4-yl-phenyl)-amide trifluoroacetic acid salt A flask was charged with 4-(4-amino-3-cyclohex-1-enyl-phenyl)-piperidine-1-carboxylic acid tert-butyl ester (0.050 g, 0.14 mmol) (as prepared in the previous step), 4-cyano-1H-pyrrole-2-carboxylic acid (0.019 g, 0.14 mmol)(as prepared in Example 2), EDCI (0.040 g, 0.21 mmol), HOBt (0.019 g, 0.14 mmol), DIEA (0.073 mL, 0.42 mmol), and DCM (0.5 mL) and stirred at 25° C. for 10 h. The reaction was loaded directly on a 10-g solid phase extraction (SPE) cartridge (silica) and the resulting intermediate was eluted with 30% EtOAc/hexane. This compound was stirred at RT for 1 h in 50% TFA/DCM (2 mL) and then concentrated and purified by RP-HPLC (C18), eluting with 30-50% $CH_3CN$ in 0.1% $TFA/H_2O$ over 12 min to give the title compound (0.052 g, 77%). $^1$H-NMR (400 MHz, $CD_3OD$): δ 7.59 (s, 1H), 7.50 (d, 1H), 7.22 (d, 1H), 7.16 (m, 2H), 5.74 (m, 1H), 3.54. (m, 2H), 3.16 (m, 2H), 2.94 (m, 1H), 2.29 (m, 2H), 2.15 (m, 4H), 1.92 (m, 2H), 1.72 (m, 4H). Mass spectrum (ESI, m/z): Calcd. for $C_{23}H_{26}N_4O$, 375.2 (M+H). found 375.1.

EXAMPLE 14

4-Cyano-1H-imidazole-2-carboxylic acid (2-cyclohex-1-enyl-4-piperidin-4-yl-phenyl)-amide trifluoroacetic acid salt

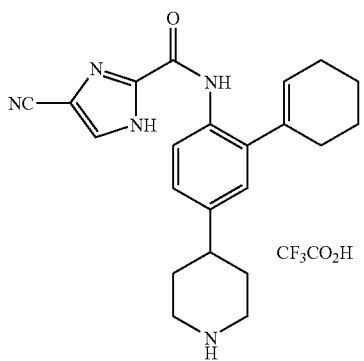

a) 4-(4-{[4-Cyano-1-(2-trimethylsilanyl-ethoxymethyl)-1H-imidazole-2-carbonyl]-amino}-3-cyclohex-1-enyl-phenyl)-piperidine-1-carboxylic acid tert-butyl ester

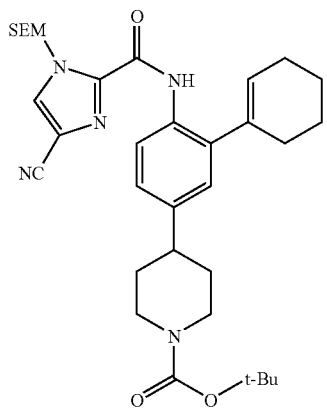

To a solution of 4-cyano-1-(2-trimethylsilanyl-ethoxymethyl)-1H-imidazole-2-carboxylate potassium salt (3.34 g, 10.9 mmol) (as prepared in Example 3, step (d)) in 20 mL DCM was added DIEA (3.8 mL, 21.8 mmol) and PyBroP (5.6 g, 12.0 mmol), and the reaction stirred at 25° C. for 15 min. A solution of 4-(4-amino-3-cyclohex-1-enyl-phenyl)-piperidine-1-carboxylic acid tert-butyl ester (3.9 g, 10.9 mmol) (as prepared in Example 13, step (d)) in 10 mL DCM was added and the reaction stirred for 8 h at 25° C. The reaction was diluted EtOAc (60 mL) and washed with $NaHCO_3$ (2×60 mL) and brine (100 mL) and the organic layer was dried over $Na_2SO_4$ and then concentrated. The title compound was purified by flash chromatography (silica gel, 2% EtOAc/DCM) to give 5.5 g (85%) of the title compound as a yellow oil. Mass spectrum (ESI, m/z): Calcd. for $C_{33}H_{47}N_5O_4Si$, 606.2 (M+H). found 606.2.

b) 4-Cyano-1H-imidazole-2-carboxylic acid (2-cyclohex-1-enyl-4-piperidin-4-yl-phenyl)-amide trifluoroacetic acid salt To a solution of 4-(4-{[4-cyano-1-(2-trimethylsilanyl-ethoxymethyl)-1H-imidazole-2-carbonyl]-amino}-3-cyclohex-1-enyl-phenyl)-piperidine-1-carboxylic acid tert-butyl ester (1.5 g, 2.5 mmol) (as prepared in the previous step) in 10 mL of DCM and 0.3 mL EtOH was added 3 mL of TFA and the solution stirred for 3 h at 25° C. The reaction was diluted with 5 mL of EtOH and then concentrated. The residue was crystallized from methanol and ethyl ether to give 0.85 g (70%) of the title compound as a white solid. $^1$H-NMR (400 MHz, $CD_3OD$) δ 8.18 (d, 1H), 8.04 (s, 1H), 7.22 (dd, 1H), 7.12 (d, 1H), 5.76 (m, 1H), 3.54. (m, 2H), 3.16 (m, 2H), 2.92 (m, 1H), 2.30 (m, 4H), 2.10 (m, 2H), 1.75 (m, 6H). Mass spectrum (ESI, m/z): Calcd. for $C_{22}H_{25}N_5O$, 376.2 (M+H). found 376.2.

EXAMPLE 15

4-Cyano-1H-pyrrole-2-carboxylic acid [4-(1-acetyl-piperidin-4-yl)-2-cyclohex-1-enyl-phenyl]-amide

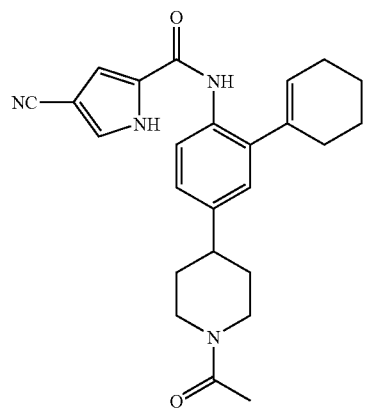

The title compound was prepared from 4-cyano-1H-pyrrole-2-carboxylic acid (2-cyclohex-1-enyl-4-piperidin-4-yl-phenyl)-amide trifluoroacetic acid salt (as prepared in Example 13, step (e)) according to the procedure in Example 37. $^1$H-NMR (400 MHz, $CDCl_3$) δ 10.82 (s, 1H), 8.28 (d, 1H), 8.18 (s, 1H), 7.48 (d, 1H), 7.16 (dd, 1H), 7.02 (s, 1H), 6.72 (s, 1H), 5.88 (m, 1H), 4.82 (m, 1H), 3.98. (m, 1H), 3.20 (m, 1H), 2.70 (m, 2H), 2.29 (m, 4H), 2.18 (s, 3H), 1.80 (m, 8H). Mass spectrum (ESI, m/z): Calcd. for $C_{25}H_{28}N_4O_2$, 417.2 (M+H). found 417.1.

EXAMPLE 16

4-Cyano-1H-imidazole-2-carboxylic acid [4-(1-acetyl-piperidin-4-yl)-2-cyclohex-1-enyl-phenyl]-amide

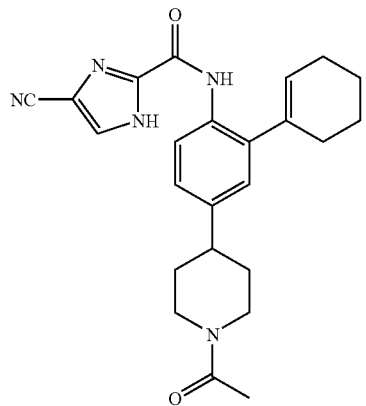

The title compound was prepared from 4-cyano-1H-imidazole-2-carboxylic acid (2-cyclohex-1-enyl-4-piperidin-4-yl-phenyl)-amide trifluoroacetic acid salt (as prepared in Example 13, step (b)) according to the procedure in Example 37: $^1$H-NMR (400 MHz, CDCl$_3$) δ 13.12 (br s, 1H), 9.58 (s, 1H), 8.34 (d, 1H), 7.76 (s, 1H), 7.21 (dd, 1H), 7.05 (d, 1H), 5.86 (s, 1H), 4.84 (m, 2H), 4.00 (m, 1H), 3.22 (m, 1H), 2.72 (m, 2H), 2.30 (m, 4H), 2.21 (s, 3H), 1.80 (m, 8H). Mass spectrum (ESI, m/z): Calcd. for $C_{24}H_{27}N_5O_2$, 418.2 (M+H). found 418.1.

EXAMPLE 17

4-Cyano-1H-imidazole-2-carboxylic acid [2-(4-methyl-cyclohex-1-enyl)-4-piperidin-4-yl-phenyl]-amide trifluoroacetic acid salt

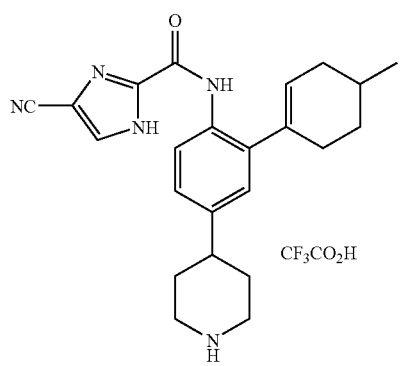

The title compound was prepared from 4-cyano-1-(2-trimethylsilanyl-ethoxymethyl)-1H-imidazole-2-carboxylate potassium salt (as prepared in Example 3, step (d)) and 4-[4-amino-3-(4-methyl-cyclohex-1-enyl)-phenyl]-piperidine-1-carboxylic acid tert-butyl ester (prepared according to the procedure in Example 13, step (d), substituting 4-methyl-1-cyclohex-1-enyl boronic acid for cyclohex-1-enyl boronic acid) according to the procedure for Example 14: $^1$H-NMR (400 MHz, CD$_3$OD): δ 8.18 (d, 1H), 8.04 (s, 1H), 7.22 (dd, 1H), 7.12 (d, 1H), 5.80 (m, 1H), 3.54. (m, 2H), 3.18 (m, 2H), 2.94 (m, 1H), 2.30 (m, 3H), 2.12 (m, 2H), 1.92 (m, 5H), 1.54 (m, 1H), 1.12 (d, 3H). Mass spectrum (ESI, m/z): Calcd. for $C_{23}H_{27}N_5O$, 390.2 (M+H). found 390.2.

EXAMPLE 18

4-Cyano-1H-imidazole-2-carboxylic acid (2-cyclopent-1-enyl-4-piperidin-4-yl-phenyl)-amide trifluoroacetic acid salt

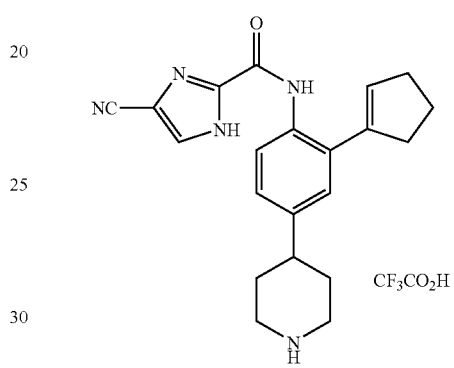

The title compound was prepared from 4-cyano-1-(2-trimethylsilanyl-ethoxymethyl)-1H-imidazole-2-carboxylate potassium salt (as prepared in Example 3, step (d)) and 4-(4-amino-3-cyclopent-1-enyl-phenyl)-piperidine-1-carboxylic acid tert-butyl ester (prepared according to the procedure in Example 13, step (d), substituting cyclopenten-1-yl boronic acid for cyclohex-1-enyl boronic acid) according to the procedure for Example 14. $^1$H-NMR (400 MHz, DMSO-d$_6$) δ 14.25 (br s, 1H), 10.00 (s, 1H), 8.36 (s, 1H), 7.72 (d, 1H), 7.18 (m, 2H), 6.06 (s, 1H), 4.12 (m, 1H), 3.42 (m, 2H), 3.18 (m, 2H), 3.00 (m, 3H), 2.80 (m, 2H), 1.92 (m, 5H). Mass spectrum (ESI, m/z): Calcd. for $C_{21}H_{23}N_5O$, 362.2 (M+H), found 362.2.

EXAMPLE 19

An alternate method for the synthesis of the intermediate described in Example 1 is described below.

5-Cyano-furan-2-carboxylic acid

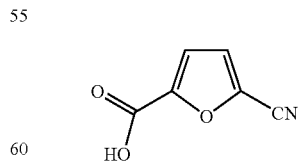

A 250-mL, three-neck, round-bottom flask equipped with a mechanical stirrer, a heating mantle, and a condenser was charged with 5-formyl-2-furancarboxylic acid (9.18 g, 65.6 mmol) and pyridine (60 mL). Hydroxylamine hydrochloride (5.01 g, 72.2 mmol) was added and the mixture was heated to 85° C. Acetic anhydride (40 mL) was added and the reaction was stirred at 85° C. for 3 h, after which time the solvent was evaporated at 40° C. under reduced pressure. The residue was dissolved in water, basified with 2.0 N NaOH solution to pH 9, and extracted with 4:1 dichloromethane/2-propanol until the pyridine was completely removed (5×200 mL). The aqueous solution was then acidified with 2.0 N HCl solution to pH 2, saturated with solid NaCl, and extracted with 4:1 dichloromethane/2-propanol (5×200 mL). The combined organic extracts were dried over $Na_2SO_4$ and concentrated in vacuo to dryness. The residue was crystallized from dichloromethane to give 6.80 g of the title compound as a white solid (76%). Mass spectrum (ESI-neg, m/z) Calcd. for $C_6H_3NO_3$, 136.0 (M−H). found 136.1. The $^1H$ NMR spectrum was consistent with the assigned structure.

EXAMPLE 20

4-Cyano-1H-imidazole-2-carboxylic acid {2-cyclohex-1-enyl-4-[1-(2-methanesulfonyl-acetyl)-piperidin-4-yl]-phenyl}-amide

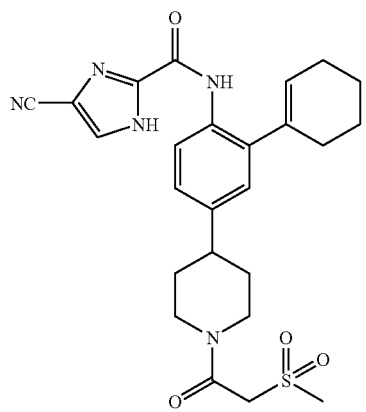

A flask was charged with methanesulfonyl-acetic acid (14 mg, 0.10 mmol), EDCI (30 mg, 0.15 mmol), HOBt (14 mg, 0.10 mmol), DIEA (36 µL, 0.20 mmol) and 0.5 mL DCM and stirred at 25° C. After 10 min, a solution containing 4-cyano-1H-imidazole-2-carboxylic acid (2-cyclohex-1-enyl-4-piperidin-4-yl-phenyl)-amide TFA salt (40 mg, 0.08 mmol) (as prepared in Example 20, step (b)) and $NEt_3$ (14 µL, 0.09 mmol) in 0.5 mL DCM was added and the reaction allowed to proceed for 10 h at 25° C. The reaction mixture was loaded on a 5-g SPE cartridge (silica) and the title compound was eluted with 10% EtOH/EtOAc to give 10 mg (25%) of a white solid. $^1H$-NMR (400 MHz, $CDCl_3$): δ 11.60 (br s, 1H), 9.52 (s, 1H), 8.30 (d, 1H), 7.74 (s, 1H), 7.60 (dd, 1H), 7.03 (d, 1H), 5.86 (m, 1H), 4.84 (m, 1H), 4.18 (s, 2H), 4.12 (m, 1H), 3.32 (m, 1H), 3.20 (s, 3H), 2.82 (m, 2H), 2.30 (m, 4H), 1.98 (m, 2H), 1.84 (m, 5H), 1.72 (m, 1H). Mass spectrum (ESI, m/z): Calcd. for $C_{25}H_{29}N_5O_4S$, 496.2 (M+H). found 496.2.

EXAMPLE 21

4-Cyano-1H-imidazole-2-carboxylic acid [2-cyclohex-1-enyl-4-(1-pyridin-2-ylmethyl-piperidin-4-yl)-phenyl]-amide trifluoroacetic acid salt

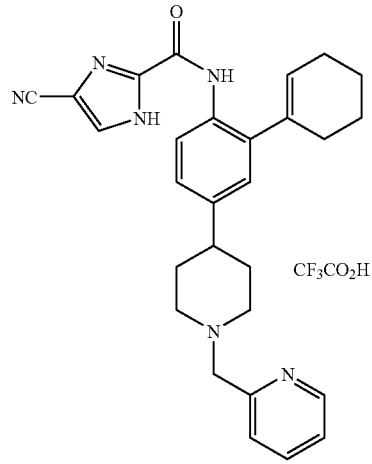

A flask was charged with 4-cyano-1H-imidazole-2-carboxylic acid (2-cyclohex-1-enyl-4-piperidin-4-yl-phenyl)-amide TFA salt (88 mg, 0.18 mmol) (as prepared in Example 14, step (b)), pyridine-2-carbaldehyde (17 µL, 0.21 mmol), $NEt_3$ (30 µL, 0.21 mmol), sodium triacetoxyborohydride (56 mg, 0.25 mmol) and 0.8 mL of 1,2-dichloroethane and stirred for 10 h at 25° C. The solvent was evaporated, and the title compound was purified by RP-HPLC (C18), eluting with 30-50% $CH_3CN$ in 0.1% $TFA/H_2O$ over 20 min to give 81 mg (78%) of a white solid. $^1H$-NMR (400 MHz, DMSO-$d_6$): δ 14.25 (br s, 1H), 9.90 (br s, 1H), 9.79 (s, 1H), 8.72 (s, 1H), 8.36 (s, 1H), 7.98 (m, 1H), 7.88 (dd, 1H), 7.58 (d, 1H), 7.52 (m, 1H), 7.20 (m, 1H), 7.12 (d, 1H), 5.76 (m, 1H), 4.56 (s, 2H), 3.40 (m, 2H), 3.18 (m, 2H), 2.88 (m, 1H), 2.20 (m, 4H), 2.00 (m, 4H), 1.72 (m, 4H). Mass spectrum (ESI, m/z): Calcd. for $C_{28}H_{30}N_6O$, 467.2 (M+H). found 467.2.

EXAMPLE 22

4-Cyano-1H-imidazole-2-carboxylic acid [2-(4-methyl-cyclohex-1-enyl)-4-(1-pyridin-2-ylmethyl-piperidin-4-yl)-phenyl]-amide trifluoroacetic acid salt

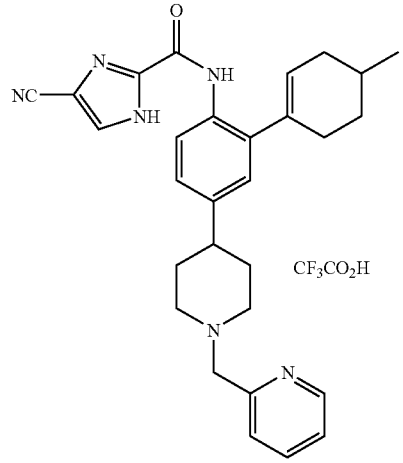

This compound was prepared according to the procedure in Example 21 from 4-cyano-1H-imidazole-2-carboxylic acid [2-(4-methyl-cyclohex-1-enyl)-4-piperidin-4-yl-phenyl]-amide (as prepared in Example 17) and pyridine-2-carbaldehyde. $^1H$-NMR (400 MHz, DMSO-$d_6$): δ 14.25 (br s, 1H), 9.90 (br s, 1H), 9.79 (s, 1H), 8.72 (s, 1H), 8.36 (s, 1H), 7.98 (m, 1H), 7.86 (dd, 1H), 7.54 (d, 1H), 7.52 (m, 1H), 7.20 (m, 1H), 7.12 (d, 1H), 5.74 (m, 1H), 4.56 (s, 2H), 3.40 (m, 2H), 3.18 (m, 2H), 2.88 (m, 1H), 2.48-2.22 (m, 3H), 2.18-2.06 (m, 4H), 1.98-1.82 (m, 3H), 1.52 (m, 1H), 1.02 (s, 3H). Mass spectrum (ESI, m/z): Calcd. for $C_{28}H_{32}N_6O$, 481.2 (M+H). found 481.2.

EXAMPLE 23

4-Cyano-1H-imidazole-2-carboxylic acid {2-cyclo-pent-1-enyl-4-[1-(1-methyl-1H-imidazol-2-ylmethyl)-piperidin-4-yl]-phenyl}-amide trifluoroacetic acid salt

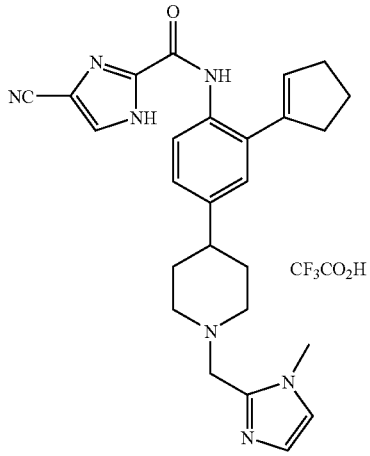

This compound was prepared from 4-cyano-1H-imidazole-2-carboxylic acid (2-cyclopent-1-enyl-4-piperidin-4-yl-phenyl)-amide TFA salt (as prepared in Example 18) and 1-methyl-1H-imidazole-2-carbaldehyde according to the procedure in Example 21. $^1$H-NMR (400 MHz, $CD_3OD$): δ 8.03 (m, 2H), 7.50 (d, 1H), 7.42 (s, 1H), 7.20 (m, 2H), 6.02 (m, 1H), 4.22 (s, 2H), 3.96 (s, 3H), 3.30 (m, 2H), 2.82-2.40 (m, 7H), 2.13-1.84 (m, 6H). Mass spectrum (ESI, m/z): Calcd. for $C_{26}H_{29}N_7O$, 456.2 (M+H). found 456.2.

EXAMPLE 24

4-{4-[(4-Cyano-1H-imidazole-2-carbonyl)-amino]-3-cyclohex-1-enyl-phenyl}-piperidine-1-carboxylic acid amide

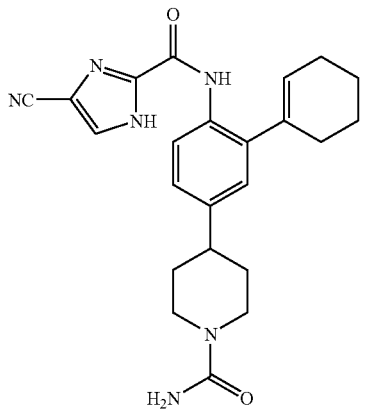

A flask was charged with 4-cyano-1H-imidazole-2-carboxylic acid (2-cyclohex-1-enyl-4-piperidin-4-yl-phenyl)-amide TFA salt (51 mg, 0.10 mmol) (as prepared in Example 14, step (b)), $NEt_3$ (22 μL, 0.15 mmol), trimethylsilyl isocyanate (16 μL, 0.11 mmol) and 1.0 mL of DCM and stirred for 10 h at 25° C. The solvent was evaporated and the title compound was purified by RP-HPLC (C18), eluting with 35-60% $CH_3CN$ in 0.1% $TFA/H_2O$ over 11 min to give 30 mg (70%) of a white solid. $^1$H-NMR (400 MHz, DMSO-$d_6$): δ 14.28 (br s, 1H), 9.76 (s, 1H), 8.34 (s, 1H), 7.84 (d, 1H), 7.18 (dd, 1H), 7.08 (d, 1H), 6.00 (br s, 2H), 5.72 (m, 1H), 4.18 (m, 2H), 2.80-2.60 (m, 3H), 2.24-2.10 (m, 4H), 1.80-1.60 (m, 6H), 1.50 (m, 2H). Mass spectrum (ESI, m/z): Calcd. for $C_{23}H_{26}N_6O$, 419.2 (M+H). found 419.0.

EXAMPLE 25

4-Cyano-1H-imidazole-2-carboxylic acid [2-cyclohex-1-enyl-4-(3,4,5,6-tetrahydro-2H-[1,2]bipyridinyl-4-yl)-phenyl]-amide trifluoroacetic acid salt

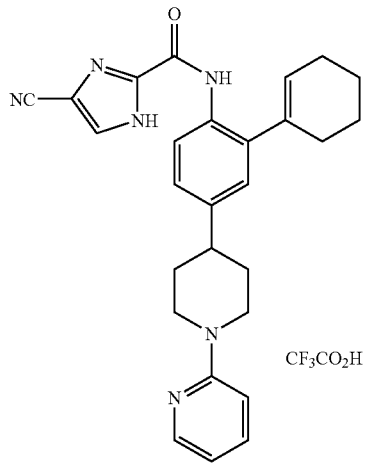

A flask was charged with 4-cyano-1H-imidazole-2-carboxylic acid (2-cyclohex-1-enyl-4-piperidin-4-yl-phenyl)-amide TFA salt (75 mg, 0.15 mmol) (as prepared in Example 14, step (b)), $K_2CO_3$ (84 mg, 0.60 mmol), 2-fluoropyridine (27 μL, 0.30 mmol) and 0.3 mL of N,N-dimethylacetamide and stirred for 8 h at 120° C. The reaction was diluted with 3 mL of $H_2O$ and the title compound was purified by RP-HPLC (C18), eluting with 30-50% $CH_3CN$ in 0.1% $TFA/H_2O$ over 9 min to give 50 mg (75%) of a white solid. $^1$H-NMR (400 MHz, $CD_3OD$): δ 8.18 (d, 1H), 8.06 (m, 1H), 8.02 (s, 1H), 7.94 (dd, 1H), 7.48 (d, 2H), 7.22 (dd, 1H), 7.12 (d, 1H), 6.98 (t, 1H), 5.82 (m, 1H), 4.32 (m, 2H), 3.46 (m, 2H), 3.00 (m, 1H), 2.30 (m, 4H), 2.18 (m, 2H), 1.96-1.74 (m, 6H). Mass spectrum (ESI, m/z): Calcd. for $C_{27}H_{28}N_6O$, 453.2 (M+H). found 453.2.

EXAMPLE 26

4-Cyano-1H-imidazole-2-carboxylic acid {2-cyclohex-1-enyl-4-[1-(2-hydroxy-ethyl)-piperidin-4-yl]-phenyl}-amide trifluoroacetic acid salt

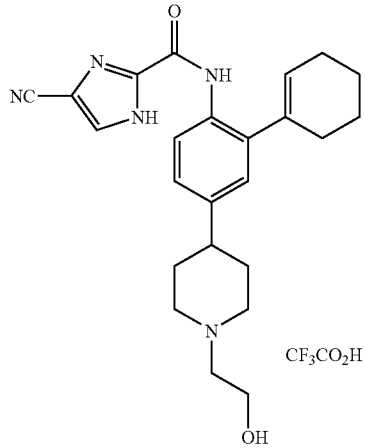

The title compound was prepared from 4-cyano-1H-imidazole-2-carboxylic acid (2-cyclohex-1-enyl-4-piperidin-4-yl-phenyl)-amide TFA salt (as prepared in Example 14, step (b)), and hydroxy-acetaldehyde according to the procedure in Example 21. $^1$H-NMR (400 MHz, CD$_3$OD): δ 8.18 (d, 1H), 8.02 (s, 1H), 7.22 (dd, 1H), 7.14 (d, 2H), 5.82 (m, 1H), 3.94 (m, 2H), 3.74 (m, 2H), 3.30 (m, 2H), 3.18 (t, 2H), 2.92 (m, 1H), 2.30 (m, 4H), 2.20-1.98 (m, 4H), 1.96-1.74 (m, 4H). Mass spectrum (ESI, m/z): Calcd. for C$_{24}$H$_{29}$N$_5$O$_2$, 420.2 (M+H). found 420.2.

EXAMPLE 27

4-Cyano-1H-imidazole-2-carboxylic acid {4-[1-(2-cyano-ethyl)-piperidin-4-yl]-2-cyclohex-1-enyl-phenyl}-amide trifluoroacetic acid salt

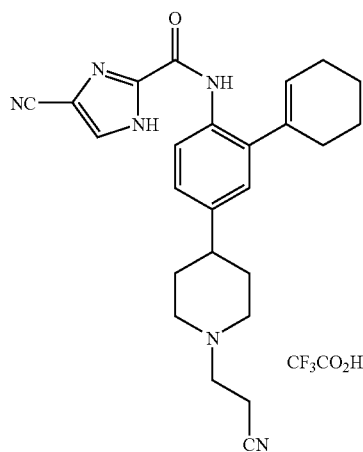

A flask was charged with 4-cyano-1H-imidazole-2-carboxylic acid (2-cyclohex-1-enyl-4-piperidin-4-yl-phenyl)-amide TFA salt (77 mg, 0.16 mmol) (as prepared in Example 14, step (b)), NEt$_3$ (24 μL, 0.16 mmol), acrylonitrile (12 μL, 0.18 mmol), 0.1 mL MeOH and 1.0 mL of 1,2-dichloroethane and stirred for 1 h at 80° C. The reaction was concentrated and the title compound was purified by RP-HPLC (C18), eluting with 30-50% CH$_3$CN in 0.1% TFA/H$_2$O over 12 min to give 83 mg (95%) of a white solid. $^1$H-NMR (400 MHz, CD$_3$OD): δ 8.18 (d, 1H), 8.06 (m, 1H), 7.22 (dd, 1H), 7.12 (d, 1H), 5.82 (m, 1H), 3.76 (m, 2H), 3.60 (m, 2H), 3.28 (t, 2H), 3.12 (t, 2H), 2.92 (m, 1H), 2.30 (m, 4H), 2.18-1.98 (m, 4H), 1.92-1.74 (m, 4H). Mass spectrum (ESI, m/z): Calcd. for C$_{25}$H$_{28}$N$_6$O, 429.2 (M+H). found 429.2.

EXAMPLE 28

4-Cyano-1H-imidazole-2-carboxylic acid [4-(1-carbamoylmethyl-piperidin-4-yl)-2-cyclohex-1-enyl-phenyl]-amide trifluoroacetic acid salt

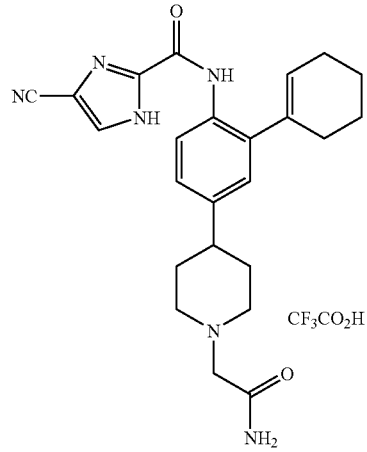

A flask was charged with 4-cyano-1H-imidazole-2-carboxylic acid (2-cyclohex-1-enyl-4-piperidin-4-yl-phenyl)-amide TFA salt (50 mg, 0.10 mmol) (as prepared in Example 14, step (b)), NEt$_3$ (32 μL, 0.23 mmol), 2-bromoacetamide (16 mg, 0.12 mmol), and 0.5 mL of DCM and stirred for 4 h at 25° C. The reaction was concentrated and the title compound was purified by RP-HPLC (C18), eluting with 30-50% CH$_3$CN in 0.1% TFA/H$_2$O over 12 min to give 42 mg (75%) of a white solid. $^1$H-NMR (400 MHz, DMSO-d$_6$): δ 14.28 (br s, 1H), 9.78 (s, 1H), 9.50 (br s, 1H), 8.34 (s, 1H), 8.00 (s, 1H), 7.88 (d, 1H), 7.72 (s, 1H), 7.18 (dd, 1H), 7.10 (d, 1H), 5.76 (m, 1H), 3.94 (s, 2H), 3.58 (m, 2H), 3.12 (m, 2H), 2.80 (m, 1H), 2.20 (m, 4H), 1.98 (m, 4H), 1.80 (m, 4H). Mass spectrum (ESI, m/z): Calcd. for C$_{24}$H$_{28}$N$_6$O$_2$, 433.2 (M+H). found 433.2.

EXAMPLE 29

4-Cyano-1H-imidazole-2-carboxylic acid {2-cyclohex-1-enyl-4-[1-(2-pyridin-2-yl-acetyl)-piperidin-4-yl]-phenyl}-amide trifluoroacetic acid salt

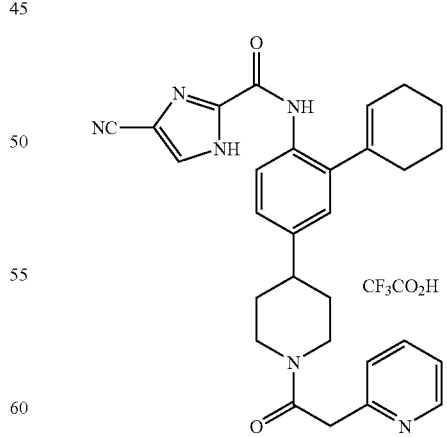

A flask was charged with 4-cyano-1H-imidazole-2-carboxylic acid (2-cyclohex-1-enyl-4-piperidin-4-yl-phenyl)-amide TFA salt (25 mg, 0.05 mmol) (as prepared in Example 14, step (b)), pyridin-2-yl-acetic acid hydrochloride (10 mg, 0.06 mmol), EDCI (12 mg, 0.06 mmol), HOBt (8.0 mg, 0.06 mmol), DIEA (36 μL, 0.20 mmol) and 0.2 mL DMF and stirred at 25° C. for 10 h. The reaction was diluted with 2 mL of $H_2O$ and the title compound was purified by RP-HPLC (C18), eluting with 30-50% $CH_3CN$ in 0.1% $TFA/H_2O$ over 9 min to give 22 mg (70%) of a white solid. $^1$H-NMR (400 MHz, $CD_3OD$): δ 8.82 (d, 1H), 8.52 (t, 1H), 8.14 (d, 1H), 8.04 (s, 1H), 7.96 (m, 3H), 7.20 (dd, 1H), 7.10 (d, 1H), 5.82 (m, 1H), 4.68 (m, 1H), 4.32 (m, 2H), 4.18 (m, 1H), 3.40 (m, 1H), 2.88 (m, 2H), 2.30 (m, 4H), 2.06-1.60 (m, 8H). Mass spectrum (ESI, m/z): Calcd. for $C_{29}H_{30}N_6O_2$, 495.2.2 (M+H). found 495.2.

EXAMPLE 30

4-Cyano-1H-imidazole-2-carboxylic acid {2-cyclohex-1-enyl-4-[1-(2-pyridin-3-yl-acetyl)-piperidin-4-yl]-phenyl}-amide trifluoroacetic acid salt

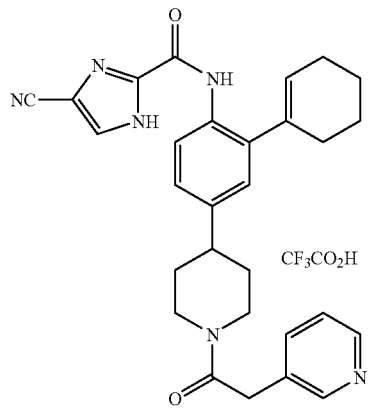

The title compound was prepared from 4-cyano-1H-imidazole-2-carboxylic acid (2-cyclohex-1-enyl-4-piperidin-4-yl-phenyl)-amide TFA salt (as prepared in Example 14, step (b)), according to the procedure in Example 29 using pyridin-3-yl-acetic acid. $^1$H-NMR (400 MHz, $CD_3OD$): δ 8.80 (m, 2H), 8.54 (d, 1H), 8.10 (d, 1H), 8.06 (t, 1H), 7.98 (s, 1H), 7.18 (dd, 1H), 7.08 (d, 1H), 5.78 (m, 1H), 4.68 (m, 1H), 4.20 (m, 1H), 4.18 (s, 2H), 3.36 (m, 1H), 2.84 (m, 2H), 2.28 (m, 4H), 2.06-1.70 (m, 7H), 1.62 (m, 1H). Mass spectrum (ESI, m/z): Calcd. for $C_{29}H_{30}N_6O_2$, 495.2 (M+H). found 495.2.

EXAMPLE 31

4-Cyano-1H-imidazole-2-carboxylic acid {2-cyclohex-1-enyl-4-[1-(2-pyridin-4-yl-acetyl)-piperidin-4-yl]-phenyl}-amide trifluoroacetic acid salt

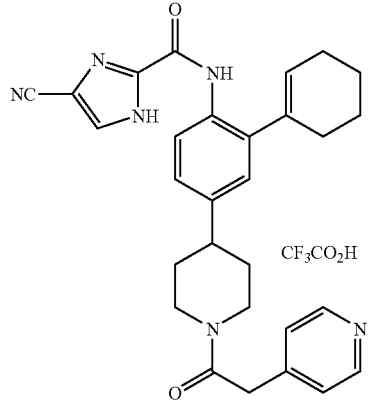

The title compound was prepared from 4-cyano-1H-imidazole-2-carboxylic acid (2-cyclohex-1-enyl-4-piperidin-4-yl-phenyl)-amide TFA salt (as prepared in Example 14, step (b)), according to the procedure in Example 29 using pyridin-4-yl-acetic acid. $^1$H-NMR (400 MHz, $CD_3OD$): δ 8.78 (d, 2H), 8.12 (d, 1H), 8.00 (m, 3H), 7.18 (dd, 1H), 7.08 (d, 1H), 5.80 (m, 1H), 4.66 (m, 1H), 4.22 (s, 2H), 4.18 (m, 1H), 3.34 (m, 1H), 2.84 (m, 2H), 2.24 (m, 4H), 2.00-1.70 (m, 7H), 1.64 (m, 1H). Mass spectrum (ESI, m/z): Calcd. for $C_{29}H_{30}N_6O_2$, 495.2 (M+H). found 495.2.

EXAMPLE 32

4-Cyano-1H-imidazole-2-carboxylic acid (2-cyclohex-1-enyl-4-{1-[2-(1-methyl-1H-imidazol-4-yl)-acetyl]-piperidin-4-yl}-phenyl)-amide trifluoroacetic acid salt

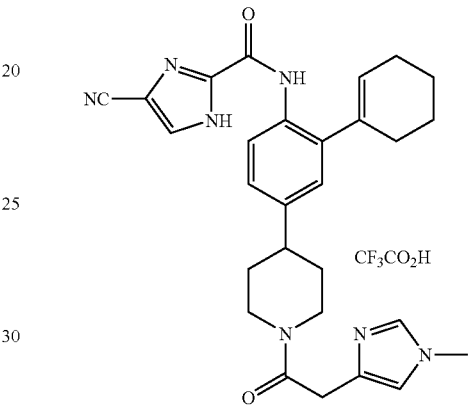

The title compound was prepared from 4-cyano-1H-imidazole-2-carboxylic acid (2-cyclohex-1-enyl-4-piperidin-4-yl-phenyl)-amide TFA salt (as prepared in Example 14, step (b)), according to the procedure in Example 29 using (1-methyl-1H-imidazol-4-yl)-acetic acid. $^1$H-NMR (400 MHz, $CD_3OD$): δ 8.82 (s, 1H), 8.10 (d, 1H), 8.00 (s, 1H), 7.42 (s, 1H), 7.16 (dd, 1H), 7.06 (d, 1H), 5.80 (m, 1H), 4.66 (m, 1H), 4.12 (m, 1H), 4.04 (m, 2H), 3.92 (s, 3H), 3.28 (m, 1H), 2.82 (m, 2H), 2.26 (m, 4H), 2.00-1.70 (m, 7H), 1.64 (m, 1H). Mass spectrum (ESI, m/z): Calcd. for $C_{28}H_{31}N_7O_2$, 498.2 (M+H). found 498.2.

EXAMPLE 33

4-Cyano-1H-imidazole-2-carboxylic acid {2-cyclohex-1-enyl-4-[1-(2-1H-imidazol-4-yl-acetyl)-piperidin-4-yl]-phenyl}-amide trifluoroacetic acid salt

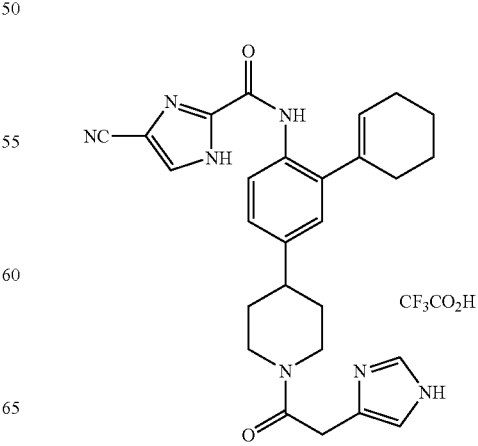

The title compound was prepared from 4-cyano-1H-imidazole-2-carboxylic acid (2-cyclohex-1-enyl-4-piperidin-4-yl-phenyl)-amide TFA salt (as prepared in Example 14, step (b)), according to the procedure in Example 29 using (1-methyl-1H-imidazol-4-yl)-acetic acid. $^1$H-NMR (400 MHz, CD$_3$OD): δ 8.88 (s, 1H), 8.12 (d, 1H), 8.02 (s, 1H), 7.44 (s, 1H), 7.20 (dd, 1H), 7.10 (d, 1H), 5.82 (m, 1H), 4.70 (m, 1H), 4.18 (m, 1H), 4.06 (m, 2H), 3.36 (m, 1H), 2.84 (m, 2H), 2.30 (m, 4H), 2.00-1.70 (m, 7H), 1.64 (m, 1H). Mass spectrum (ESI, m/z): Calcd. for C$_{27}$H$_{29}$N$_7$O$_2$, 484.2 (M+H). found 484.2.

EXAMPLE 34

4-Cyano-1H-imidazole-2-carboxylic acid {2-cyclohex-1-enyl-4-[1-(2-morpholin-4-yl-ethyl)-piperidin-4-yl]-phenyl}-amide di-trifluoroacetic acid salt

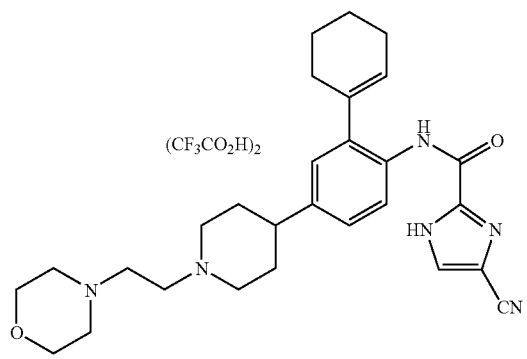 [SMILES: N#Cc1c[nH]c(C(=O)Nc2ccc(C3CCN(CCN4CCOCC4)CC3)cc2C2=CCCCC2)n1 ; "(CF3CO2H)2"]

a) 4-Cyano-1-(2-trimethylsilanyl-ethoxymethyl)-1H-imidazole-2-carboxylic acid {2-cyclohex-1-enyl-4-[1-(2-morpholin-4-yl-ethyl)-piperidin-4-yl]-phenyl}-amide

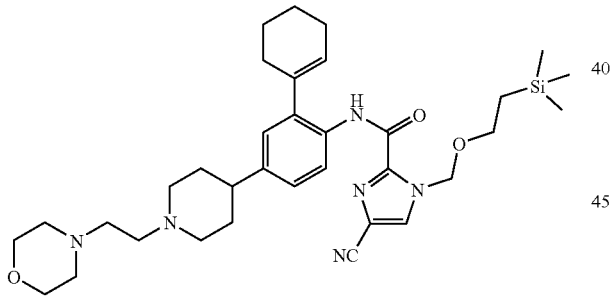

A flask was charged with 4-cyano-1-(2-trimethylsilanyl-ethoxymethyl)-1H-imidazole-2-carboxylic acid (2-cyclohex-1-enyl-4-piperidin-4-yl-phenyl)-amide TFA salt (830 mg, 1.34 mmol) (as prepared in Example 39, step (a)), K$_2$CO$_3$ (600 mg, 4.34 mmol), sodium iodide (40 mg, 0.27 mmol), 4-(2-chloro-ethyl)-morpholine hydrochloride (260 mg, 1.40 mmol), and 5.0 mL of N,N-dimethylacetamide and stirred for 8 h at 80° C. The reaction was diluted with EtOAc (50 mL) and washed with NaHCO$_3$ (2×50 mL), brine (50 mL) and concentrated. The title compound was purified by flash chromatography (silica gel, 5% MeOH/DCM) to give 650 mg (78%) of a white solid. Mass spectrum (ESI, m/z): Calcd. for C$_{34}$H$_{50}$N$_6$O$_3$Si, 619.4 (M+H). found 619.3.

b) 4-Cyano-1H-imidazole-2-carboxylic acid {2-cyclohex-1-enyl-4-[1-(2-morpholin-4-yl-ethyl)-piperidin-4-yl]-phenyl}-amide trifluoroacetic acid salt To a solution of 4-cyano-1-(2-trimethylsilanyl-ethoxymethyl)-1H-imidazole-2-carboxylic acid {2-cyclohex-1-enyl-4-[1-(2-morpholin-4-yl-ethyl)-piperidin-4-yl]-phenyl}-amide (650 mg, 1.05 mmol) (as prepared in the previous step) in 10 mL of DCM was added 0.3 mL of EtOH and 3.0 mL of TFA, and the reaction was allowed to proceed for 2 h at 25° C. The reaction was diluted with 10 mL of EtOH and concentrated. The title compound was purified by RP-HPLC (C18), eluting with 30-50% CH$_3$CN in 0.1% TFA/H$_2$O over 9 min to give 600 mg (80%) of a white solid. $^1$H-NMR (400 MHz, CD$_3$OD): δ 8.18 (d, 1H), 8.04 (s, 1H), 7.24 (dd, 1H), 7.14 (d, 1H), 5.84 (m, 1H), 3.84 (m, 4H), 3.76 (m, 2H), 3.50 (m, 2H), 3.30-3.10 (m, 4H), 2.92 (m, 5H), 2.30 (m, 4H), 2.20-2.00 (m, 4H), 1.90-1.74 (m, 4H). Mass spectrum (ESI, m/z): Calcd. for C$_{28}$H$_{36}$N$_6$O$_2$, 489.2. found 489.2.

EXAMPLE 35

4-Cyano-1H-imidazole-2-carboxylic acid [2-(1,1-dioxo-1,2,3,6-tetrahydro-1λ$^6$-thiopyran-4-yl)-4-piperidin-4-yl-phenyl]-amide

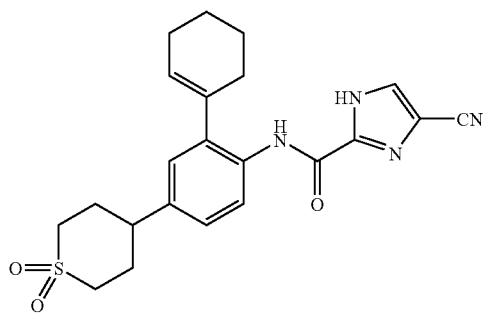 [SMILES: N#Cc1c[nH]c(C(=O)Nc2ccc(C3CCS(=O)(=O)CC3)cc2C2=CCCCC2)n1]

a) Trifluoromethanesulfonic acid 3,6-dihydro-2H-thiopyran-4-yl ester

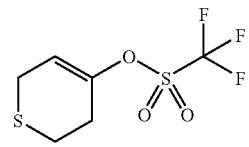 [SMILES: O=S(=O)(OC1=CCSCC1)C(F)(F)F]

A solution of tetrahydro-thiopyran-4-one (1.00 g, 8.61 mmol) in 10 ml of THF was added to a solution of LDA (2.0 M, 4.52 ml, 9.04 mmol) in 20 ml of THF at −78° C. under Ar. The mixture was warmed to RT and stirred for 0.5 h, then cooled to −78° C. again. A solution of N-phenyltrifluoromethanesulfonimide (3.42 g, 9.47 mmol) in 10 ml of THF was added. The resulting mixture was warmed to RT and stirred for 0.5 h under Ar. Treated with 200 ml of EtOAc, the mixture was washed with H$_2$O (3×50 mL), brine (50 mL) and dried (Na$_2$SO$_4$). Removal of the solvent under reduced pressure followed by flash chromatography of the residue on silica gel (hexane-3% EtOAc/hexane) gave 810 mg (38%) of the title compound as a colorless oil. $^1$H-NMR (CDCl$_3$; 400 MHz): δ 6.01 (m, 1H), 3.30 (m, 2H), 2.86 (dd, 2H, J=5.7, 5.7 Hz), 2.58-2.64 (m, 2H). Mass spectrum (ESI, m/z): Calcd. for C$_6$H$_7$F$_3$O$_3$S$_2$, 249.0 (M+H). found 249.3.

b) 4-(4-Nitro-phenyl)-3,6-dihydro-2H-thiopyran

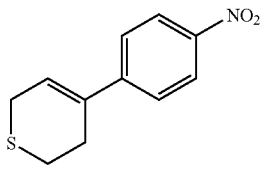 [SMILES: O=[N+]([O-])c1ccc(C2=CCSCC2)cc1]

To a mixture of 4-nitrophenylboronic acid (418 mg, 2.50 mmol), trifluoro-methanesulfonic acid 3,6-dihydro-2H-thiopyran-4-yl ester (as prepared in the previous step, 931 mg, 3.75 mmol), Pd(PPh$_3$)$_4$ (433 mg, 0.375 mmol) and lithium chloride (LiCl) (212 mg, 5.0 mmol) in 20 mL of 1,4-dioxane was added 2.0 M aq Na$_2$CO$_3$ solution (3.13 mL, 6.25 mmol). The resulting mixture was stirred at 80° C. for 2 h and then cooled to RT. Treated with 200 mL of EtOAc, the mixture was washed with H$_2$O (2×30 mL), brine (30 mL) and dried (Na$_2$SO$_4$). Removal of the solvent under reduced pressure followed by flash chromatography of the residue on silica gel (1-3% EtOAc/hexane) gave 470 mg (85%) of the title compound as a light brown oil. $^1$H-NMR (CDCl$_3$; 400 MHz): δ 8.19 (d, 2H, J=9.1 Hz), 7.48 (d, 2H, J=9.1 Hz), 6.36 (m, 1H), 3.39 (m, 2H), 2.91 (t, 2H, J=5.7 Hz), 2.72 (m, 2H). Mass spectrum (ESI, m/z): Calcd. for C$_1$H$_{11}$NO$_2$S, 222.1 (M+H). found 222.3.

c) 4-(4-Nitro-phenyl)-3,6-dihydro-2H-thiopyran 1,1-dioxide

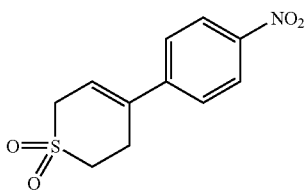 [SMILES: O=[N+]([O-])c1ccc(C2=CCS(=O)(=O)CC2)cc1]

A solution of 3-chloroperoxybenzoic acid (1.04 g, 4.62 mmol, 77%) in 15 mL of dichloromethane (DCM) was added slowly to a solution of 4-(4-nitro-phenyl)-3,6-dihydro-2H-thiopyran (as prepared in the previous step, 465 mg, 2.10 mmol) in 15 mL of DCM at −78° C. under Ar. The mixture was stirred at −78° C. for 0.5 h, and then warmed to RT. Treated with 100 mL of EtOAc, the mixture was washed with 10% Na$_2$SO$_3$ (2×15 mL), satd aq NaHCO$_3$ solution (20 mL), H$_2$O (20 mL), brine (20 mL) and dried (Na$_2$SO$_4$). Removal of the solvent under reduced pressure followed by flash chromatography of the residue on silica gel (2-5% EtOAc/DCM) gave 518 mg (97%) of the title compound as a white solid. $^1$H-NMR (CDCl$_3$; 400 MHz): δ 8.23 (d, 2H, J=9.0 Hz), 7.52 (d, 2H, J=9.0 Hz), 6.04 (m, 1H), 3.86 (m, 2H), 3.26-3.31 (m, 2H), 3.18-3.23 (m, 2H).

d) 4-(1,1-Dioxo-hexahydro-1λ$^6$-thiopyran-4-yl)-phenylamine

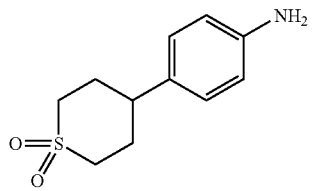 [SMILES: Nc1ccc(C2CCS(=O)(=O)CC2)cc1]

A mixture of 4-(4-nitro-phenyl)-3,6-dihydro-2H-thiopyran 1,1-dioxide (as prepared in the previous step, 502 mg, 1.98 mmol) and 10% Pd/C (250 mg, 50 wt %) in 15 mL of MeOH was stirred at RT under H$_2$ (balloon pressure) for 2 h. The Pd catalyst was removed by filtration on Celite, and the filtrate was concentrated to give 314 mg (70%) of the title compound as a slightly yellow solid. $^1$H-NMR (CDCl$_3$; 400 MHz): δ 7.03 (d, 2H, J=8.3 Hz), 6.67 (d, 2H, J=8.3 Hz), 3.51-3.79 (brs, 2H), 3.11-3.17 (m, 4H), 2.70 (dddd, 1H, J=12.3, 12.3, 2.9, 2.9 Hz), 2.31-2.43 (m, 2H), 2.15-2.23 (m, 2H).

e) 2-Bromo-4-(1,1-dioxo-hexahydro-1λ$^6$-thiopyran-4-yl)-phenylamine

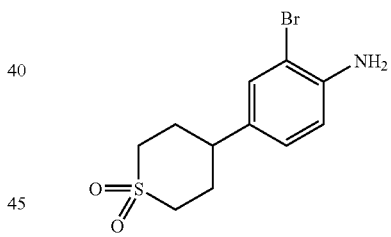

To a suspension of 4-(1,1-dioxo-hexahydro-1×6-thiopyran-4-yl)-phenylamine (as prepared in the previous step, 174 mg, 0.77 mmol) in 20 mL of 3:1 DCM/MeOH at 0° C. was added N-bromosuccinimide (NBS) (137 mg, 0.77 mmol) in 5 mL of DCM under Ar. The mixture was warmed to RT and stirred for 1 h under Ar. Treated with 100 mL of EtOAc, the mixture was washed with H$_2$O (2×20 mL), brine (20 mL) and dried (Na$_2$SO$_4$). Removal of the solvent under reduced pressure followed by flash chromatography of the residue on silica gel (2-3% EtOAc/DCM) gave 155 mg (66%) of the title compound as a white solid. $^1$H-NMR (CDCl$_3$; 400 MHz): δ 7.28 (d, 1H, J=2.0 Hz), 6.97 (dd, 1H, J=8.3, 2.0 Hz), 6.73 (d, 1H, J=8.3 Hz), 4.07 (br s, 2H), 3.09-3.14 (m, 4H), 2.66 (dddd, 1H, J=12.1, 12.1, 3.3, 3.3 Hz), 2.26-2.39 (m, 2H), 2.12-2.21 (m, 2H). Mass spectrum (ESI, m/z): Calcd. for C$_{11}$H$_{14}$BrNO$_2$S, 304.0 (M+H). found 304.1.

f) 2-Cyclohex-1-enyl-4-(1,1-dioxo-hexahydro-1λ⁶-thiopyran-4-yl)-phenylamine

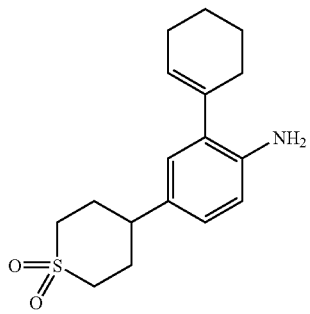 [SMILES: Nc1ccc(C2CCS(=O)(=O)CC2)cc1C1=CCCCC1]

To a mixture of 2-bromo-4-(1,1-dioxo-hexahydro-1×6-thiopyran-4-yl)-phenylamine (as prepared in the previous step, 150 mg, 0.493 mmol), cyclohexen-1-yl boronic acid (70 mg, 0.542 mmol) and Pd(PPh$_3$)$_4$ (57 mg, 0.0493 mmol) in 5 mL of 1,4-dioxane was added 2.0 M aq Na$_2$CO$_3$ solution (2.0 mL, 4.0 mmol). The resulting mixture was stirred at 80° C. for 8 h under Ar, and then cooled to RT. Treated with 50 mL of EtOAc, the mixture was washed with H$_2$O (3×15 mL), brine (20 mL) and dried (Na$_2$SO$_4$). Removal of the solvent under reduced pressure followed by flash chromatography of the residue on silica gel (2-5% EtOAc/DCM) gave 130 mg (86%) of the title compound as a brown solid. ¹H-NMR (CDCl$_3$; 400 MHz): δ 6.89 (dd, 1H, J=8.4, 2.3 Hz), 6.84 (d, 1H, J=2.3 Hz), 6.65 (d, 1H, J=8.4 Hz), 5.74 (m, 1H), 3.74 (br s, 2H), 3.08-3.17 (m, 4H), 2.66 (dddd, 1H, J=12.1, 12.1, 3.1, 3.1 Hz), 2.29-2.42 (m, 2H), 2.13-2.25 (m, 6H), 1.73-1.81 (m, 2H), 1.65-1.73 (m, 2H). Mass spectrum (ESI, m/z): Calcd. for C$_{17}$H$_{23}$NO$_2$S, 306.1 (M+H). found 306.1.

g) 4-Cyano-1-(2-trimethylsilanyl-ethoxymethyl)-1H-imidazole-2-carboxylic acid [2-cyclohex-1-enyl-4-(1,1-dioxo-hexahydro-1λ⁶-thiopyran-4-yl)-phenyl]-amide

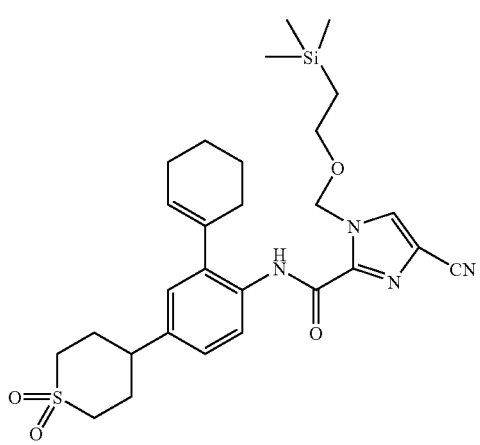 [SMILES: C[Si](C)(C)CCOCn1cc(C#N)nc1C(=O)Nc1ccc(C2CCS(=O)(=O)CC2)cc1C1=CCCCC1]

To a mixture of 2-cyclohex-1-enyl-4-(1,1-dioxo-hexahydro-1λ⁶-thiopyran-4-yl)-phenylamine (as prepared in the previous step, 122 mg, 0.50 mmol), potassium 4-cyano-1-(2-trimethylsilanyl-ethoxymethyl)-1H-imidazole-2-carboxylate (as prepared in Example 3, step (d), 134 mg, 0.44 mmol) and bromotri(pyrrolidino)phosphonium hexafluorophosphate (PyBroP) (205 mg, 0.44 mmol) in 5 mL of DMF was added DIEA (209 µL, 1.20 mmol). The resulting mixture was stirred at RT for 18 h under Ar, cooled to RT. Treated with 50 mL of EtOAc, the mixture was washed with H$_2$O (3×10 mL), brine (10 mL) and dried (Na$_2$SO$_4$). Removal of the solvent under reduced pressure followed by flash chromatography of the residue on silica gel (1-3% EtOAc/DCM) gave 161 mg (73%) of the title compound as a colorless oil. ¹H-NMR (CDCl$_3$; 400 MHz): δ 9.69 (s, 1H), 8.29 (d, 1H, J=8.4 Hz), 7.78 (s, 1H), 7.14 (dd, 1H, J=8.4, 2.2 Hz), 7.04 (d, 1H, J=2.2 Hz), 5.95 (s, 2H), 5.83 (m, 1H), 3.66 (t, 2H, J=8.2 Hz), 3.11-3.20 (m, 4H), 2.77 (dddd, 1H, J=12.1, 12.1, 3.2, 3.2 Hz), 2.35-2.47 (m, 2H), 2.17-2.33 (m, 6H), 1.74-1.89 (m, 4H), 0.97 (t, 2H, J=8.2 Hz), 0.00 (s, 9H). Mass spectrum (ESI, m/z): Calcd. for C$_{28}$H$_{38}$N$_4$O$_4$SSi, 555.2 (M+H). found 555.3.

h) 4-Cyano-1H-imidazole-2-carboxylic acid [2-cyclohex-1-enyl-4-(1,1-dioxo-hexahydro-1λ⁶-thiopyran-4-yl)-phenyl]-amide

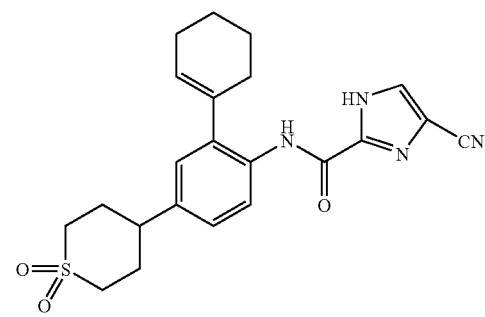 [SMILES: N#Cc1c[nH]c(C(=O)Nc2ccc(C3CCS(=O)(=O)CC3)cc2C2=CCCCC2)n1]

To a solution of 4-cyano-1-(2-trimethylsilanyl-ethoxymethyl)-1H-imidazole-2-carboxylic acid [2-cyclohex-1-enyl-4-(1,1-dioxo-hexahydro-1λ⁶-thiopyran-4-yl)-phenyl]-amide (as prepared in the previous step, 145 mg, 0.261 mmol) in 6 mL of DCM was added 0.20 mL of EtOH followed by 2 mL of TFA. The resulting solution was stirred at RT for 3 h. Removal of the solvent under reduced pressure followed by flash chromatography of the residue on silica gel (20-25% EtOAc/DCM) gave 83 mg (90%) of the title compound as a white solid. ¹H-NMR (CDCl$_3$; 400 MHz): δ 12.34 (s, 1H), 9.60 (s, 1H), 8.35 (d, 1H, J=8.4 Hz), 7.75 (s, 1H), 7.30 (dd, 1H, J=8.4, 2.2 Hz), 7.08 (d, 1H, J=2.2 Hz), 5.86 (m, 1H), 3.11-3.23 (m, 4H), 2.80 (dddd, 1H, J=12.2, 12.2, 2.8, 2.8 Hz), 2.40-2.57 (m, 2H), 2.17-2.35 (m, 6H), 1.74-1.91 (m, 4H). Mass spectrum (ESI, m/z): Calcd. for C$_{22}$H$_{24}$N$_4$O$_3$S, 425.2 (M+H). found 425.6.

EXAMPLE 36

4-Cyano-1H-imidazole-2-carboxylic acid [2-(1,1-dioxo-1,2,3,6-tetrahydro-1λ6-thiopyran-4-yl)-4-piperidin-4-yl-phenyl]-amide trifluoroacetic acid salt

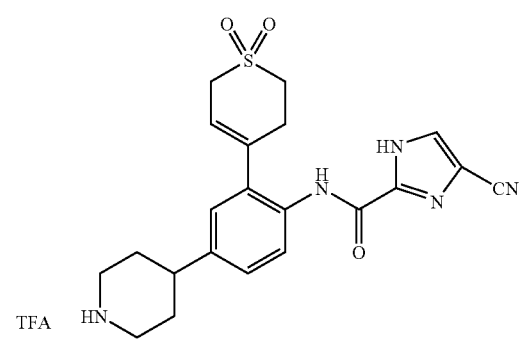 [SMILES: N#Cc1c[nH]c(C(=O)Nc2ccc(C3CCNCC3)cc2C2=CCS(=O)(=O)CC2)n1]

a) 2-(3,6-Dihydro-2H-thiopyran-4-yl)-5,5-dimethyl-[1,3,2]dioxaborinane

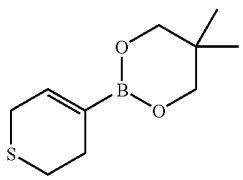

A mixture of trifluoromethanesulfonic acid 3,6-dihydro-2H-thiopyran-4-yl ester (as prepared in Example 35, step (a), 500 mg, 2.01 mmol), bis(neopentyl glycolato)diboron (478 mg, 2.11 mmol), Pd(dppf)Cl$_2$ (147 mg, 0.20 mmol) and KOAc (592 mg, 6.03 mmol) in 8 mL of 1,4-dioxane was stirred at 80° C. for 8 h under Ar, and then cooled to RT. Treated with 50 mL of EtOAc, the mixture was washed with H$_2$O (2×10 mL), brine (10 mL) and dried (Na$_2$SO$_4$). Removal of the solvent under reduced pressure followed by flash chromatography of the residue on silica gel (0-5% EtOAc/DCM) gave 351 mg (82%) of the title compound as a colorless oil. $^1$H-NMR (CDCl$_3$; 400 MHz): δ 6.62 (m, 1H), 3.63 (s, 4H), 3.21 (m, 2H), 2.68 (t, 2H, J=5.8 Hz), 2.37 (m, 2H), 0.96 (s, 6H). Mass spectrum (ESI, m/z): Calcd. for C$_{10}$H$_{17}$BO$_2$S, 213.1 (M+H). found 213.1.

b) 4-[4-Amino-3-(3,6-dihydro-2H-thiopyran-4-yl)-phenyl]-piperidine-1-carboxylic acid tert-butyl ester

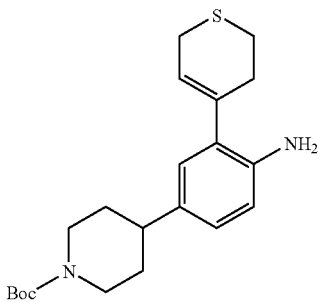 [SMILES: CC(C)(C)OC(=O)N1CCC(c2ccc(N)c(C3=CCSCC3)c2)CC1]

To a mixture of 4-(4-amino-3-bromo-phenyl)-piperidine-1-carboxylic acid tert-butyl ester (as prepared in Example 13, step (c), 200 mg, 0.563 mmol), 2-(3,6-dihydro-2H-thiopyran-4-yl)-5,5-dimethyl-[1,3,2]dioxaborinane (as prepared in the previous step, 131 mg, 0.619 mmol) and Pd(PPh$_3$)$_4$ (65 mg, 0.056 mmol) in 5 mL of 1,4-dioxane was added 2.0 M aq Na$_2$CO$_3$ solution (2.25 mL, 4.5 mmol). The resulting mixture was stirred at 80° C. for 7 h under Ar, and then cooled to RT. Treated with 50 mL of EtOAc, the mixture was washed with H$_2$O (3×15 mL), brine (20 mL) and dried (Na$_2$SO$_4$). Removal of the solvent under reduced pressure followed by flash chromatography of the residue on silica gel (15-30% EtOAc/hexane) gave 141 mg (67%) of the title compound as a colorless oil. $^1$H-NMR (CDCl$_3$; 400 MHz): δ 6.91 (dd, 1H, J=8.2, 2.2 Hz), 6.81 (d, 1H, J=2.2 Hz), 6.65 (d, 1H, J=8.2 Hz), 5.91 (m, 1H), 4.22 (br s, 2H), 3.66 (br s, 2H), 3.29-3.31 (m, 2H), 2.87 (dd, 2H, J=5.7, 5.7 Hz), 2.77 (m, 2H), 2.47-2.56 (m, 3H), 1.78 (d, 2H, J=12.6 Hz), 1.50-1.63 (m, 2H), 1.48 (s, 9H). Mass spectrum (ESI, m/z): Calcd. for C$_{21}$H$_{30}$N$_2$O$_2$S, 375.2 (M+H). found 375.2.

c) 4-[4-{[4-Cyano-1-(2-trimethylsilanyl-ethoxymethyl)-1H-imidazole-2-carbonyl]-amino}-3-(3,6-dihydro-2H-thiopyran-4-yl)-phenyl]-piperidine-1-carboxylic acid tert-butyl ester To a mixture of 4-[4-amino-3-(3,6-dihydro-2H-thiopyran-4-yl)-phenyl]-piperidine-1-carboxylic acid tert-butyl ester (as prepared in the previous step, 45 mg, 0.12 mmol), potassium 4-cyano-1-(2-trimethylsilanyl-ethoxymethyl)-1H-imidazole-2-carboxylate (as prepared in Example 3, step (d), 44 mg, 0.144 mmol) and PyBroP (67 mg, 0.144 mmol) in 2 mL of DMF was added DIEA (42 µL, 0.24 mmol). The resulting mixture was stirred at RT for 4 h under Ar. Treated with 30 mL of EtOAc, the mixture was washed with H$_2$O (3×10 mL), brine (10 mL) and dried (Na$_2$SO$_4$). Removal of the solvent under reduced pressure followed by flash chromatography of the residue on silica gel (1-2% EtOAc/DCM) gave 64 mg (85%) of the title compound as a light yellow oil. $^1$H-NMR (CDCl$_3$; 400 MHz): δ 9.51 (s, 1H), 8.21 (d, 1H, J=8.5 Hz), 7.78 (s, 1H), 7.16 (dd, 1H, J=8.5, 2.1 Hz), 7.02 (d, 1H, J=2.1 Hz), 6.00 (m, 1H), 5.92 (s, 2H), 4.25 (br s, 2H), 3.66 (t, 2H, J=8.2), 3.42 (m, 2H), 2.93 (dd, 2H, J=5.7, 5.7 Hz), 2.79 (m, 2H), 2.63 (dddd, 1H, J=12.3, 12.3, 3.3, 3.3 Hz), 2.49-2.56 (m, 2H), 1.82 (d, 2H, J=12.8 Hz), 1.56-1.66 (m, 2H), 1.49 (s, 9H), 0.97 (t, 2H, J=8.2 Hz), 0.00 (s, 9H).

d) 4-[4-{[4-Cyano-1-(2-trimethylsilanyl-ethoxymethyl)-1H-imidazole-2-carbonyl]-amino}-3-(1,1-dioxo-1,2,3,6-tetrahydro-1λ$^6$-thiopyran-4-yl)-phenyl]-piperidine-1-carboxylic acid tert-butyl ester

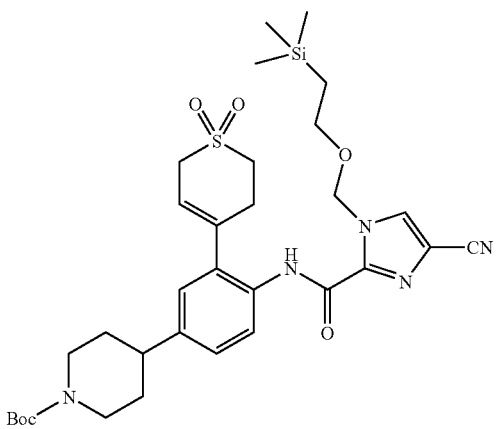 [SMILES: CC(C)(C)OC(=O)N1CCC(c2ccc(NC(=O)c3nc(C#N)cn3COCC[Si](C)(C)C)c(C3=CCS(=O)(=O)CC3)c2)CC1]

A solution of 3-chloroperoxybenzoic acid (91 mg, 0.404 mmol, 77%) in 1 mL of DCM was added slowly to 4-[4-{[4-cyano-1-(2-trimethylsilanyl-ethoxymethyl)-1H-imidazole-2-carbonyl]-amino}-3-(3,6-dihydro-2H-thiopyran-4-yl)-phenyl]-piperidine-1-carboxylic acid tert-butyl ester (as prepared in the previous step, 120 mg, 0.192 mmol) in 3 mL of DCM at −78° C. under Ar. The mixture was stirred at −78° C. for 15 min, and then warmed to RT. Treated with 40 mL of EtOAc, the mixture was washed with 15% Na$_2$SO$_3$ (5 mL), satd aq NaHCO$_3$ solution (2×10 mL), H$_2$O (10 mL), brine (10 mL) and dried (Na$_2$SO$_4$). Removal of the solvent under reduced pressure followed by flash chromatography of the residue on silica gel (2-10% EtOAc/DCM) gave 85 mg (67%) of the title compound as a colorless oil. $^1$H-NMR (CDCl$_3$; 400 MHz): δ 9.23 (s, 1H), 8.03 (d, 1H, J=8.3 Hz), 7.80 (s, 1H), 7.21 (dd, 1H, J=8.3, 2.0 Hz), 7.06 (d, 1H, J=2.0 Hz), 5.93 (s, 2H), 5.75 (t, 1H, J=4.1 Hz), 4.25 (br s, 2H), 3.86 (br s, 2H), 3.66 (t, 2H, J=8.2 Hz), 3.29 (t, 2H, J=6.3 Hz), 3.03 (t, 2H, J=5.4 Hz), 2.74-2.86 (m, 2H), 2.64 (dddd, 1H, J=12.3, 12.3, 3.3, 3.3 Hz), 1.82 (d, 2H, J=12.3 Hz), 1.55-1.65 (m, 2H), 1.49 (s, 9H), 0.98 (t, 2H, J=8.2 Hz), 0.01 (s, 9H). Mass spectrum (ESI, m/z): Calcd. for C$_{32}$H$_{45}$N$_5$O$_6$SSi, 656.3 (M+H). found 656.7.

e) 4-Cyano-1H-imidazole-2-carboxylic acid [2-(1,1-dioxo-1,2,3,6-tetrahydro-1λ6-thiopyran-4-yl)-4-piperidin-4-yl-phenyl]-amide, trifluoroacetic acid salt

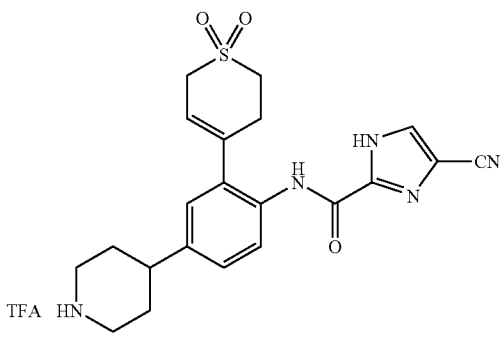 [SMILES: N#Cc1c[nH]c(C(=O)Nc2ccc(C3CCNCC3)cc2C2=CCS(=O)(=O)CC2)n1]

To a solution of 4-[4-{[4-cyano-1-(2-trimethylsilanyl-ethoxymethyl)-1H-imidazole-2-carbonyl]-amino}-3-(1,1-dioxo-1,2,3,6-tetrahydro-1λ$^6$-thiopyran-4-yl)-phenyl]-piperidine-1-carboxylic acid tert-butyl ester (as prepared in the previous step, 81 mg, 0.123 mmol) in 6 mL of DCM was added 0.20 mL of EtOH followed by 2 mL of TFA. The resulting solution was stirred at RT for 3 h. Removal of the solvent under reduced pressure gave 64 mg (96%) of the title compound as a white solid. $^1$H-NMR (CD$_3$OD; 400 MHz): δ 8.02 (s, 1H), 7.78 (d, 1H, J=8.3 Hz), 7.29 (dd, 1H, J=8.3, 2.0 Hz), 7.21 (d, 1H, J=2.0 Hz), 5.71 (t, 1H, J=4.2 Hz), 3.83 (br s, 2H), 3.51 (d, 2H, J=12.4 Hz), 3.33 (t, 2H, J=6.0 Hz), 3.15 (td, 2H, J=13.1, 2.6 Hz), 3.01 (m, 2H), 2.94 (dddd, 1H, J=12.2, 12.2, 3.5, 3.5 Hz), 2.08 (d, 2H, J=12.9 Hz), 1.91 (m, 2H, J=13.3, 13.3, 13.3, 3.8 Hz). Mass spectrum (ESI, m/z): Calcd. for C$_{21}$H$_{23}$N$_5$O$_3$S, 426.2 (M+H). found 426.2.

EXAMPLE 37

4-Cyano-1H-imidazole-2-carboxylic acid [4-(1-acetyl-piperidin-4-yl)-2-(1,1-dioxo-1,2,3,6-tetrahydro-1λ$^6$-thiopyran-4-yl)-phenyl]-amide

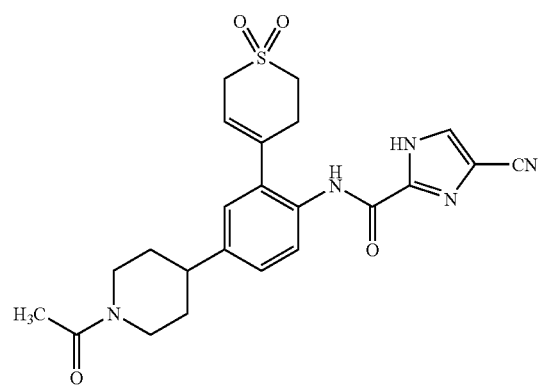 [SMILES: CC(=O)N1CCC(c2ccc(NC(=O)c3nc(C#N)c[nH]3)c(C3=CCS(=O)(=O)CC3)c2)CC1]

To a suspension of 4-cyano-1H-imidazole-2-carboxylic acid [2-(1,1-dioxo-1,2,3,6-tetrahydro-1×6-thiopyran-4-yl)-4-piperidin-4-yl-phenyl]-amide trifluoroacetic acid salt (as prepared in Example 36, step (e), 62 mg, 0.115 mmol) in 4 mL of 1:1 DCM/DMF at RT was added DIEA (60 µL, 0.345 mmol). The mixture was stirred for 5 min, then acetic anhydride (11 µL, 0.121 mmol) was added slowly to the mixture, and the resulting mixture was stirred at RT for 0.5 h. Treated with 40 mL of EtOAc, the mixture was washed with H$_2$O (2×20 mL). The aqueous layers were extracted with EtOAc (4×10 mL). The combined organic layers were concentrated in vacuo. The residue was purified by flash chromatography on silica gel (1-4% MeOH/DCM) yielding 50.9 mg (95%) of the title compound as a white solid. $^1$H-NMR (CDCl$_3$; 400 MHz): δ 13.0 (s, 1H), 9.10 (s, 1H), 8.13 (d, 1H, J=8.4 Hz), 7.77 (d, 1H, J=2.3 Hz), 7.26 (dd, 1H, J=8.4, 2.0 Hz), 7.08 (d, 1H, J=2.0 Hz), 5.77 (t, 1H, J=4.3 Hz), 4.84 (dt, 1H, J=13.3, 2.1 Hz), 4.00 (dt, 1H, J=13.3, 2.1 Hz), 3.89 (br s, 2H), 3.31 (t, 2H, J=6.2 Hz), 3.23 (td, 1H, J=13.2, 2.5 Hz), 3.02 (m, 2H), 2.77 (dddd, 1H, J=11.9, 11.9, 3.4, 3.4 Hz), 2.68 (ddd, 1H, J=12.6, 12.6, 2.9 Hz), 2.18 (s, 3H), 1.70-1.97 (m, 4H). Mass spectrum (ESI, m/z): Calcd. for C$_{23}$H$_{25}$N$_5$O$_4$S, 468.2 (M+H). found 468.1.

EXAMPLE 38

4-Cyano-1H-imidazole-2-carboxylic acid {2-cyclohex-1-enyl-4-[1-(2-dimethylamino-acetyl)-piperidin-4-yl]-phenyl}-amide

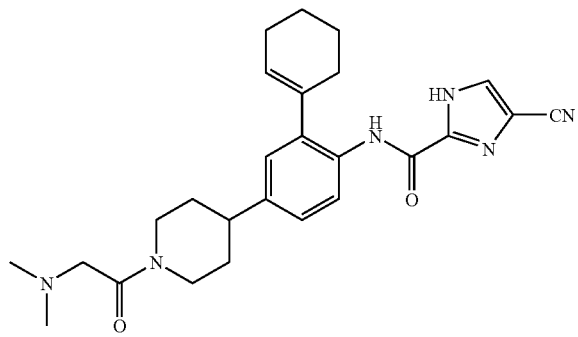 [SMILES: CN(C)CC(=O)N1CCC(c2ccc(NC(=O)c3nc(C#N)c[nH]3)c(C3=CCCCC3)c2)CC1]

A mixture of 4-cyano-1H-imidazole-2-carboxylic acid (2-cyclohex-1-enyl-4-piperidin-4-yl-phenyl)-amide trifluoroacetic acid salt (as prepared in Example 14, step (b), 655 mg, 1.30 mmol) in DCM (15 mL) was cooled to 0° C. and DIEA (0.92 mL, 5.2 mmol) was added. Dimethylaminoacetyl chloride hydrochloride (211 mg, 1.3 mol) was then added portion wise over 10 min. The reaction mixture was stirred at 0° C. for 30 min and allowed to warm to RT and stirred for 2 h. Solvent was removed in vacuo and the resulting residue was partitioned between brine and DCM. The organic layer was separated, dried ($Na_2SO_4$) and concentrated. The residue obtained was purified on silica (5% MeOH: DCM) to obtain 432 mg (70%) of the title compound as a white solid. $^1$H-NMR ($CDCl_3$; 400 MHz): δ 9.49 (s, 1H), 8.24 (d, 1H, J=2.3 Hz), 7.70 (s, 1H), 7.12 (dd, 1H, J=8.4, 2.1 Hz), 7.01 (s, 1H), 5.82 (m, 1H), 4.75 (d, 1H, J=13.4 Hz), 4.13 (d, 1H, J=13.4 Hz), 3.57 (d, 1H, J=14.2 Hz), 3.18 (d, 1H, J=14.2 Hz), 3.12 (td, 1H, J=13.3, 2.4 Hz), 2.73 (dddd, 1H, J=11.9, 11.9, 3.8, 3.8 Hz), 2.65 (ddd, 1H, J=13.3, 13.3, 2.4 Hz), 2.40 (s, 6H), 2.18-2.32 (m, 4H), 1.60-1.98 (m, 8H). Mass spectrum (ESI, m/z): Calcd. for $C_{26}H_{32}N_6O_2$, 461.3 (M+H). found 461.2.

EXAMPLE 38b

4-Cyano-1H-imidazole-2-carboxylic acid {2-cyclohex-1-enyl-4-[1-(2-methylamino-acetyl)-piperidin-4-yl]-phenyl}-amide

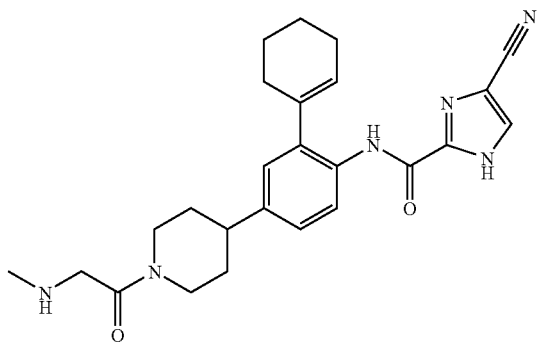 [SMILES: CNCC(=O)N1CCC(c2ccc(NC(=O)c3nc(C#N)c[nH]3)c(C3=CCCCC3)c2)CC1]

HPLC purification of Example 38a also afforded a small amount of 4-cyano-1H-imidazole-2-carboxylic acid {2-cyclohex-1-enyl-4-[1-(2-methylamino-acetyl)-piperidin-4-yl]-phenyl}-amide. $^1$H-NMR ($CD_3OD$; 400 MHz): δ 8.02 (d, 1H, J=8.4 Hz), 7.92 (s, 1H), 7.07 (dd, 1H, J=8.4 Hz, J=2.4 Hz), 6.98 (d, 1H, J=2.4 Hz), 5.73-5.68 (m, 1H), 4.60-4.51 (m, 1H), 3.76-3.68 (m, 1H), 3.20-3.11 (m, 1H), 2.81-2.70 (m, 2H), 2.67 (s, 3H), 2.22-2.13 (m, 4H), 1.88-1.66 (m, 6H), 1.66-1.46 (m, 2H). Mass spectrum (ESI, m/z): Calcd. for $C_{25}H_{30}N_6O_2$, 447.2 (M+H). found 447.3.

EXAMPLE 39

4-{4-[(4-Cyano-1H-imidazole-2-carbonyl)-amino]-3-cyclohex-1-enyl-phenyl}-piperidine-1-carboxylic acid (2-hydroxy-ethyl)-amide

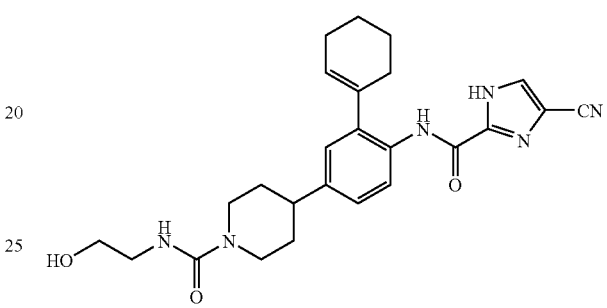

a) 4-Cyano-1-(2-trimethylsilanyl-ethoxymethyl)-1H-imidazole-2-carboxylic acid (2-cyclohex-1-enyl-4-piperidin-4-yl-phenyl)-amide, trifluoroacetic acid salt

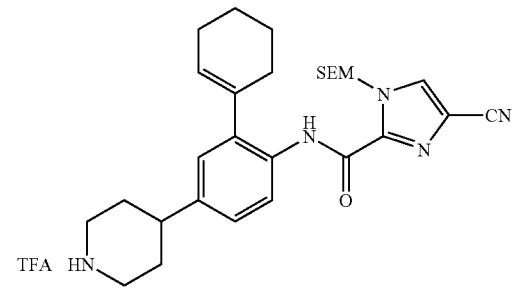 [SMILES: C[Si](C)(C)CCOCn1cc(C#N)nc1C(=O)Nc1ccc(C2CCNCC2)cc1C1=CCCCC1]

To a solution of 4-(4-{[4-cyano-1-(2-trimethylsilanyl-ethoxymethyl)-1H-imidazole-2-carbonyl]-amino}-3-cyclohex-1-enyl-phenyl)-piperidine-1-carboxylic acid tert-butyl ester (as prepared in Example 14, step (a), 81 mg, 0.123 mmol) in 18 mL of DCM was added 1 mL of EtOH followed by 5 mL of TFA at 0° C. The resulting solution was stirred at RT for 0.5 h, treated with 20 mL of EtOH followed by 20 mL of n-PrOH and 5 mL of $H_2O$, the mixture was then concentrated under reduced pressure to give a slightly yellow solid. Flash chromatography of the compound on silica gel (2-4% MeOH/DCM) gave 0.87 g (85%) of the title compound as a white solid. $^1$H-NMR ($CDCl_3$; 400 MHz): δ 9.70 (s, 1H), 9.66 (br s, 1H), 9.15 (br s, 1H), 8.29 (d, 1H, J=8.3 Hz), 7.78 (s, 1H), 7.13 (dd, 1H, J=8.3, 2.2 Hz), 7.03 (d, 1H, J=2.2 Hz), 5.95 (s, 2H), 5.83 (m, 1H), 3.66 (t, 2H, J=8.4 Hz), 3.55 (d, 2H, J=12.3 Hz), 2.95-3.11 (m, 2H), 2.76 (m, 1H), 2.18-2.33 (m, 4H), 1.99-2.15 (m, 4H), 1.82 (m, 4H), 0.97 (t, 2H, J=8.3 Hz), 0.00 (s, 9H). Mass spectrum (ESI, m/z): Calcd. for $C_{28}H_{39}N_5O_2Si$, 506.3 (M+H). found 506.1.

b) 4-(4-{[4-Cyano-1-(2-trimethylsilanyl-ethoxymethyl)-1H-imidazole-2-carbonyl]-amino}-3-cyclohex-1-enyl-phenyl)-piperidine-1-carboxylic acid (2-hydroxy-ethyl)-amide

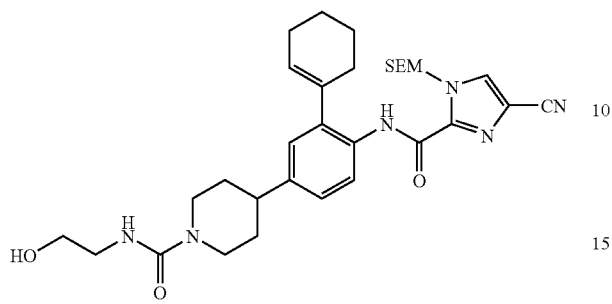

A solution of 4-cyano-1-(2-trimethylsilanyl-ethoxymethyl)-1H-imidazole-2-carboxylic acid (2-cyclohex-1-enyl-4-piperidin-4-yl-phenyl)-amide trifluoroacetic acid salt (as prepared in the previous step, 116 mg, 0.192 mmol) and DIEA (134 μL, 0.770 mmol) in 4 mL of DCM was added slowly to solution of triphosgene (23 mg, 0.0768 mmol) in 4 mL of DCM at −78° C. under Ar. The mixture was stirred at −78° C. for 15 min, warmed to RT and stirred for 15 min and cooled to −78° C. again. A suspension of 2-amino-ethanol (350 μL, 5.77 mmol) in 4 mL of THF was added and the resulting mixture was warmed to RT and stirred for 20 h under Ar. Treated with 100 mL of EtOAc, the mixture was washed with H$_2$O (3×20 mL), brine (20 mL) and dried (Na$_2$SO$_4$). Removal of the solvent in vacuo followed by flash chromatography of the residue on silica gel (10% EtOAc/DCM then 5% MeOH/DCM) gave 95 mg (83%) of the title compound as a colorless oil. $^1$H-NMR (CDCl$_3$; 400 MHz): δ 9.68 (s, 1H), 8.25 (d, 1H, J=8.4 Hz), 7.77 (s, 1H), 7.12 (dd, 1H, J=8.4, 2.2 Hz), 7.01 (d, 1H, J=2.2 Hz), 5.94 (s, 2H), 5.83 (m, 1H), 4.96 (t, 1H, J=5.6 Hz), 4.11 (d, 2H, J=13.3 Hz), 3.75 (ddd, 2H, J=4.4 Hz), 3.66 (t, 2H, J=8.3 Hz), 3.44 (ddd, 2H, J=5.0 Hz), 3.36 (t, 1H, J=4.6 Hz), 2.91 (ddd, 2H, J=13.0, 2.2 Hz), 2.66 (dddd, 1H, J=12.2, 12.2, 3.3, 3.3 Hz), 2.18-2.33 (m, 4H), 1.75-1.91 (m, 6H), 1.67 (dddd, 2H, J=12.9, 12.9, 12.9, 4.0 Hz), 0.97 (t, 2H, J=8.3 Hz), 0.00 (s, 9H). Mass spectrum (ESI, m/z): Calcd. for C$_{31}$H$_{44}$N$_6$O$_4$Si, 593.3 (M+H). found 593.1.

c) 4-{4-[(4-Cyano-1H-imidazole-2-carbonyl)-amino]-3-cyclohex-4-enyl-phenyl}-piperidine-1-carboxylic acid (2-hydroxy-ethyl)-amide

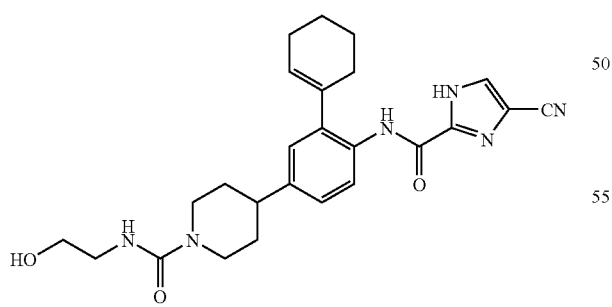

To a solution of 4-(4-{[4-cyano-1-(2-trimethylsilanyl-ethoxymethyl)-1H-imidazole-2-carbonyl]-amino}-3-cyclohex-1-enyl-phenyl)-piperidine-1-carboxylic acid (2-hydroxy-ethyl)-amide (as prepared in the previous step, 95 mg, 0.16 mmol) in 3 mL of DCM was added 0.10 mL of EtOH followed by 1.0 mL of TFA. The resulting solution was stirred at RT for 6 h. Removal of the solvent under reduced pressure followed by flash chromatography of the residue on silica gel (2-8% MeOH/DCM) gave 68 mg (92%) of the title compound as a white solid. $^1$H-NMR (CD$_3$OD; 400 MHz): δ 8.09 (d, 1H, J=8.4 Hz), 8.00 (s, 1H), 7.15 (dd, 1H, J=8.4, 2.2 Hz), 5.79 (m, 1H), 4.15 (dd, 2H, J=13.3, 1.1 Hz), 3.61 (t, 2H, J=5.9 Hz), 3.27-3.32 (m, 2H), 2.90 (ddd, 2H, J=13.0, 13.0, 2.5 Hz), 2.73 (dddd, 1H, J=12.1, 12.1, 2.6, 2.6 Hz), 2.26 (m, 4H), 1.73-1.88 (m, 6H), 1.62 (dddd, 2H, J=12.6, 12.6, 12.6, 4.0 Hz). Mass spectrum (ESI, m/z): Calcd. for C$_{25}$H$_{30}$N$_6$O$_3$, 463.2 (M+H). found 463.2.

EXAMPLE 40

4-Cyano-1H-imidazole-2-carboxylic acid {2-cyclohex-1-enyl-4-[1-(2-methanesulfonyl-ethyl)-piperidin-4-yl]-phenyl}-amide

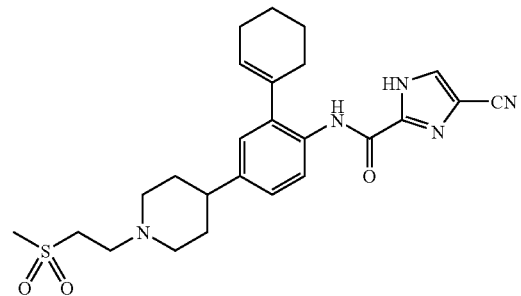 [SMILES: CS(=O)(=O)CCN1CCC(c2ccc(NC(=O)c3nc(C#N)c[nH]3)c(C3=CCCCC3)c2)CC1]

a) Methanesulfonic acid 2-methanesulfonyl-ethyl ester

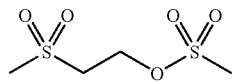

To a solution of methanesulfonyl chloride (484 mg, 4.23 mmol) in 15 mL of DCM at 0° C. was added 2-methanesulfonyl-ethanol (500 mg, 4.03 mmol) in 10 mL of DCM followed by DIEA (1.05 mL, 6.05 mmol) under Ar. The mixture was warmed to RT and stirred for 20 h under Ar. The mixture was treated with 100 mL of EtOAc and washed with H$_2$O (3×20 mL), brine (20 mL) and dried (Na$_2$SO$_4$). Removal of the solvent in vacuo gave 534 mg (66%) of the title compound as a brown oil. $^1$H-NMR (CDCl$_3$; 400 MHz): δ 4.67 (d, 2H, J=5.5 Hz), 3.46 (d, 2H, J=5.5 Hz), 3.11 (s, 3H), 3.04 (s, 3H).

b) 4-Cyano-1H-imidazole-2-carboxylic acid {2-cyclohex-1-enyl-4-[1-(2-methanesulfonyl-ethyl)-piperidin-4-yl]-phenyl}-amide

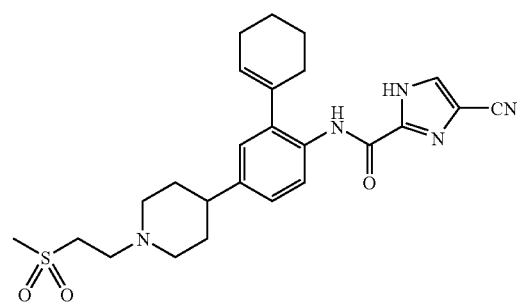 [SMILES: CS(=O)(=O)CCN1CCC(c2ccc(NC(=O)c3nc(C#N)c[nH]3)c(C3=CCCCC3)c2)CC1]

To a solution of 4-cyano-1H-imidazole-2-carboxylic acid (2-cyclohex-1-enyl-4-piperidin-4-yl-phenyl)-amide trifluoroacetic acid salt (as prepared in Example 14, step (b), 85 mg, 0.174 mmol) and DIEA (91 µL, 0.521 mmol) in 3 mL of DCM at RT was added 2-methanesulfonic acid 2-methanesulfonyl-ethyl ester (as prepared in the previous step, 42 mg, 0.208 mmol). The resulting mixture was stirred at RT for 3 h. Treated with 50 mL of EtOAc, the mixture was washed with H$_2$O (2×20 mL), brine (10 mL) and dried (Na$_2$SO$_4$). Removal of the solvent in vacuo followed by flash chromatography of the residue on silica gel (1-3% MeOH/DCM) gave 54 mg (65%) of the title compound as a white solid. $^1$H-NMR (CDCl$_3$; 400 MHz): δ 9.54 (s, 1H), 8.25 (d, 1H, J=8.4 Hz), 7.72 (s, 1H), 7.15 (dd, 1H, J=8.4, 2.0 Hz), 7.04 (d, 1H, J=2.0 Hz), 5.85 (m, 1H), 3.21 (t, 1H, J=6.5 Hz), 3.09 (s, 3H), 3.02-3.11 (m, 2H), 2.92 (t, 2H, J=6.5 Hz), 2.52 (dddd, 1H, J=12.1, 12.1, 3.3, 3.3 Hz), 2.18-2.34 (m, 4H), 2.18 (t, 2H, J=10.8 Hz), 1.64-1.94 (m, 8H). Mass spectrum (ESI, m/z): Calcd. for C$_{25}$H$_{31}$N$_5$O$_3$S, 482.2 (M+H). found 482.2.

The following compounds have been prepared according to the examples as indicated:

EXAMPLE 43

4-Cyano-1H-imidazole-2-carboxylic acid {2-cyclohex-1-enyl-4-[1-(pyridine-3-carbonyl)-piperidin-4-yl]-phenyl}-amide

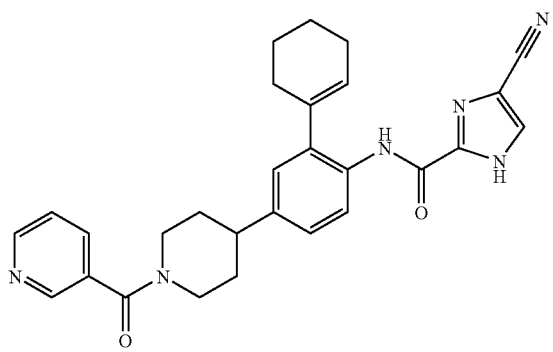

A solution of 4-cyano-1H-imidazole-2-carboxylic acid (2-cyclohex-1-enyl-4-piperidin-4-yl-phenyl)-amide trifluoroacetic acid salt (as prepared in Example 14, step (b), 75.0 mg, 0.15 mmol) in CH$_2$Cl$_2$ (10 mL) was treated with Et$_3$N (64.1 µL, 0.46 mmol) and cooled to 0° C. The mixture was treated with nicotinoyl chloride hydrochloride (0.030 g, 0.17

| Example | Structure | Mass Spectrum [M + H]$^+$ Calcd. | Found | Formula | Proc. Of Ex |
|---|---|---|---|---|---|
| 41 | 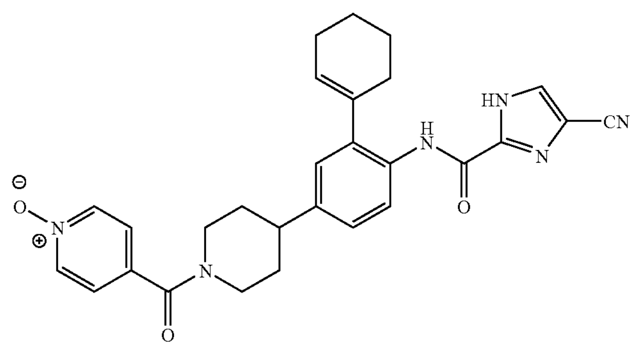 [SMILES: N#Cc1c[nH]c(C(=O)Nc2ccc(C3CCN(C(=O)c4cc[n+]([O-])cc4)CC3)cc2C2=CCCCC2)n1] | 497.2 | 497.2 | C$_{28}$H$_{28}$N$_6$O$_3$ | 29 |
| 42 | | 497.2 | 497.3 | C$_{28}$H$_{28}$N$_6$O$_3$ | 29 | mmol) and stirred at 0° C. for 15 min then at room temperature for 17 h. The reaction mixture was adsorbed directly onto silica gel. Silica gel chromatography (10% MeOH in EtOAc) afforded the title compound (61.0 mg, 83%) as a white solid. $^1$H-NMR (CDCl$_3$; 400 MHz): δ 9.51 (br s, 1H), 8.77 (s, 1H), 8.70-8.66 (m, 1H), 8.32 (d, 1H, J=8.4 Hz), 7.86-7.81 (m, 1H), 7.70 (s, 1H), 7.42-7.37 (m, 1H), 7.17 (d, 1H, J=8.4 Hz), 7.06-7.04 (m, 1H), 5.87-5.82 (m, 1H), 4.98-4.87 (m, 1H), 3.94-3.84 (m, 1H), 3.29-3.18 (m, 1H), 2.98-2.86 (m, 1H), 2.86-2.76 (m, 1H), 2.34-2.20 (m, 4H), 1.94-1.72 (m, 9H). LC-MS (ESI, m/z): Calcd. for C$_{28}$H$_{28}$N$_6$O$_2$, 481.2 (M+H). found 481.3.

EXAMPLE 44

4-Cyano-1H-imidazole-2-carboxylic acid (2-cyclohex-1-enyl-4-{1-[2-(2-hydroxy-ethylamino)-acetyl]-piperidin-4-yl}-phenyl)-amide trifluoroacetic acid salt

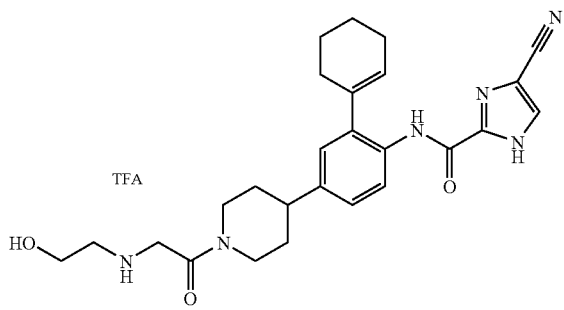 [SMILES: N#Cc1c[nH]c(C(=O)Nc2ccc(C3CCN(C(=O)CNCCO)CC3)cc2C2=CCCCC2)n1]

a) [2-(4-{4-[(4-Cyano-1H-imidazole-2-carbonyl)-amino]-3-cyclohex-1-enyl-phenyl}-piperidin-1-yl)-2-oxo-ethyl]-carbamic acid tert-butyl ester

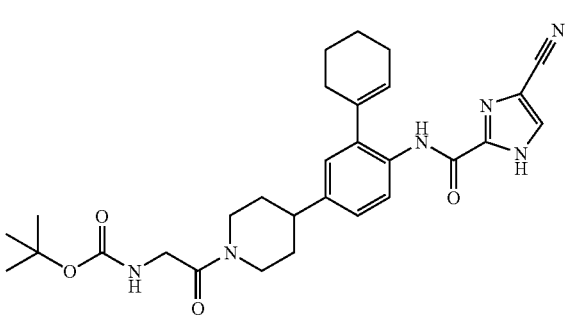 [SMILES: CC(C)(C)OC(=O)NCC(=O)N1CCC(c2ccc(NC(=O)c3nc(C#N)c[nH]3)c(C3=CCCCC3)c2)CC1]

A solution of N—BOC-glycine (0.29 g, 1.63 mmol) in CH$_2$Cl$_2$ (10 mL) was treated with DIEA (0.85 mL, 4.90 mmol), HOBt (0.26 g, 1.96 mmol), and EDCI (0.38 g, 1.96 mmol). The mixture was stirred at room temperature for 10 min and added to a suspension of 4-cyano-1H-imidazole-2-carboxylic acid (2-cyclohex-1-enyl-4-piperidin-4-yl-phenyl)-amide trifluoroacetic acid salt (as prepared in Example 14, step (b), 0.80 g, 1.63 mmol) in CH$_2$Cl$_2$ (20 mL). The solution was stirred at room temperature for 17 h. Solvents were evaporated in vacuo. Silica gel chromatography (50% EtOAc in hexanes) afforded the title compound (0.41 g, 47%) as a white solid. $^1$H-NMR (CDCl$_3$; 400 MHz): δ 9.53 (s, 1H), 8.26 (d, 1H, J=8.4 Hz), 7.80-7.78 (m, 1H), 7.71 (s, 1H), 7.45-7.43 (m, 1H), 7.06 (d, 1H, J=8.4 Hz), 7.00 (s, 1H), 5.83 (br s, 1H), 5.76 (br s, 1H), 4.78-4.68 (m, 1H), 3.96-3.85 (m, 2H), 3.17-3.03 (m, 1H), 2.78-2.63 (m, 2H), 2.29 (br s, 2H), 2.22 (br s, 2H), 1.95-1.87 (m, 2H), 1.86-1.72 (m, 4H), 1.70-1.55 (m, 2H), 1.44 (s, 9H). LC-MS (ESI, m/z): Calcd. for C$_{29}$H$_{36}$N$_6$O$_4$ 533.3 (M+H). found 532.9.

b) 4-Cyano-1H-imidazole-2-carboxylic acid {4-[1-(2-amino-acetyl)-piperidin-4-yl]-2-cyclohex-1-enyl-phenyl}-amide trifluoroacetic acid salt

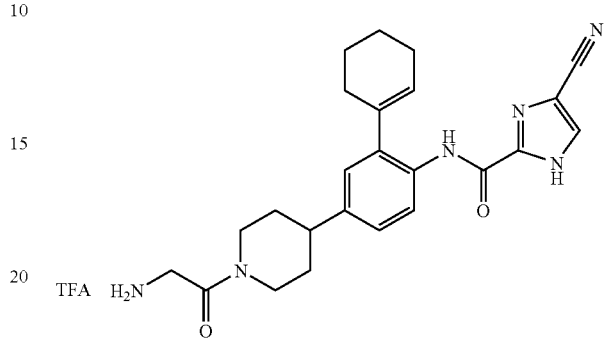

A solution of [2-(4-{4-[(4-cyano-1H-imidazole-2-carbonyl)-amino]-3-cyclohex-1-enyl-phenyl}-piperidin-1-yl)-2-oxo-ethyl]-carbamic acid tert-butyl ester (as prepared in the previous step, 0.41 g, 0.77 mmol) in CH$_2$Cl$_2$ (20 mL) was treated with EtOH (0.2 mL) and TFA (6 mL). The mixture stirred at room temperature for 45 min, and the solvents were evaporated in vacuo. The crude material was used directly in the next step. LC-MS (ESI, m/z): Calcd. for C$_{24}$H$_{28}$N$_6$O$_2$ 433.2 (M+H). found 433.2.

c) 4-Cyano-1H-imidazole-2-carboxylic acid (2-cyclohex-1-enyl-4-{1-[2-(2-hydroxy-ethylamino)-acetyl]-piperidin-4-yl}-phenyl)-amide trifluoroacetic acid salt

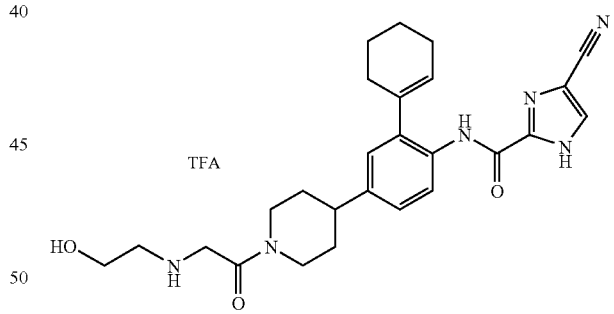

A suspension of 4-cyano-1H-imidazole-2-carboxylic acid {4-[1-(2-amino-acetyl)-piperidin-4-yl]-2-cyclohex-1-enyl-phenyl}-amide trifluoroacetic acid salt (as prepared in the previous step, 0.42 g, 0.77 mmol) in CH$_2$Cl$_2$ (20 mL) was treated with Na(OAc)$_3$BH (0.33 g, 1.54 mmol) and solid glyoxal (44.6 mg, 0.77 mmol). The mixture stirred at room temperature for 1 h, and the solvent was evaporated in vacuo. The residue was taken up in MeOH and the solids filtered off, and the filtrate was concentrated in vacuo. Reverse phase HPLC (C-18 column) (20% to 60% acetonitrile in water with 0.1% TFA over 30 min) afforded the title compound (83 mg, 19% over two steps) as a white solid. $^1$H-NMR (CD$_3$OD; 400 MHz): δ 8.16-8.09 (m, 1H), 8.05-8.01 (m, 1H), 7.22-7.15 (m, 1H), 7.11-7.06 (m, 1H), 5.84-5.79 (m, 1H), 4.72-4.62 (m, 1H), 4.24-3.91 (m, 2H), 3.89-3.80 (m, 2H), 3.28-3.18 (m, 2H), 2.92-2.79 (m, 2H), 2.28 (br s, 4H), 1.98-1.89 (m, 2H), 1.89-1.76 (m, 4H), 1.76-1.57 (m, 2H). LC-MS (ESI, m/z): Calcd. for $C_{26}H_{32}N_6O_3$ 477.2 (M+H). found 477.2.

EXAMPLE 45

4-Cyano-1H-imidazole-2-carboxylic acid (2-cyclohex-1-enyl-4-{1-[2-(2-hydroxy-ethyl)-methyl-amino-acetyl]-piperidin-4-yl}-phenyl)-amide trifluoroacetic acid salt

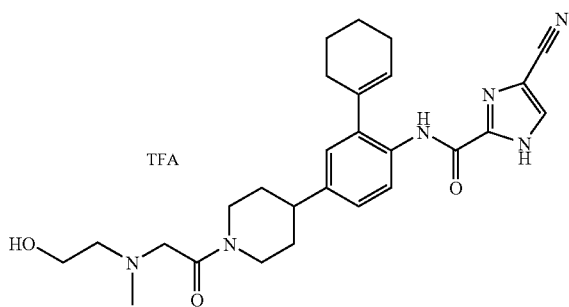 [SMILES: CN(CCO)CC(=O)N1CCC(c2ccc(NC(=O)c3nc(C#N)c[nH]3)c(C3=CCCCC3)c2)CC1]

A solution of 4-cyano-1H-imidazole-2-carboxylic acid (2-cyclohex-1-enyl-4-{1-[2-(2-hydroxy-ethylamino)-acetyl]-piperidin-4-yl}-phenyl)-amide trifluoroacetic acid salt (as prepared in Example 44, step (c), 50.0 mg, 0.085 mmol) in MeOH (3 mL) was treated with Na(OAc)$_3$BH (39.5 mg, 0.19 mmol) and 37% aqueous formaldehyde (8.2 µL, 0.10 mmol). The mixture was stirred at room temperature for 5.5 h, and the solvents were removed in vacuo. Reverse phase HPLC (C-18 column) (10% to 50% acetonitrile in water with 0.1% TFA over 30 min) afforded the title compound (19.5 mg, 47%) as a white solid. $^1$H-NMR (CD$_3$OD; 400 MHz): δ 8.12 (d, 1H, J=8.4 Hz), 8.02 (s, 1H), 7.19 (dd, 1H, J=8.4, 2.0 Hz), 7.09 (d, 1H, J=2.0 Hz), 5.84-5.79 (m, 1H), 4.72-4.64 (m, 1H), 4.39-4.23 (m, 2H), 3.84-3.79 (m, 1H), 3.31-3.21 (m, 1H), 3.03-2.94 (m, 6H), 2.92-2.80 (m, 2H), 2.32-2.24 (m, 4H), 2.00-1.90 (m, 2H), 1.90-1.76 (m, 5H), 1.78-1.59 (m, 2H). LC-MS (ESI, m/z): Calcd. for $C_{27}H_{34}N_6O_3$ 491.3 (M+H). found 491.2.

EXAMPLE 46

4-Cyano-1H-imidazole-2-carboxylic acid [4-(1-acetyl-piperidin-4-yl)-2-(1,2,5,6-tetrahydro-pyridin-3-yl)-phenyl]-amide trifluoroacetic acid salt

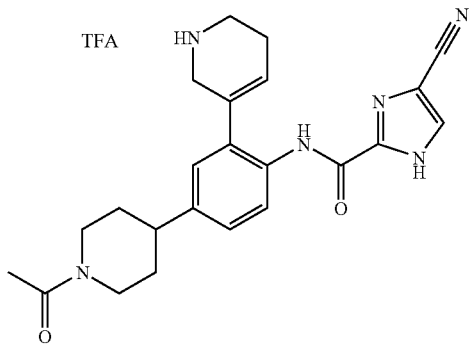 [SMILES: CC(=O)N1CCC(c2ccc(NC(=O)c3nc(C#N)c[nH]3)c(C3=CCCNC3)c2)CC1]

a) 5-Trifluoromethanesulfonyloxy-3,6-dihydro-2H-pyridine-1-carboxylic acid tert-butyl ester

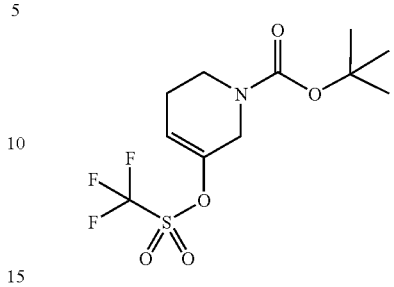

A solution of LDA (23.4 mL, 35.1 mmol, 1.5 M in cyclohex) in THF (50 mL) was cooled to −78° C. under Ar. The solution was treated with 3-oxo-piperidine-1-carboxylic acid tert-butyl ester (5.00 g, 25.1 mmol) as a solution in THF (15 mL) via drop wise addition and stirred for 15 min. The mixture was treated with 1,1,1-trifluoro-N-phenyl-N—[(trifluoromethyl)sulfonyl]methanesulfonimide (12.5 g, 35.1 mmol) as a solution in THF (40 mL). The mixture was allowed to warm to room temperature and stir 2.5 h. The reaction was quenched with saturated aqueous NaHCO$_3$, diluted with Et$_2$O, and washed with water. The organic layer was dried over MgSO$_4$ and concentrated in vacuo. Silica gel chromatography (5% EtOAc in hexanes) afforded the title compound (2.45 g, 30%) as a colorless oil. $^1$H-NMR (CDCl$_3$; 400 MHz): δ 5.97-5.89 (m, 1H), 4.09-4.01 (m, 2H), 3.54-3.45 (m, 2H), 2.36-2.26 (m, 2H), 1.48 (s, 9H). LC-MS (ESI, m/z): Calcd. for $C_{11}H_{16}F_3NO_5S$ 332.1 (M+H). found 332.1.

b) 5-(4,4,5,5-Tetramethyl-[1,3,2]dioxaborolan-2-yl)-3,6-dihydro-2H-pyridine-1-carboxylic acid tert-butyl ester

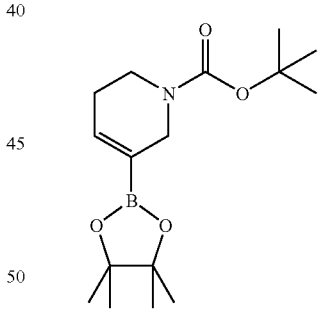

PdCl$_2$dppf (0.16 g, 0.22 mmol), KOAc (2.18 g, 22.2 mmol), 4,4,5,5,4',4',5',5'-octamethyl-[2,2']bi[[1,3,2]dioxaborolanyl] (2.07 g, 8.13 mmol), and dppf (0.12 g, 0.22 mmol) were placed in a round-bottomed flask, and the flask was flushed with Ar. A degassed solution of 5-trifluoromethanesulfonyloxy-3,6-dihydro-2H-pyridine-1-carboxylic acid tert-butyl ester (as prepared in the previous step, 2.45 g, 7.40 mmol) in dioxane (70 mL) was added to the flask and heated to 80° C. for 16 h. The mixture was filtered through a glass-fritted funnel to remove the solid KOAc, and the filtrate was concentrated in vacuo. Silica gel chromatography (5% EtOAc in hexanes) afforded the title compound (1.62 g, 71%) as a colorless oil. $^1$H-NMR (CDCl$_3$; 400 MHz): δ 6.69-6.60 (m, 1H), 3.98 (br s, 2H), 3.49-3.42 (m, 2H), 2.24-2.16 (m, 2H), 1.47 (s, 9H), 1.27 (s, 12H). LC-MS (ESI, m/z): Calcd. for C₁₈H₂₈BNO₄ 310.2 (M+H). found 311.0.

c) 4-(4-Nitro-phenyl)-3,6-dihydro-2H-pyridine-1-carboxylic acid tert-butyl ester

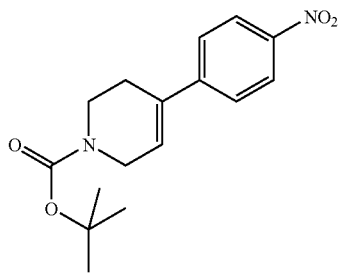 [SMILES: CC(C)(C)OC(=O)N1CC=C(c2ccc([N+](=O)[O-])cc2)CC1]

The title compound was prepared by the Suzuki coupling procedure of Example 35, step (b) using 4-nitrophenylboronic acid (167 mg, 1.00 mmol) and 4-trifluoromethanesulfonyloxy-3,6-dihydro-2H-pyridine-1-carboxylic acid tert-butyl ester (as prepared in Example 13, step (a), 295 mg, 1.00 mmol). Silica gel chromatography (10% EtOAc in hexanes) afforded the title compound (273 mg, 90%) as an oil. ¹H-NMR (CDCl₃; 400 MHz): δ 8.19 (d, 2H, J=8.8 Hz), 7.50 (d, 2H, J=8.8 Hz), 6.23 (m, 1H), 4.12 (m, 2H), 3.66 (m, 2H), 2.54 (m, 2H), 1.49 (s, 9H).

d) 1-[4-(4-Amino-phenyl)-piperidin-1-yl]-ethanone

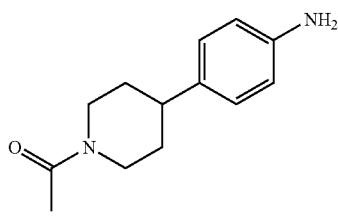 [SMILES: CC(=O)N1CCC(c2ccc(N)cc2)CC1]

A solution of 4-(4-nitro-phenyl)-3,6-dihydro-2H-pyridine-1-carboxylic acid tert-butyl ester (as prepared in the previous step, 304 mg, 1.00 mmol) in a 1:1 mixture of DCM/TFA (10 mL) was stirred at room temperature for 3 h and concentrated. The residue was dried in vacuo overnight, was taken up in CH₂Cl₂ (10 mL) and was cooled to 0° C. To this solution, Et₃N (280 µL, 2 mmol) was added drop wise, followed by acetic anhydride (102 µL, 1 mmol). The resulting mixture was stirred at 0° C. for 1 h and allowed to warm to room temperature. The reaction mixture was washed with brine, and the organic layer was separated, dried and concentrated. The resulting product was reduced to obtain the title compound (143 mg, 65%) using a procedure similar to Example 4, step (d). ¹H-NMR (CDCl₃; 400 MHz): δ 6.97 (d, 2H, J=8.4 Hz), 6.64 (d, 2H, J=8.4 Hz), 4.75 (m, 1H), 3.93 (m, 1H), 3.13 (m, 3H), 2.66 (m, 2H), 2.12 (s, 3H), 1.84 (m, 2H), 1.57 (m, 2H).

e) 1-[4-(4-Amino-3-bromo-phenyl)-piperidin-1-yl]-ethanone

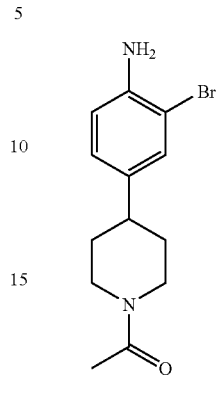

A solution of 1-[4-(4-amino-phenyl)-piperidin-1-yl]-ethanone (as prepared in the previous step, 0.36 g, 1.66 mmol) in CH₂Cl₂ (10 mL) was cooled to −78° C. and treated with NBS (0.28 g, 1.58 mmol) as a suspension in CH₂Cl₂ (4 mL). The reaction was allowed to warm to room temperature and stir for 30 min. The reaction was diluted with CH₂Cl₂ and washed with saturated aqueous NaHCO₃. The organic layer was dried over MgSO₄ and concentrated in vacuo. The crude material was used directly in the next reaction. LC-MS (ESI, m/z): Calcd. for C₁₃H₁₇BrN₂O 297.1 (M+H). found 297.1.

f) 5-[5-(1-Acetyl-piperidin-4-yl)-2-amino-phenyl]-3,6-dihydro-2H-pyridine-1-carboxylic acid tert-butyl ester

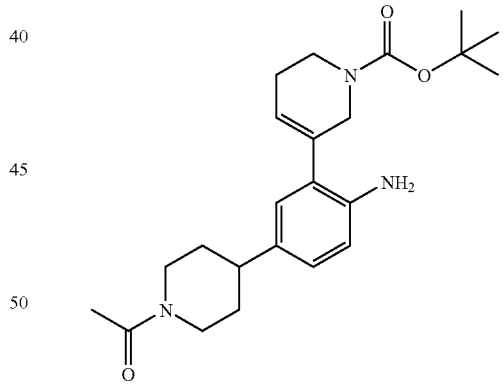

A solution of 5-(4,4,5,5-tetramethyl-[1,3,2]dioxaborolan-2-yl)-3,6-dihydro-2H-pyridine-1-carboxylic acid tert-butyl ester (as prepared in Example 46, step (b), 0.62 g, 2.02 mmol) and 1-[4-(4-amino-3-bromo-phenyl)-piperidin-1-yl]-ethanone (as prepared in the previous step, 0.20 g, 0.67 mmol) in toluene:EtOH (2:1, 9 mL) was treated with 2.0 M aqueous Na₂CO₃ (2.7 mL, 5.38 mmol) and was degassed with sonication under Ar. The mixture was heated to 80° C., treated with Pd(PPh₃)₄ (54 mg, 0.05 mmol), and stirred at 80° C. for 4.5 h. The reaction was cooled to room temperature, diluted with EtOAc, and washed with saturated aqueous NaHCO₃. The organic layer was dried over MgSO₄ and concentrated in vacuo to afford the title compound (0.25 g, 93%) as an off-white solid. LC-MS (ESI, m/z): Calcd. for $C_{23}H_{33}N_3O_3$ 422.2 (M+Na). found 422.0.

g) 5-(5-(1-Acetyl-piperidin-4-yl)-2-{[4-cyano-1-(2-trimethylsilanyl-ethoxymethyl)-1H-imidazole-2-carbonyl]-amino}-phenyl)-3,6-dihydro-2H-pyridine-1-carboxylic acid tert-butyl ester

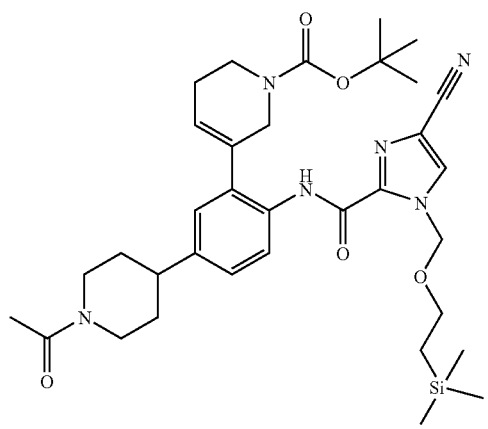 [SMILES: CC(=O)N1CCC(c2ccc(NC(=O)c3nc(C#N)cn3COCC[Si](C)(C)C)c(C3=CCCN(C(=O)OC(C)(C)C)C3)c2)CC1]

A solution of 5-[5-(1-acetyl-piperidin-4-yl)-2-amino-phenyl]-3,6-dihydro-2H-pyridine-1-carboxylic acid tert-butyl ester (as prepared in the previous step, 0.25 g, 0.63 mmol) in $CH_2Cl_2$ was treated with PyBroP (0.44 g, 0.94 mmol) and 4-cyano-1-(2-trimethylsilanyl-ethoxymethyl)-1H-imidazole-2-carboxylic acid, potassium salt (as prepared in Example 3, step (d), 0.21 g, 0.69 mmol). The resulting slurry was cooled to 0° C. and treated with DIEA (0.33 mL, 1.88 mmol). The ice bath was removed and the mixture stirred at room temperature for 18 h. The reaction was diluted with $CH_2Cl_2$ and washed with saturated aqueous $NaHCO_3$. The organic layer was dried over $MgSO_4$ and concentrated in vacuo. Silica gel chromatography (25-45% EtOAc in hexanes then 100% EtOAc) afforded the title compound (399 mg, 98%) as a white solid. LC-MS (ESI, m/z): Calcd. for $C_{34}H_{48}N_6O_5Si$ 649.4 (M+H). found 649.9.

h) 4-Cyano-1H-imidazole-2-carboxylic acid [4-(1-acetyl-piperidin-4-yl)-2-(1,2,5,6-tetrahydro-pyridin-3-yl)-phenyl]-amide trifluoroacetic acid salt

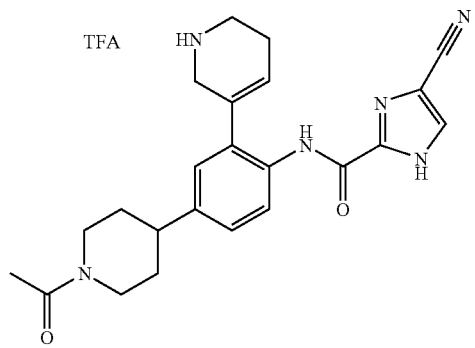 [SMILES: CC(=O)N1CCC(c2ccc(NC(=O)c3nc(C#N)c[nH]3)c(C3=CCCNC3)c2)CC1]

A solution of 5-(5-(1-acetyl-piperidin-4-yl)-2-{[4-cyano-1-(2-trimethylsilanyl-ethoxymethyl)-1H-imidazole-2-carbonyl]-amino}-phenyl)-3,6-dihydro-2H-pyridine-1-car- boxylic acid tert-butyl ester (as prepared in the previous step, 0.40 g, 0.61 mmol) in $CH_2Cl_2$ (20 mL) and EtOH (0.4 mL) was treated with TFA (3 mL). The solution was stirred at room temperature for 0.5 h. The solvents were evaporated in vacuo, and the residue was immediately taken up in EtOH (25 mL) and stored at 5° C. for 11 h. The solution was concentrated in vacuo, and the residue was taken up in $CH_2Cl_2$ (20 mL) and EtOH (0.4 mL) then treated with TFA (6 mL). The reaction was stirred at room temperature for 2 h, and the solvents were evaporated in vacuo. Reverse phase HPLC (C-18 column) (10 to 80% acetonitrile in water with 0.1% TFA over 30 min) afforded the title compound (56.9 mg, 22%) as a white solid. $^1$H-NMR (CDCl$_3$; 400 MHz): δ 8.06 (s, 1H), 7.81 (d, 1H, J=8.4 Hz), 7.32 (d, 1H, J=8.4 Hz), 7.22 (s, 1H), 6.10-6.03 (m, 1H), 4.74-4.64 (m, 2H), 4.11-4.02 (m, 1H), 3.95 (s, 2H), 3.50-3.37 (m, 2H), 3.29-3.20 (m, 1H), 2.93-2.82 (m, 1H), 2.80-2.69 (m, 1H), 2.62-2.53 (m, 2H), 2.16 (s, 3H), 1.98-1.84 (m, 2H), 1.78-1.54 (m, 2H). LC-MS (ESI, m/z): Calcd. for $C_{23}H_{26}N_6O_2$ 419.2 (M+H). found 419.2.

EXAMPLE 47

(4-{4-[(4-Cyano-1H-imidazole-2-carbonyl)-amino]-3-cyclohex-1-enyl-phenyl}-piperidin-1-yl)-acetic acid trifluoroacetic acid salt

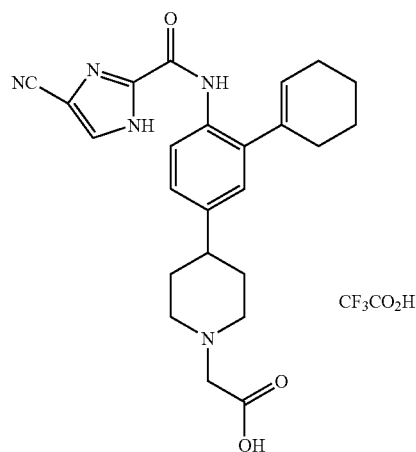

A flask was charged with 4-cyano-1H-imidazole-2-carboxylic acid (2-cyclohex-1-enyl-4-piperidin-4-yl-phenyl)-amide TFA salt (33 mg, 0.067 mmol) (as prepared in Example 14, step (b)), t-butyl bromoacetate (10 µL, 0.067 mmol), NEt$_3$ (20 µL, 0.135 mmol) and 0.25 mL of DCM and stirred for 10 h at 25° C. The reaction mixture was loaded on a 5 g SPE cartridge (silica) and 23 mg (70%) of (4-{4-[(4-cyano-1H-imidazole-2-carbonyl)-amino]-3-cyclohex-1-enyl-phenyl}-piperidin-1-yl)-acetic acid tert-butyl ester was eluted with 25% EtOAc/DCM. This compound was dissolved in 1 mL of DCM and 20 µL of EtOH and 1 mL of TFA were added and the reaction stirred for 3 h at 25° C. The title compound was purified by RP-HPLC (C18), eluting with 30-50% CH$_3$CN in 0.1% TFA/H$_2$O over 12 min to give 10 mg (40%) of a white solid. $^1$H-NMR (400 MHz, CD$_3$OD): δ 8.16 (d, 1H), 8.02 (s, 1H), 7.22 (dd, 1H), 7.10 (d, 1H), 5.72 (m, 1H), 4.04. (s, 2H), 3.76 (m, 2H), 3.22 (m, 2H), 2.90 (m, 1H), 2.29 (m, 4H), 2.10 (m, 4H), 1.82 (m, 4H). Mass spectrum (ESI, m/z): Calcd. for $C_{24}H_{27}N_5O_3$, 434.2 (M+H). found 434.2.

EXAMPLE 48

4-Cyano-1H-imidazole-2-carboxylic acid {4-[1-(3-amino-3-methyl-butyryl)-piperidin-4-yl]-2-cyclohex-1-enyl-phenyl}-amide trifluoroacetic acid salt

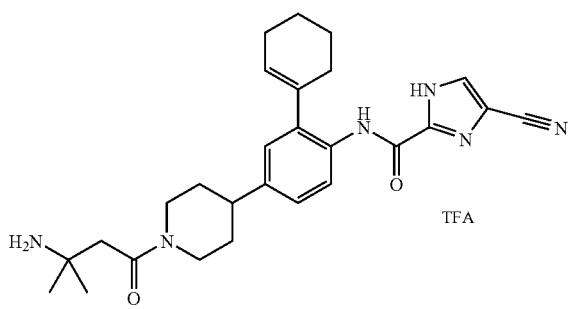 [SMILES: CC(C)(N)CC(=O)N1CCC(c2ccc(NC(=O)c3nc(C#N)c[nH]3)c(C3=CCCCC3)c2)CC1]

a) [3-(4-{4-[(4-Cyano-1H-imidazole-2-carbonyl)-amino]-3-cyclohex-1-enyl-phenyl}-piperidin-1-yl)-1,1-dimethyl-3-oxo-propyl]-carbamic acid tert-butyl ester

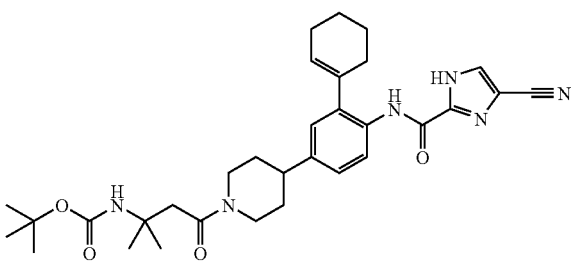 [SMILES: CC(C)(CC(=O)N1CCC(c2ccc(NC(=O)c3nc(C#N)c[nH]3)c(C3=CCCCC3)c2)CC1)NC(=O)OC(C)(C)C]

To a mixture of 4-cyano-1H-imidazole-2-carboxylic acid (2-cyclohex-1-enyl-4-piperidin-4-yl-phenyl)-amide trifluoroacetic acid salt (as prepared in Example 14, step (b), 40.0 mg, 0.0818 mmol), 3-tert-butoxycarbonylamino-3-methyl-butyric acid (*J. Med. Chem.*, 34(2), 633-642, (1991), 21.4 mg, 0.0981 mmol) and PyBroP (55.0 mg, 0.0981 mmol) in dichloroethane (2 mL) was added DIEA (43 µL, 0.25 mmol) and the resulting mixture was stirred at RT for 1 day under Ar. The mixture was diluted with EtOAc (30 mL) and washed with H$_2$O (2×10 mL), brine (10 mL), dried over Na$_2$SO$_4$ and then concentrated in vacuo. The residue was purified by flash chromatography (silica gel, 10-40% EtOAc/hexane) to give 33.0 mg (70%) of the title compound as a colorless oil. Mass spectrum (ESI, m/z): Calcd. for C$_{32}$H$_{42}$N$_6$O$_4$, 575.3 (M+H). found 574.8.

b) 4-Cyano-1H-imidazole-2-carboxylic acid {4-[1-(3-amino-3-methyl-butyryl)-piperidin-4-yl]-2-cyclohex-1-enyl-phenyl}-amide trifluoroacetic acid salt

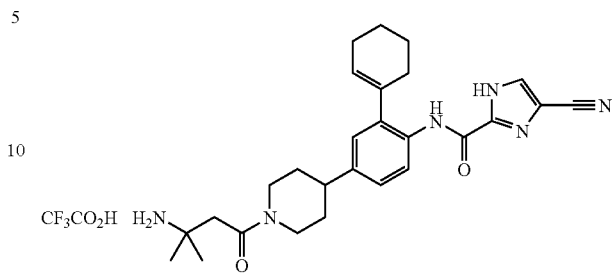

To a solution of [3-(4-{4-[(4-cyano-1H-imidazole-2-carbonyl)-amino]-3-cyclohex-1-enyl-phenyl}-piperidin-1-yl)-1,1-dimethyl-3-oxo-propyl]-carbamic acid tert-butyl ester (33.0 mg, 0.0574 mmol) (as prepared in the previous step) in 3 mL of DCM and 0.10 mL EtOH at 0° C. was added 1.0 mL of TFA, the mixture was warmed to RT and stirred for 3 h. The reaction was diluted with 3 mL of n-PrOH and then concentrated in vacuo. The residue was purified by flash chromatography (silica gel, 3-8% MeOH/DCM) to give 33.5 mg (99%) of the title compound as a white solid. $^1$H-NMR (400 MHz, CDCl$_3$): δ 13.3 (s, 1H), 9.52 (s, 1H), 8.57 (br s, 3H), 8.26 (d, 1H, J=8.6 Hz), 7.69 (s, 1H), 7.02 (dd, 1H, J=8.6, 1.7 Hz), 6.98 (d, 1H, J=1.7 Hz), 5.78 (m, 1H), 4.67 (br d, 1H, J=13.4 Hz), 3.88 (br d, 1H, J=13.4 Hz), 3.10 (m, 1H), 2.55-2.85 (m, 4H), 2.23 (m, 4H), 1.72-2.01 (m, 8H), 1.50 (s, 6H). Mass spectrum (ESI, m/z): Calcd. for C$_{27}$H$_{34}$N$_6$O$_2$, 475.3 (M+H), found 475.1.

EXAMPLE 49

4H-[1,2,4]-triazole-3-carboxylic acid (2-cyclohex-1-enyl-4-piperidin-4-yl-phenyl)-amide bis trifluoroacetic acid salt

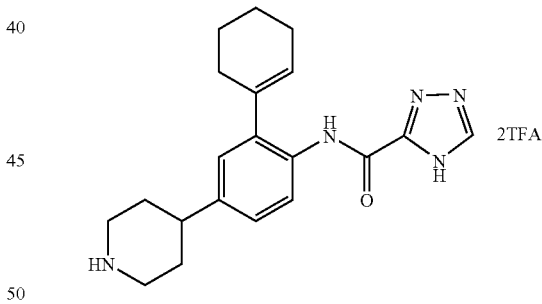

a) 1-(2-Trimethylsilanyl-ethoxymethyl)-1H-[1,2,4]-triazole-3-carboxylic acid methyl ester

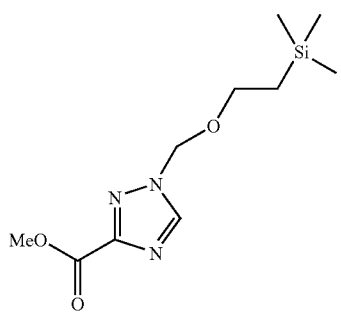 [SMILES: COC(=O)c1ncn(COCC[Si](C)(C)C)n1]

To a suspension of NaH (60% dispersion) (200 mg, 5.00 mmol) in DMF (5 mL) at 0° C., a solution of methyl-1H-1,2,4-triazolecarboxylate (635 mg, 5.00 mmol) in DMF (5 mL) was added dropwise. The resulting suspension was stirred at the same temperature for 30 min and treated with SEMCl (0.90 mL, 5.0 mmol). The resulting solution was stirred at RT for 30 min and poured onto ice. The product was extracted with ether (3×20 mL). The ether layers were combined, dried (Na$_2$SO$_4$) and concentrated in vacuo. The residue obtained was chromatographed on silica (10% EtOAc/hexane) to obtain the title compound (530 mg, 41%). Mass spectrum (ESI, m/z): Calcd. for C$_{10}$H$_{19}$N$_3$O$_3$Si, 258.1 (M+H). found 258.2.

b) 4-(3-Cyclohex-1-enyl-4-{[1-(2-trimethylsilanyl-ethoxymethyl)-1H-[1,2,4-]triazole-3-carbonyl]-amino}-phenyl)-piperidine-1-carboxylic acid tert-butyl ester

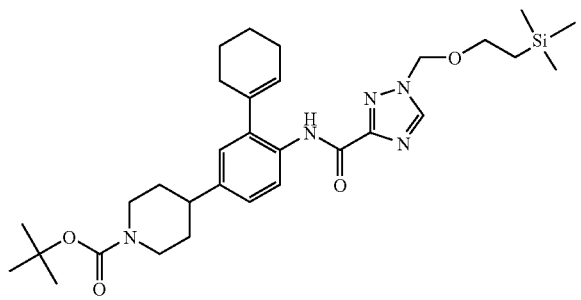 [SMILES: CC(C)(C)OC(=O)N1CCC(c2ccc(NC(=O)c3ncn(COCC[Si](C)(C)C)n3)c(C3=CCCCC3)c2)CC1]

To a solution of 1-(2-trimethylsilanyl-ethoxymethyl)-1H-[1,2,4]-triazole-3-carboxylic acid methyl ester (as prepared in the previous step, 257 mg, 1.00 mmol) in EtOH (2 mL), 2 N KOH (0.5 mL, 1 mmol) was added. The resulting solution was stirred at RT for 20 min and concentrated in vacuo. The residue obtained was suspended in ether (10 mL) and sonicated for 5 min. The ether was then removed in vacuo and the resulting residue was dried for 4 hr to obtain 1-(2-trimethyl-silanyl-ethoxymethyl)-1H-[1,2,4]-triazole-3-carboxylic acid potassium salt (273 mg, 97%) which was directly used in the next step without any further purification.

A mixture of 1-(2-trimethylsilanyl-ethoxymethyl)-1H-[1,2,4]-triazole-3-carboxylic acid potassium salt (as prepared above, 28 mg, 0.10 mmol), DIEA (34 µL, 0.20 mmol), 4-(4-amino-3-cyclohex-1-enyl-phenyl)-piperidine-1-carboxylic acid tert-butyl ester (as prepared in Example 14, step (b), 35.6 mg, 0.100 mmol) and PyBroP (69.9 mg, 0.150 mmol) in DCM (2 mL) was stirred at RT for 12 h. The reaction mixture was diluted with DCM (5 mL) and washed with saturated aqueous NaHCO$_3$ (10 mL) and water (10 mL). The organic layer was separated, dried (Na$_2$SO$_4$) and concentrated in vacuo. The product was chromatographed on silica (20-40% EtOAc/hexane) to obtain the title compound (31.9 mg, 55%). Mass spectrum (ESI, m/z): Calcd. for C$_{31}$H$_{47}$N$_5$O$_4$Si, 481.2 (M-BOC+2H). found. 481.2.

c) 4H-[1,2,4-]-triazole-3-carboxylic acid (2-cyclohex-1-enyl-4-piperidin-4-yl-phenyl)-amide bis trifluoroacetic acid salt

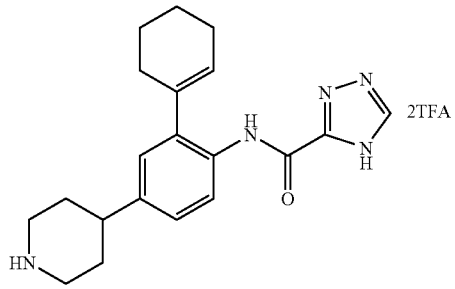 [SMILES: O=C(Nc1ccc(C2CCNCC2)cc1C1=CCCCC1)c1nnc[nH]1 ; "2TFA"]

To a solution of 4-(3-cyclohex-1-enyl-4-{[1-(2-trimethyl-silanyl-ethoxymethyl)-1H-[1,2,4]-triazole-3-carbonyl]-amino}-phenyl)-piperidine-1-carboxylic acid tert-butyl ester (as prepared in the previous step, 81.9 mg, 0.140 mmol) in DCM (0.4 mL) and EtOH (13 µL), was added TFA (0.13 mL). The resulting solution was stirred at RT for 3 h and concentrated in vacuo. The residue obtained was dried under vacuum for 1 h, suspended in ether (10 mL) and sonicated for 5 min. The solid formed was collected by suction filtration to obtain the title compound (56 mg, 68%). $^1$H-NMR (CD$_3$OD; 400 MHz): δ 8.53 (br s, 1H), 8.20 (d, 1H, J=8.4 Hz), 7.21 (dd, 1H, J=8.4, 2.1 Hz), 7.11 (d, 1H, J=2.1 Hz), 5.83 (br s, 1H), 3.45 (m, 2H), 3.19 (m, 2H), 2.98 (m, 1H), 2.28 (m, 4H), 2.14 (m, 2H), and 1.95-1.75 (m, 6H). Mass spectrum (ESI, m/z): Calcd. for C$_{20}$H$_{25}$N$_5$O, 352.4 (M+H). found 352.2.

EXAMPLE 50

5-Chloro-4H-[1,2,4]-triazole-3-carboxylic acid (2-cyclohex-1-enyl-4-piperidin-4-yl-phenyl)-amide trifluoroacetic acid salt

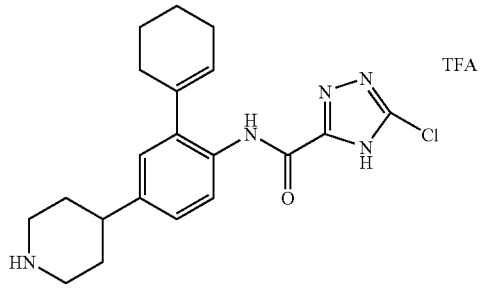 [SMILES: "TFA" ; O=C(Nc1ccc(C2CCNCC2)cc1C1=CCCCC1)c1nnc(Cl)[nH]1]

a) 5-Chloro-1-(2-trimethylsilanyl-ethoxymethyl)-1H-[1,2,4]-triazole-3-carboxylic acid methyl ester

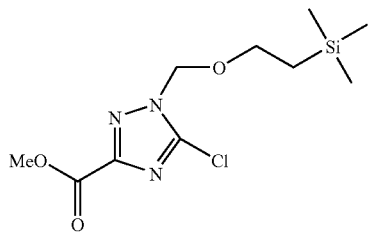 [SMILES: COC(=O)c1nc(Cl)n(COCC[Si](C)(C)C)n1]

To a suspension of NaH (60% dispersion, 53.9 mg, 1.34 mmol) in DMF (5 mL) at 0° C., a solution of 5-chloro-1H-

[1,2,4]-triazole-3-carboxylic acid methyl ester (*Bull. Pharm. Sci.,* 20(1): 47-61, (1997), 218 mg, 1.35 mmol) in DMF (10 mL) was added dropwise. The resulting suspension was stirred at the same temperature for 30 min and then treated with SEMCl (0.24 mL, 1.4 mmol). The resulting solution was stirred at RT for 30 min and poured onto ice. The mixture was extracted with ether (3×20 mL) and the ether layers were combined, dried (Na$_2$SO$_4$) and concentrated in vacuo. The residue obtained was chromatographed on silica (10% EtOAc/hexane) to obtain the title compound (227 mg, 58%). Mass spectrum (ESI, m/z): Calcd. for C$_{10}$H$_{18}$ClN$_3$O$_3$Si, 292.0 and 294.0 (M+H). found 291.5 and 293.6.

b) 4-(4-{[5-Chloro-1-(2-trimethylsilanyl-ethoxymethyl)-1H-[1,2,4]-triazole-3-carbonyl}-amino]-3-cyclohex-1-enyl-phenyl)-piperidine-1-carboxylic acid tert-butyl ester

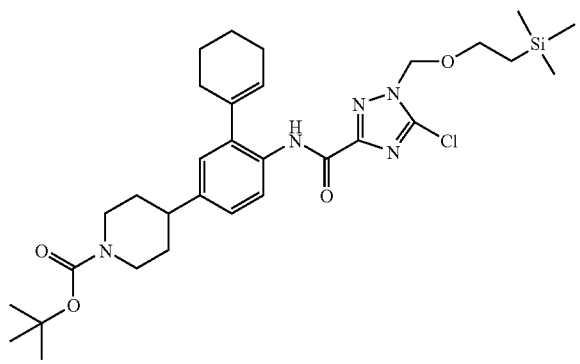 [SMILES: CC(C)(C)OC(=O)N1CCC(c2ccc(NC(=O)c3nc(Cl)n(COCC[Si](C)(C)C)n3)c(C3=CCCCC3)c2)CC1]

To a solution of 4-(4-{[5-chloro-1-(2-trimethylsilanyl-ethoxymethyl)-1H-[1,2,4]triazole-3-carboxylic acid methyl ester (as prepared in the previous step, 227 mg, 0.780 mmol) in EtOH (2 mL), 2 N KOH (0.4 mL, 0.8 mmol) was added. The resulting solution was stirred at RT for 20 min and concentrated in vacuo. The residue obtained was suspended in ether (10 mL) and sonicated for 5 min. The ether was then removed and the resulting residue was dried in vacuo for 4 h to obtain 4-(4-{[5-chloro-1-(2-trimethylsilanyl-ethoxymethyl)-1H-[1,2,4]triazole-3-carboxylic acid potassium salt (223 mg, 91%) which was directly used in the next step without any further purification.

A mixture of 4-(4-{[5-chloro-1-(2-trimethylsilanyl-ethoxymethyl)-1H-[1,2,4]-triazole-3-carboxylic acid potassium salt (as prepared above, 35 mg, 0.10 mmol), DIEA (34 µL, 0.10 mmol), 4-(4-amino-3-cyclohex-1-enyl-phenyl)-piperidine-1-carboxylic acid tert-butyl ester (as prepared in Example 14, step (b), 35.6 mg, 0.100 mmol) and PyBroP (69.9 mg, 0.150 mmol) in DCM (2 mL) was stirred at RT for 12 h. The reaction mixture was diluted with DCM (5 mL) and washed with saturated aqueous NaHCO$_3$ (10 mL) and water (10 mL). The organic layer was separated, dried (Na$_2$SO$_4$) and concentrated in vacuo. The product was chromatographed on silica (20-40% EtOAc/hexane) to obtain the title compound (52 mg, 85%). $^1$H-NMR (CDCl$_3$; 400 MHz): δ 9.60 (s, 1H), 8.29 (d, 1H, J=8.4 Hz), 7.18 (dd, 1H, J=8.4, 2.2 Hz), 7.13 (d, 1H, J=2.2 Hz), 5.99 (s, 2H), 5.84 (br s, 1H), 4.18-4.25 (m, 2H), 3.72-3.76 (m, 2H), 2.58-2.67 (m, 2H), 2.51-2.64 (m, 1H), 2.18-2.33 (m, 4H), 1.78-1.92 (m, 6H), 1.55-1.65 (m, 2H), 1.49 (s, 9H), 0.93-0.98 (m, 2H), 0.10 (s, 9H).

c) 5-Chloro-1H-[1,2,4-]-triazole-3-carboxylic acid (2-cyclohex-1-enyl-4-piperidin-4-yl-phenyl)-amide trifluoroacetic acid salt

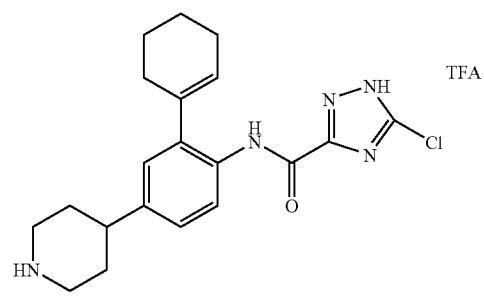 [SMILES: "TFA" ; O=C(Nc1ccc(C2CCNCC2)cc1C1=CCCCC1)c1n[nH]c(Cl)n1]

To a solution of 4-(4-{[5-chloro-1-(2-trimethylsilanyl-ethoxymethyl)-1H-[1,2,4]-triazole-3-carbonyl]-amino}-3-cyclohex-1-enyl-phenyl)-piperidine-1-carboxylic acid tert-butyl ester (as prepared in the previous step, 63.3 mg, 0.102 mmol) in DCM (0.5 mL) and EtOH (11 µL) was added TFA (0.1 mL). After stirring the resulting mixture at RT for 12 h, another 0.1 mL of TFA was added. The reaction mixture was stirred for an additional 5 h at RT, the solvents were evaporated, and the title compound was purified by RP-HPLC (C18) eluting with 20-70% CH$_3$CN in 0.1% TFA/H$_2$O over 20 min to obtain the title compound (30 mg, 58%). $^1$H-NMR (CD$_3$OD; 400 MHz): δ 8.14 (d, 1H, J=8.4 Hz), 7.20 (dd, 1H, J=8.4, 2.1 Hz), 7.13 (d, 1H, J=2.1 Hz), 5.82 (br s, 1H), 3.45 (m, 2H), 3.19 (m, 2H), 2.98 (m, 1H), 2.28 (m, 4H), 2.14 (m, 2H), and 1.95-1.75 (m, 6H). Mass spectrum (ESI, m/z): Calcd. for C$_{20}$H$_{24}$ClN$_5$O, 386.1 and 388.1 (M+H). found 386.2 and 388.1.

EXAMPLE 51

5-Cyano-1H-imidazole-2-carboxylic acid [2-cyclohex-1-enyl-4-(cis-2,6-dimethyl-piperidin-4-yl)-phenyl]-amide bis trifluoroacetic acid salt, and 5-cyano-1H-imidazole-2-carboxylic acid [2-cyclohex-1-enyl-4-(trans-2,6-dimethyl-piperidin-4-yl)-phenyl]-amide bis trifluoroacetic acid salt

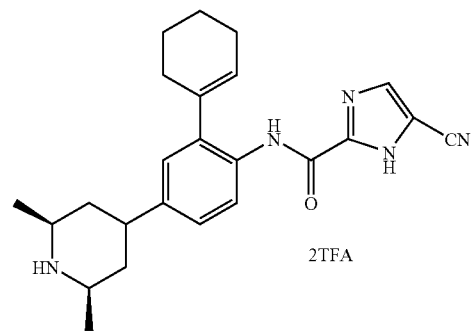

-continued

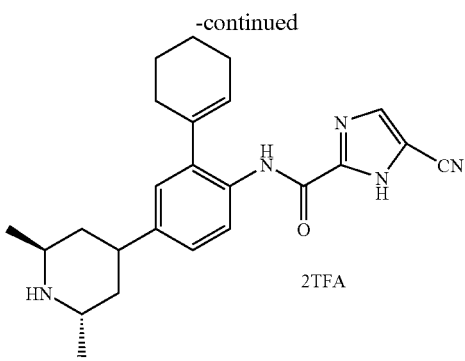

a) Cis/trans 2,6-Dimethyl-4-oxo-piperidine-1-carboxylic acid tert-butyl ester

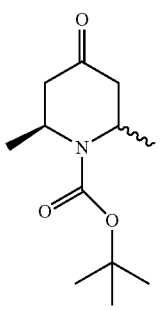

A solution of cis/trans-2,6-dimethylpiperidinone (*Coll. Czech. Chem. Commun.*: 31(111), 4432-41, (1966), 1.27 g, 10.0 mmol) in ether (100 mL) was treated with aq 1 N NaOH (11 mL, 11 mmol) and (BOC)$_2$O (2.18 g, 10.0 mmol). The resulting mixture as stirred at RT for 48 hr. The ether layer was separated, dried and concentrated. The residue was chromatographed on silica (10% EtOAc-hexane) to obtain the title compound (1.10 g, 50%): LC-MS (ESI, m/z): Calcd. for C$_{12}$H$_{21}$NO$_3$, 128.1 (M-BOC+2H). found 128.1.

b) 4-(4-Amino-phenyl)-cis/trans 2,6-dimethyl-piperidine-1-carboxylic acid tert-butyl ester

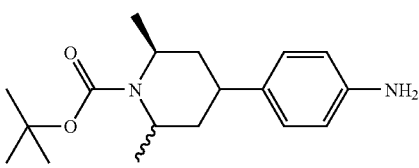 [SMILES: CC1CC(c2ccc(N)cc2)C[C@H](C)N1C(=O)OC(C)(C)C]

A solution of cis/trans N-Boc-2,6-dimethylpiperidinone (as prepared in the previous step, 1.14 g, 5.00 mmol) in THF (20 mL) was cooled to −78° C. and treated with LDA (1.5 M solution in cyclohex, THF and ethylbenzene, 4.4 mL, 6.5 mmol) under Ar. The resulting mixture was stirred at the same temperature for 30 min and treated with N-phenyltrifluoromethanesulfonimide (2.34 g, 6.55 mmol) in THF (20 mL). The reaction mixture was stirred for another 30 min and allowed to warm to RT. After 30 min. at RT the reaction mixture was concentrated in vacuo and the residue was taken up in ether (20 mL) and washed with cold water (2×10 mL). The ether layer was dried (Na$_2$SO$_4$) and concentrated to afforded cis/trans-2,6-dimethyl-4-trifluoromethanesulfonyloxy-3,6-dihydro-2H-pyridine-1-carboxylic acid tert-butyl ester (890 mg, 49%) which was directly used in next step.

The title compound was then prepared according to the Suzuki coupling procedure of Example 35, step (b) using 4-aminophenylboronic acid (219 mg, 1.00 mmol) and cis/trans-2,6-dimethyl-4-trifluoromethanesulfonyloxy-3,6-dihydro-2H-pyridine-1-carboxylic acid tert-butyl ester (as prepared above, 321 mg, 1.00 mmol). Silica gel chromatography (10-20% EtOAc/hexanes) afforded 4-(4-amino-phenyl)-2,6-dimethyl-3,6-dihydro-2H-pyridine-1-carboxylic acid tert-butyl ester (172 mg, 57%): Mass spectrum (ESI, m/z): Calcd. for C$_{18}$H$_{26}$N$_2$O$_2$, 303.2 (M+H) found 303.1.

A solution of 4-(4-amino-phenyl)-2,6-dimethyl-3,6-dihydro-2H-pyridine-1-carboxylic acid tert-butyl ester (as prepared above, 380 mg, 1.25 mmol) in MeOH (10 mL) was hydrogenated over 10% Pd/C (190 mg) at 20 psi for 1 h. The solution was filtered through a pad of Celite and concentrated to give the title compound (360 mg, 94%). Mass spectrum (ESI, m/z): Calcd. for C$_{18}$H$_{28}$N$_2$O$_2$, 305.2 (M+H). found 305.6.

c) 4-(4-Amino-3-cyclohex-1-enyl-phenyl)-cis/trans 2,6-dimethyl-piperidine-1-carboxylic acid tert-butyl ester

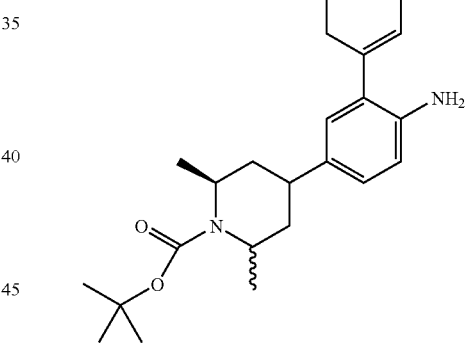

To a solution of 4-(4-amino-phenyl)-2,6-dimethyl-piperidine-1-carboxylic acid tert-butyl ester (as prepared in previous step, 334 mg, 1.09 mmol) in DCM (10 mL) was added NBS (195 mg, 1.09 mmol) and the reaction mixture was stirred at RT for 12 h. The reaction mixture was diluted with DCM (10 mL) and washed with saturated aqueous NaHCO$_3$ (10 mL) and water (10 mL). The organic layer was separated, dried (Na$_2$SO$_4$) and concentrated in vacuo to obtain 4-(4-amino-3-bromo-phenyl)-cis/trans-2,6-dimethyl-piperidine-1-carboxylic acid tert-butyl ester (367 mg, 87%). Mass spectrum (ESI, m/z): Calcd. for C$_{18}$H$_{27}$BrN$_2$O$_2$, 327.0 and 329.0 (M-t-Bu+H). found 327.0 and 328.9.

The title compound was then prepared according to the Suzuki coupling procedure of Example 12, step (d) using cyclohexan-1-enyl boronic acid (157 mg, 1.25 mmol) and 4-(4-amino-3-bromo-phenyl)-2,6-dimethyl-piperidine-1-carboxylic acid tert-butyl ester (as prepared above, 382 mg, 1.00 mmol) and chromatographed on silica (20% EtOAc/ hexanes) to afford 254 mg (66%). Mass spectrum (ESI, m/z): Calcd. for $C_{24}H_{36}N_2O_2$, 384.2 (M+H). found 385.1.

d) 4-(4-{[4-Cyano-1-(2-trimethylsilanyl-ethoxymethyl)-1H-imidazole-2-carbonyl]-amino}-3-cyclohex-1-enyl-phenyl)-cis-2,6-dimethyl-piperidine-1-carboxylic acid tert-butyl ester and 4-(4-{[4-cyano-1-(2-trimethylsilanyl-ethoxymethyl)-1H-imidazole-2-carbonyl]-amino}-3-cyclohex-1-enyl-phenyl)-trans-2,6-dimethyl-piperidine-1-carboxylic acid tert-butyl ester

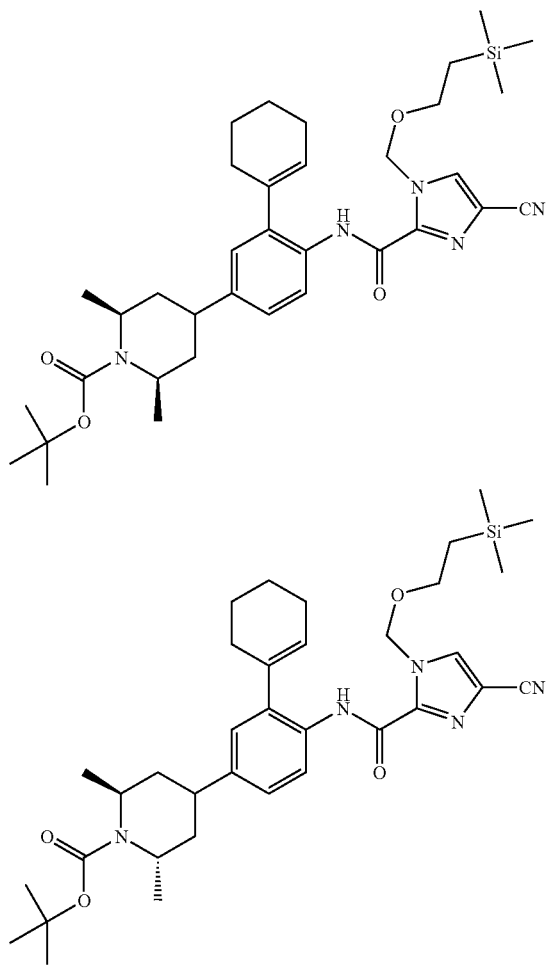

A mixture of 4-cyano-1-(2-trimethylsilanyl-ethoxymethyl)-1H-imidazole-2-carboxylic acid, potassium salt (as prepared in Example 3, step (d), 384 mg, 1.00 mmol), DIEA (0.34 µL, 2.0 mmol), 4-(4-amino-3-cyclohex-1-enyl-phenyl)-2,6-dimethyl-piperidine-1-carboxylic acid tert-butyl ester (as prepared in the previous step, 384 mg, 1.00 mmol) and PyBroP (699 mg, 1.50 mmol) in DCM (20 mL) was stirred at RT for 12 h. The reaction mixture was diluted with DCM (10 mL) and washed with saturated aqueous $NaHCO_3$ (10 mL) and water (10 mL). The organic layer was separated, dried ($Na_2SO_4$) and concentrated in vacuo to obtained a mixture of the above two title compounds (321 mg, 50.7%). The mixture was chromatographed on silica (10-20% EtOAc/hexane) to obtain the individual title compounds.

4-(4-{[4-cyano-1-(2-trimethylsilanyl-ethoxymethyl)-1H-imidazole-2-carbonyl]-amino}-3-cyclohex-1-enyl-phenyl)-trans-2,6-dimethyl-piperidine-1-carboxylic acid tert-butyl ester (31 mg). Mass spectrum (ESI, m/z): Calcd. for $C_{35}H_{51}N_5O_4Si$, 634.3 (M+H). found 634.1.

4-(4-{[4-cyano-1-(2-trimethylsilanyl-ethoxymethyl)-1H-imidazole-2-carbonyl]-amino}-3-cyclohex-1-enyl-phenyl)-cis-2,6-dimethyl-piperidine-1-carboxylic acid tert-butyl ester contaminated with 10% of 4-(4-{[4-cyano-1-(2-trimethylsilanyl-ethoxymethyl)-1H-imidazole-2-carbonyl]-amino}-3-cyclohex-1-enyl-phenyl)-trans-2,6-dimethyl-piperidine-1-carboxylic acid tert-butyl ester (290 mg). Mass spectrum (ESI, m/z): Calcd. for $C_{35}H_{51}N_5O_4Si$, 634.3 (M+H). found 634.1.

e) 5-Cyano-1H-imidazole-2-carboxylic acid [2-cyclohex-1-enyl-4-(cis-2,6-dimethyl-piperidin-4-yl)-phenyl]-amide bis trifluoroacetic acid salt and 5-cyano-1H-imidazole-2-carboxylic acid [2-cyclohex-1-enyl-4-(trans-2,6-dimethyl-piperidin-4-yl)-phenyl]-amide bis trifluoroacetic acid salt

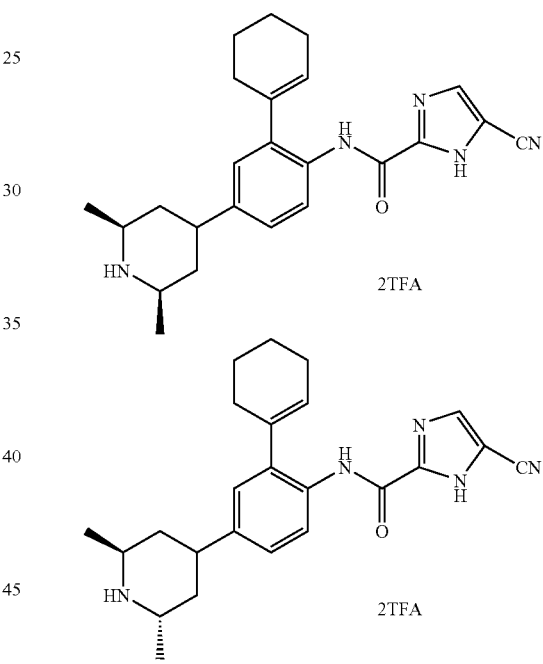

The title compounds were prepared from 290 mg (0.457 mmol) of 4-(4-{[4-cyano-1-(2-trimethylsilanyl-ethoxymethyl)-1H-imidazole-2-carbonyl]-amino}-3-cyclohex-1-enyl-phenyl)-cis-2,6-dimethyl-piperidine-1-carboxylic acid tert-butyl ester and 31 mg (0.048 mmol) of 4-(4-{[4-cyano-1-(2-trimethylsilanyl-ethoxymethyl)-1H-imidazole-2-carbonyl]-amino}-3-cyclohex-1-enyl-phenyl)-trans-2,6-dimethyl-piperidine-1-carboxylic acid tert-butyl ester according to the procedure in Example 14, step (b).

5-Cyano-1H-imidazole-2-carboxylic acid [2-cyclohex-1-enyl-4-(cis-2,6-dimethyl-piperidin-4-yl)-phenyl]-amide bis trifluoroacetic acid salt (93 mg, 32%): $^1$H-NMR ($CD_3OD$; 400 MHz): δ 8.17 (d, 1H, J=8.4 Hz), 8.03 (s, 1H), 7.22 (d, 1H, J=8.4 Hz), 7.11 (s, 1H), 5.72 (br s, 1H), 3.87 (m, 1H), 3.78 (m, 1H), 3.45 (m, 1H), 3.23 (m, 1H), 3.07 (m, 1H), 2.22 (m, 4H), 2.19 (m, 2H), 1.75-1.92 (m, 4H), 1.56 (m, 3H), 1.37 (m, 6H). Mass spectrum, ESI, m/z): Calcd. for $C_{24}H_{29}N_5O$, 404.2 (M+H). found 404.2.

5-Cyano-1H-imidazole-2-carboxylic acid [2-cyclohex-1-enyl-4-(trans-2,6-dimethyl-piperidin-4-yl)-phenyl]-amide bis trifluoroacetic acid salt (17.3 mg, 56%). $^1$H-NMR (CDCl$_3$; 400 MHz): δ 13.9 (br s, 1H), 10.3 (br s, 1H), 9.98 (s, 1H), 8.41 (d, 1H, J=8.4 Hz), 7.75 (br s, 1H), 7.26 (dd, 1H, J=8.4, 2.0 Hz), 7.15 (d, 1H, J=2 Hz), 5.92 (br s, 1H), 4.12 (m, 1H), 3.59 (m, 1H), 3.1-3.3 (m, 4H), 2.25-2.42 (m, 6H), 2.05-1.78 (m, 6H), 1.62 (d, 3H, J=7.1 Hz), 1.43 (d, 3H, J=6.3 Hz). Mass spectrum (ESI, m/z): Calcd. for C$_{24}$H$_{29}$N$_5$O, 404.2 (M+H). found 404.2.

EXAMPLE 52

5-Cyano-1H-imidazole-2-carboxylic acid {2-cyclohex-1-enyl-4-[1-(R)-(+)-(2,3-dihydroxy-propionyl)-piperidin-4-yl]-phenyl}-amide

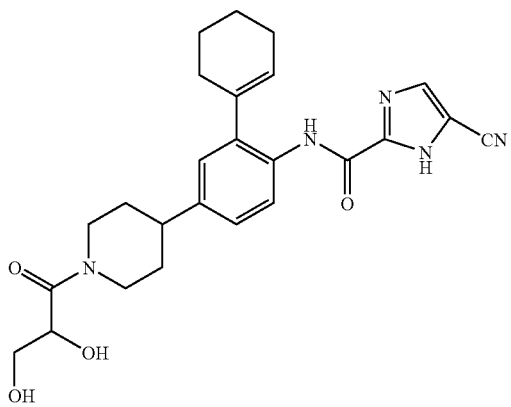 [SMILES: N#Cc1cnc(C(=O)Nc2ccc(C3CCN(C(=O)C(O)CO)CC3)cc2C2=CCCCC2)[nH]1]

a) 5-Cyano-1H-imidazole-2-carboxylic acid {2-cyclohex-1-enyl-4-[1-(R)-(+)2,2-dimethyl-[1,3]dioxolane-4-carbonyl)-piperidin-4-yl]-phenyl}-amide

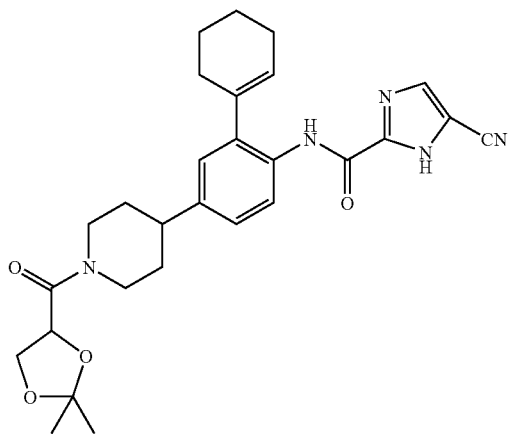 [SMILES: CC1(C)OCC(C(=O)N2CCC(c3ccc(NC(=O)c4ncc(C#N)[nH]4)c(C4=CCCCC4)c3)CC2)O1]

To a solution of methyl(R)-(+)-2,2-dimethyl-1,3-dioxolane-4-carboxylate (0.16 mL, 1.0 mmol) in MeOH (2 mL), 2 N KOH (0.5 mL, 1 mmol) was added. The resulting solution was stirred at RT for 20 min and concentrated in vacuo. The residue obtained was suspended in ether (10 mL) and sonicated for 5 min. The ether was then removed and the resulting residue was dried in vacuo for 4 h to obtain (R)-(+)-2,2-dimethyl-1,3-dioxolane-4-carboxylic acid potassium salt (173 mg, 94%) which was directly used in the next step without purification.

To a solution of 4-cyano-1H-imidazole-2-carboxylic acid (2-cyclohex-1-enyl-4-piperidin-4-yl-phenyl)-amide, trifluoroacetic acid salt (as prepared in Example 14, step (b), 40 mg, 0.08 mmol) in DCM (1.5 mL) was added to a mixture of (R)-(+)-2,2-dimethyl-1,3-dioxalane-4-carboxylic acid potassium salt (as prepared above, 18 mg, 0.090 mmol), EDCI (18.8 mg, 0.0900 mmol), HOBt (13.2 mg, 0.0900 mmol) and DIEA (42 μL, 0.24 mmol). The resulting mixture was stirred at RT for 6 h. Water (10 mL) was added and DCM layer was separated, dried (Na$_2$SO$_4$) and concentrated. The residue obtained was chromatographed on silica (2% MeOH/DCM) to obtain title compound (47 mg, 97%). Mass spectrum (ESI, m/z): Calcd. for C$_{28}$H$_{33}$N$_5$O$_4$, 504.2 (M+H). found 503.9.

b) 5-Cyano-1H-imidazole-2-carboxylic acid {2-cyclohex-1-enyl-4-[1-(R)-(+)-(2,3-dihydroxy-propionyl)-piperidin-4-yl]-phenyl}-amide

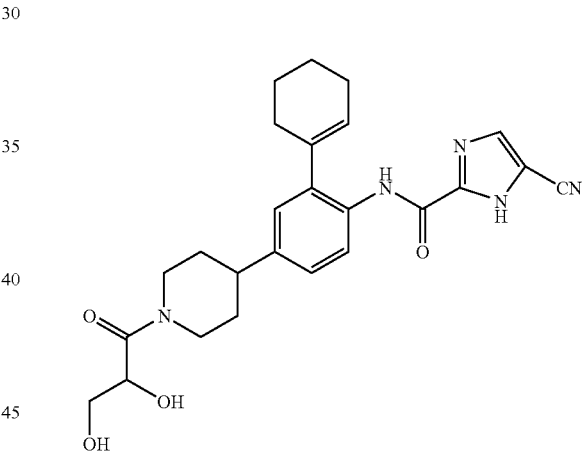

To a solution of 5-cyano-1H-imidazole-2-carboxylic acid {2-cyclohex-1-enyl-4-[1-(R)-(2,2-dimethyl-[1,3]dioxolane-4-carbonyl)-piperidin-4-yl]-phenyl}-amide (as prepared in the previous step, 45 mg, 0.090 mmol) in MeOH (1 mL) was added aq 2 N HCl (2 mL). The resulting mixture was stirred at RT for 12 hr. Solvents were removed in vacuo and the resulting residue was dried for 4 h. The ether (10 mL) was added and sonicated for 5 min. The ether was removed in vacuo and the residue was dried for 12 h to obtain the title compound (21.3 mg, 52%). $^1$H-NMR (DMSO; 400 MHz): δ 14.1 (br s, 1H), 9.85 (s, 1H), 8.32 (s, 1H), 7.92 (d, 1H, J=8.4 Hz), 7.18 (dd, 1H, J=8.4, 2.1 Hz), 7.13 (d, 1H, J=2.1 Hz), 5.72 (br s, 1H), 4.51 (m, 1H), 4.33 (m, 1H), 4.15 (m, 1H), 3.55 (m, 1H), 3.43 (m, 1H), 3.08 (m, 1H), 2.81 (m, 1H), 2.63 (m, 1H), 2.12-2.24 (m, 4H), 1.31-1.38 (m, 10H). mass spectrum (ESI, m/z): Calcd. for C$_{25}$H$_{29}$N$_5$O$_4$, 464.2 (M+H). found 464.1.

EXAMPLE 53

5-Cyano-1H-imidazole-2-carboxylic acid [2-cyclo-hex-1-enyl-4-(1-methoxy-piperidin-4-yl)-phenyl]-amide trifluoroacetic acid salt

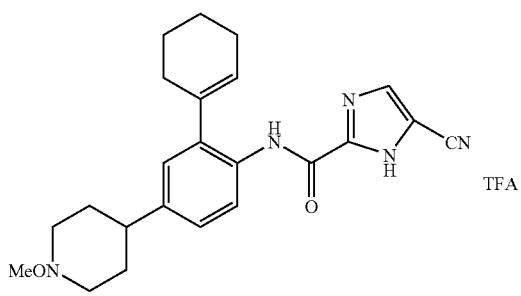

a) 4-(1-Methoxy-1,2,3,6-tetrahydro-pyridin-4-yl)-phenylamine

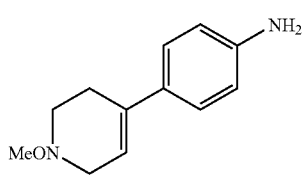

A solution of N-methoxypiperidinone (J. Org. Chem., 26, 1867, (1961), 650 mg, 5.00 mmol) in THF (20 mL)) was cooled to −78° C. and treated with LDA (1.5 M solution in cyclohex, THF and ethylbenzene, 4.3 mL, 6.4 mmol) under Ar. The resulting mixture was stirred at same temperature for 30 min and treated with N-phenyltrifluoromethane-sulfonimide (2.3 g, 6.4 mmol) in THF (20 mL). The reaction mixture was stirred for another 30 min and allowed to warm to RT. After 30 min at RT, the reaction mixture was concentrated in vacuo and the residue obtained was taken up in EtOAc (20 mL) and washed with cold water (2×10 mL). EtOAc layer was dried (Na$_2$SO$_4$) and concentrated to afforded trifluoromethanesulfonic acid 1-methoxy-1,2,3,6-tetrahydro-pyridin-4-yl ester (980 mg, 71%) as a white foam which was directly used in next step.

The title compound was then prepared according to Suzuki coupling procedure of Example 35, step (b) using 4-aminophenylboronic acid (219 mg, 1.00 mmol) and trifluoromethanesulfonic acid 1-methoxy-1,2,3,6-tetrahydro-pyridin-4-yl ester (as prepared above, 261 mg, 1.00 mmol). Silica gel chromatography (20-50% EtOAc/hexanes) afforded 60 mg (29%). Mass spectrum (ESI, m/z): Calcd. for C$_{12}$H$_{16}$N$_2$O, 205.1 (M+H). found 205.2.

b) 2-Cyclohex-1-enyl-4-(1-methoxy-piperidin-4-yl)-phenylamine

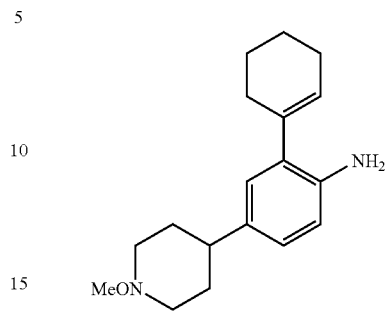

A solution of 4-(1-methoxy-1,2,3,6-tetrahydro-pyridin-4-yl)-phenylamine (as prepared in previous step) (40.8 mg, 0.200 mmol) in MeOH (5 mL) was hydrogenated over 10% Pd/C (20.4 mg) at 20 psi for 1 h. The solution was filtered through a pad of Celite and concentrated to give 4-(1-methoxy-piperidin-4-yl)-phenylamine (38 mg, 92%) which was directly used in the next step without purification.

To a solution of 4-(1-methoxy-piperidin-4-yl)-phenylamine (as prepared above, 42 mg, 0.20 mmol) in DCM (2 mL) was added NBS (36.2 mg, 0.20 mmol) and the reaction mixture was stirred at RT for 12 h. The reaction mixture was diluted with DCM (10 mL) and washed with saturated aqueous NaHCO$_3$ (10 mL) and water (10 mL). The organic layer was separated, dried (Na$_2$SO$_4$) and concentrated in vacuo to obtain 2-bromo-4-(1-methoxy-1,2,3,6-tetrahydro-pyridin-4-yl)-phenylamine (43 mg, 74.5%) which was used in the next step without purification.

The title compound was then prepared according to Suzuki coupling procedure of Example 12, step (d) using cyclohex-1-enyl boronic acid (27.9 mg, 1.00 mmol) and 2-bromo-4-(1-methoxy-1,2,3,6-tetrahydro-pyridin-4-yl)-phenylamine (as prepared above, 44 mg, 0.15 mmol) and chromatographed on silica (20-50% EtOAc/hexanes) afforded 2-cyclohex-1-enyl-4-(1-methoxy-piperidin-4-yl)-phenylamine (33 mg, 74%). Mass spectrum, (ESI, m/z): Calcd. for C$_{18}$H$_{26}$N$_2$O, 287.2 (M+H). found 286.8.

c) 4-Cyano-1-(2-trimethylsilanyl-ethoxymethyl)-1H-imidazole-2-carboxylic acid [2-cyclohex-1-enyl-4-(1-methoxy-piperidin-4-yl)-phenyl]-amide

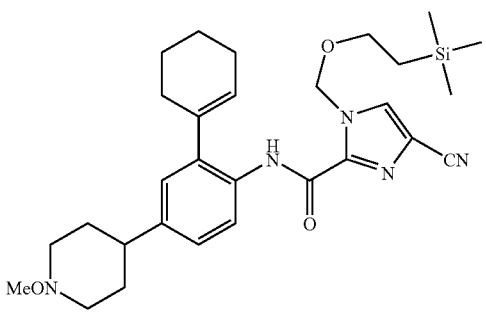

A mixture of 4-cyano-1-(2-trimethylsilanyl-ethoxymethyl)-1H-imidazole-2-carboxylic acid, potassium salt (as prepared in Example 3, step (d), 35.6 mg, 0.100 mmol), DIEA (0.34 µL, 0.20 mmol), 2-cyclohex-1-enyl-4-(1-methoxy-piperidin-4-yl)-phenylamine (as prepared in previous step, 28.6 mg, 0.1 mmol) and PyBroP (69.9 mg, 0.150 mmol) in DCM (2 mL) was stirred at RT for 12 h. The reaction mixture was diluted with DCM (10 mL) and washed with saturated aqueous NaHCO$_3$ (10 mL) and water (10 mL). The organic layer was separated, dried (Na$_2$SO$_4$) and concentrated in vacuo. The product was chromatographed on silica (20-40% EtOAc/hexane) to obtain the title compound (26 mg, 48%). Mass spectrum (ESI, m/z): Calcd. for C$_{29}$H$_{41}$N$_5$O$_3$Si, 536.3 (M+H). found 536.2.

d) 5-Cyano-1H-imidazole-2-carboxylic acid [2-cyclohex-1-enyl-4-(1-methoxy-piperidin-4-yl)-phenyl]-amide trifluoroacetic acid salt

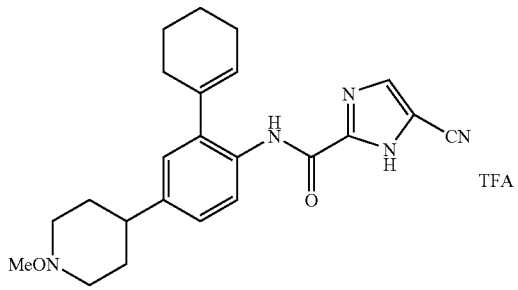

To a solution of 4-cyano-1-(2-trimethylsilanyl-ethoxymethyl)-1H-imidazole-2-carboxylic acid [2-cyclohex-1-enyl-4-(1-methoxy-piperidin-4-yl)-phenyl]-amide (as prepared in previous step, 31 mg, 0.020 mmol) in DCM (0.5 mL) and EtOH (11 µL) was added TFA (0.1 mL). The resulting solution was stirred at RT for 6 h. The reaction mixture was concentrated in vacuo and the resulting residue was dried for 1 h, suspended in ether (10 mL) and sonicated for 5 min. The solid formed was collected by suction filtration to obtain the title compound (17.3 mg, 58%). $^1$H-NMR (DMSO; 400 MHz): δ 9.70 (s, 1H), 8.30 (s, 1H), 7.83 (d, 1H, J=8.4 Hz), 7.14 (d, 1H, J=8.4 Hz), 7.05 (s, 1H), 5.71 (br s, 1H), 3.30-3.55 (m, 5H), 2.41-2.62 (m, 2H), 2.12-2.19 (m, 4H), 1.60-1.85 (m, 8H). Mass spectrum (ESI, m/z): Calcd. for C$_{23}$H$_{27}$N$_5$O$_2$, 406.2 (M+H). found 406.1.

EXAMPLE 54

4-Cyano-1H-imidazole-2-carboxylic acid [6-(4,4-dimethyl-cyclohex-1-enyl)-1',2',3',4',5',6'-hexahydro-[2,4]bipyridinyl-5-yl]-amide trifluoroacetic acid salt

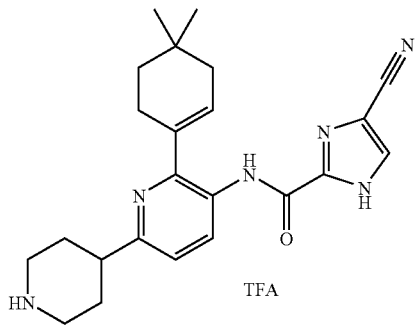 [SMILES: "TFA" ; CC1(C)CC=C(c2nc(C3CCNCC3)ccc2NC(=O)c2nc(C#N)c[nH]2)CC1]

a) 5-Nitro-3',6'-dihydro-2'H-[2,4]bipyridinyl-1'-carboxylic acid tert-butyl ester

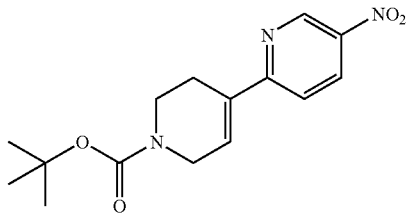 [SMILES: CC(C)(C)OC(=O)N1CC=C(c2ccc([N+](=O)[O-])cn2)CC1]

A solution of 202 mg (0.994 mmol) 2-bromo-5-nitropyridine in 4 mL of toluene and 2 mL of EtOH was treated with 338 mg (1.09 mmol) 4-trifluoromethane-sulfonyloxy-3,6-dihydro-2H-pyridine-1-carboxylic acid tert-butyl ester (Synthesis, 993, (1991)) and 1.49 mL (2.981 mmol) 2 M aqueous Na$_2$CO$_3$. The mixture was degassed via sonication, placed under argon, treated with 80.3 mg (0.00700 mmol) Pd(PPh$_3$)$_4$ and heated to 80° C. for 4 h. The mixture was diluted with EtOAc and washed with water. The organic layer was dried over MgSO$_4$ and concentrated in vacuo. The resulting residue was chromatographed on a 50-g silica Varian MegaBond Elut column with 10-25% EtOAc-hexane to afford 226 mg (75%) of the title compound as a light yellow solid: Mass spectrum (ESI, m/z): Calcd. for C$_{15}$H$_{19}$N$_3$O$_4$, 306.1 (M+H). found 305.7.

b) 5-Amino-3',4',5',6'-tetrahydro-2'H-[2,4]bipyridinyl-1'-carboxylic acid tert-butyl ester

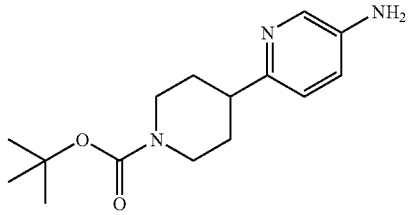 [SMILES: CC(C)(C)OC(=O)N1CCC(c2ccc(N)cn2)CC1]

A solution of 226 mg (0.740 mmol) 5-nitro-3',6'-dihydro-2'H-[2,4']bipyridinyl-1'-carboxylic acid tert-butyl ester (as prepared in the previous step) in 15 mL MeOH was treated with 110 mg 10% Pd/C (Degussa type E101-NE/W, Aldrich, 50% by weight water) and 1 atm H$_2$ at room temperature for 18 h. The mixture was filtered through Celite, and the filter cake was washed with MeOH. Concentration afforded 220 mg (107%) of the title compound as a colorless glassy solid. Mass spectrum (ESI, m/z): Calcd. for C$_{15}$H$_{23}$N$_3$O$_2$, 278.2 (M+H). found 278.0.

c) 5-Amino-6-bromo-3',4',5',6'-tetrahydro-2'H-[2,4]bipyridinyl-1'-carboxylic acid tert-butyl ester

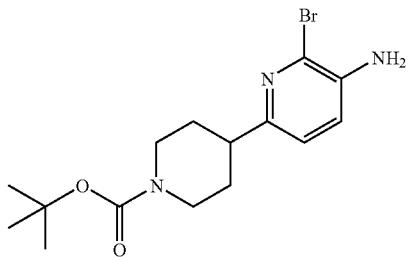 [SMILES: CC(C)(C)OC(=O)N1CCC(c2ccc(N)c(Br)n2)CC1]

A solution of 220 mg (0.793 mmol) 5-amino-3',4',5',6'-tetrahydro-2'H-[2,4']bipyridinyl-1'-carboxylic acid tert-butyl ester (as prepared in the previous step) in 10 mL CH$_2$Cl$_2$ was treated with 134 mg (0.753 mmol) N-bromosuccinimide at room temperature for 20 min. The mixture was diluted with CH$_2$Cl$_2$ and washed with saturated aqueous NaHCO$_3$. The organic layer was dried over MgSO$_4$ and concentrated in vacuo. Chromatography of the residue on a 50-g silica Varian MegaBond Elut column with 10-35% EtOAc-hexanes afforded 209 mg (74%) of the title compound as a colorless glassy solid. $^1$H-NMR (CDCl$_3$; 400 MHz): δ 6.97 (d, 1H, J=8.0 Hz), 6.91 (d, 1H, J=8.0 Hz), 4.28-4.15 (br s, 2H), 4.06-3.90 (m, 2H), 2.85-2.75 (m, 2H), 2.77-2.68 (m, 1H), 1.92-1.83 (m, 2H), 1.68-1.54 (m, 2H), 1.47 (s, 9H).

d) 5-Amino-6-(4,4-dim ethyl-cyclohex-1-enyl)-3',4',5',6'-tetrahydro-2'H-[2,4]bipyridinyl-1'-carboxylic acid tert-butyl ester

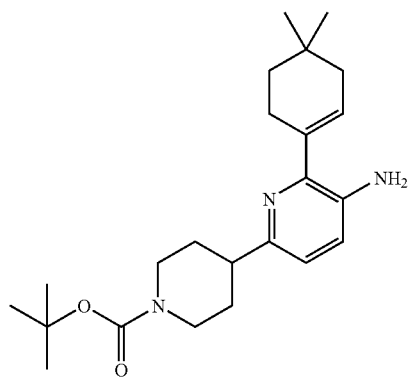 [SMILES: CC1(C)CC=C(c2nc(C3CCN(C(=O)OC(C)(C)C)CC3)ccc2N)CC1]

A solution of 209 mg (0.587 mmol) 5-amino-6-bromo-3',4',5',6'-tetrahydro-2'H-[2,4']bipyridinyl-1'-carboxylic acid tert-butyl ester (as prepared in the previous step) in 5 mL of toluene and 2.5 mL of EtOH was treated with 99.3 mg (0.645 mmol) 4,4-dicyclohex-1-enylboronic acid and 2.34 mL (4.69 mmol) 2 M aqueous Na$_2$CO$_3$. The mixture was degassed via sonication, placed under argon, treated with 47.4 mg (0.0410 mmol) Pd(PPh$_3$)$_4$, and heated to 80° C. for 16 h. The mixture was diluted with EtOAc and washed with water. The aqueous layer was extracted with additional EtOAc, and the combined organic layers were dried over MgSO$_4$ and concentrated in vacuo. Chromatography of the residue on a 50-g silica Varian MegaBond Elut column with 25% EtOAc-hexanes afforded 150 mg (66%) of the title compound as a white foamy solid. Mass spectrum (ESI, m/z): Calcd. for C$_{23}$H$_{35}$N$_3$O$_2$, 386.3 (M+H). found 386.3.

e) 5-{[4-Cyano-1-(2-trimethylsilanyl-ethoxymethyl)-1H-imidazole-2-carbonyl]-amino}-6-(4,4-dimethyl-cyclohex-1-enyl)-3',4',5',6'-tetrahydro-2'H-[2,4]bipyridinyl-1'-carboxylic acid tert-butyl ester

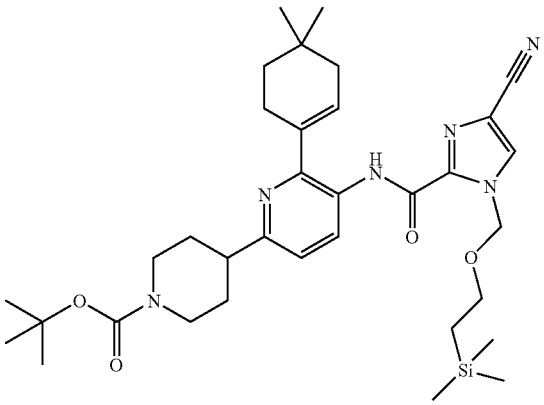 [SMILES: CC1(C)CC=C(c2nc(C3CCN(C(=O)OC(C)(C)C)CC3)ccc2NC(=O)c2nc(C#N)cn2COCC[Si](C)(C)C)CC1]

A solution of 150 mg (0.389 mmol) 5-amino-6-(4,4-dimethyl-cyclohex-1-enyl)-3',4',5',6'-tetrahydro-2'H-[2,4']bipyridinyl-1'-carboxylic acid tert-butyl ester (as prepared in the previous step) in 15 mL of CH$_2$Cl$_2$ was treated with 131 mg (0.428 mmol) of 4-cyano-1-(2-trimethylsilanyl-ethoxymethyl)-1H-imidazole-2-carboxylate potassium salt (as prepared in Example 3, step (b)), 272 mg (0.584 mmol) PyBroP, and 203 μL (1.17 mmol) DIEA at room temperature for 3 h. The mixture was diluted with CH$_2$Cl$_2$ and washed with saturated aqueous NaHCO$_3$. The organic layer was dried over MgSO$_4$ and concentrated in vacuo. Chromatography of the residue on a 50-g silica Varian MegaBond Elut column with 50% EtOAc-hexanes afforded 215 mg (87%) of the title compound as a white solid. Mass spectrum (ESI, m/z): Calcd. for C$_{34}$H$_{50}$N$_6$O$_4$Si, 635.4 (M+H). found 635.3.

f) 4-Cyano-1H-imidazole-2-carboxylic acid [6-(4,4-dimethyl-cyclohex-1-enyl)-1',2',3', 4',5',6'-hexahydro-[2,4]bipyridinyl-5-yl]-amide trifluoroacetic acid salt

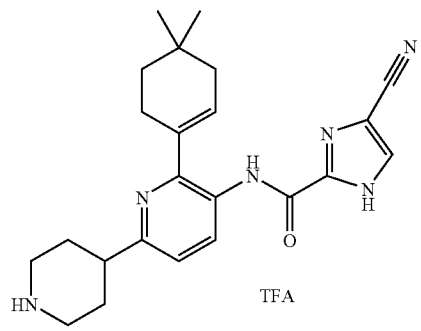 [SMILES: "TFA" ; CC1(C)CC=C(c2nc(C3CCNCC3)ccc2NC(=O)c2nc(C#N)c[nH]2)CC1]

A solution of 215 mg (0.339 mmol) 5-{[4-cyano-1-(2-trimethylsilanyl-ethoxymethyl)-1H-imidazole-2-carbonyl]-amino}-6-(4,4-dimethyl-cyclohex-1-enyl)-3',4',5' 6'-tetrahydro-2'H-[2,4']bipyridinyl-1'-carboxylic acid tert-butyl ester (as prepared in the previous step) in 10 mL of CH$_2$Cl$_2$ was treated with three drops MeOH and 3 mL TFA at room temperature for 4 h. MeOH (10 mL) was added and the solvents evaporated in vacuo. Chromatography of the residue on a 50-g silica Varian MegaBond Elut column with 10% MeOH—CH$_2$Cl$_2$ afforded 210 mg (97%) of the title compound as a white solid. $^1$H-NMR (CD$_3$OD; 400 MHz): δ 8.59 (d, 1H, J=8.4 Hz), 8.04 (s, 1H), 7.28 (d, 1H, J=8.4 Hz), 6.02-5.93 (m, 1H), 3.58-3.48 (m, 2H), 3.32-3.03 (m, 3H), 2.54-2.42 (m, 2H), 2.23-2.02 (m, 6H), 1.11 (s, 6H). Mass spectrum (ESI, m/z): Calcd. for C$_{23}$H$_{28}$N$_6$O, 405.2 (M+H). found 405.2.

EXAMPLE 55

4-Cyano-1H-imidazole-2-carboxylic acid [1'-(2-dimethylamino-acetyl)-6-(4,4-dimethyl-cyclohex-1-enyl)-1',2',3',4',5',6'-hexahydro-[2,4]bipyridinyl-5-yl]-amide trifluoroacetic acid salt

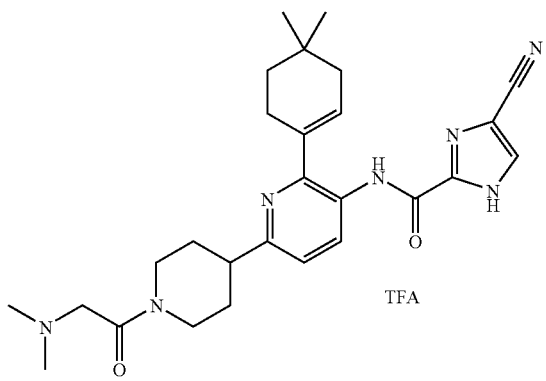 [SMILES: CN(C)CC(=O)N1CCC(c2ccc(NC(=O)c3nc(C#N)c[nH]3)c(C3=CCC(C)(C)CC3)n2)CC1 ; "TFA"]

A suspension of 20.9 mg (0.203 mmol) N,N-dimethylglycine in 4 mL CH$_2$Cl$_2$ was treated with 49.8 mg (0.197 mmol) bis(2-oxo-3-oxazolidinyl)phosphinic chloride (BOP-Cl) and 75 μL (0.54 mmol) Et$_3$N at room temperature for 1 h. The mixture was then treated with 70.0 mg (0.135 mmol) 4-cyano-1H-imidazole-2-carboxylic acid [6-(4,4-dimethyl-cyclohex-1-enyl)-1',2',3',4', 5',6'-hexahydro-[2,4']bipyridinyl-5-yl]-amide trifluoroacetate (as prepared in Example 54, step (f)) at room temperature for 18 h. The mixture was diluted with CH$_2$Cl$_2$ and washed with water. The organic layer was dried over MgSO$_4$ and concentrated in vacuo. The residue was purified by RP-HPLC (C18) with 10-80% CH$_3$CN in 0.1% TFA/H$_2$O over 30 min to afford 34.9 mg (53%) of the title compound as a white solid. $^1$H-NMR (CD$_3$OD; 400 MHz): δ 8.38 (d, 1H, J=8.4 Hz), 8.05 (s, 1H), 7.33 (d, 1H, J=8.4 Hz), 6.05-5.98 (m, 1H), 4.68 (d, 1H, J=15.2 Hz), 3.82 (d, 1H, J=15.2 Hz), 3.16-3.05 (m, 1H), 3.01-2.94 (m, 6H), 2.52-2.40 (m, 2H), 2.39 (s, 6H), 2.17-2.10 (m, 2H), 2.09-1.87 (m, 2H), 1.67-1.59 (m, 2H), 1.12 (s, 6H). Mass spectrum (ESI, m/z): Calcd. for C$_{27}$H$_{35}$N$_7$O$_2$, 490.3 (M+H). found 490.4.

EXAMPLE 56

4-Cyano-1H-imidazole-2-carboxylic acid [6-(4,4-dimethyl-cyclohex-1-enyl)-1'-(2-methanesulfonyl-ethyl)-1',2',3',4',5',6'-hexahydro-[2,4]bipyridinyl-5-yl]-amide trifluoroacetic acid salt

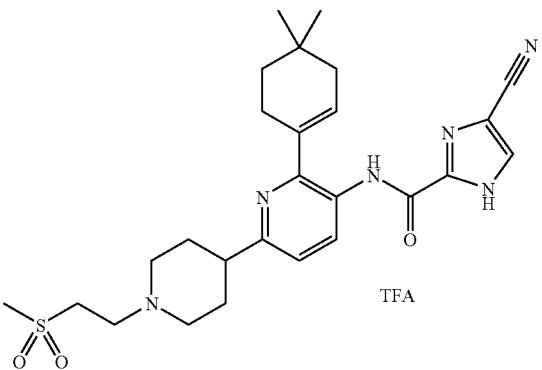 [SMILES: CC1(C)CC=C(c2nc(C3CCN(CCS(C)(=O)=O)CC3)ccc2NC(=O)c2nc(C#N)c[nH]2)CC1 ; "TFA"]

A solution of 70.0 mg (0.135 mmol) 4-cyano-1H-imidazole-2-carboxylic acid [6-(4,4-dimethyl-cyclohex-1-enyl)-1',2',3',4', 5',6'-hexahydro-[2,4']bipyridinyl-5-yl]-amide (as prepared in Example 54, step (f)) in 10 mL of CH$_2$Cl$_2$ was treated with 32.7 mg (0.162 mmol) methanesulfonic acid 2-methanesulfonyl-ethyl ester (as prepared in Example 40, step (a)) and 70.5 μL (0.405 mmol) DIEA at room temperature for 6 h. The mixture was diluted with CH$_2$Cl$_2$ and washed with water. The organic layer was dried over MgSO$_4$ and concentrated in vacuo. The residue was purified by RP-HPLC (C18) with 20-60% CH$_3$CN in 0.1% TFA/H$_2$O over 30 min to afford 48 mg (85%) of the title compound as a white solid. $^1$H-NMR (CD$_3$OD; 400 MHz): δ 8.65 (d, 1H, J=8.4 Hz), 8.05 (s, 1H), 7.34 (d, 1H, J=8.4 Hz), 6.05-5.98 (m, 1H), 3.85-3.66 (m, 6H), 3.29-3.21 (m, 2H), 3.20-3.01 (m, 1H), 3.14 (s, 3H), 2.53-2.45 (m, 2H), 2.30-2.15 (m, 4H), 2.15-2.10 (m, 2H), 1.62 (t, 2H, J=6.4 Hz), 1.11 (s, 6H). Mass spectrum (ESI, m/z): Calcd. for C$_{26}$H$_{34}$N$_6$O$_3$S, 511.2 (M+H). found 511.3.

EXAMPLE 57

5-Cyano-1H-imidazole-2-carboxylic acid {4-[1-(2-amino-2-methyl-propionyl)-piperidin-4-yl]-2-cyclohex-1-enyl-phenyl}-amide trifluoroacetic acid salt

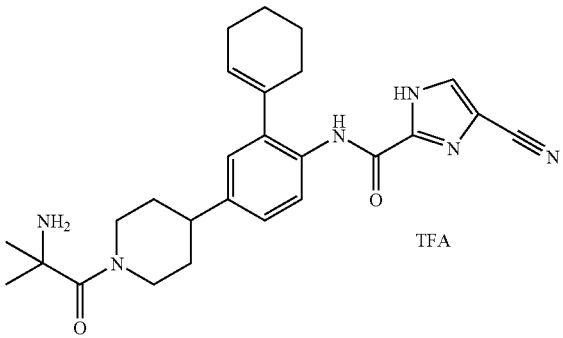 [SMILES: "TFA" ; CC(C)(N)C(=O)N1CCC(c2ccc(NC(=O)c3nc(C#N)c[nH]3)c(C3=CCCCC3)c2)CC1]

a) {2-[4-(4-{[4-Cyano-1-(2-trimethylsilanyl-ethoxymethyl)-1H-imidazole-2-carbonyl]-amino}-3-cyclohex-1-enyl-phenyl)-piperidin-1-yl]-1,1-dimethyl-2-oxo-ethyl}-carbamic acid tert-butyl ester

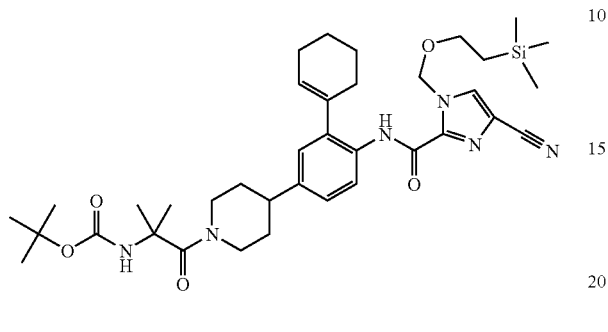

To a solution of 4-(4-{[4-cyano-1-(2-trimethylsilanyl-ethoxymethyl)-1H-imidazole-2-carbonyl]-amino}-3-cyclohex-1-enyl-phenyl)-piperidine-1-carboxylic acid tert-butyl ester (231 mg, 0.380 mmol) (as prepared in Example 14, step (a)) in 2.5 mL of DCM and 0.4 mL EtOH was added 700 µL of TFA and the solution stirred for 3 h at 25° C. The reaction was diluted with 4 mL of EtOH and then concentrated to give ca. a 2:1 mixture of 5-cyano-1-(2-trimethylsilanyl-ethoxymethyl)-1H-imidazole-2-carboxylic acid (2-cyclohex-1-enyl-4-piperidin-4-yl-phenyl)-amide trifluoroacetic acid salt to starting material by $^1$H-NMR and LC/MS which was used in the following step without further purification. The mixture in 3 mL of DCM was added to a solution of 2-tert-butoxycarbonylamino-2-methyl-propionic acid (53 mg, 0.70 mmol), DIEA (122 µL, 0.700 mmol) and PyBroP (144 mg, 0.300 mmol) in 3 mL of DCM and the reaction was stirred at 25° C. overnight. The reaction was diluted with EtOAc (25 mL) and washed with satd aq NaHCO$_3$ (1×25 mL) and brine (25 mL) and the organic layer was dried over Na$_2$SO$_4$ and then concentrated. Purification of the residue by preparative TLC (50% EtOAc-hexanes) afforded 40 mg (15%) of the title compound as a white solid. Mass Spectrum (ESI, m/z): Calcd. for $C_{37}H_{55}N_6O_5Si$, 691.3 (M+H). found 691.1.

b) 5-Cyano-1H-imidazole-2-carboxylic acid {4-[1-(2-amino-2-methyl-propionyl)-piperidin-4-yl]-2-cyclohex-1-enyl-phenyl}-amide trifluoroacetic acid salt To a solution of {2-[4-(4-{[4-cyano-1-(2-trimethylsilanyl-ethoxymethyl)-1H-imidazole-2-carbonyl]-amino}-3-cyclohex-1-enyl-phenyl)-piperidin-1-yl]-1,1-dimethyl-2-oxo-ethyl}-carbamic acid tert-butyl ester (40 mg, 0.050 mmol) in 2 mL of DCM and 20 µL of EtOH was added 1.5 mL of TFA. The solution was stirred for 3 h at 25° C., diluted with 2 mL of EtOH and concentrated in vacuo. Trituration of the residue with ether afforded 8.4 mg (29%) of the title compound as a white solid. $^1$H-NMR (CD$_3$OD; 400 MHz): δ 8.10 (d, 1H, J=8.4 Hz), 8.00 (s, 1H), 7.16 (d, 1H, J=8.4 Hz), 7.07 (s, 1H), 5.79 (s, 1H), 4.55-4.48 (m, 1H), 3.30 (s, 6H), 2.89-2.87 (m, 2H), 2.40-2.25 (m, 4H), 1.96-1.93 (m, 2H), 1.86-1.83 (m, 6H), 1.64-1.61 (m, 2H). Mass Spectrum (ESI, m/z): Calcd. for $C_{26}H_{33}N_6O_2$, 461.2 (M+H). found 461.3.

EXAMPLE 58

5-Cyano-1H-imidazole-2-carboxylic acid [6-cyclohex-1-enyl-1'-(2-methanesulfonyl-ethyl)-1',2',3',4',5',6'-hexahydro-[2,4]bipyridinyl-5-yl]-amide

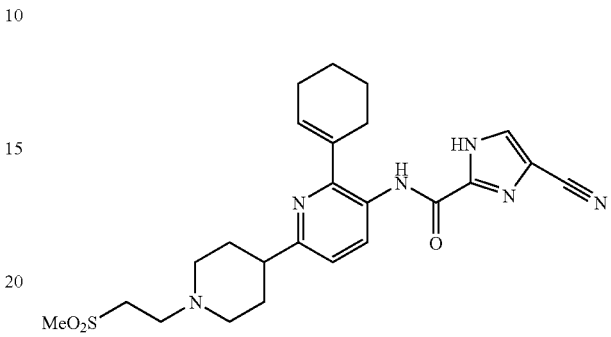

a) 5-Amino-6-cyclohex-1-enyl-3',4',5',6'-tetrahydro-2'H-[2,4]bipyridinyl-1'-carboxylic acid tert-butyl ester

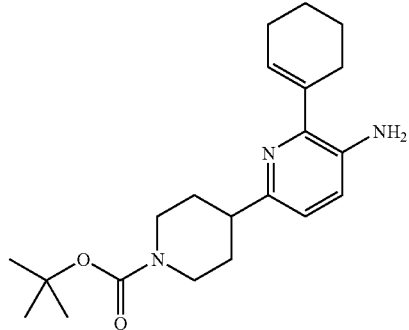 [SMILES: CC(C)(C)OC(=O)N1CCC(c2ccc(N)c(C3=CCCCC3)n2)CC1]

To a mixture of 5-amino-6-bromo-3',4',5',6'-tetrahydro-2'H-[2,4]bipyridinyl-1'-carboxylic acid tert-butyl ester (331 mg, 0.93 mmol) (as prepared in Example 54, step (c)) and cyclohexen-1-yl boronic acid (141 mg, 1.11 mmol) in 5 mL of EtOH, 10 mL of toluene and 5 mL of 2 M Na$_2$CO$_3$, was added Pd(PPh$_3$)$_4$ (107 mg, 0.0930 mmol) and the result was heated at 80° C. for 16 h. The reaction was diluted with 100 mL of ether and 100 mL of brine and the layers were separated. The organic layer was dried (Na$_2$SO$_4$) and concentrated in vacuo. Purification of the residue by column chromatography (silica gel, 30-60% ether-hexanes) afforded 248 mg (74%) the title compound as an light brown oil LC-MS (ESI, m/z): Calcd. for $C_{21}H_{32}N_3O_2$ (M+H), 358.2. found 358.1.

b) 5-{[4-Cyano-1-(2-trimethylsilanyl-ethoxymethyl)-1H-imidazole-2-carbonyl]-amino}-6-cyclohex-1-enyl-3',4',5',6'-tetrahydro-2'H-[2,4]bipyridinyl-1'-carboxylic acid tert-butyl ester

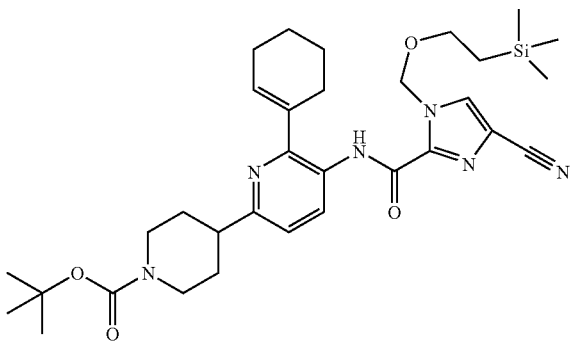 [SMILES: CC(C)(C)OC(=O)N1CCC(c2ccc(NC(=O)c3nc(C#N)cn3COCC[Si](C)(C)C)c(C3=CCCCC3)n2)CC1]

To a solution of 4-cyano-1-(2-trimethylsilanyl-ethoxymethyl)-1H-imidazole-2-carboxylate potassium salt (296 mg, 0.970 mmol) (as prepared in Example 3, step (d)) in 8 mL DCM was added DIEA (291 μL, 1.72 mmol) and PyBroP (512 mg, 1.10 mmol), and the reaction was stirred at 25° C. for 15 min. A solution of 5-amino-6-cyclohex-1-enyl-3',4',5',6'-tetrahydro-2'H-[2,4']bipyridinyl-1'-carboxylic acid tert-butyl ester (233 mg, 0.65 mmol) (as prepared in the previous step) in 4 mL DCM was added and the reaction stirred overnight at 25° C. The reaction was diluted with EtOAc (25 mL) and washed with NaHCO$_3$ (1×25 mL) and brine (25 mL) and the organic layer was dried over Na$_2$SO$_4$ and then concentrated. The residue was purified by flash chromatography (silica gel, 5% MeOH—CHCl$_3$) to afford 167 mg (40%) of the title compound as a white solid. Mass Spectrum (ESI, m/z): Calcd. for C$_{32}$H$_{46}$N$_6$O$_4$Si, 607.3 (M+H). found 607.3.

c) 5-Cyano-1H-imidazole-2-carboxylic acid (6-cyclohex-1-enyl-2',3',4',5',6'-hexahydro-[2,4]bipyridinyl-5-yl)-amide trifluoroacetic acid salt

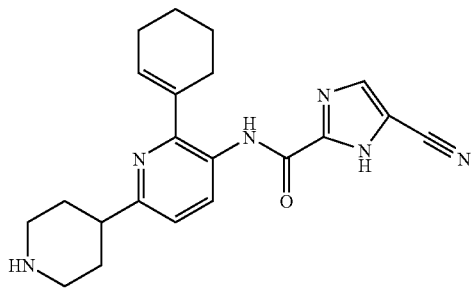 [SMILES: N#Cc1cnc(C(=O)Nc2ccc(C3CCNCC3)nc2C2=CCCCC2)[nH]1]

The title compound was prepared from 5-{[4-cyano-1-(2-trimethylsilanyl-ethoxymethyl)-1H-imidazole-2-carbonyl]-amino}-6-cyclohex-1-enyl-3',4',5',6'-tetrahydro-2'H-[2,4']bipyridinyl-1'-carboxylic acid tert-butyl ester (167 mg, 0.27 mmol) using a procedure similar to Example 14, step (b) to afford 57 mg (43%) of the title compound as a white solid. LC-MS (ESI, m/z): Calcd. for C$_{21}$H$_{24}$N$_6$O, 377.2 (M+H). found 377.2.

d) 5-Cyano-1H-imidazole-2-carboxylic acid [6-cyclohex-1-enyl-1'-(2-methanesulfonyl-ethyl)-1' 2',3',4',5',6'-hexahydro-[2,4']bipyridinyl-5-yl]-amide To a slurry of 5-cyano-1H-imidazole-2-carboxylic acid (6-cyclohex-1-enyl-1',2',3',4',5',6'-hexahydro-[2,4']bipyridinyl-5-yl)-amide trifluoroacetic acid salt (57 mg, 0.11 mmol) in 5 mL of DCM was added DIEA (50.4 μL, 0.290 mmol) followed by 30.5 mg (0.150 mmol) of methanesulfonic acid 2-methanesulfonyl-ethyl ester (as prepared in Example 40, step (a)). The reaction was allowed to stir overnight, diluted with 20 mL of DCM, washed with satd aq NaHCO$_3$ (1×20 mL) and dried over Na$_2$SO$_4$. Purification by preparative TLC (silica gel, 40% EtOAc-hexanes) afforded 22.3 mg (40%) of the title compound as a white solid. $^1$H-NMR (DMSO; 400 MHz): δ 10.02 (s, 1H), 8.24 (s, 1H), 8.11 (d, 1H, J=8.4 Hz), 7.18 (d, 1H, J=8.4 Hz), 5.96 (s, 1H), 3.04 (s, 3H), 3.02-2.99 (m, 3H), 2.73 (t, 2H, J=2.7 Hz), 2.39-2.37 (m, 2H), 2.11-2.05 (m, 4H), 1.85-1.64 (m, 10H). Mass Spectrum (ESI, m/z): Calcd. for C$_{24}$H$_{31}$N$_6$O$_3$S, 483.2 (M+H). found 483.3.

EXAMPLE 59

An Alternate Method for the Synthesis of the Intermediate Described in Example 3 is Described Below 4-Cyano-1-(2-trimethylsilanyl-ethoxy ethyl)-1H-imidazole-2-carboxylic acid potassium salt

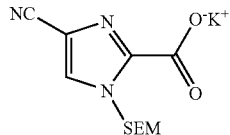

a) 1H-Imidazole-4-carbonitrile

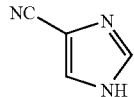

A 22-L, four-neck, round-bottom flask equipped with a mechanical stirrer, a temperature probe, a condenser, and an addition funnel with a nitrogen inlet was charged with 1H-imidazole-4-carboxaldehyde (Aldrich, 1.10 kg, 11.5 mol) and pyridine (3.0 L, 3.0 mol). The reaction flask was cooled to 8° C. with an ice bath and hydroxylamine hydrochloride (871 g, 12.5 mol) was added slowly in portions to maintain the internal temperature below 30° C. The reaction was allowed to cool to ambient temperature and stirred for 2 h at ambient temperature. The resulting thick yellow solution was heated to 80° C. with a heating mantle and acetic anhydride (2.04 L, 21.6 mol) was added dropwise over 200 min to maintain the temperature below 110° C. during the addition. The reaction mixture was heated at 100° C. for 30 min, after which time it was allowed to cool to ambient temperature and then further cooled in an ice bath. The pH was adjusted to 8.0 (pH meter) by the addition of 25 wt % NaOH (5.5 L) at such a rate that the internal temperature was maintained below 30° C. The reaction mixture was then transferred into a 22-L separatory funnel and extracted with ethyl acetate (6.0 L). The combined organic layer was washed with brine (2×4.0 L), dried over MgSO₄, filtered, and concentrated to dryness under reduced pressure at 35° C. to give the crude product as a yellow semisolid. The resulting semisolid was suspended in toluene (3.0 L) and stirred for 1 h, after which time it was filtered to give a light yellow solid, which was resuspended in toluene (3.0 L) and stirred for 1 h. The resulting slurry was filtered and the filter cake washed with toluene (2×500 mL) to give the title compound as a light yellow solid [870 g, 82%). The ¹H and ¹³C NMR spectra were consistent with the assigned structure.

b) 1-(2-Trimethylsilanyl-ethoxymethyl)-1H-imidazole-4-carbonitrile and 3-(2-trimethylsilanyl-ethoxymethyl)-3H-imidazole-4-carbonitrile

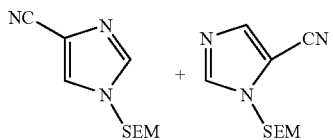

A 22-L, four-neck, round-bottom flask equipped with a mechanical stirrer, a temperature probe, and an addition funnel with a nitrogen inlet was charged with 1H-imidazole-4-carbonitrile (830 g, 8.91 mol, as prepared in the previous step), potassium carbonate (2.47 kg, 17.8 mol), and acetone (6.0 L). Agitation was initiated and the mixture was cooled to 10° C. with an ice bath. SEMCl (1.50 kg, 9.00 mol) was added through the addition funnel over 210 min to maintain the internal temperature below 15° C. The reaction was then allowed to warm to ambient temperature and stirred at ambient temperature overnight (20 h). The reaction mixture was then cooled in an ice bath to 10° C. and quenched by the slow addition of water (8.0 L) over 30 min to maintain the internal temperature below 30° C. The resulting mixture was transferred to a 22-L separatory funnel and extracted with ethyl acetate (2×7.0 L). The combined organics were concentrated under reduced pressure at 35° C. to give the crude product as a dark brown oil, which was purified through a plug of silica gel (16.5×20 cm, 2.4 kg silica gel) using 2:1 heptane/ethyl acetate (15 L) as eluent. The fractions containing the product were combined and concentrated under reduced pressure at 35° C. to afford a mixture of the title compounds as a light brown oil [1785 g, 90%). The ¹H NMR spectrum was consistent with the assigned structure and indicated the presence of a 64:36 ratio of regioisomers.

c) 2-Bromo-1-(2-trimethylsilanyl-ethoxymethyl)-1H-imidazole-4-carbonitrile

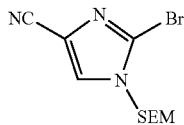

A 22-L, four-neck, round-bottom flask equipped with a mechanical stirrer, a temperature probe, and a condenser with a nitrogen inlet was charged with a mixture of 1-(2-trimethylsilanyl-ethoxymethyl)-1H-imidazole-4-carbonitrile and 3-(2-trimethylsilanyl-ethoxymethyl)-3H-imidazole-4-carbonitrile [600 g, 2.69 mol, as prepared in the previous step) and carbon tetrachloride (1.8 L). Agitation was initiated and the mixture was heated to 60° C. At this point N-bromosuccinimide (502 g, 2.82 mol) was added in several portions over 30 min, which resulted in an exotherm to 74° C. The reaction was allowed to cool to 60° C. and further stirred at 60° C. for 1 h. The reaction was allowed to cool slowly to ambient temperature and the resulting slurry was filtered and the filtrate washed with satd NaHCO₃ solution (4.0 L). The organics were passed through a plug of silica gel (8×15 cm, silica gel; 600 g) using 2:1 heptane/ethyl acetate (6.0 L) as eluent. The fractions containing the product (based on TLC analysis) were combined and concentrated under reduced pressure to give a crystalline light yellow solid, which was then filtered and washed with heptane (500 mL) to give the title compound as a crystalline white solid [593 g, 73%). The ¹H and ¹³C NMR spectra were consistent with the assigned structure and showed no evidence of the minor regioisomer.

d) 4-Cyano-]-(2-trimethylsilanyl-ethoxy ethyl)-1H-imidazole-2-carboxylic acid ethyl ester

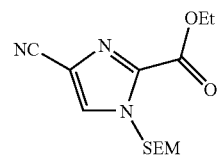

A 12-L, four-neck, round-bottom flask equipped with a mechanical stirrer, a temperature probe, and an addition funnel with a nitrogen inlet was charged with 2-bromo-1-(2-trimethylsilanyl-ethoxymethyl)-1H-imidazole-4-carbonitrile [390 g, 1.29 mol, as prepared in the previous step) and anhydrous tetrahydrofuran (4.0 L). Agitation was initiated and the reaction mixture was cooled to −50° C. using a dry ice/acetone bath. Isopropylmagnesium chloride (2.0 M in THF, 760 mL, 1.52 mol) was added through the addition funnel over 30 min to maintain the internal temperature below −40° C. The reaction was stirred for a further 30 min at −43° C., after which time it was cooled to −78° C. Ethyl chloroformate (210 mL, 2.20 mol) was added through the addition funnel over 10 min to maintain the internal temperature below −60° C. The reaction was stirred for a further 40 min at −70° C., at which point the dry ice/acetone bath was removed and the reaction was allowed to warm to ambient temperature over 1.5 h. The reaction mixture was cooled in an ice bath to 0° C. and quenched by the slow addition of satd ammonium chloride solution (1.8 L) at such a rate that the internal temperature was maintained below 10° C. The reaction mixture was transferred into a 12-L separatory funnel, diluted with ethyl acetate (4.0 L), and the layers were separated. The organic layer was washed with brine (2×2.0 L) and concentrated under reduced pressure at 35° C. to give a brown oil. The crude oil was dissolved in dichloromethane (300 mL) and purified by chromatography (15×22 cm, 1.5 kg of silica gel, 10:1 to 4:1 heptane/ethyl acetate) to give a yellow oil, which was dissolved in EtOAc (100 mL), diluted with heptane (2.0 L), and stored in a refrigerator for 5 h. The resulting slurry was filtered to give the title compound as a crystalline white solid (141 g, 37%). The ¹H and ¹³C NMR spectra were consistent with the assigned structure.

e) 4-Cyano-1-(2-trimethylsilanyl-ethoxymethyl)-1H-imidazole-2-carboxylic acid potassium salt

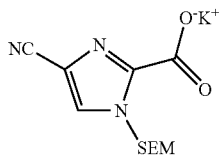

A 5-L, three-neck, round-bottom flask equipped with a mechanical stirrer, a temperature probe, and an addition funnel with a nitrogen inlet was charged with 5 [400 g, 1.35 mol) and ethanol (4.0 L). Agitation was initiated and a water bath was applied after all of the solid had dissolved. A solution of 6 N KOH (214.0 mL, 1.29 mol) was added through the addition funnel over 15 min to maintain the internal temperature below 25° C. and the reaction was stirred for 5 min at room temperature. The solution was then concentrated to dryness under reduced pressure at 20° C. to give a white solid. The resulting solid was suspended in methyl t-butyl ether (MTBE, 4.0 L) and stirred for 30 min, after which time the slurry was filtered and the filter cake washed with MTBE (1.0 L) to give the title compound as a white solid, which was further dried under vacuum at ambient temperature for 4 d [366 g, 89%). The $^1$H NMR, $^{13}$C NMR, and mass spectra were consistent with the assigned structure. Anal. Calcd for $C_{11}H_{16}KN_3O_3Si$: C, 43.25; H, 5.28; N, 13.76. Found: C, 42.77; H, 5.15; N, 13.37. Karl Fisher: 1.3% $H_2O$.

Biological Activity of FLT3 Inhibitors of Formula I'

The following representative assays were performed in determining the biological activities of the FLT3 inhibitors of Formula I'. They are given to illustrate the invention in a non-limiting fashion.

In Vitro Assays

The following representative in vitro assays were performed in determining the FLT3 biological activity of the compounds of Formula I'. They are given to illustrate the invention in a non-limiting fashion.

Inhibition of FLT3 enzyme activity, MV4-11 proliferation and Baf3-FLT3 phosphorylation exemplify the specific inhibition of the FLT3 enzyme and cellular processes that are dependent on FLT3 activity. Inhibition of Baf3 cell proliferation is used as a test of FLT3 independent cytotoxicity. All of the examples herein show significant and specific inhibition of the FLT3 kinase and FLT3-dependent cellular responses. The compounds of the present invention are also cell permeable.

FLT3 Fluorescence Polarization Kinase Assay

To determine the activity of the compounds of the present invention in an in vitro kinase assay, inhibition of the isolated kinase domain of the human FLT3 receptor (a.a. 571-993) was performed using the following fluorescence polarization (FP) protocol. The FLT3 FP assay utilizes the fluorescein-labeled phosphopeptide and the anti-phosphotyrosine antibody included in the Panvera Phospho-Tyrosine Kinase Kit (Green) supplied by Invitrogen. When FLT3 phosphorylates polyGlu$_4$Tyr, the fluorescein-labeled phosphopeptide is displaced from the anti-phosphotyrosine antibody by the phosphorylated poly Glu$_4$Tyr, thus decreasing the FP value. The FLT3 kinase reaction is incubated at room temperature for 30 minutes under the following conditions: 10 nM FLT3 571-993, 20 ug/mL poly Glu$_4$Tyr, 150 uM ATP, 5 mM MgCl$_2$, 1% compound in DMSO. The kinase reaction is stopped with the addition of EDTA. The fluorescein-labeled phosphopeptide and the anti-phosphotyrosine antibody are added and incubated for 30 minutes at room temperature.

Data points are an average of triplicate samples. Inhibition and IC$_{50}$ data analysis was done with GraphPad Prism using a non-linear regression fit with a multiparamater, sigmoidal dose-response (variable slope) equation. The IC$_{50}$ for kinase inhibition represents the dose of compound that results in a 50% inhibition of kinase activity compared to DMSO vehicle control.

Inhibition of MV4-11 and Baf3 Cell Proliferation

To assess the cellular potency of compounds of the present invention, FLT3 specific growth inhibition was measured in the leukemic cell line MV4-11 (ATCC Number: CRL-9591). MV4-11 cells are derived from a patient with childhood acute myelomonocytic leukemia with an 11q23 translocation resulting in a MLL gene rearrangement and containing an FLT3-ITD mutation (AML subtype M4)(1,2). MV4-11 cells cannot grow and survive without active FLT3ITD.

The IL-3 dependent, murine b-cell lymphoma cell line, Baf3, were used as a control to confirm the selectivity of compounds of the present invention by measuring non-specific growth inhibition by the compounds of the present invention.

To measure proliferation inhibition by compounds of the present invention, the luciferase based CellTiterGlo reagent (Promega), which quantifies total cell number based on total cellular ATP concentration, was used. Cells are plated at 10,000 cells per well in 100 ul of in RPMI media containing penn/strep, 10% FBS and 1 ng/ml GM-CSF or 1 ng/ml IL-3 for MV4-11 and Baf3 cells respectively.

Compound dilutions or 0.1% DMSO (vehicle control) are added to cells and the cells are allowed to grow for 72 hours at standard cell growth conditions (37° C., 5% CO$_2$). For activity measurements in MV4-11 cells grown in 50% plasma, cells were plated at 10,000 cells per well in a 1:1 mixture of growth media and human plasma (final volume of 100 µL). To measure total cell growth an equal volume of CellTiterGlo reagent was added to each well, according to the manufacturer's instructions, and luminescence was quantified. Total cell growth was quantified as the difference in luminescent counts (relative light units, RLU) of cell number at Day 0 compared to total cell number at Day 3 (72 hours of growth and/or compound treatment). One hundred percent inhibition of growth is defined as an RLU equivalent to the Day 0 reading. Zero percent inhibition was defined as the RLU signal for the DMSO vehicle control at Day 3 of growth.

Data points are an average of triplicate samples. The IC$_{50}$ for growth inhibition represents the dose of a compound of the present invention that results in a 50% inhibition of total cell growth at day 3 of the DMSO vehicle control. Inhibition and IC$_{50}$ data analysis was done with GraphPad Prism using a non-linear regression fit with a multiparamater, sigmoidal dose-response (variable slope) equation. MV4-11 cells express the FLT3 internal tandem duplication mutation, and thus are entirely dependent upon FLT3 activity for growth. Strong activity against the MV4-11 cells is anticipated to be a desirable quality of the invention. In contrast, the Baf3 cell proliferation is driven by the cytokine IL-3 and thus is used as a non-specific toxicity control. FLT3 Inhibitor Compound #38 of the present invention showed <50% inhibition at a 3 µM dose (data is not included), suggesting that it is not cytotoxic and has good selectivity for FLT3.

Cell-Based FLT3 Receptor Elisa

Specific cellular inhibition of FLT ligand-induced wild-type FLT3 phosphorylation was measured in the following manner: Baf3 FLT3 cells overexpressing the FLT3 receptor were obtained from Dr. Michael Heinrich (Oregon Health and Sciences University). The Baf3 FLT3 cell lines were created by stable transfection of parental Baf3 cells (a murine B cell lymphoma line dependent on the cytokine IL-3 for growth) with wild-type FLT3. Cells were selected for their ability to grow in the absence of IL-3 and in the presence of FLT3 ligand.

Baf3 cells were maintained in RPMI 1640 with 10% FBS, penn/strep and 10 ng/ml FLT ligand at 37° C., 5% $CO_2$. To measure direct inhibition of the wild-type FLT3 receptor activity and phosphorylation a sandwich ELISA method was developed similar to those developed for other RTKs (3,4). 200 μL of Baf3FLT3 cells ($1 \times 10^6$/mL) were plated in 96 well dishes in RPMI 1640 with 0.5% serum and 0.01 ng/mL IL-3 for 16 hours prior to 1 hour compound or DMSO vehicle incubation. Cells were treated with 100 ng/mL Flt ligand (R&D Systems Cat# 308-FK) for 10 min. at 37° C. Cells were pelleted, washed and lysed in 100 uL lysis buffer (50 mM Hepes, 150 mM NaCl, 10% Glycerol, 1% Triton —X-100, 10 mM NaF, 1 mM EDTA, 1.5 mM $MgCl_2$, 10 mM Na Pyrophosphate) supplemented with phosphatase (Sigma Cat# P2850) and protease inhibitors (Sigma Cat #P8340). Lysates were cleared by centrifugation at 1000×g for 5 minutes at 4° C. Cell lysates were transferred to white wall 96well microtiter (Costar #9018) plates coated with 50 ng/well anti-FLT3 antibody (Santa Cruz Cat# sc-480) and blocked with SeaBlock reagent (Pierce Cat#37527). Lysates were incubated at 4° C. for 2 hours. Plates were washed 3× with 200 uL/well PBS/0.1% Triton-X-100. Plates were then incubated with 1:8000 dilution of HRP-conjugated anti-phosphotyrosine antibody (Clone 4G10, Upstate Biotechnology Cat#16-105) for 1 hour at room temperature. Plates were washed 3× with 200 uL/well PBS/0.1% Triton-X-100. Signal detection with Super Signal Pico reagent (Pierce Cat#37070) was done according to manufacturer's instruction with a Berthold microplate luminometer.

Data points are an average of triplicate samples. The total relative light units (RLU) of Flt ligand stimulated FLT3 phosphorylation in the presence of 0.1% DMSO control was defined as 0% inhibition and 100% inhibition was the total RLU of lysate in the basal state. Inhibition and $IC_{50}$ data analysis was done with GraphPad Prism using a non-linear regression fit with a multiparamater, sigmoidal dose-response (variable slope) equation.

1. Drexler H G. *The Leukemia-Lymphoma Cell Line Factsbook*. Academic Press: San Diego, Calif., 2000.
2. Quentmeier H, Reinhardt J, Zaborski M, Drexler H G. FLT3 mutations in acute myeloid leukemia cell lines. Leukemia. 2003 January; 17:120-124.
3. Sadick, M D, Sliwkowski, M X, Nuijens, A, Bald, L, Chiang, N, Lofgren, J A, Wong W L T. Analysis of Heregulin-Induced ErbB2 Phosphorylation with a High-Throughput Kinase Receptor Activation Enzyme-Linked Immunsorbent Assay, Analytical Biochemistry. 1996; 235:207-214.
4. Baumann C A, Zeng L, Donatelli R R, Maroney A C. Development of a quantitative, high-throughput cell-based enzyme-linked immunosorbent assay for detection of colony-stimulating factor-1 receptor tyrosine kinase inhibitors. J Biochem Biophys Methods. 2004; 60:69-79.

The activity of selected compounds of the present invention is presented below. All activities are in EM and have the following uncertainties: FLT3 kinase: ±10%; MV4-11 and Baf3-FLT3: ±20%.

| | Structure | Flt-3 IC50 (μM) | MV4-11 IC50 (μM) | Baf3 IC50 (μM) |
|---|---|---|---|---|
| 5 | 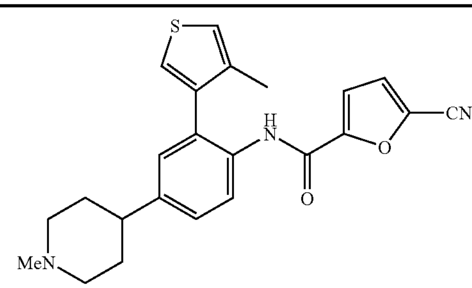 | 0.01 | 0.666 | N/A |
| 6 | 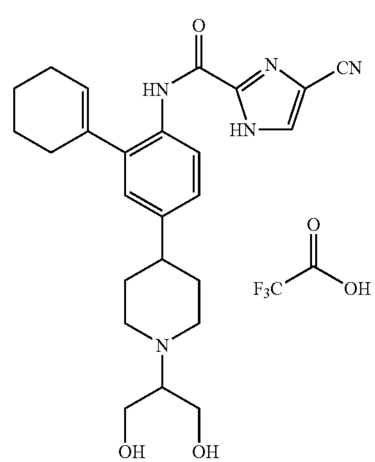 [SMILES: N#Cc1c[nH]c(C(=O)Nc2ccc(C3CCN(C(CO)CO)CC3)cc2C2=CCCCC2)n1 ; O=C(O)C(F)(F)F] | 0.082 | N/A | N/A |

-continued

| | Structure | Flt-3 IC50 (μM) | MV4-11 IC50 (μM) | Baf3 IC50 (μM) |
|---|---|---|---|---|
| 7 | 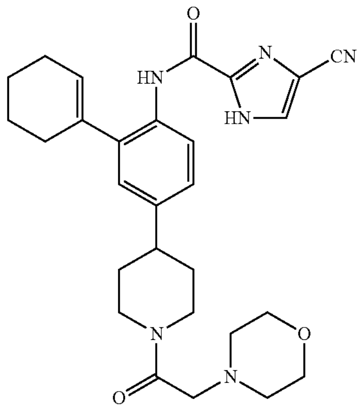 [SMILES: N#Cc1c[nH]c(C(=O)Nc2ccc(C3CCN(C(=O)CN4CCOCC4)CC3)cc2C2=CCCCC2)n1] | 0.14 | N/A | N/A |
| 9 | 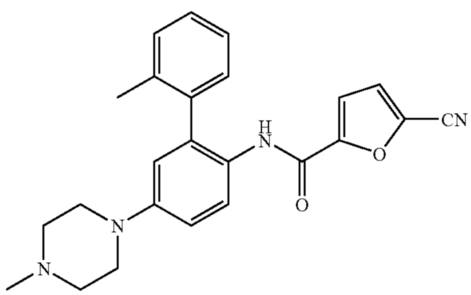 [SMILES: Cc1ccccc1-c1cc(N2CCN(C)CC2)ccc1NC(=O)c1ccc(C#N)o1] | 0.097 | 1.00 | N/A |
| 11 | 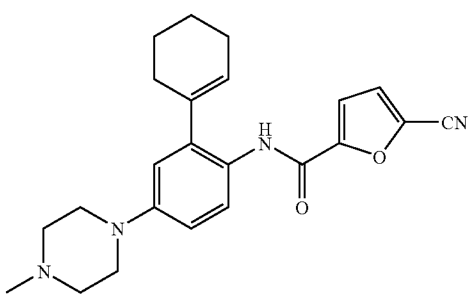 [SMILES: CN1CCN(c2ccc(NC(=O)c3ccc(C#N)o3)c(C3=CCCCC3)c2)CC1] | 0.26 | 0.131 | 1.30 |
| 12 | 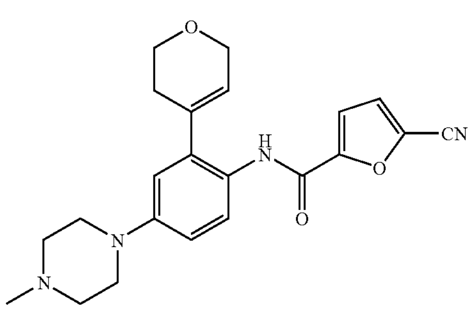 [SMILES: CN1CCN(c2ccc(NC(=O)c3ccc(C#N)o3)c(C3=CCOCC3)c2)CC1] | 1.24 | >10 | N/A |

-continued

| | Structure | Flt-3 IC50 (μM) | MV4-11 IC50 (μM) | Baf3 IC50 (μM) |
|---|---|---|---|---|
| 13 | 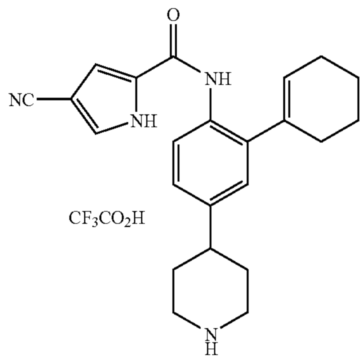 | 0.034 | N/A | N/A |
| 14 | 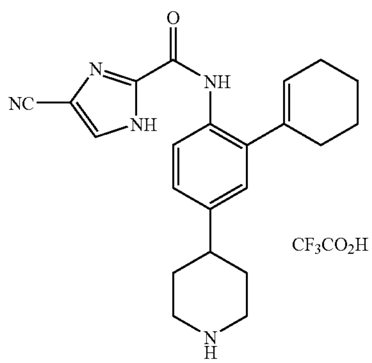 | 0.032 | N/A | 0.770 |
| 16 | 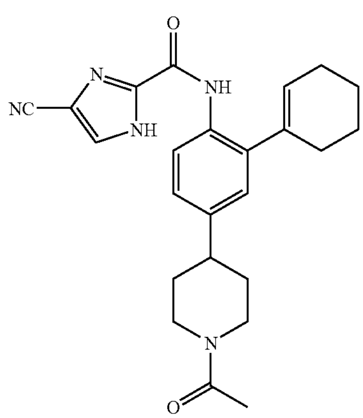 | 0.039 | N/A | N/A |
| 17 | 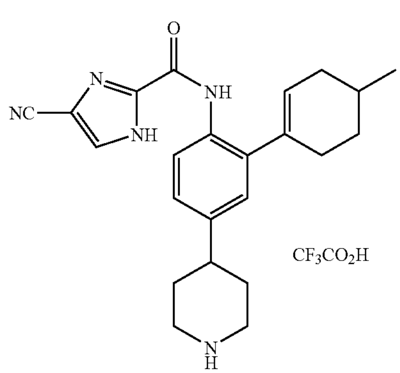 | 0.013 | N/A | N/A |

-continued

| | Structure | Flt-3 IC50 (μM) | MV4-11 IC50 (μM) | Baf3 IC50 (μM) |
|---|---|---|---|---|
| 20 | 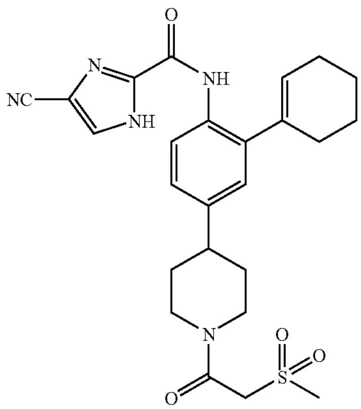 | 0.13 | N/A | N/A |
| 23 | 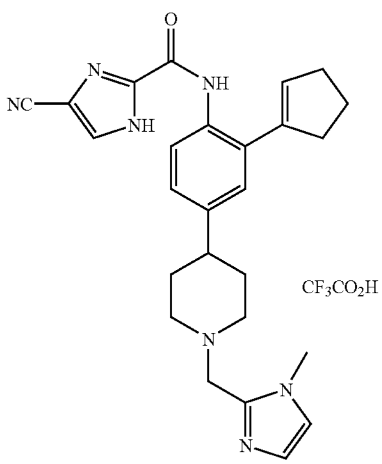 | 0.016 | 0.115 | N/A |
| 24 | 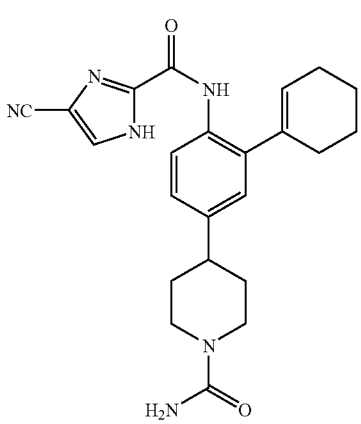 | 0.37 | N/A | N/A |

-continued

| | Structure | Flt-3 IC50 (μM) | MV4-11 IC50 (μM) | Baf3 IC50 (μM) |
|---|---|---|---|---|
| 25 | 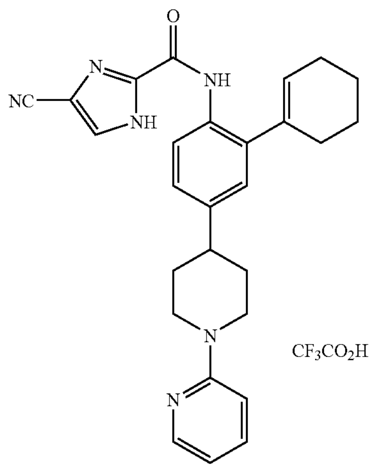 | 2.9 | N/A | N/A |
| 26 | 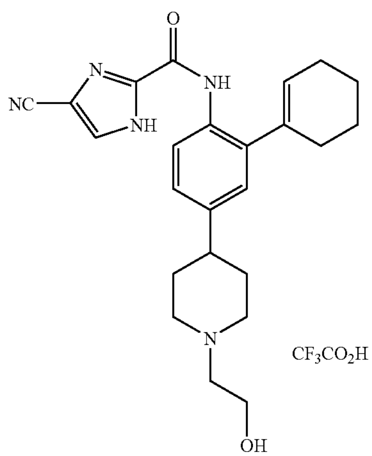 | 0.053 | N/A | N/A |
| 34 | 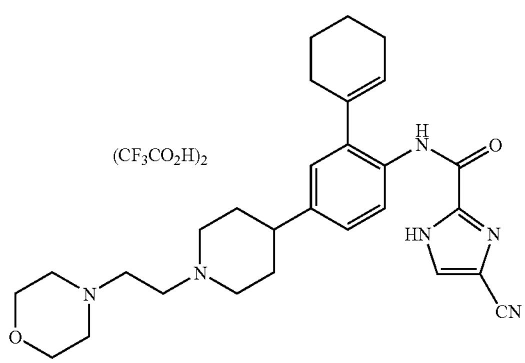 [SMILES: "(CF3CO2H)2" ; N#Cc1c[nH]c(C(=O)Nc2ccc(C3CCN(CCN4CCOCC4)CC3)cc2C2=CCCCC2)n1] | 0.018 | 0.00800 | 0.205 |
| 35 | 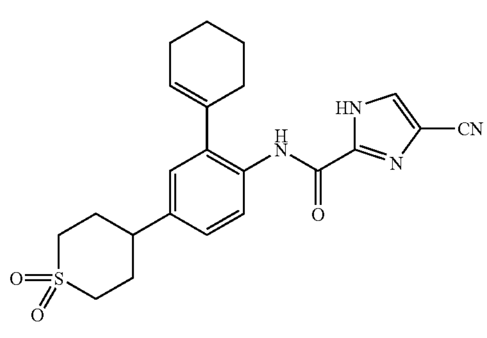 [SMILES: N#Cc1c[nH]c(C(=O)Nc2ccc(C3CCS(=O)(=O)CC3)cc2C2=CCCCC2)n1] | 0.120 | 0.192 | N/A |

-continued

| | Structure | Flt-3 IC50 (μM) | MV4-11 IC50 (μM) | Baf3 IC50 (μM) |
|---|---|---|---|---|
| 36 | 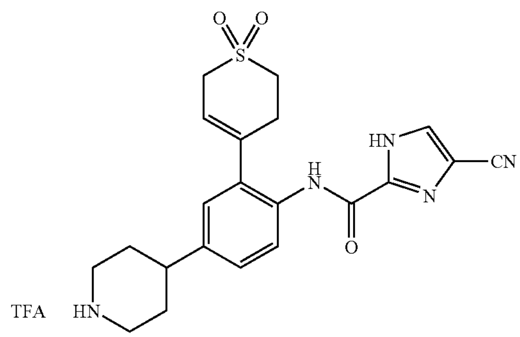 [SMILES: "TFA" ; N#Cc1c[nH]c(C(=O)Nc2ccc(C3CCNCC3)cc2C2=CCS(=O)(=O)CC2)n1] | 9.1 | 0.192 | N/A |
| 38 | 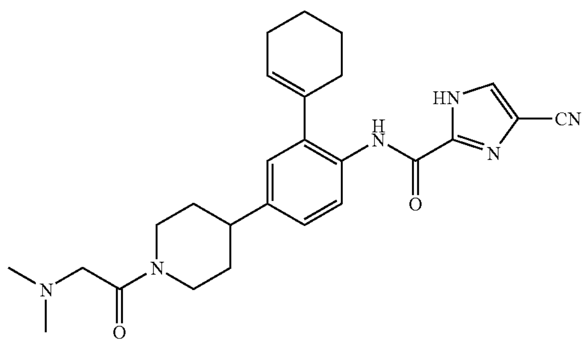 [SMILES: CN(C)CC(=O)N1CCC(c2ccc(NC(=O)c3nc(C#N)c[nH]3)c(C3=CCCCC3)c2)CC1] | 0.0142 | 0.0235 | 0.0760 |
| 40 | 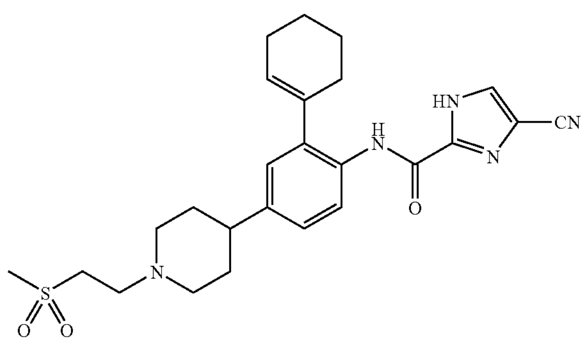 [SMILES: CS(=O)(=O)CCN1CCC(c2ccc(NC(=O)c3nc(C#N)c[nH]3)c(C3=CCCCC3)c2)CC1] | 0.092 | 0.116 | 0.292 |
| 47 | 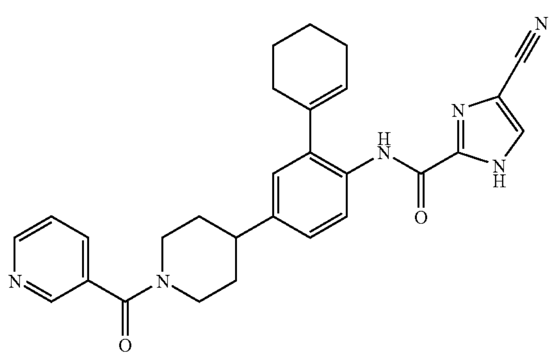 [SMILES: N#Cc1c[nH]c(C(=O)Nc2ccc(C3CCN(C(=O)c4cccnc4)CC3)cc2C2=CCCCC2)n1] | 0.11 | N/A | N/A |

-continued

| | Structure | Flt-3 IC50 (μM) | MV4-11 IC50 (μM) | Baf3 IC50 (μM) |
|---|---|---|---|---|
| 46 | 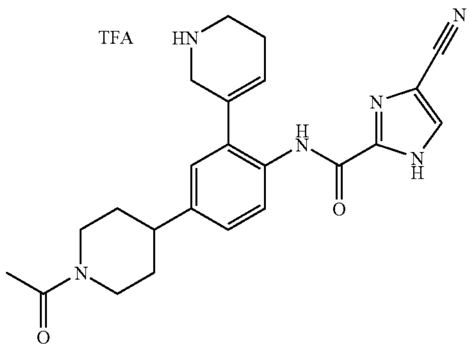 [SMILES: CC(=O)N1CCC(c2ccc(NC(=O)c3nc(C#N)c[nH]3)c(C3=CCCNC3)c2)CC1] | 0.039 | N/A | N/A |
| 47 | 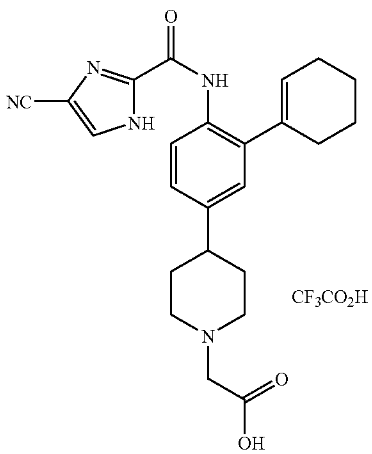 | 0.083 | N/A | N/A |
| 51a | 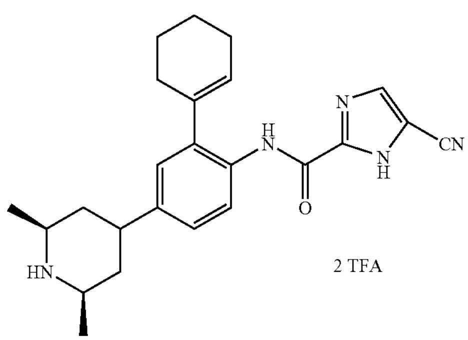 [SMILES: C[C@@H]1CC(c2ccc(NC(=O)c3ncc(C#N)[nH]3)c(C3=CCCCC3)c2)C[C@H](C)N1 ; "2 TFA"] | 0.0023 | 0.00472 | N/A |
| 55 | 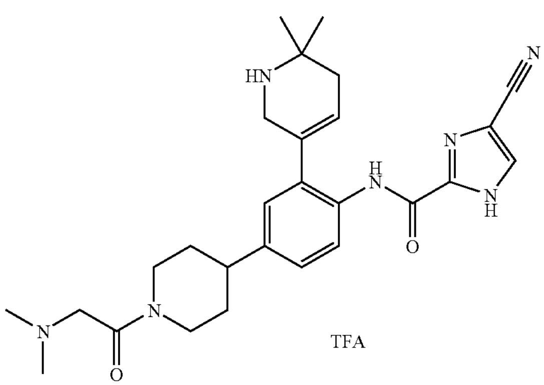 [SMILES: CN(C)CC(=O)N1CCC(c2ccc(NC(=O)c3nc(C#N)c[nH]3)c(C3=CCC(C)(C)NC3)c2)CC1] | 0.034 | N/A | N/A |

| Structure | Flt-3 IC50 (μM) | MV4-11 IC50 (μM) | Baf3 IC50 (μM) |
|---|---|---|---|
| 56 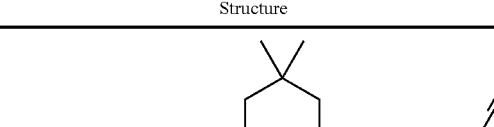 TFA | 0.14 | N/A | N/A |

In Vivo Assays

The oral anti-tumor efficacy of FLT3 Inhibitor Compound #38 of the present invention was evaluated in vivo using a nude mouse MV4-11 human tumor xenograft regression model. The experimental procedure and results are discussed in the Anti-Tumor Effect of FLT3 Inhibitor Compound D Alone Experimental section below (See also, FIGS. 18-21). Note: Compound D corresponds to compound #38 of the aforementioned FLT3 inhibitors of Formula I' of the present invention.

Formulation

The FLT3 kinase inhibitors and the farnesyl transferase inhibitors of the present invention can be prepared and formulated by methods known in the art, and as described herein. In addition to the preparation and formulations described herein, the farnesyltransferase inhibitors of the present invention can be prepared and formulated into pharmaceutical compositions by methods described in the art, such as the publications cited herein. For example, for the farnesyltransferase inhibitors of formulae (I), (II) and (III) suitable examples can be found in WO-97/21701. The farnesyltransferase inhibitors of formulae (IV), (V), and (VI) can be prepared and formulated using methods described in WO 97/16443, farnesyltransferase inhibitors of formulae (VII) and (VIII) according to methods described in WO 98/40383 and WO 98/49157 and farnesyltransferase inhibitors of formula (IX) according to methods described in WO 00/39082 respectively. Tipifarnib (R115777) and its less active enantiomer can be synthesized by methods described in WO 97/21701. Tipifarnib (R115777) is expected to be available commercially as ZARNESTRA™ in the near future, and is currently available upon request (by contract) from Johnson & Johnson Pharmaceutical Research & Development, L.L.C. (Titusville, N.J.).

Where separate pharmaceutical compositions are utilized, the FLT3 kinase inhibitor or farnesyl transferase inhibitor, as the active ingredient, is intimately admixed with a pharmaceutical carrier according to conventional pharmaceutical compounding techniques, which carrier may take a wide variety of forms depending on the form of preparation desired for administration, e.g., oral or parenteral such as intramuscular. A unitary pharmaceutical composition having both the FLT3 kinase inhibitor and farnesyl transferase inhibitor as active ingredients can be similarly prepared.

In preparing either of the individual compositions, or the unitary composition, in oral dosage form, any of the usual pharmaceutical media may be employed. Thus, for liquid oral preparations, such as for example, suspensions, elixirs and solutions, suitable carriers and additives include water, glycols, oils, alcohols, flavoring agents, preservatives, coloring agents and the like; for solid oral preparations such as, for example, powders, capsules, caplets, gelcaps and tablets, suitable carriers and additives include starches, sugars, diluents, granulating agents, lubricants, binders, disintegrating agents and the like. Because of their ease in administration, tablets and capsules represent the most advantageous oral dosage unit form, in which case solid pharmaceutical carriers are obviously employed. If desired, tablets may be sugar coated or enteric coated by standard techniques. For parenterals, the carrier will usually comprise sterile water, though other ingredients, for example, for purposes such as aiding solubility or for preservation, may be included. Injectable suspensions may also be prepared, in which case appropriate liquid carriers, suspending agents and the like may be employed. In preparation for slow release, a slow release carrier, typically a polymeric carrier, and a compound of the present invention are first dissolved or dispersed in an organic solvent. The obtained organic solution is then added into an aqueous solution to obtain an oil-in-water-type emulsion. Preferably, the aqueous solution includes surface-active agent(s). Subsequently, the organic solvent is evaporated from the oil-in-water-type emulsion to obtain a colloidal suspension of particles containing the slow release carrier and the compound of the present invention.

The pharmaceutical compositions herein will contain, per dosage unit, e.g., tablet, capsule, powder, injection, teaspoonful and the like, an amount of the active ingredient necessary to deliver an effective dose as described above. The pharmaceutical compositions herein will contain, per unit dosage unit, e.g., tablet, capsule, powder, injection, suppository, teaspoonful and the like, from about 0.01 mg to 200 mg/kg of body weight per day. Preferably, the range is from about 0.03 to about 100 mg/kg of body weight per day, most preferably, from about 0.05 to about 10 mg/kg of body weight per day. The compounds may be administered on a regimen of 1 to 5 times per day. The dosages, however, may be varied depending upon the requirement of the patients, the severity of the condition being treated and the compound being employed. The use of either daily administration or post-periodic dosing may be employed. Preferably these compositions are in unit dosage forms such as tablets, pills, capsules, powders, granules, sterile parenteral solutions or suspensions, metered aerosol or liquid sprays, drops, ampoules, auto-injector devices or suppositories; for oral parenteral, intranasal, sublingual or rectal administration, or for administration by inhalation or insufflation. Alternatively, the composition may be presented in a form suitable for once-weekly or once-monthly administration; for example, an insoluble salt of the active compound, such as the decanoate salt, may be adapted to provide a depot preparation for intramuscular injection. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective dosage forms such as tablets, pills and capsules. This solid preformulation composition is then subdivided into unit dosage forms of the type described above containing from 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of material can be used for such enteric layers or coatings, such materials including a number of polymeric acids with such materials as shellac, acetyl alcohol and cellulose acetate.

The liquid forms in which the FLT3 kinase inhibitor and the farnesyl transferase inhibitor individually (or both in the case of a unitary composition) may be incorporated for administration orally or by injection include, aqueous solutions, suitably flavored syrups, aqueous or oil suspensions, and flavored emulsions with edible oils such as cottonseed oil, sesame oil, coconut oil or peanut oil, as well as elixirs and similar pharmaceutical vehicles. Suitable dispersing or suspending agents for aqueous suspensions, include synthetic and natural gums such as tragacanth, acacia, alginate, dextran, sodium carboxymethylcellulose, methylcellulose, polyvinyl-pyrrolidone or gelatin. The liquid forms in suitably flavored suspending or dispersing agents may also include the synthetic and natural gums, for example, tragacanth, acacia, methyl-cellulose and the like. For parenteral administration, sterile suspensions and solutions are desired. Isotonic preparations which generally contain suitable preservatives are employed when intravenous administration is desired.

Advantageously, the FLT3 kinase inhibitor and the farnesyl transferase inhibitor may be administered in a single daily dose (individually or in a unitary composition), or the total daily dosage may be administered in divided doses of two, three or four times daily. Furthermore, compounds for the present invention (individually or in a unitary composition) can be administered in intranasal form via topical use of suitable intranasal vehicles, or via transdermal skin patches well known to those of ordinary skill in that art. To be administered in the form of a transdermal delivery system, the dosage administration will, of course, be continuous rather than intermittent throughout the dosage regimen.

For instance, for oral administration in the form of a tablet or capsule, the active drug component (the FLT3 kinase inhibitor and the farnesyl transferase inhibitor individually, or together in the case of a unitary composition) can be combined with an oral, non-toxic pharmaceutically acceptable inert carrier such as ethanol, glycerol, water and the like. Moreover, when desired or necessary, suitable binders; lubricants, disintegrating agents and coloring agents can also be incorporated into the mixture. Suitable binders include, without limitation, starch, gelatin, natural sugars such as glucose or beta-lactose, corn sweeteners, natural and synthetic gums such as acacia, tragacanth or sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

The daily dosage of the products of the present invention may be varied over a wide range from 1 to 5000 mg per adult human per day. For oral administration, the compositions are preferably provided in the form of tablets containing, 0.01, 0.05, 0.1, 0.5, 1.0, 2.5, 5.0, 10.0, 15.0, 25.0, 50.0, 100, 150, 200, 250 and 500 milligrams of the active ingredient for the symptomatic adjustment of the dosage to the patient to be treated. An effective amount of the drug is ordinarily supplied at a dosage level of from about 0.01 mg/kg to about 200 mg/kg of body weight per day. Particularly, the range is from about 0.03 to about 15 mg/kg of body weight per day, and more particularly, from about 0.05 to about 10 mg/kg of body weight per day. The FLT3 kinase inhibitor and the farnesyl transferase inhibitor individually, or together in the case of a unitary composition, may be administered on a regimen up to four or more times per day, preferably of 1 to 2 times per day.

Optimal dosages to be administered may be readily determined by those skilled in the art, and will vary with the particular compound used, the mode of administration, the strength of the preparation, the mode of administration, and the advancement of the disease condition. In addition, factors associated with the particular patient being treated, including patient age, weight, diet and time of administration, will result in the need to adjust dosages.

The FLT3 kinase inhibitor and the farnesyl transferase inhibitor of the present invention can also be administered (individually or in a unitary composition) in the form of liposome delivery systems, such as small unilamellar vesicles, large unilamellar vesicles, and multilamellar vesicles. Liposomes can be formed from a variety of lipids, including but not limited to amphipathic lipids such as phosphatidylcholines, sphingomyelins, phosphatidylethanolamines, phophatidylcholines, cardiolipins, phosphatidylserines, phosphatidylglycerols, phosphatidic acids, phosphatidylinositols, diacyl trimethylammonium propanes, diacyl dimethylammonium propanes, and stearylamine, neutral lipids such as triglycerides, and combinations thereof. They may either contain cholesterol or may be cholesterol-free.

The FLT3 kinase inhibitor and the farnesyl transferase inhibitor of the present invention can also be administered (individually or in a unitary composition) locally. Any delivery device, such as intravascular drug delivery catheters, wires, pharmacological stents and endoluminal paving, may be utilized. The delivery system for such a device may comprise a local infusion catheter that delivers the compound at a rate controlled by the administor.

The present invention provides a drug delivery device comprising an intraluminal medical device, preferably a stent, and a therapeutic dosage of the FLT3 kinase inhibitor and the farnesyl transferase inhibitor of the invention. Alternatively, the present invention provides for individual administration of a therapeutic dosage of one or both of the FLT3 kinase inhibitor and the farnesyl transferase inhibitor of the invention by means of a drug delivery device comprising an intraluminal medical device, preferably a stent The term "stent" refers to any device capable of being delivered by a catheter. A stent is routinely used to prevent vascular closure due to physical anomalies such as unwanted inward growth of vascular tissue due to surgical trauma. It often has a tubular, expanding lattice-type structure appropriate to be left inside the lumen of a duct to relieve an obstruction. The stent has a lumen wall-contacting surface and a lumen-exposed surface. The lumen-wall contacting surface is the outside surface of the tube and the lumen-exposed surface is the inner surface of the tube. The stent can be polymeric, metallic or polymeric and metallic, and it can optionally be biodegradable.

The FLT3 kinase inhibitor and farnesyl transferase inhibitor of the present invention (individually or in a unitary composition) can be incorporated into or affixed to the stent in a number of ways and in utilizing any number of biocompatible materials. In one exemplary embodiment, the compound is directly incorporated into a polymeric matrix, such as the polymer polypyrrole, and subsequently coated onto the outer surface of the stent. The compound elutes from the matrix by diffusion through the polymer. Stents and methods for coating drugs on stents are discussed in detail in the art. In another exemplary embodiment, the stent is first coated with as a base layer comprising a solution of the compound, ethylene-co-vinylacetate, and polybutylmethacrylate. Then, the stent is further coated with an outer layer comprising only polybutylmethacrylate. The outlayer acts as a diffusion barrier to prevent the compound from eluting too quickly and entering the surrounding tissues. The thickness of the outer layer or topcoat determines the rate at which the compound elutes from the matrix. Stents and methods for coating are discussed in detail in WIPO publication WO9632907, U.S. Publication No. 2002/0016625 and references disclosed therein.

To better understand and illustrate the invention and its exemplary embodiments and advantages, reference is made to the following experimental section.

EXPERIMENTALS

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

Inhibition of AML cell growth with the combination of an FTI and a FLT3 inhibitor was tested. Two FTIs, Tipifarnib and FTI Compound 176 ("FTI-176), and eight novel FLT3 inhibitors: Compounds A, B, C, D, E, F G and H were used to inhibit the growth of FLT3-dependent cell types in vitro (see FIG. 5 depicting the test compounds). Note: Compound D corresponds to FLT3 inhibitor compound #38 of Formula I'.

The cell lines that were tested included those that are dependent on FLT3ITD mutant activity for growth (MV4-11 and Baf3-FLT3ITD), FLT3 wt activity for growth (Baf3FLT3) and those that grow independent of FLT3 activity (THP-1). MV4-11 (ATCC Number: CRL-9591) cells are derived from a patient with childhood acute myelomonocytic leukemia with an 11q23 translocation resulting in a MLL gene rearrangement and containing an FLT3-ITD mutation (AML subtype M4) (see Drexler H G. The Leukemia-Lymphoma Cell Line Factsbook. Academic Press: San Diego, Calif., 2000 and Quentmeier H, Reinhardt J, Zaborski M, Drexler H G. FLT3 mutations in acute myeloid leukemia cell lines. Leukemia. 2003 January; 17:120-124.). Baf3-FLT3 and Baf3-FLT3ITD cell lines were obtained from Dr. Michael Henrich and the Oregon Health Sciences University. The Baf3 FLT3 cell lines were created by stable transfection of parental Baf3 cells (a murine B cell lymphoma line dependent on the cytokine IL-3 for growth) with either wild-type FLT3 or FLT3 containing the ITD insertion in the juxatamembrane domain of the receptor resulting in its constitutive activation. Cells were selected for their ability to grow in the absence of IL-3 and in either the presence of FLT3 ligand (Baf3-FLT3) or independent of any growth factor (Baf3-ITD). THP-1 (ATCC Number: TIB-202) cells were isolated from a childhood AML patient with an N-Ras mutation and no FLT3 abnormality. Although the cells express a functional FLT3 receptor, THP-1 cells are not dependent on FLT3 activity for viability and growth (data not shown).

Dose responses for the individual compounds alone were determined for each cell line using a standard 72-hour cell proliferation assay (see FIGS. 6.1-6.8). The standard chemotherapeutic agent Cytarabine was used as a control cytotoxic agent in all experiments. The FTI Tipifamib has a potency range of high nanomolar to high picomolar range depending on the cell type. The FLT3 inhibitors, Compounds A, B, C, D, E, F G and H, individually have good potency (sub-micromolar) for the inhibition of FLT3 driven proliferation (compared to the first line cytotoxic agent Cytarabine and Tipifarnib) in cells that depend on FLT3 for growth. Each of these chemically distinct compounds alone has potential for the treatment of disorders related to FLT3, such as FLT3 positive AML. Cytarabine inhibition of proliferation is comparable (1-2CM) to previous reports of its in vitro activity in MV4-11 cells (Levis, M., et al. (2004) "In vitro studies of a FLT3 inhibitor combined with chemotherapy: sequence of administration is important to achieve synergistic cytotoxic effects." Blood. 104(4): 1145-50). The FLT3 inhibitors tested had no effect on THP-1 proliferation. The $IC_{50}$ calculation for each compound in each cell line was used in subsequent combination experiments to calculate synergistic effects of compound combinations on cell proliferation. (See FIGS. 10.1-10.8 and Tables 1-3, hereafter.)

The effect of a single (sub-$IC_{50}$) dose of the FLT3 inhibitor Compound A on Tipifarnibpotency was then examined. Each cell line was simultaneously treated with one dose of the FLT3 inhibitor Compound A and varying doses of Tipifamib and the proliferation of the cells was evaluated in the standard 72-hour cell proliferation protocol. The $IC_{50}$ for Tipifarnib was then calculated according to the procedure described in the Biological Activity section hereafter (see FIGS. 7a-c depicting results for FLT3 inhibitor Compound A and Tipifarnib combination.) The cell lines that were tested included those that are dependent on FLT3ITD mutant activity for growth (MV4-11 and Baf3-FLT3ITD), FLT3 wt activity for growth (Baf3FLT3) and those that grow independent of FLT3 activity (THP-1).

The FLT3 inhibitor Compound A significantly increased the potency of the FTI Tipifarnib for the inhibition of AML (MV4-11) and FLT3 dependent (Baf3-ITD and Baf3-FLT3) cell proliferation. With a single sub-$IC_{50}$ dose of FLT3 inhibitor Compound A in (a) MV4-11 (50 nM); (b) Baf3-ITD (50 nM) and (c) Baf3-FLT3 (100 nM) cells, Tipifarnib increased in potency by more than 3-fold in each cell line tested. This is indicative of significant synergy.

Next, single dose combinations of the FTI Tipifamib and the FLT3 inhibitor Compound A were evaluated in the MV4-11, Baf3-ITD and Baf3-FLT3 cell lines. This single dose combination scenario more closely represents dosing strategies for chemotherapeutic combinations that are used in the clinic. With this method cells are simultaneously treated with a single sub-$IC_{50}$ of dose of each compound or a combination of compounds and inhibition of proliferation was monitored. Using this method it is observed that combinations of a sub-$IC_{50}$ dose of the FTI Tipifarnib and the FLT3 inhibitor Compound A are beyond additive in inhibiting the growth of the AML cell line MV4-11 and other FLT3-dependent cells (see FIGS. 8a-d). This synergistic effect with Tipifarnib is not observed in cells that do not depend on FLT3 for proliferation (THP-1). This synergistic effect was also observed for combinations of FLT3 inhibitor Compound A and Cytarabine.

Additionally, single dose combinations of a FLT3 inhibitor and a FTI were examined to determine if this activity was compound specific or mechanism based. A single sub-$IC_{50}$ of dose of either FLT3 inhibitor Compound B or D with Tipifarnib was tested for its inhibition of MV4-11 proliferation. It is observed, similar to combinations of Tipifarnib and FLT3 inhibitor Compound A, that the combinations of either FLT3 inhibitor Compound B or D with Tipifarnib inhibits the proliferation of FLT3-dependent MV4-11 cells with greater that additive efficacy. This suggests that the combination of any FLT3 inhibitor and FTI will synergistically inhibit the proliferation of FLT3-dependent AML cells. This observation is novel and non-obvious to those skilled in the art. Synergy was also observed with the combination of either FLT3 inhibitor Compound B or D and cytarabine.

To statistically evaluate the synergy of a FLT3 inhibitor and an FTI in FLT3 dependent cell lines, dosing combinations were evaluated by the method of Chou and Talalay. See Chou T C, Talalay P. (1984) "Quantitative analysis of dose-effect relationships: the combined effects of multiple drugs or enzyme inhibitors." Adv Enzyme Regul. 22:27-55. Using this method inhibitors are added simultaneously to cells in a ratio of the $IC_{50}$ dose of each compound alone. The data is collected and subject to isobolar analysis of fixed ratio dose combinations as described by Chou and Talalay. This analysis is used to generate a combination index or CI. The CI value of 1 corresponds to compounds that behave additively; CI values <0.9 are considered synergistic and CI values of >1.1 are considered antagonistic. Using this method, multiple FTI and FLT3 combinations were evaluated. For each experimental combination $IC_{50}$, were calculated for each individual compound (see FIGS. 6.1-6.8) in each of the FLT3 dependent cell lines and then fixed ratio dosing (at dose ranges including 9, 3, 1, 1/3, 1/9× the individual compound $IC_{50}$) was performed in the standard cell proliferation assay. FIGS. 10.1-10.8 summarizes the raw data from isobolar analysis fixed ratio dosing according to the method of Chou and Talalay, obtained using Calcusyn software (Biosoft). Using the isobologram, synergy can be graphically represented. Data points for combinations that are additive lie along the isobolar line at a given dose affect (CI=1). Data points for combinations that are synergistic fall to the left, or under, the isobolar line for a given dose effect (CI<0.9). Data points for combinations that are antagonistic fall to the right, or over, the isobolar line for a given dose effect (CI>1.1). FIG. 10.1a-c summarizes the isobolar analysis for the combination of FLT3 inhibitor Compound A and Tipifarnib in MV4-11, Baf3-ITD and Baf3-wtFLT3. From the isobolar analysis, synergy was observed at all experimentally determined data points including the combination doses that resulted in a 50% inhibition of cell proliferation (ED50), a 75% inhibition of cell proliferation (ED75) and a 90% inhibition of cell proliferation (ED90). Each of these points falls significantly to the left of the isobolar (or additive) line, indicating significant synergy. The combination of FLT3 inhibitor Compound A and Tipifarnib resulted in significant synergy for proliferation inhibition in each FLT3 dependent cell lines tested. The combination indecies for the isobolograms depicted in FIGS. 10.1a-c are found in Tables 1-3 hereafter.

Additionally, FIGS. 10.2a-b summarizes the isobolar analysis with the combination of a chemically distinct FLT3 inhibitor, FLT3 inhibitor Compound B and Tipifarnib. Similar to the FLT3 inhibitor Compound A and Tipifarnib combination, the FLT3 inhibitor Compound H and Tipifarnib combination was synergistic for inhibiting cellular proliferation at all doses tested and in all FLT3-dependent cell lines tested. The combination indecies for the isobolargrams depicted in FIGS. 5.2a-c are found in Tables 1-3 hereafter. Furthermore, FIGS. 5.3a-c summarizes the isobolar analysis of a combination of Tipifarnib and another chemically distinct FLT3 inhibitor (FLT3 inhibitor Compound E). As with the other combinations tested, the combination of FLT3 inhibitor compound E and Tipifarnib synergistically inhibited FLT3-dependent proliferation in three different cell lines at all doses tested. The combination indecies for the isobolargrams depicted in FIGS. 5.3a-c are found in Tables 1-3 hereafter. To further expand the combination studies, each of the FLT3 inhibitors shown to demonstrate synergy with Tipifarnib were also tested in combination with another farnesyl transferase inhibitor, FTI-176. Tables 1-3 summarize the results of all the combinations tested in the three FLT3-dependent cell lines described above. The combination indecies for each combination are contained within Tables 1-3.

TABLE 1

Table 1: The combination of a FLT3 inhibitor and an FTI (all combinations tested) synergistically inhibits the proliferation of MV4-11 AML cells as measured by the Combination Index (CI). Combinations were performed at a fixed ratio of the individual compound $IC_{50s}$ for proliferation as summarized in Biological Activity Measurments section hereafter. $IC_{50}$ and CI values were calculated by the method of Chou and Talalay using Calcusyn software (Biosoft). CI and $IC_{50}$ values are an average of three independent experiments with three replicates per data point.

| MV4-11 cells | CI - ED50 | CI - ED75 | CI - ED90 | FTI IC50 (nM) | FLT3 inhibitor IC50 (nM) |
|---|---|---|---|---|---|
| Tipifarnib | | | | 15.41 | |
| FTI-176 | | | | 17.73 | |
| FLT3 inhibitor Compound A | | | | | 92.53 |
| FLT3 inhibitor Compound B | | | | | 31.3 |
| FLT3 inhibitor Compound C | | | | | 18.1 |
| FLT3 inhibitor Compound D | | | | | 13.8 |
| FLT3 inhibitor Compound H | | | | | 166.93 |
| FLT3 inhibitor Compound E | | | | | 32.81 |

TABLE 1-continued

Table 1: The combination of a FLT3 inhibitor and an FTI (all combinations tested) synergistically inhibits the proliferation of MV4-11 AML cells as measured by the Combination Index (CI). Combinations were performed at a fixed ratio of the individual compound $IC_{50s}$ for proliferation as summarized in Biological Activity Measurments section hereafter. $IC_{50}$ and CI values were calculated by the method of Chou and Talalay using Calcusyn software (Biosoft). CI and $IC_{50}$ values are an average of three independent experiments with three replicates per data point.

| MV4-11 cells | CI - ED50 | CI - ED75 | CI - ED90 | FTI IC50 (nM) | FLT3 inhibitor IC50 (nM) |
|---|---|---|---|---|---|
| Tipifarnib + FLT3 inhibitor Compound A | 0.58 | 0.52 | 0.46 | 3.96 | 28.12 |
| Tipifarnib + FLT3 inhibitor Compound B | 0.79 | 0.66 | 0.60 | 4.48 | 9.86 |
| Tipifarnib + FLT3 inhibitor Compound C | 0.78 | 0.62 | 0.55 | 3.65 | 3.86 |
| Tipifarnib + FLT3 inhibitor Compound D | 0.67 | 0.62 | 0.59 | 4.19 | 3.75 |
| Tipifarnib + FLT3 inhibitor Compound H | 0.56 | 0.51 | 0.48 | 4.39 | 64.81 |
| Tipifarnib + FLT3 inhibitor Compound E | 0.67 | 0.62 | 0.59 | 4.19 | 1.75 |
| Tipifarnib + FLT3 inhibitor Compound F | 0.69 | 0.59 | 0.55 | 4.23 | 11.67 |
| Tipifarnib + FLT3 inhibitor Compound G | 0.75 | 0.61 | 0.68 | 4.84 | 145.15 |
| FTI 176 + FLT3 inhibitor Compound A | 0.62 | 0.60 | 0.59 | 4.63 | 30.12 |
| FTI 176 + FLT3 inhibitor Compound H | 0.66 | 0.63 | 0.61 | 5.81 | 50.94 |
| FTI 176 + FLT3 inhibitor Compound E | 0.68 | 0.64 | 0.61 | 5.69 | 9.37 |
| FTI 176 + FLT3 inhibitor Compound D | 0.71 | 0.63 | 0.60 | 4.72 | 5.48 |

TABLE 2

Table 2: The combination of a FLT3 inhibitor and an FTI (all combinations tested) synergistically inhibits the proliferation of Baf3-FLT3 cells stimulated with 100 ng/ml FLT ligand as measured by the Combination Index (CI). Combinations were performed at a fixed ratio of the individual compound IC50s for proliferation as summarized in Biological Activity Measurments section hereafter. IC50 and CI values were calculated by the method of Chou and Talalay using Calcusyn software (Biosoft). CI and $IC_{50}$ values are an average of three independent experiments with three replicates per data point.

| Baf3-FLT3 | CI - ED50 | CI - ED75 | CI - ED90 | FTI IC50 (nM) | FLT3 inhibitor IC50 (nM) |
|---|---|---|---|---|---|
| Tipifarnib | | | | 1.85 | |
| FTI-176 | | | | 1.35 | |
| FLT3 inhibitor Compound A | | | | | 169.77 |
| FLT3 inhibitor Compound B | | | | | 173.1 |
| FLT3 inhibitor Compound C | | | | | 91.3 |
| FLT3 inhibitor Compound D | | | | | 39.90 |
| FLT3 inhibitor Compound H | | | | | 451.37 |
| FLT3 inhibitor Compound E | | | | | 29.40 |
| Tipifarnib + FLT3 inhibitor Compound A | 0.45 | 0.40 | 0.37 | 0.333 | 48.24 |
| Tipifarnib + FLT3 inhibitor Compound B | 0.78 | 0.67 | 0.62 | 0.431 | 23.26 |
| Tipifarnib + FLT3 inhibitor Compound C | 0.81 | 0.71 | 0.65 | 0.442 | 63.41 |
| Tipifarnib + FLT3 inhibitor Compound D | 0.60 | 0.53 | 0.49 | 0.360 | 12.31 |
| Tipifarnib + FLT3 inhibitor Compound H | 0.38 | 0.36 | 0.35 | 0.277 | 125.28 |
| Tipifarnib + FLT3 inhibitor Compound E | 0.42 | 0.39 | 0.38 | 0.360 | 23.26 |
| FTI 176 + FLT3 inhibitor Compound A | 0.55 | 0.40 | 0.32 | 0.374 | 56.33 |
| FTI 176 + FLT3 inhibitor Compound D | 0.60 | 0.56 | 0.48 | 0.380 | 11.61 |
| FTI 176 + FLT3 inhibitor Compound H | 0.44 | 0.34 | 0.27 | 0.290 | 145.11 |

TABLE 2-continued

Table 2: The combination of a FLT3 inhibitor and an FTI (all combinations tested) synergistically inhibits the proliferation of Baf3-FLT3 cells stimulated with 100 ng/ml FLT ligand as measured by the Combination Index (CI). Combinations were performed at a fixed ratio of the individual compound IC50s for proliferation as summarized in Biological Activity Measurments section hereafter. IC50 and CI values were calculated by the method of Chou and Talalay using Calcusyn software (Biosoft). CI and $IC_{50}$ values are an average of three independent experiments with three replicates per data point.

| Baf3-FLT3 | CI - ED50 | CI - ED75 | CI - ED90 | FTI IC50 (nM) | FLT3 inhibitor IC50 (nM) |
|---|---|---|---|---|---|
| FTI 176 + FLT3 inhibitor Compound E | 0.49 | 0.39 | 0.33 | 0.391 | 25.16 |

TABLE 3

Table 3: The combination of a FLT3 inhibitor and an FTI (all combinations tested) synergistically inhibits the proliferation of Baf3-ITD cells as measured by the Combination Index (CI). Combinations were performed at a fixed ratio of the individual compound IC50s for proliferation as summarized in Biological Activity Measurments section hereafter. IC50 and CI values were calculated by the method of Chou and Talalay using Calcusyn software (Biosoft). CI and $IC_{50}$ values are an average of three independent experiments with three replicates per data point.

| Baf3-FLT3 cells | CI - ED50 | CI - ED75 | CI - ED90 | FTI IC50 (nM) | FLT3 inhibitor IC50 (nM) |
|---|---|---|---|---|---|
| Tipifarnib | | | | 547.87 | |
| FTI-176 | | | | 667.86 | |
| FLT3 inhibitor Compound A | | | | | 76.12 |
| FLT3 inhibitor Compound D | | | | | 14.56 |
| FLT3 inhibitor Compound H | | | | | 200.17 |
| FLT3 inhibitor Compound E | | | | | 29.40 |
| Tipifarnib + FLT3 inhibitor Compound A | 0.72 | 0.63 | 0.62 | 146.83 | 27.19 |
| Tipifarnib + FLT3 inhibitor Compound D | 0.68 | 0.65 | 0.63 | 165.60 | 4.87 |
| Tipifarnib + FLT3 inhibitor Compound H | 0.92 | 0.87 | 0.84 | 172.80 | 71.49 |
| Tipifarnib + FLT3 inhibitor Compound E | 0.82 | 0.78 | 0.75 | 189.10 | 11.85 |
| FTI 176 + FLT3 inhibitor Compound A | 0.74 | 0.62 | 051 | 224.36 | 25.37 |
| FTI 176 + FLT3 inhibitor Compound D | 0.75 | 0.69 | 0.63 | 231.68 | 4.12 |
| FTI 176 + FLT3 inhibitor Compound H | 0.62 | 0.60 | 0.58 | 183.38 | 68.54 |
| FTI 176 + FLT3 inhibitor Compound E | 0.51 | 0.50 | 0.50 | 220.80 | 8.91 |

Synergy of combination dosing is observed with all FTI and FLT3 combinations tested in all FLT3 dependent cell lines used. The combination of an FTI and FLT3 inhibitor reduces the individual compounds antiproliferative effect by an average of 3-4-fold. It can be concluded that the synergy observed for combinations of a FLT3 inhibitor and an FTI is a mechanism based phenomena and not related to the specific chemical structures of individual FTIs or FLT3 inhibitors. Accordingly, synergistic growth inhibition would be observed with any combination of a FLT3 inhibitor and Tipifamib or any other FTI.

The ultimate goal of treatment for FLT3 related disorders is to kill the disease causative cells and to cause regression of disease. To examine if the FTI/FLT3 inhibitor combination is synergistic for cell death of FLT3 dependent disease causative cells, particularly AML, ALL and MDS cells, the combination of Tipifamib and the FLT3 inhibitor Compound A was tested for its ability to induce an increase in fluorescent labeled Annexin V staining in MV4-11 cells. Annexin V binding to phosphotidyl serine that has translocated from the inner leaflet of the plasma membrane to the outer leaflet of the plasma membrane and is a well established way to measure apoptosis of cells. See van Engeland M., L. J. Nieland, et al. (1998) "Annexin V-affinity assay: a review on an apoptosis detection system based on phosphatidylserine exposure." Cytometry. 31(1):1-9.

Tipifarnib and FLT3 inhibitor Compound A were incubated with MV4-11 cells alone or in a fixed ratio (4:1 based on the calculated $EC_{50}$ for each agent alone) for 48 hours in standard cell culture conditions. After the compound incubations, treated cells were harvested and stained with Annexin V-PE and 7-AAD using the Guava Nexin apoptosis kit according to the protocol in the Biological Activity Measurements section hereafter. Annexin V staining peaks at 60% because cells late in apoptosis begin to fall apart and are considered debris. However, $EC_{50}$, can be calculated from this data because of its consistent sigmoidal kinetics. From the data summarized in FIG. 11a, it is concluded that the combination of Tipifarnib and FLT3 inhibitor Compound A is significantly more potent than either agent alone for inducing apoptosis of MV4-11 cells. The $EC_{50}$ for the induction of annexin V staining shifted more than 4-fold for the FLT3 inhibitor FLT3 inhibitor Compound A. The $EC_{50}$ for induction of annexin V staining shifted by more than eight-fold for the FTI Tipifarnib. Statistical analysis using the above described method of Chou and Talalay was also performed to determine the synergy of the combination. FIG. 11b depicts the isobolar analysis of the Tipifamib and FLT3 inhibitor Compound A combination in inducing annexin V staining. All data points lie significantly to the left of the isobolar line. The CI values for the combination are listed in the table in FIG. 11c. The synergy that was observed for annexin V staining (and induction of apoptosis) were more significant than the synergies that were observed for the FLT3 inhibitor and FTI combinations for proliferation. The magnitude of the synergistic induction of apoptosis of MV4-11 cells by the combination of an FTI and a FLT3 inhibitor could not be predicted by those skilled in the art. Thus, based on the data from proliferation, any combination of a FLT3 inhibitor and an FTI would also be synergistic for inducing apoptosis of FLT3 dependent cells (i.e. causative cells for FLT3 disorders, particularly AML, ALL and MDS).

To confirm that the combination of a FLT3 inhibitor and an FTI synergistically activates apoptosis of FLT3 dependent cells, the combination of several FLT3 inhibitors and the FTI Tipifamib was tested for its ability to induce the activity of caspase 3/7 in MV4-11 cells. Caspase activation, a critical step in the final execution of the apoptotic cellular death process, can be induced by a variety of cellular stimuli including growth factor withdrawal or growth factor receptor inhibition See Hengartner, M O. (2000) "The biochemistry of apoptosis." Nature 407:770-76 and Nunez G, Benedict M A, Hu Y, Inohara N. (1998) "Caspases: the proteases of the apoptotic pathway." Oncogene 17:3237-45. Cellular caspase activation can be monitored using a synthetic caspase 3/7 substrate that is cleaved to release a substrate for the enzyme luciferase, that may convert the substrate to a luminescent product. See Lovborg H, Gullbo J, Larsson R. (2005) "Screening for apoptosis-classical and emerging techniques." Anticancer Drugs 16:593-9. Caspase activation was monitored using the Caspase Glo technology from Promega (Madison, Wis.) according to the protocol in the Biological Activity Measurement section hereafter.

Individual $EC_{50}$ determinations were done to establish dose ratios for combination analysis of synergy. FIG. 12a-d summarizes the $EC_{50}$ determinations of each individual agent. For combination experiments, Tipifarnib and FLT3 inhibitor Compounds B, C and D were incubated with MV4-11 cells in a fixed ratio (based on the calculated $EC_{50}$ for each agent alone) at various doses (ranges including 9, 3, 1, 1/3, 1/9 x the individual compound $EC_{50}$) for 24 hours in standard cell culture conditions. After 24 hours the caspase 3/7 activity was measured according to the manufacture's instructions and detailed in the Biological Activity Measurement section hereafter. FIGS. 13.1-13.3 summarizes the synergy of caspase activation (by the method previously described method of Chou and Talalay) that was observed with the Tipifarnib and FLT3 inhibitor Compounds B, C and D combinations in MV4-11 cells. Synergy was observed at all doses tested and in all combinations tested. The synergy that was observed for caspase activation (and induction of apoptosis) was even more significant than the synergies that were observed for the FLT3 inhibitor and FTI combinations for proliferation in MV4-11 cells. The magnitude of the synergistic induction of apoptosis of MV4-11 cells by the combination of an FTI and a FLT3 inhibitor could not be predicted by those skilled in the art. Thus, based on the data from proliferation, any combination of a FLT3 Inhibitor and an FTI would also be synergistic for inducing apoptosis of FLT3 dependent cells (i.e. causative cells for FLT3 disorders, particularly AML, ALL and MDS).

It is well established that phosphorylation of the FLT3 receptor and downstream kinases such as MAP kinase are required for proliferative effects of FLT3 receptor. See Scheijen, B. and J. D. Griffin (2002) "Tyrosine kinase oncogenes in normal hematopoiesis and hematological disease." Oncogene 21(21): 3314-33. We postulate that the molecular mechanism of the synergy observed with a FLT3 inhibitor and an FTI is related to the compound induced decrease of FLT3 receptor signaling required for AML cell proliferation and survival. To test this we looked at phosphorylation state of both the FLT3-ITD receptor and a downstream target of FLT3 receptor activity, MAP kinase (erk1/2) phosphorylation in MV4-11 cells, using commercially available reagents according to the protocol detailed in the Biological Activity Measurements section hereafter. MV4-11 cells were treated with indicated concentrations of FLT3 inhibitor Compound A alone or in combination with Tipifarnib for 48 hours under standard cell growth conditions. For analysis of FLT3 phosphorylation, cells were harvested and FLT3 was immunoprecipitated and separated by SDS-PAGE. For analysis of MAP kinase (erk1/2) phosphorylation, cells were harvested, subjected to lysis, separated by SDS-Page and transferred to nitrocellulose for immunoblot analysis. For quantitative analysis of FLT3 phosphorylation, immunoblots were probed with phosphotyrosine antibody and the phophoFLT3 signal was quantified using Molecular Dynamics Typhoon Image Analysis. The immunoblots were then stripped and reprobed to quantify the total FLT3 protein signal. This ratio of phosphorylation to total protein signal was used to calculate the approximate $IC_{50}$ of the compound dose responses. For quantitative analysis of MAP kinase (ERK1/2) phosphorylation, immunoblots were probed with a phosphospecific ERK1/2 antibody and the phophoERK1/2 signal was quantified using Molecular Dynamics Typhoon Image Analysis. The immunoblots were then stripped and reprobed to quantify the total ERK1/2 protein signal. This ratio of phosphorylation to total protein signal was used to calculate the approximate $IC_{50}$ of the compound dose responses. $IC_{50}$ values were calculated using GraphPad Prism software. The result of this work is summarized in FIG. 14.

It is observed that the combination of Tipifamib and FLT3 inhibitor Compound A increases the potency of FLT3 inhibitor Compound A two to three fold for both inhibition of FLT3 phosphorylation and MAP kinase phosphorylation. This is consistent with the increase in potency of the compounds anti-proliferative effects. The effect of FLT3 phosphorylation that was observed with the FTI/FLT3 inhibitor combination has not been reported previously. The mechanism for this effect on FLT3 phosphorylation is unknown but would be predicted to occur for any FTI/FLT3 inhibitor combination based on the experimental data collected for proliferation inhibition described above.

In Vitro Biological Activity Measurements

Reagents and Antibodies. Cell Titerglo proliferation reagent was obtained from Promega Corporation. Proteases inhibitor cocktails and phosphatase inhibitor cocktails II were purchased from Sigma (St. Louis, Mo.). The GuavaNexin apoptosis reagent was purchased from Guava technologies (Hayward, Calif.). Superblock buffer and SuperSignal Pico reagent were purchased from Pierce Biotechnology (Rockford, Ill.). Fluorescence polarization tyrosine kinase kit (Green) was obtained from Invitrogen. Mouse anti-phosphotyrosine (4G10) antibody was purchased from Upstate Biotechnology, Inc (Charlottesville, Va.). Anti-human FLT3 (rabbit IgG) was purchased from Santa Cruz biotechnology (Santa Cruz, Calif.). Anti-phospho Map kinase and total p42/44 Map kinase antibodies were purchased form Cell Signaling Technologies (Beverly, Mass.) Alkaline phosphatase-conjugated goat-anti-rabbit IgG, and goat-anti-mouse IgG antibody purchased from Novagen (San Diego, Calif.). DDAO phosphate was purchased from Molecular Probes (Eugene, Oreg.). All tissue culture reagents were purchase from BioWhittaker (Walkersville, Md.).

Cell lines. THP-1 (Ras mutated, FLT3 wild type) and human MV4-11 (expressing constitutively FLT3-Internal tandem duplication or ITD mutant isolated from an AML patient with a t15;17 translocation) AML cells)(see Drexler H G. The Leukemia-Lymphoma Cell Line Factsbook. Academic Press: San Diego, Calif., 2000 and Quentmeier H, Reinhardt J, Zaborski M, Drexler H G. FLT3 mutations in acute myeloid leukemia cell lines. Leukemia. 2003 January; 17:120-124.) were obtained from ATCC (Rockville, Md.). The IL-3 dependent murine B-cell progenitor cell line Baf3 expressing human wild-type FLT3 (Baf3-FLT3) and ITD-mutated FLT3 (Baf3-ITD) were obtained from Dr. Michael Heinrich (Oregon Health Sciences University). Cells were maintained in RPMI media containing penn/strep, 10% FBS alone (THP-1, Baf3-ITD) and 2 ng/ml GM-CSF (MV4-11) or 10 ng/ml FLT ligand (Baf3-FLT3). MV4-11, Baf3-ITD and Baf3-FLT3 cells are all absolutely dependent on FLT3 activity for growth. GM-CSF enhances the activity of the FLT3-ITD receptor in the MV4-11 cells.

Cell proliferation assay for MV4-11, Baf3-ITD, Baf3-FLT3 and THP-1 cells. To measure proliferation inhibition by test compounds the luciferase based CellTiterGlo reagent (Promega) was used. Cells are plated at 10,000 cells per well in 100 ul of in RPMI media containing penn/strep, 10% FBS alone (THP-1, Baf3-ITD) and 0.2 ng/ml GM-CSF (MV4-11) or 10 ng/ml FLT ligand (Baf3-FLT3). Compound dilutions or 0.1% DMSO (vehicle control) are added to cells and the cells are allowed to grow for 72 hours at standard cell growth conditions (37° C., 5% $CO_2$). In combination experiments test agents were added simultaneously to the cells. Total cell growth is quantified as the difference in luminescent counts (relative light units, RLU) of cell number at Day 0 compared to total cell number at Day 3 (72 hours of growth and/or compound treatment). One hundred percent inhibition of growth is defined as an RLU equivalent to the Day 0 reading. Zero percent inhibition is defined as the RLU signal for the DMSO vehicle control at Day 3 of growth. All data points are an average of triplicate samples. The $IC_{50}$ for growth inhibition represents the dose of a compound that results in a 50% inhibition of total cell growth at Day 3 of the DMSO vehicle control. $IC_{50}$ data analysis was done with GraphPad Prism using a non-linear regression fit with a multiparameter, sigmoidal dose-response (variable slope) equation.

Immunoprecipitation and Quantitative Immunoblot Analysis. MV4-11 cells were grown in DMEM supplemented with 10% fetal bovine serum, 2 ng/ml GM-CSF and kept between $1\times10^5$ and $1\times10^6$ cells/ml. For western blot analysis of Map Kinase phosphorylation $1\times10^6$ MV4-11 cells per condition were used. For immunoprecipitation experiments examining FLT3-ITD phosphorylation, $1\times10^7$ cells were used for each experimental condition. After compound treatment, MV4-11 cells were washed once with cold 1×PBS and lysed with HNTG lysis buffer (50 mM Hepes, 150 mM NaCl, 10% Glycerol, 1% Triton —X-100, 10 mM NaF, 1 mM EDTA, 1.5 mM $MgCl_2$, 10 mM NaPyrophosphate)+4 ul/ml Protease Inhibitor Cocktail (Sigma cat.#P8340)+4 ul/ml Phosphatase Inhibitor Cocktail (Sigma Cat#P2850). Nuclei and debris were removed from cell lysates by centrifugation (5000 rpm for 5 min. at 4° C.). Cell lysates for immunoprecipitation were cleared with agarose-Protein A/G for 30 minutes at 4° C. and immunoprecipitated using the 3 ug of FLT3 antibody for 1 hours at 4° C. Immune complexes were then incubated with agarose-Protein A/G for 1 hour at 4° C. Protein A/G immunoprecipitates were washed three times in 1.0 ml of HNTG lysis buffer. Immunoprecipitates and cell lysates (40 ug total protein) were resolved on a 10% SDS-PAGE gel, and the proteins were transferred to nitrocellulose membrane. For anti-phosphotyrosine immunoblot analysis, membranes were blocked with SuperBlock (Pierce) and blotted for 2 hours with anti-phosphotyrosine (clone 4G10, Upstate Biotechnologies) followed by alkaline phosphatase-conjugated goat anti-mouse antibody. For anti-phosphoMAP kinase western blotting, membranes were blocked Super block for 1 hour and blotted overnight in primary antibody, followed by an incubation with an AP conjugated goat-anti rabbit secondary antibody. Detection of protein was done by measuring the fluorescent product of the alkaline phosphatase reaction with the substrate 9H-(1,3-dichloro-9,9-dimethylacridin-2-one-7-yl) phosphate, diammonium salt (DDAO phosphate) (Molecular Probes) using a Molecular Dynamics Typhoon Imaging system (Molecular Dynamics, Sunnyvale, Calif.). Blots were stripped and reprobed with anti-FLT3 antibody for normalization of phosphorylation signals. Quantitation of DDAO phosphate signal and $IC_{50}$ determinations were done with Molecular Dynamics ImageQuant and GraphPad Prism software.

Annexin V Staining. To examine the apoptosis of the leukemic MV4-11 cell line, cells were treated with Tipifarnib and/or FLT3 inhibitor Compound A, and Annexin V binding to phosphotidylserine on the outer leaflet of the plasma membrane of apoptotic cells was monitored using the GuavaNexin assay reagent and the Guava personal flow cytometry system (Guava Technologies; Hayward, Calif.). MV4-11 cells were plated at 200,000 cells per ml in tissue culture media containing varying concentrations of Tipifarnib and/or FLT3 inhibitor Compound A and incubated for 48 hours at 37° C., 5% $CO_2$. Cells were harvested by centrifugation at 400×g for 10 minutes at 4° C. Cells were then washed with 1×PBS and resuspended in 1× Nexin buffer at $1\times10^6$ cells/ml. 5 µl of Annexin V-PE ad 5 µl of 7-AAD was added to 40 µl of cell suspension and incubated on ice for 20 minutes protected from light. 450 ml of cold 1× Nexin buffer was added to each sample and the cells were then acquired on the Guava cytometer according to the manufacturer's instructions. All annexin positive cells were considered apoptotic- and percent Annexin positive cells was calculated.

Caspase 3/7 Activation Assay. MV4-11 cells were grown in RPMI media containing pen/strep, 10% FBS and 1 ng/mL GM-CSF. Cells were maintained between $2\times10^5$ cells/mL and $8\times10^5$ cells/mL feeding/splitting every 2-3 days. Cells were centrifuged and resuspend at $2\times10^5$ cells/mL RPMI media containing Penn/Strep, 10% FBS and 0.1 ng/mL GM-CSF. MV4-11 cells were plated at 20,000 cells per well in 100 µL of in RPMI media containing penn/strep, 10% FBS alone and 0.1 ng/mL GM-CSF (Corning Costar Cat # 3610) in the presence of various concentrations of test compounds or DMSO. In combination experiments test agents were added simultaneously to the cells. Cells were incubated for 24 hours at 37° C., 5% $CO_2$. After 24-hour incubation, caspase activity was measured with the Promega CaspaseGlo reagent (Cat# G8090) according to the manufacture's instructions. Briefly, CaspaseGlo substrate is diluted with 10 mL Caspase Glo buffer. One volume of diluted Caspase Glo reagent was added to one volume of tissue culture media and mixed for two minutes on rotating orbital shaker. Following incubation at room temperature for 60 minutes, light emission was measured on a Berthold luminometer with the 1 second program. Baseline caspase activity was defined as an RLU equivalent to DMSO vehicle (0.1% DMSO) treated cells. $EC_{50}$ data analysis was completed with GraphPad Prism using a non-linear regression fit with a multiparameter, sigmoidal dose-response (variable slope) equation.

Combination Index Analysis. To determine growth inhibition synergy of a FTI and FLT3 inhibitor combination based on the method of Chou and Talalay (Chou and Talalay. See Chou T C, Talalay P. (1984) "Quantitative analysis of dose-effect relationships: the combined effects of multiple drugs or enzyme inhibitors." Adv Enzyme Regul. 22:27-55.), fixed ratio combination dosing with isobolar statistical analysis was performed. Test agents were combined at a fixed ratio of the individual $IC_{50}$ for proliferation for each cell line and dosed at varying concentrations including 9, 3, 1, 1/3, 1/9 times the determined $IC_{50}$ dose. To measure proliferation inhibition by test combinations the luciferase based CellTiterGlo reagent (Promega) was used. Cells are plated at 10,000 cells per well in 100 ul of in RPMI media containing penn/strep, 10% FBS alone (THP-1, Baf3-ITD) and 0.1 ng/ml GM-CSF (MV4-11) or 100 ng/ml FLT ligand (Baf3-FLT3). Total cell growth is quantified as the difference in luminescent counts (relative light units, RLU) of cell number at Day 0 compared to total cell number at Day 3 (72 hours of growth and/or compound treatment). All data points are an average of triplicate samples. One hundred percent inhibition of growth is defined as an RLU equivalent to the Day 0 reading. Zero percent inhibition is defined as the RLU signal for the DMSO vehicle control at Day 3 of growth. Inhibition data was analyzed using Calcsyn (BioSoft, Ferguson, Mo.) and the combination index (C.I.) calculated. C.I. values <0.9 are considered synergistic.

In Vivo Combination Studies

The effect of combination treatment of the FLT3 Inhibitor FLT3 inhibitor compounds and Tipifarnib (Zarnestra™) on the growth of MV-4-11 human AML tumor xenografts in nude mice was tested using FLT3 inhibitor Compounds B and D. The in vivo study was designed to extend the in vitro observations to evaluate the potential for a synergistic anti-tumor effect of FLT3 inhibitor Compounds B and D each administered orally together with Tipifarnib to nude mice bearing established MV-4-11 tumor xenografts.

Anti-Tumor Effect of FLT3 Inhibitor Compound B Alone

Female athymic nude mice (CD-1, nu/nu, 9-10 weeks old) were obtained from Charles River Laboratories (Wilmington, Mass.) and were maintained according to NIH standards. All mice were group housed (5 mice/cage) under clean-room conditions in sterile micro-isolator cages on a 12-hour light/dark cycle in a room maintained at 21-22° C. and 40-50% humidity. Mice were fed irradiated standard rodent diet and water ad libitum. All animals were housed in a Laboratory Animal Medicine facility that is fully accredited by the American Association for Assessment and Accreditation of Laboratory Animal Care (AAALAC). All procedures involving animals were conducted in compliance with the NIH *Guide for the Care and Use of Laboratory Animals* and all protocols were approved by an Internal Animal Care and Use Committee (IACUC).

The human leukemic MV4-11 cell line was obtained from the American Type Culture Collection (ATCC Number: CRL-9591) and propagated in RPMI medium containing 10% FBS (fetal bovine serum) and 5 ng/mL GM-CSF (R&D Systems). MV4-11 cells are derived from a patient with childhood acute myelomonocytic leukemia with an 11q23 translocation resulting in a MLL gene rearrangement and containing an FLT3-ITD mutation (AML subtype M4)(1,2). MV4-11 cells express constitutively active phosphorylated FLT3 receptor as a result of a naturally occurring FLT3/ITD mutation. Strong anti-tumor activity against MV4-11 tumor growth in the nude mouse tumor xenograft model is anticipated to be a desirable quality of the invention.

In pilot growth studies, the following conditions were identified as permitting MV4-11 cell growth in nude mice as subcutaneous solid tumor xenografts: Immediately prior to injection, cells were washed in PBS and counted, suspended 1:1 in a mixture of PBS:Matrigel (BD Biosciences) and then loaded into pre-chilled 1 cc syringes equipped with 25 gauge needles. Female athymic nude mice weighing no less than 20-21 grams were inoculated subcutaneously in the left inguinal region of the thigh with $5 \times 10^6$ tumor cells in a delivery volume of 0.2 mL. For regression studies, the tumors were allowed to grow to a pre-determined size prior to initiation of dosing. Approximately 3 weeks after tumor cell inoculation, mice bearing subcutaneous tumors ranging in size from $10^6$ to 439 $mm^3$ (60 mice in this range) were randomly assigned to treatment groups such that all treatment groups had similar starting mean tumor volumes of ~200 $mm^3$. Mice were dosed orally by gavage with vehicle (control group) or compound at various doses twice-daily (b.i.d.) during the week and once-daily (q.d.) on weekends. Dosing was continued for 11 consecutive days, depending on the kinetics of tumor growth and size of tumors in vehicle-treated control mice. If tumors in the control mice reached ~10% of body weight (~2.0 grams), the study was to be terminated. FLT3 inhibitor compounds were prepared fresh daily as a clear solution (@1, 3 and 10 mg/mL) in 20% HPβCD/2% NMP/10 mM Na Phosphate, pH 3-4 (NMP=Pharmasolve, ISP Technologies, Inc.) or other suitable vehicle and administered orally as described above. During the study, tumor growth was measured three times-a-week (M, W, F) using electronic Vernier calipers. Tumor volume ($mm^3$) was calculated using the formula $(L \times W)^2/2$, where L=length (mm) and W=width (shortest distance in mm) of the tumor. Body weight was measured three times-a-week and a loss of body weight >10% was used as an indication of lack of compound tolerability. Unacceptable toxicity was defined as body weight loss >20% during the study. Mice were closely examined daily at each dose for overt clinical signs of adverse, drug-related side effects.

On the day of study termination, a final tumor volume and final body weight were obtained on each animal. Mice were euthanized using 100% $CO_2$ and tumors were immediately excised intact and weighed, with final tumor wet weight (grams) serving as a primary efficacy endpoint.

The time course of the inhibitory effects of FLT3 inhibitor compounds on the growth of MV4-11 tumors is illustrated in FIG. 1. Values represent the mean (±sem) of 15 mice per treatment group. Percent inhibition (%I) of tumor growth was calculated versus tumor growth in the vehicle-treated Control group on the last study day. Statistical significance versus Control was determined by Analysis of Variance (ANOVA) followed by Dunnett's t-test: * $p<0.05$; ** $p<0.01$.

A similar reduction of final tumor weight was noted at study termination. (See FIG. 2). Values represent the mean (±sem) of 15 mice per treatment group, except for the high dose group where only 5 of 15 mice were sacrificed on the day of study termination. Percent Inhibition was calculated versus the mean tumor weight in the vehicle-treated control group. Statistical significance versus Control was determined by ANOVA followed by Dunnett's t-test: ** $p<0.01$.

FIG. 1: FLT3 inhibitor Compound B administered orally by gavage at doses of 10, 30 and 100 mg/kg b.i.d. for 11 consecutive days, produced statistically significant, dose-dependent inhibition of growth of MV4-11 tumors grown subcutaneously in nude mice. On the last day of treatment (Day 11), mean tumor volume was dose-dependently decreased by 44%, 84% ($p<0.01$) and 94% ($p<0.01$) at doses of 10, 30 and 100 mg/kg, respectively, compared to the mean tumor volume of the vehicle-treated group. Tumor regression was observed at doses of 30 mg/kg and 100 mg/kg, with statistically significant decreases of 42% and 77%, respectively, versus the starting mean tumor volumes on Day 1. At the lowest dose tested of 10 mg/kg, modest growth delay was observed (44% I vs Control), however this effect did not achieve statistical significance.

FIG. 2: Following eleven consecutive days of oral dosing, FLT3 inhibitor Compound B produced statistically significant, dose-dependent reductions of final tumor weight compared to the mean tumor weight of the vehicle-treated group, with 48%, 85% ($p<0.01$) and 99% ($p<0.01$) decreases at 10, 30 and 100 mg/kg doses, respectively. In some mice, at the high dose of FLT3 inhibitor Compound B, final tumors had regressed to non-palpable, non-detectable tumors.

Mice were weighed three times each week (M, W, F) during the study and were examined daily at the time of dosing for overt clinical signs of any adverse, drug-related side effects. No overt toxicity was noted for FLT3 inhibitor Compound B and no significant adverse effects on body weight were observed during the 11-day treatment period at doses up to 200 mg/kg/day. Overall, across all dose groups for FLT3 inhibitor Compound B the mean loss of body weight was <3% of initial body weight, indicating that the FLT3 inhibitor compounds were well-tolerated.

To establish further that FLT3 inhibitor compounds reached the expected target in tumor tissue, the level of FLT3 phosphorylation in tumor tissue obtained from vehicle- and compound-treated mice was measured. Results for FLT3 inhibitor Compound B is shown in FIG. 3. For this pharmacodynamic study, a sub-set of 10 mice from the vehicle-treated control group were randomized into two groups of 5 mice each and then treated with another dose of vehicle or compound (100 mg/kg, po). Tumors were harvested 2 hours later and snap frozen for assessment of FLT3 phosphorylation by immunobloting.

Harvested tumors were processed for immunoblot analysis of FLT3 phosphorylation in the following manner: 100 mg of tumor tissue was dounce homogenized in lysis buffer (50 mM Hepes, 150 mM NaCl, 10% Glycerol, 1% Triton —X-100, 10 mM NaF, 1 mM EDTA, 1.5 mM $MgCl_2$, 10 mM NaPyrophosphate) supplemented with phosphatase (Sigma Cat# P2850) and protease inhibitors (Sigma Cat #P8340). Insoluble debris was removed by centrifugation at 1000×g for 5 minutes at 4° C. Cleared lysates (15 mg of total protein at 10 mg/ml in lysis buffer) were incubated with 10 μg of agarose conjugated anti-FLT3 antibody, clone C-20 (Santa Cruz cat #sc-479ac), for 2 hours at 4° C. with gentle agitation. Immunoprecipitated FLT3 from tumor lysates were then washed four times with lysis buffer and separated by SDS-PAGE. The SDS-PAGE gel was transferred to nitrocellulose and immunoblotted with anti-phosphotyrosine antibody (clone-4G10, UBI cat. #05-777), followed by alkaline phosphatase-conjugated goat anti-mouse secondary antibody (Novagen cat. # 401212). Detection of protein was done by measuring the fluorescent product of the alkaline phosphatase reaction with the substrate 9H-(1,3-dichloro-9,9-dimethylacridin-2-one-7-yl) phosphate, diammonium salt (DDAO phosphate) (Molecular Probes cat. # D 6487) using a Molecular Dynamics Typhoon Imaging system (Molecular Dynamics, Sunnyvale, Calif.). Blots were then stripped and reprobed with anti-FLT3 antibody for normalization of phosphorylation signals.

As illustrated in FIG. 3, a single dose of FLT3 inhibitor Compound B at 100 mg/kg produced a biologically significant reduction in the level of FLT3 phosphorylation in MV4-11 tumors compared to tumors from vehicle-treated mice. (Total FLT3 is shown in the bottom plot.) These results further demonstrate that the compounds of the present invention are in fact interacting with the expected FLT3 target in the tumor.

MV-4-11 tumor-bearing nude mice were prepared as described above, in the aforementioned in vivo evaluation of the oral anti-tumor efficacy of FLT3 inhibitor Compound B.
Anti-Tumor Effect of FLT3 Inhibitor Compound B Administered with Tipifarnib MV-4-11 tumor-bearing nude mice were prepared as described above, in the aforementioned in vivo evaluation of the oral anti-tumor efficacy of FLT3 inhibitor Compound B alone.

Nude mice with MV-4-11 tumors were randomized to five treatment groups of 15 mice each with mean tumor size was equivalent in each treatment group. Tumor volume (mm3) was calculated using the formula (L×W)2/2, where L=length (mm) and W=width (shortest distance in mm) of the tumor. The starting mean tumor volume for each treatment group was approximately 250 mm3.

Mice were dosed orally twice-daily (bid) during the week and once-daily (qd) on weekends with either Vehicle (20% HP RCD/2% NMP/10 mM Na Phosphate, pH 3-4 (NMP=Pharmasolve, ISP Technologies, Inc.), a sub-efficacious dose of FLT3 inhibitor Compound B (10 mg/kg), an efficacious dose of FLT3 inhibitor Compound B (20 mg/kg) and Tipifarnib (50 mg/kg) alone or in combination with each dose of FLT3 inhibitor Compound B. Dosing was continued for nine consecutive days. Tumor growth was measured three times during the study using electronic Vernier calipers. Body weight was measured three times during the study and a loss of body weight >10% was used as an indication of lack of compound tolerability.

The time course of the effect of treatment with FLT3 inhibitor Compound B and Tipifarnib alone and in combination on the growth of MV-4-11 tumors is illustrated in FIG. 15. As shown, FLT3 inhibitor Compound B administered at a dose of 10 mg/kg bid produced marginal significant inhibition of tumor growth compared to the Vehicle-treated group that reached tumors volumes of approximately 800 $mm^3$. FLT3 inhibitor Compound B administered at a dose of 20 mg/kg bid provided significant inhibition of tumor growth compared to the Vehicle-treated group and completely controlled tumor growth compared to the control. This dose was observed to produce tumor growth stasis but induced no tumor regression (defined as a tumor size less than the tumor size at study initiation). As illustrated in FIG. 15, on the final day of treatment (Day 9), tumor volume was not significantly reduced by Tipifarnib (50 mg/kg) alone when compared to control. Values represent the mean (±sem) of 15 mice per treatment group. Percent inhibition of tumor growth was calculated versus tumor growth in the Vehicle-treated Control group on the last study day. Statistical significance versus Control was determined by ANOVA followed by Dunnett's t-test: * p<0.01.

Again as shown in FIG. 15, Tipifarnib administered as a single agent at a dose of 50 mg/kg was ineffective. However, when both agents were administered orally in combination, there was a statistically significant regression of tumor volume from the mean starting tumor volume on Day 1 when FLT3 inhibitor Compound B was administered at either 10 or 20 mg/kg. On day 9, the mean tumor volume of the group was inhibited by 95% compared to the Vehicle-treated control group. Thus, combination treatment produced an inhibitory effect (ie. tumor regression) that was much greater than either agent administered alone. In point of fact, Tipifarnib (50 mg/kg) and FLT3 inhibitor Compound B alone at 10 mg/kg were essentially inactive while the combination, remarkably provided essentially complete tumor regression.

FIG. 15 illustrates the effects on tumor volume of orally administered FLT3 inhibitor Compound B and Tipifarnib alone or in combination on the growth of MV-4-11 tumor xenografts in nude mice.

FIG. 16 illustrates the effects of orally administered FLT3 inhibitor Compound B and Tipifarnib alone or in combination on the final volume of MV-4-11 tumor xenografts in nude mice on the final study day. As shown in FIG. 16, at study termination, synergy was noted with combination treatment when the final tumor volumes of each treatment group were compared with the exception that the final tumor weight reached statistical significance.

FIG. 17 illustrates the effects of orally administered FLT3 inhibitor Compound B and Tipifarnib alone or in combination on the final tumor weight of MV-4-11 tumor xenografts in nude mice on the terminal study day. As shown in FIG. 17, at study termination, synergy was confirmed by tumor weight measurement in the 10 mg/kg FLT3 inhibitor Compound B/50 mg/kg Tipifarnib combination treatment group when compared to the final tumor weight of the appropriate treatment group when the agents were administered alone.

No overt toxicity was noted and no significant adverse effects on body weight were observed during the 9-day treatment period with either agent alone or in combination. In summary, combination treatment with FLT3 inhibitor Compound B and Tipifarnib produced significantly greater inhibition of tumor growth compared to either FLT3 inhibitor Compound B or Tipifarnib administered alone.

Anti-Tumor Effect of FLT3 Inhibitor Compound D Alone

The oral anti-tumor efficacy of FLT3 inhibitor Compound D of the present invention was evaluated in vivo using a nude mouse MV4-11 human tumor xenograft regression model in athymic nude mice using the method as described above, in the aforementioned in vivo evaluation of the oral anti-tumor efficacy of FLT3 inhibitor Compound B.

MV-4-11 tumor-bearing nude mice were prepared as described above, in the aforementioned in vivo evaluation of the oral anti-tumor efficacy of FLT3 inhibitor Compound B alone.

Female athymic nude mice weighing no less than 20-21 grams were inoculated subcutaneously in the left inguinal region of the thigh with $5 \times 10^6$ tumor cells in a delivery volume of 0.2 mL. For regression studies, the tumors were allowed to grow to a pre-determined size prior to initiation of dosing. Approximately 3 weeks after tumor cell inoculation, mice bearing subcutaneous tumors ranging in size from 100 to 586 mm$^3$ (60 mice in this range; mean of 288±133 mm$^3$ (SD) were randomly assigned to treatment groups such that all treatment groups had statistically similar starting mean tumor volumes (mm$^3$). Mice were dosed orally by gavage with vehicle (control group) or compound at various doses twice-daily (b.i.d.) during the week and once-daily (qd) on weekends. Dosing was continued for 11 consecutive days, depending on the kinetics of tumor growth and size of tumors in vehicle-treated control mice. If tumors in the control mice reached 10% of body weight (~2.0 grams), the study was to be terminated. FLT3 inhibitor Compound D was prepared fresh daily as a clear solution (@1, 5 and 10 mg/mL) in 20% HPβCD/D5W, pH 3-4 or other suitable vehicle and administered orally as described above. During the study, tumor growth was measured three times-a-week (M, W, F) using electronic Vernier calipers. Tumor volume (mm$^3$) was calculated using the formula $(L \times W)^2/2$, where L=length (mm) and W=width (shortest distance in mm) of the tumor. Body weight was measured three times-a-week and a loss of body weight >10% was used as an indication of lack of compound tolerability. Unacceptable toxicity was defined as body weight loss >20% during the study. Mice were closely examined daily at each dose for overt clinical signs of adverse, drug-related side effects.

On the day of study termination (Day 12), a final tumor volume and final body weight were obtained on each animal. Mice were euthanized using 100% $CO_2$ and tumors were immediately excised intact and weighed, with final tumor wet weight (grams) serving as a primary efficacy endpoint.

The time course of the inhibitory effects of FLT3 inhibitor Compound D of the present invention on the growth of MV-4-11 tumors is illustrated in FIG. 18. Values represent the mean (±sem) of 15 mice per treatment group. Percent inhibition (% I) of tumor growth was calculated versus tumor growth in the vehicle-treated Control group on the last study day. Statistical significance versus Control was determined by Analysis of Variance (ANOVA) followed by Dunnett's t-test: * $p<0.05$; ** $p<0.01$.

As seen in FIG. 18, FLT3 inhibitor Compound D of the present invention, administered orally by gavage at doses of 10, 50 and 100 mg/kg b.i.d. for 11 consecutive days, produced statistically significant, dose-dependent inhibition of growth of MV4-11 tumors grown subcutaneously in nude mice. On the last day of treatment (Day 11), mean tumor volume was dose-dependently decreased with nearly 100% inhibition ($p<0.001$) at doses of 50 and 100 mg/kg, compared to the mean tumor volume of the vehicle-treated group. FLT3 inhibitor Compound D of the present invention produced tumor regression at doses of 50 mg/kg and 100 mg/kg, with statistically significant decreases of 98% and 93%, respectively, versus the starting mean tumor volumes on Day 1. At the lowest dose tested of 10 mg/kg, no significant growth delay was observed compared to the vehicle-treated control group. When dosing was stopped on Day 12 in the 100 mg/kg treated dose group and the tumor was allowed to re-grow, only 6/12 mice showed palpable, measurable tumor on study day 34.

FLT3 inhibitor Compound D of the present invention produced virtually complete regression of tumor mass as indicated by no measurable remnant tumor at study termination. (See FIG. 19). Bars on the graph of FIG. 19 represent the mean (±sem) of 15 mice per treatment group. As shown, there was no significant decrease in final tumor weight at the 10 mg/kg dose, consistent with the tumor volume data in FIG. 18. At the dose of 50 mg/kg, there is no bar represented on the graph since there was no measurable tumor mass detectable in these mice at termination, consistent with the complete regression of tumor volume noted in FIG. 18. The 100 mg/kg dose group is not represented on this graph since these mice were taken off drug and remnant tumor was allowed to regrow as stated above.

Following eleven consecutive days of oral dosing, FLT3 inhibitor Compound D of the present invention produced dose-dependent reductions of final tumor weight compared to the mean tumor weight of the vehicle-treated group, with complete regression of tumor mass noted at the 50 mg/kg dose. (See FIG. 19).

Mice were weighed three times each week (M, W, F) during the study and were examined daily at the time of dosing for overt clinical signs of any adverse, drug-related side effects. No overt toxicity was noted for FLT3 inhibitor Compound D of the present invention and no significant adverse effects on body weight were observed during the 11-day treatment period at doses up to 200 mg/kg/day (See FIG. 20). Overall, across all dose groups, there was no significant loss of body weight compared to the starting body weight, indicating that FLT3 inhibitor Compound D of the present invention was well-tolerated.

To establish further that FLT3 inhibitor Compound D of the present invention reached the expected target in tumor tissue, the level of FLT3 phosphorylation in tumor tissue obtained from vehicle- and compound-treated mice was measured. Results for FLT3 inhibitor Compound D of the present invention are shown in FIG. 21. For this pharmacodynamic study, a sub-set of 6 mice from the vehicle-treated control group were randomized into three groups of 2 mice each and then treated with another dose of vehicle or compound (10 and 100 mg/kg, po). Tumors were harvested 6 hours later and snap frozen for assessment of FLT3 phosphorylation by western blots.

Harvested tumors were frozen and processed for immunoblot analysis of FLT3 phosphorylation in the following manner: 200 mg of tumor tissue was dounce homogenized in lysis buffer (50 mM Hepes, 150 mM NaCl, 10% Glycerol, 1% Triton —X-100, 10 mM NaF, 1 mM EDTA, 1.5 mM $MgCl_2$, 10 mM NaPyrophosphate) supplemented with phosphatase (Sigma Cat# P2850) and protease inhibitors (Sigma Cat #P8340). Insoluble debris was removed by centrifugation at 1000×g for 5 minutes at 4° C. Cleared lysates (15 mg of total protein at 10 mg/ml in lysis buffer) were incubated with 10 μg of agarose conjugated anti-FLT3 antibody, clone C-20 (Santa Cruz cat #sc-479ac), for 2 hours at 4° C. with gentle agitation.

Immunoprecipitated FLT3 from tumor lysates were then washed four times with lysis buffer and separated by SDS-PAGE. The SDS-PAGE gel was transferred to nitrocellulose and immunoblotted with anti-phosphotyrosine antibody (clone-4G 10, UBI cat. #05-777), followed by alkaline phosphatase-conjugated goat anti-mouse secondary antibody (Novagen cat. # 401212). Detection of protein was done by measuring the fluorescent product of the alkaline phosphatase reaction with the substrate 9H-(1,3-dichloro-9,9-dimethylacridin-2-one-7-yl) phosphate, diammonium salt (DDAO phosphate) (Molecular Probes cat. # D 6487) using a Molecular Dynamics Typhoon Imaging system (Molecular Dynamics, Sunnyvale, Calif.). Blots were then stripped and reprobed with anti-FLT3 antibody for normalization of phosphorylation signals.

As illustrated in FIG. 21, a single dose of FLT3 inhibitor Compound D of the present invention at 100 mg/kg produced a biologically significant reduction in the level of FLT3 phosphorylation (top panel, tumor 5 and 6) in MV4-11 tumors compared to tumors from vehicle-treated mice (tumor 1 and 2). (Total FLT3 is shown in the bottom plot.) There was also a partial reduction of phosphorylation in animals treated with 10 mg/kg of the compound (tumor 3-4). These results further demonstrate that the compound of the present invention is in fact interacting with the expected FLT3 target in the tumor.

Anti-Tumor Effect of FLT3 Inhibitor Compound D Administered with Tipifarnib

To demonstrate in vivo synergy of the combination of FLT3 inhibitor Compound D and Tipifarnib in MV-4-11 xenograft model, tumor-bearing nude mice were prepared as described above, in the aforementioned in vivo evaluation of the oral anti-tumor efficacy of FLT3 inhibitor Compound B alone.

Nude mice with MV-4-11 tumors were randomized to four treatment groups of 10 mice each with mean tumor size was equivalent in each treatment group. Tumor volume (mm3) was calculated using the formula (L×W)2/2, where L=length (mm) and W=width (shortest distance in mm) of the tumor. The starting mean tumor volume for each treatment group was approximately 250 mm3.

Mice were dosed orally twice-daily (bid) during the week and once-daily (qd) on weekends with either Vehicle (20% HPB-CD, pH 3-4) or sub-efficacious doses of FLT3 inhibitor Compound D (25 mg/kg) or Tipifarnib (50 mg/kg) alone or in combination. Dosing was continued for sixteen consecutive days. Tumor growth was measured three times-a-week (Monday, Wednesday, Friday) using electronic Vernier calipers. Body weight was measured three times-a-week and a loss of body weight >10% was used as an indication of lack of compound tolerability.

The time course of the effect of treatment with FLT3 inhibitor Compound D and Tipifarnib alone and in combination on the growth of MV-4-11 tumors is illustrated in FIG. 22. As shown, FLT3 inhibitor Compound D administered at a dose of 25 mg/kg bid produced stasis of tumor growth compared to the Vehicle-treated group which reached tumors volumes of approximately 1500 $mm^3$. As illustrated in FIG. 22, on the final day of treatment (Day 16), tumor volume was significantly inhibited by 76% compared to the vehicle-treated control group. Values represent the mean (±sem) of 10 mice per treatment group. Percent inhibition of tumor growth was calculated versus tumor growth in the Vehicle-treated Control group on the last study day. Statistical significance versus Control was determined by ANOVA followed by Dunnett's t-test: * $p<0.01$.

As shown in FIG. 22, Tipifarnib administered as a single agent at a dose of 50 mg/kg was ineffective. However, when both agents were administered orally in combination, there was a statistically significant regression of tumor volume from the mean starting tumor volume on Day 1. On day 16, the mean tumor volume of the group was inhibited by 95% compared to the Vehicle-treated control group. Thus, combination treatment produced an inhibitory effect (ie. tumor regression) that was approximately 1.3 times the additive effect of each agent given alone, indicating synergy (see FIG. 22).

FIG. 23 illustrates the effects on tumor volume of orally administered FLT3 inhibitor Compound D and Tipifarnib alone or in combination on the growth of MV-4-11 tumor xenografts in nude mice. FIG. 24 illustrates the effects of orally administered FLT3 inhibitor Compound D and Tipifarnib alone or in combination on the final weight of MV-4-11 tumor xenografts in nude mice. As shown in FIG. 24, at study termination, similar synergy was noted with combination treatment when the final tumor weights of each treatment group were compared.

No overt toxicity was noted and no significant adverse effects on body weight were observed during the 16-day treatment period with either agent alone or in combination. Plasma and tumor samples were collected two hours after the last dose of compounds for determination of drug levels. In summary, combination treatment with FLT3 inhibitor Compound D and Tipifarnib produced significantly greater inhibition of tumor growth compared to either FLT3 inhibitor Compound D or Tipifarnib administered alone.

Conclusions

Herein we provide significant evidence that the combination of an FTI and a FLT3 inhibitor synergistically inhibits the growth of and induces the death of FLT3-dependent cells in vitro and in vivo (such as AML cells derived from patients with FLT3-ITD mutations). In vitro studies, in multiple FLT3-dependent cell lines, demonstrated synergistic inhibition of AML cell proliferation with the FTI/FLT3 inhibitor combination by both the combination index method of Chou and Talalay and the median effect method using a combination of single sub-optimal doses of each compound. Additionally, the combination of an FTI and a FLT3 inhibitor induced dramatic cell death in FLT3-dependent AML cells. This effect on apoptosis induction was significantly greater than either agent alone. This synergistic effect of an FTI/FLT3 inhibitor combination was observed for multiple, structurally distinct FLT3 inhibitors and two different FTIs. Accordingly, this synergistic inhibition of proliferation and induction of apoptosis would occur for any FLT3 inhibitor/FTI combination. Interestingly, the combination of the FTI Tipifarnib with a FLT3 inhibitor significantly increases the potency of FLT3 inhibitor mediated decrease in FLT3 receptor signaling. Furthermore, the synergy observed using in vitro methods was recapitulated in an in vivo tumor model using FLT3-dependent AML cells (MV4-11) with the combination of the FTI Tipifarnib and two chemically distinct FLT3 inhibitors (FLT3 inhibitor Compounds B and D). Accordingly, this effect would be seen for any FLT3 inhibitor/FTI combination. To our knowledge, this is the first time that synergistic AML cell killing has been observed with the combination of an FTI and a FLT3 inhibitor. Additionally, the synergies observed in the combination were not obvious to those skilled in the art based on previous data. The observed synergy is likely related to FTIs known inhibition small GTPase (Ras and Rho) and NfkB driven proliferation and survival and the FLT3 inhibitors' ability to decrease proliferation and survival signaling by the FLT3 receptor. Additionally, the FTI/FLT3 inhibitor combination had significant effects on the activity of the FLT3 receptor itself. Although the mechanism for this is currently unknown, it is likely to have a significant role in both the inhibition of cell proliferation and activation of cell death observed with the FLT3 inhibitor/FTI combination. In sum, these studies represent a novel treatment paradigm for FLT3 disorders, particularly hematological malignancies expressing wild-type or mutant FLT3 and the basis for the design of clinical trials to test FTI and FLT3 inhibitor combinations for the treatment of FLT3 disorders, particularly AML, ALL and MDS.

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

What is claimed is:

1. A method of treating a disorder selected from the group consisting of acute myeloid leukemia, acute lymphocytic leukemia and myelodysplastic syndrome comprising administering to a subject in need thereof a therapeutically effective amount of (1) a FLT3 kinase inhibitor that is:

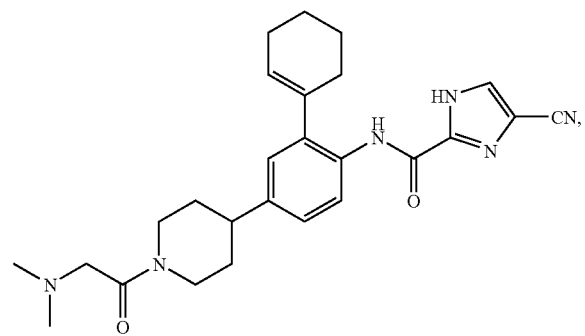

or a pharmaceutically acceptable salt thereof and (2) a farnesyl transferase inhibitor that is (+)-6-[amino(4-chlorophenyl)(1-methyl-1H-imidazol-5-yl)methyl]-4-(3-chlorophenyl)-1-methyl-2(1H)-quinolinone, or a pharmaceutically acceptable acid addition salt thereof.

2. The method of claim 1 further comprising administering to the subject a therapeutically effective amount of chemotherapy.

3. The method of claim 1 further comprising administering to the subject a therapeutically effective amount of radiation therapy.

4. The method of claim 1 further comprising administering to the subject a therapeutically effective amount of gene therapy.

5. The method of claim 1 further comprising administering to the subject a therapeutically effective amount of immunotherapy.

6. A method of treating a disorder selected from the group consisting of acute myeloid leukemia, acute lymphocytic leukemia and myelodysplastic syndrome comprising administering to a subject in need thereof a therapeutically effective amount of (1) a first pharmaceutical composition comprising a FLT3 kinase inhibitor that is:

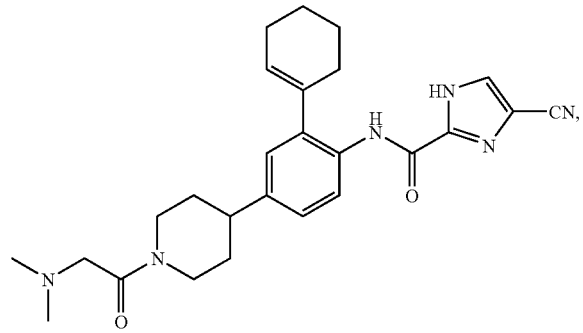

or a pharmaceutically acceptable salt thereof and a pharmaceutically acceptable carrier, and (2) a second pharmaceutical composition comprising a farnesyl transferase inhibitor that is (+)-6-[amino(4-chlorophenyl)(1-methyl-1H-imidazol-5-yl)methyl]-4-(3-chlorophenyl)-1-methyl-2(1H)-quinolinone, or a pharmaceutically acceptable acid addition salt thereof and a pharmaceutically acceptable carrier.

7. The method of claim 6 further comprising administering to the subject a prophylactically effective amount of chemotherapy.

8. The method of claim 6 further comprising administering to the subject a prophylactically effective amount of radiation therapy.

9. The method of claim 6 further comprising administering to the subject a prophylactically effective amount of gene therapy.

10. The method of claim 6 further comprising administering to the subject a prophylactically effective amount of immunotherapy.

11. A method of treating a disorder selected from the group consisting of acute myeloid leukemia, acute lymphocytic leukemia and myelodysplastic syndrome comprising administering to a subject in need thereof a therapeutically effective amount of a pharmaceutical composition comprising a FLT3 kinase inhibitor that is:

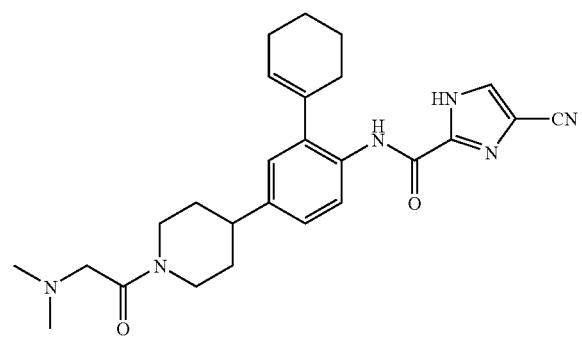 [SMILES: CN(C)CC(=O)N1CCC(c2ccc(NC(=O)c3nc(C#N)c[nH]3)c(C3=CCCCC3)c2)CC1]

or a pharmaceutically acceptable salt thereof, a farnesyl transferase inhibitor that is (+)-6-[amino(4-chlorophenyl)(1-methyl-1H-imidazol-5-yl)methyl]-4-(3-chlorophenyl)-1-methyl-2(1H)-quinolinone or a pharmaceutically acceptable acid addition salt thereof, and a pharmaceutically acceptable carrier.

12. The method of claim 11 further comprising administering to the subject a therapeutically effective amount of chemotherapy.

13. The method of claim 11 further comprising administering to the subject a therapeutically effective amount of radiation therapy.

14. The method of claim 11 further comprising administering to the subject a therapeutically effective amount of gene therapy.

15. The method of claim 11 further comprising administering to the subject a therapeutically effective amount of immunotherapy.

* * * * *